(12) United States Patent
Bieniarz et al.

(10) Patent No.: US 12,092,643 B2
(45) Date of Patent: Sep. 17, 2024

(54) DETECTING TARGETS USING MASS TAGS AND MASS SPECTROMETRY

(71) Applicant: Ventana Medical Systems, Inc., Tucson, AZ (US)

(72) Inventors: Christopher Bieniarz, Tucson, AZ (US); Jan Froehlich, Oro Valley, AZ (US); Brian Daniel Kelly, Tucson, AZ (US); Rui Hong, Oro Valley, AZ (US); Mark Lefever, Oro Valley, AZ (US); Phillip Miller, Tucson, AZ (US); Hong Wang, Oro Valley, AZ (US)

(73) Assignee: Ventana Medic Systems, Inc., Tucson, AZ (US)

( * ) Notice: Subject to any disclaimer, the term of this patent is extended or adjusted under 35 U.S.C. 154(b) by 577 days.

(21) Appl. No.: 17/021,659

(22) Filed: Sep. 15, 2020

(65) Prior Publication Data
US 2021/0063411 A1    Mar. 4, 2021

Related U.S. Application Data

(60) Division of application No. 16/055,046, filed on Aug. 4, 2018, now Pat. No. 10,883,999, which is a continuation of application No. 14/981,181, filed on Dec. 28, 2015, now Pat. No. 10,078,083, which is a continuation of application No. 13/805,983, filed on Jan. 25, 2013, now Pat. No. 9,291,597, which is a continuation of application No. PCT/US2011/042853, filed on Jul. 1, 2011.

(60) Provisional application No. 61/464,937, filed on Mar. 11, 2011, provisional application No. 61/464,977, filed on Mar. 11, 2011, provisional application No. 61/398,944, filed on Jul. 2, 2010, provisional application No. 61/398,942, filed on Jul. 2, 2010.

(51) Int. Cl.
*G01N 33/68*       (2006.01)

(52) U.S. Cl.
CPC .............. *G01N 33/6848* (2013.01)

(58) Field of Classification Search
CPC .................... G01N 33/6848; G01N 27/62
See application file for complete search history.

(56) References Cited

U.S. PATENT DOCUMENTS

| 7,132,519 B2 | 11/2006 | Monforte et al. |
| 9,291,597 B2 | 3/2016 | Hong et al. |
| 2005/0100976 A1 | 5/2005 | Bieniarz |

OTHER PUBLICATIONS

Toth et al. Simultaneous Visualization of Multiple Antigens With Tyramide Signal Amplification Using Antibodies From the Same Species. Journal or Histochemistry & Cytochemistry 2007, vol. 55, No. 6, pp. 545-554. (Year: 2007).*

* cited by examiner

*Primary Examiner* — Shafiqul Haq
(74) *Attorney, Agent, or Firm* — Charney IP Law LLC; Thomas M. Finetti

(57) ABSTRACT

Particular disclosed embodiments disclosed herein concern using a one or more various mass tags, which can be specifically deposited at targets through direct or indirect enzymatic-catalyzed transformation, to provide a method for identifying targets in tissue samples. The mass tags may be labeled with stable isotopes to produce mass tags having the same chemical structure but different masses. Mass codes produced by ionizing the mass tags are detected and/or quantified using mass spectrometry. The method can be used for multiplexed detection of multiple targets in a particular sample. In some embodiments, a map divided into sections representing sections of the tissue sample may be prepared, with the map sections including data corresponding to quantification data wherein the size of a mass peak is determined and correlated with the amount of a target for the corresponding tissue sample section.

18 Claims, 64 Drawing Sheets
Specification includes a Sequence Listing.

Exp. 1 - ER(L), PR(H)

Exp. 2 - ER(H), PR(L)

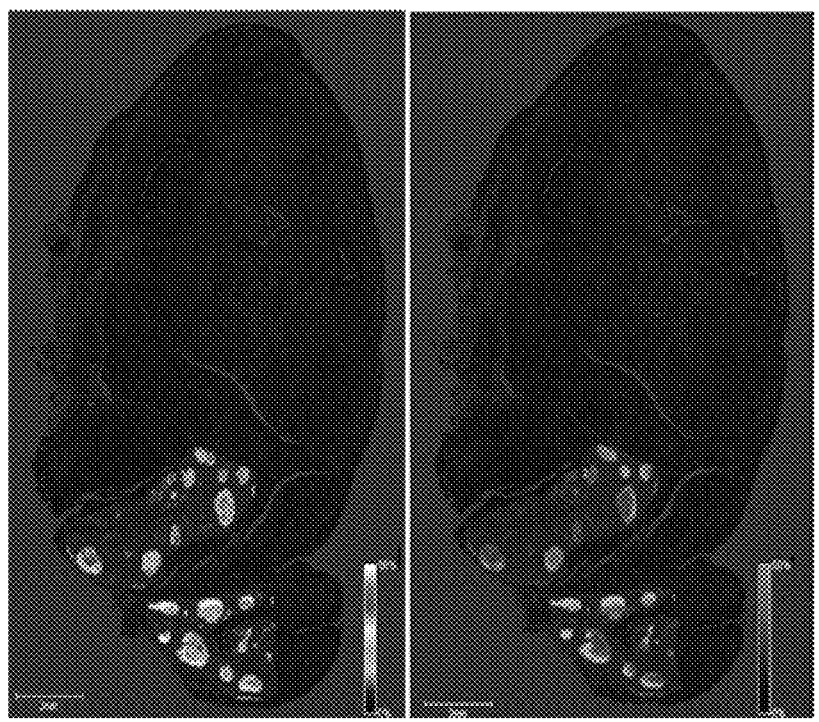
FIG. 21A   FIG. 21B   FIG. 21C

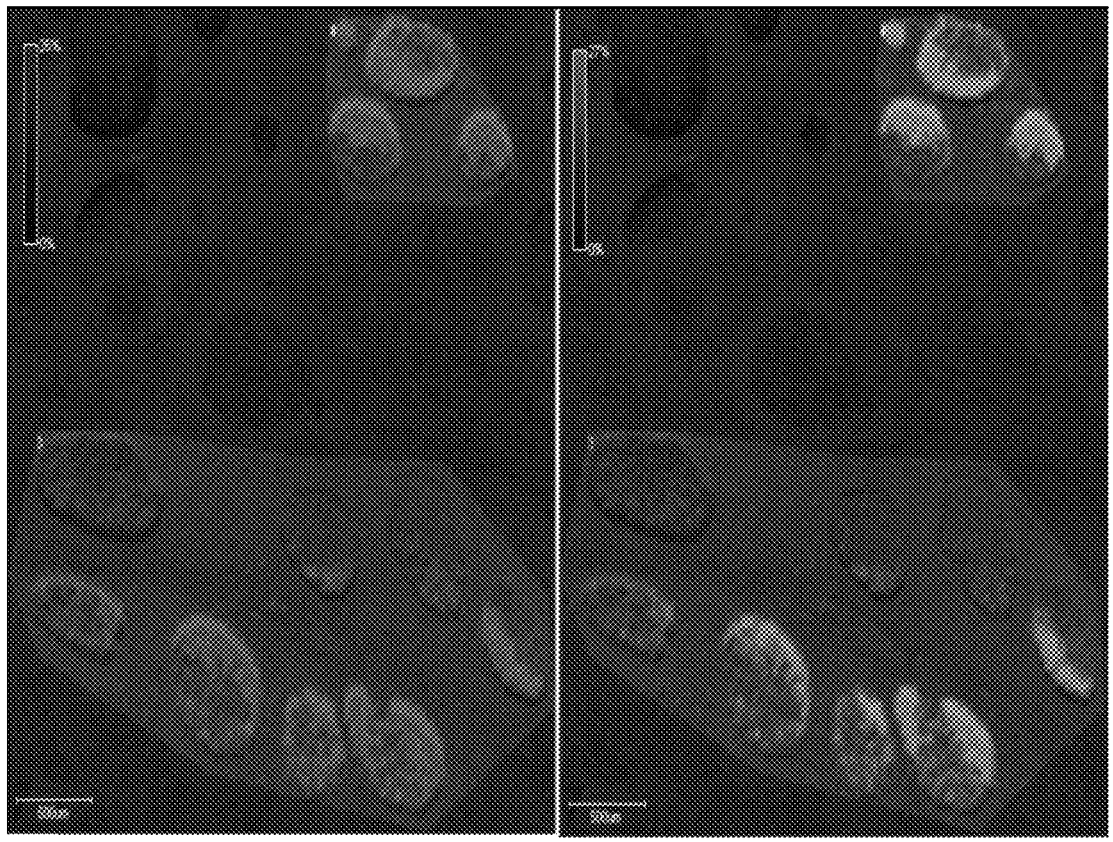
FIG. 24A  FIG. 24B
FIG. 24C
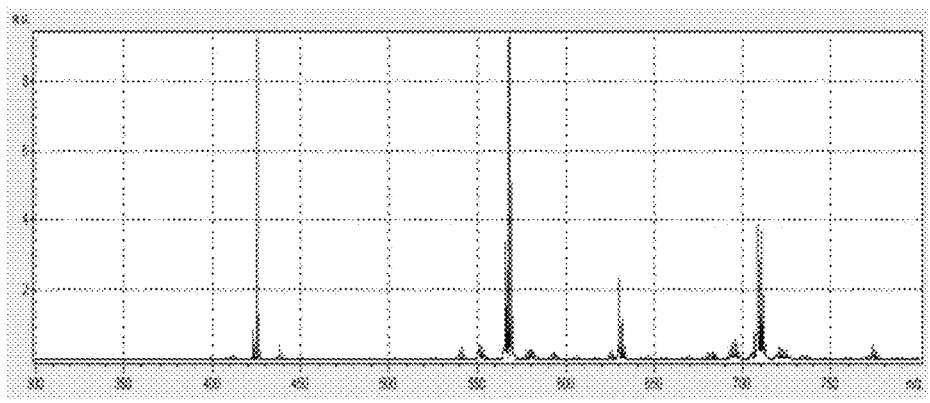

FIG. 25A
FIG. 25B
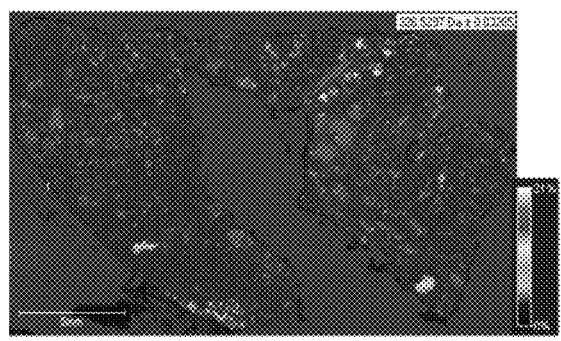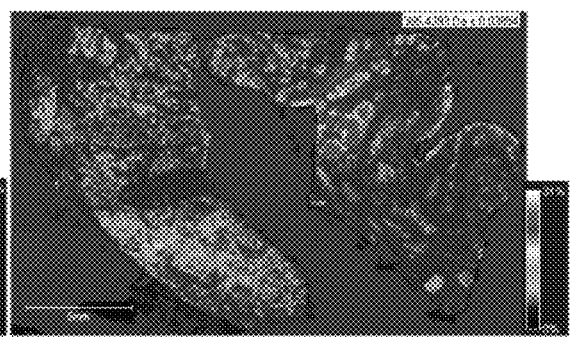
FIG. 25C
FIG. 25D
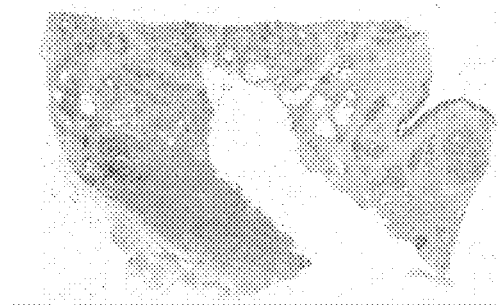
FIG. 25E
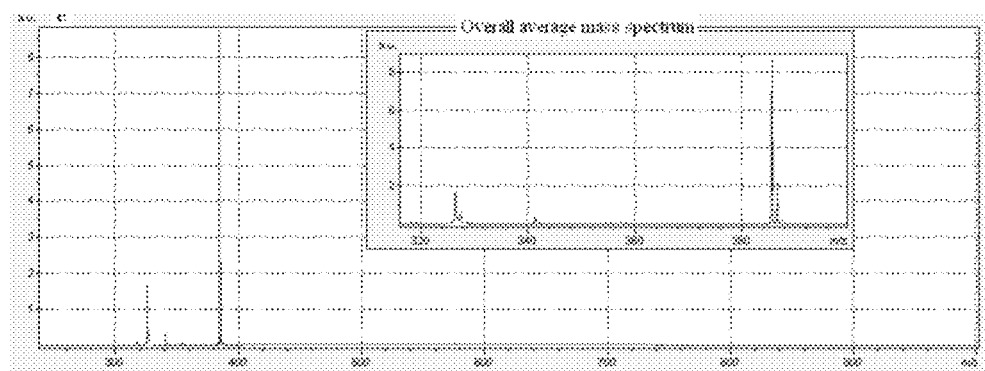

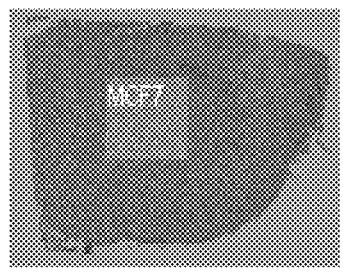
FIG. 26A
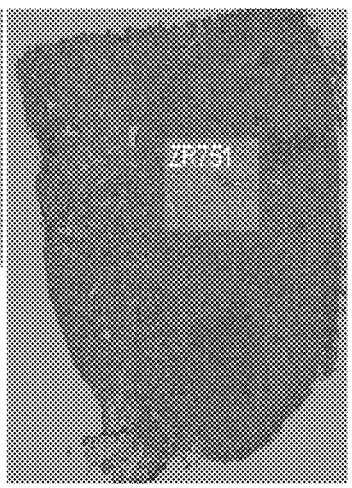
FIG. 26B
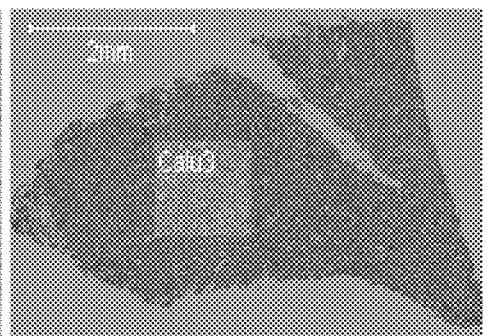
FIG. 26C
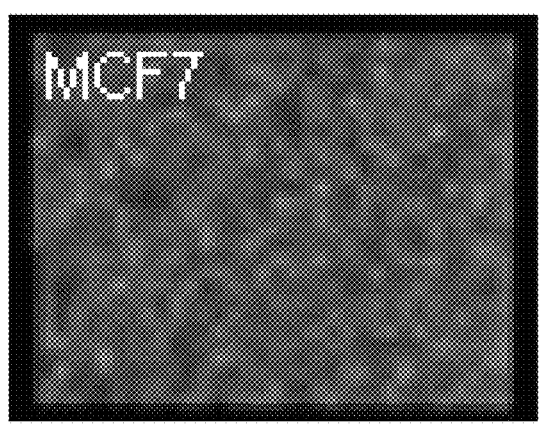
FIG. 27A
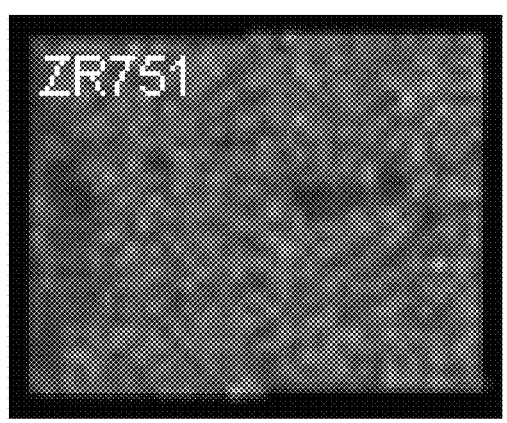
FIG. 27B
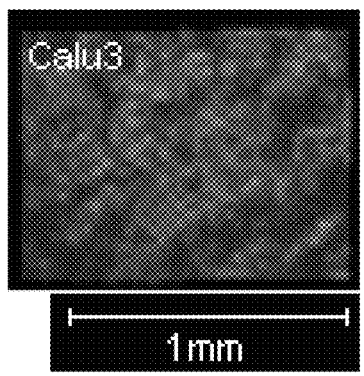
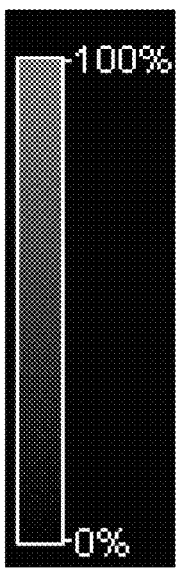
FIG. 27C

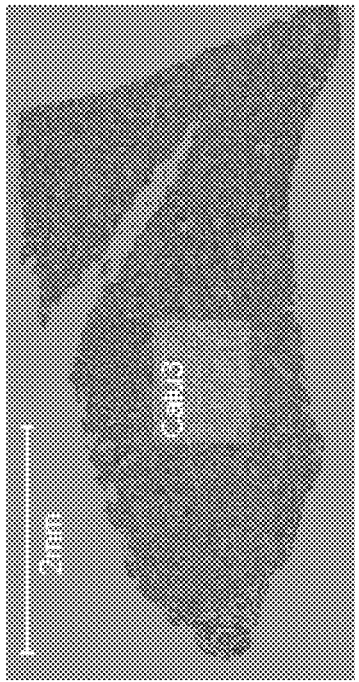
FIG. 29A
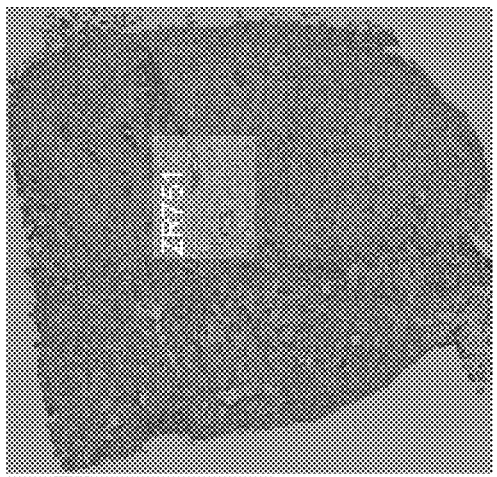
FIG. 29B
FIG. 29C
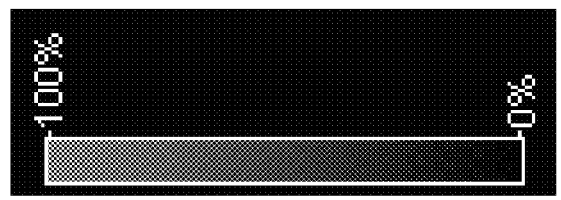
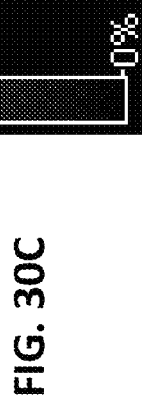
FIG. 30C
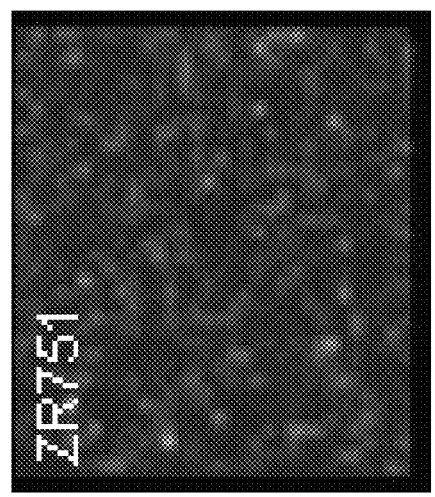
FIG. 30B
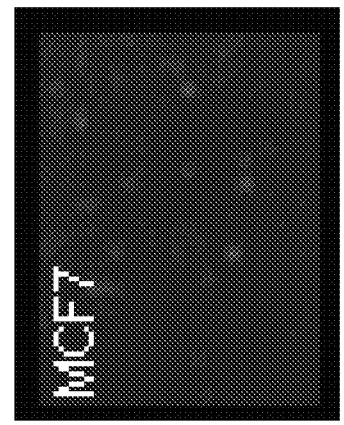
FIG. 30A

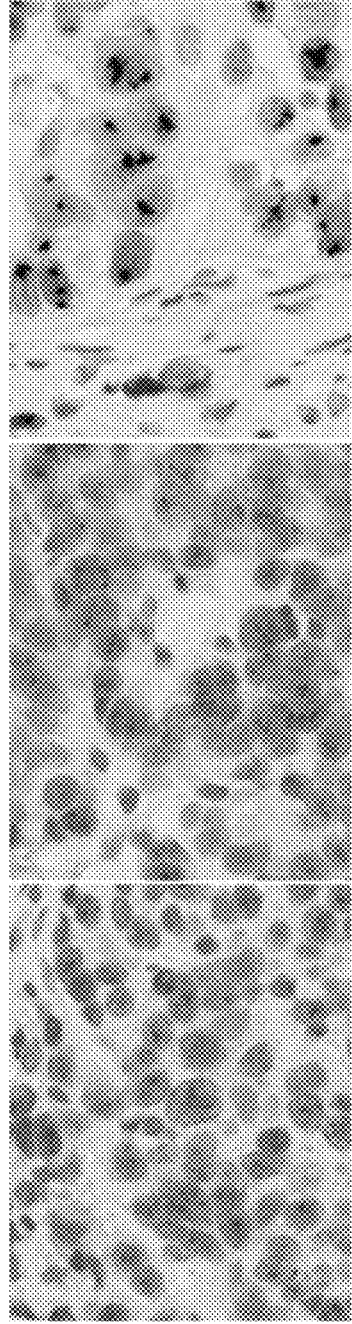
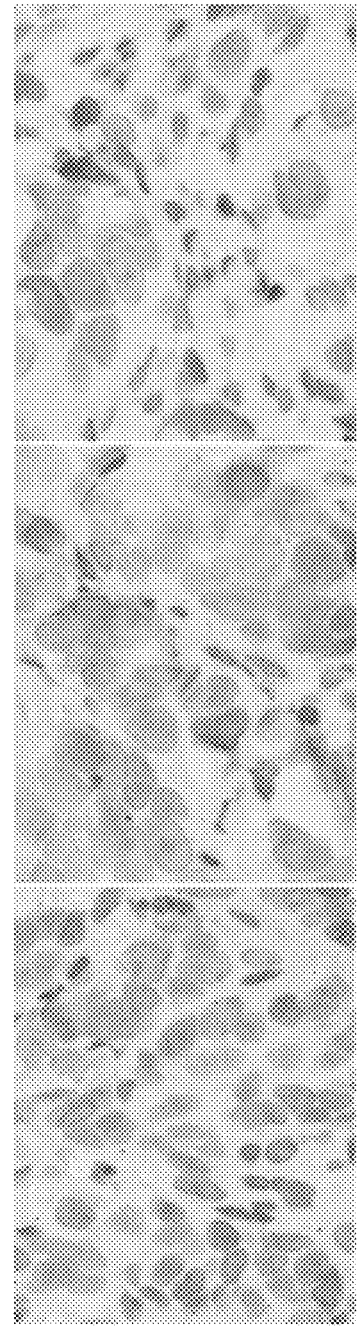

Prior Art

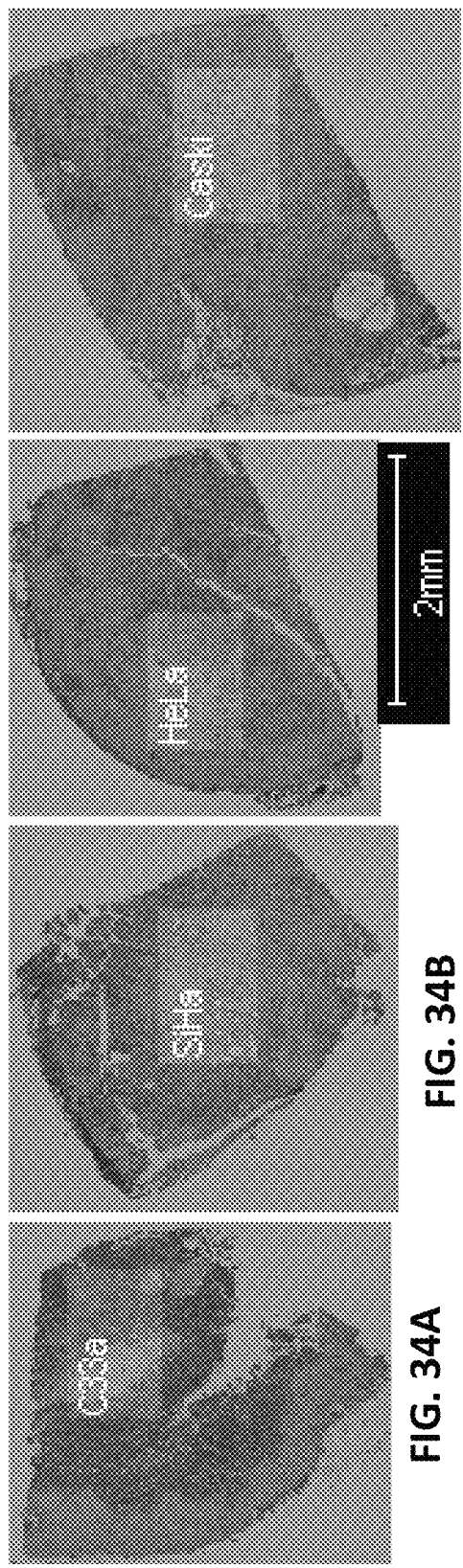

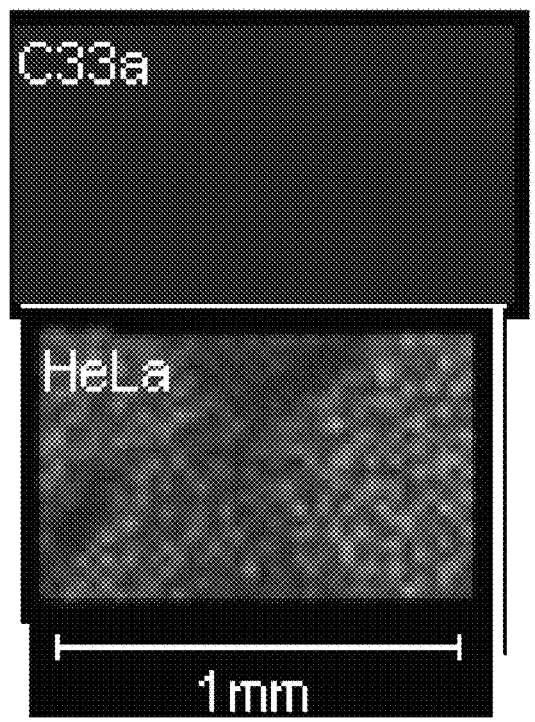
FIG. 35A
FIG. 35C
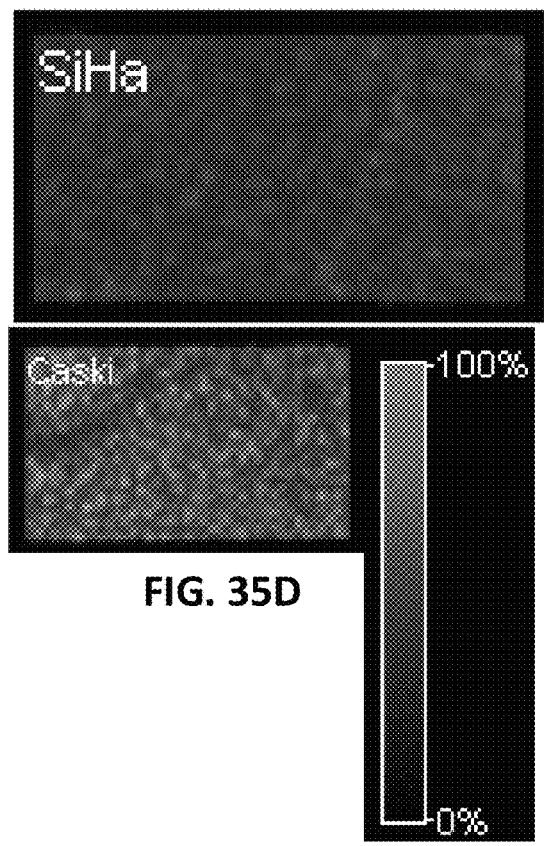
FIG. 35B
FIG. 35D

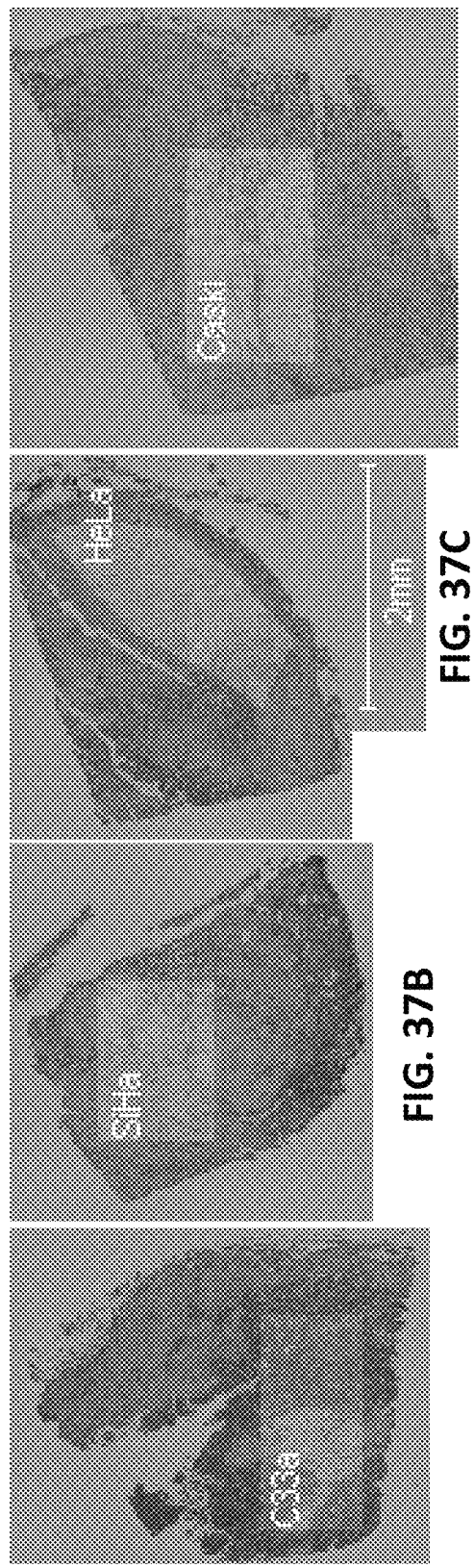

FIG. 38A
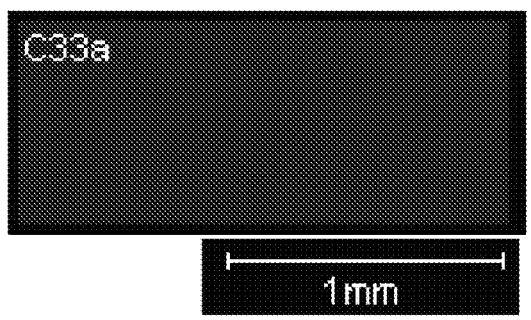
FIG. 38B
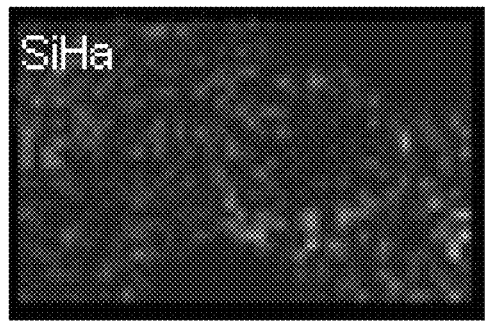
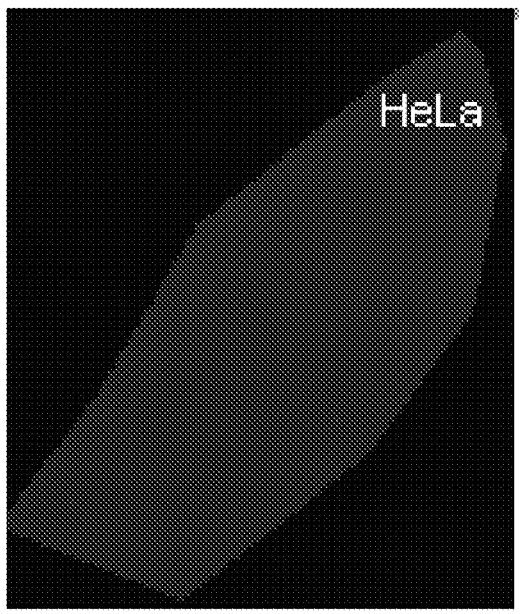
FIG. 38C
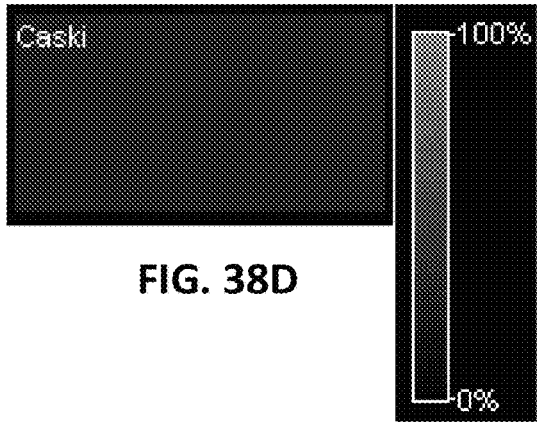
FIG. 38D

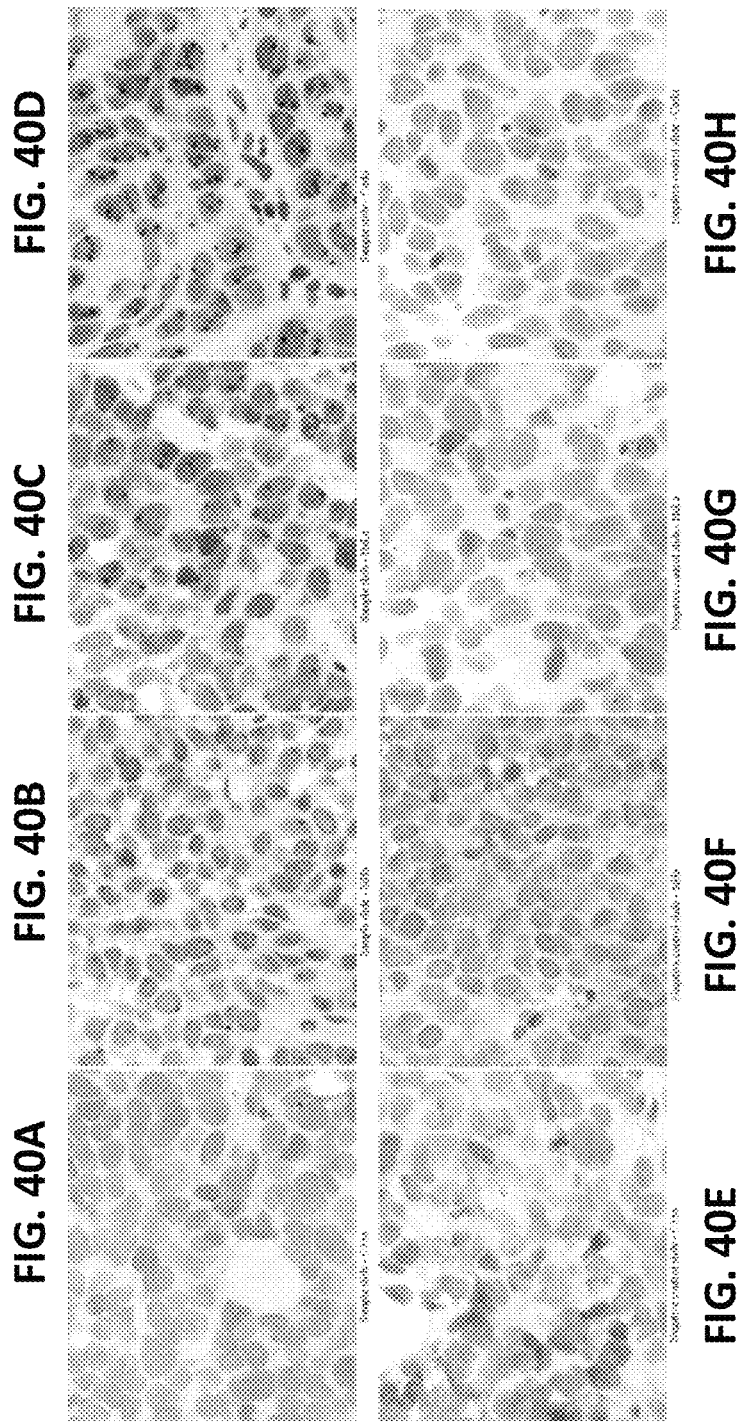

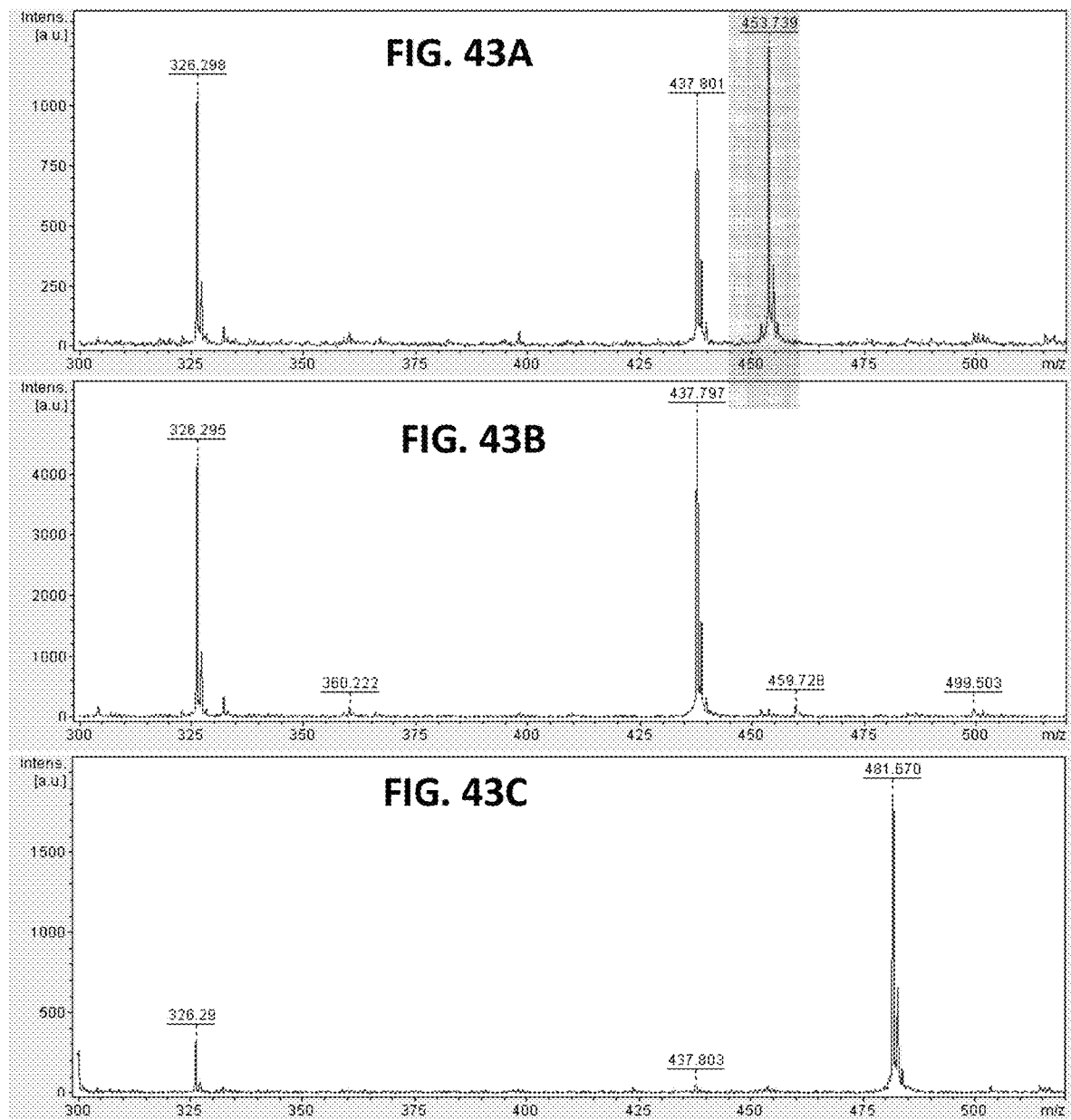

FIG. 45A
FIG. 45B
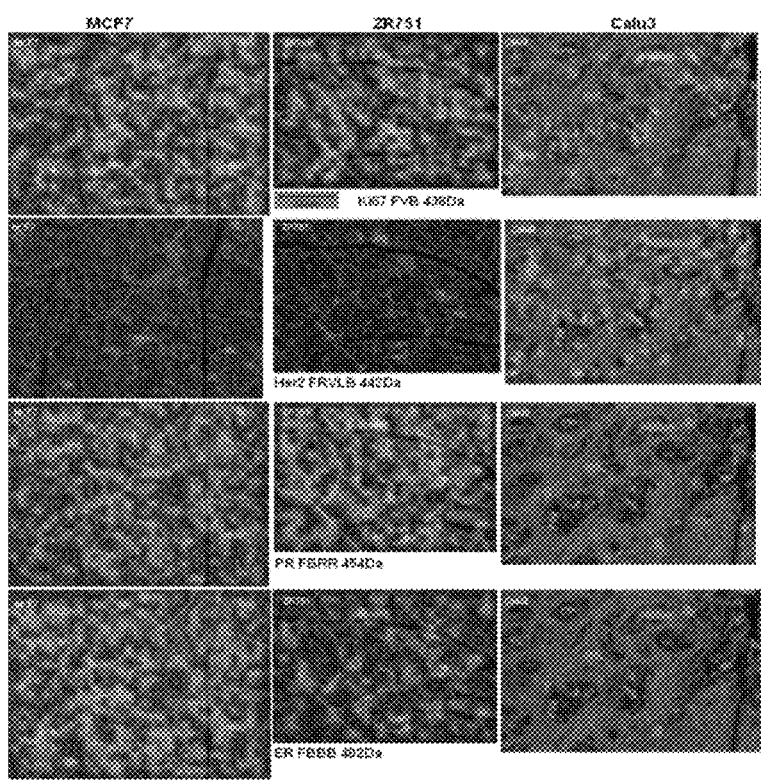
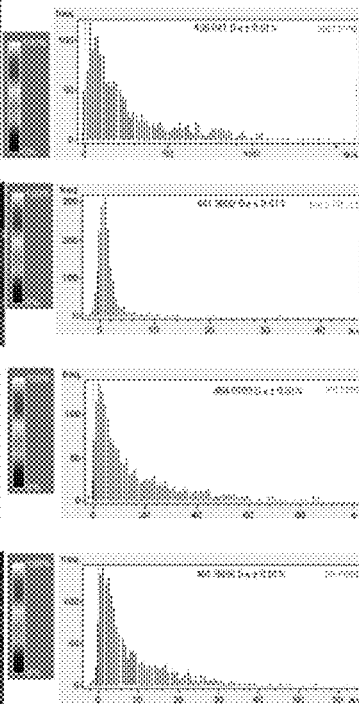
FIG. 45C
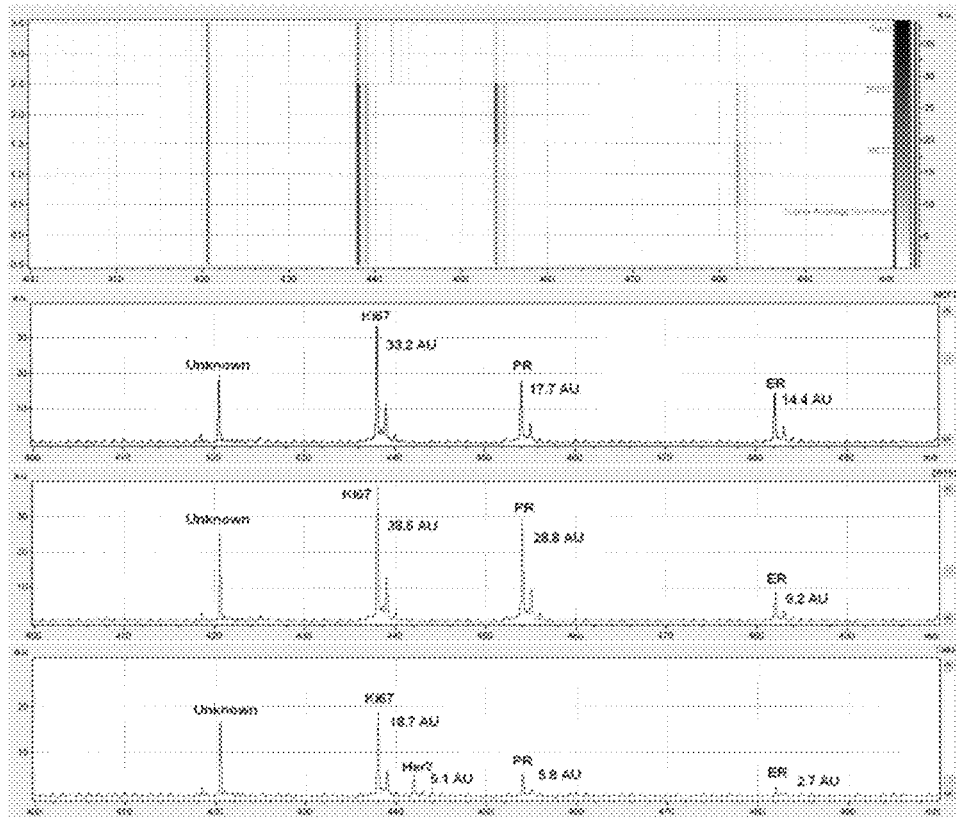

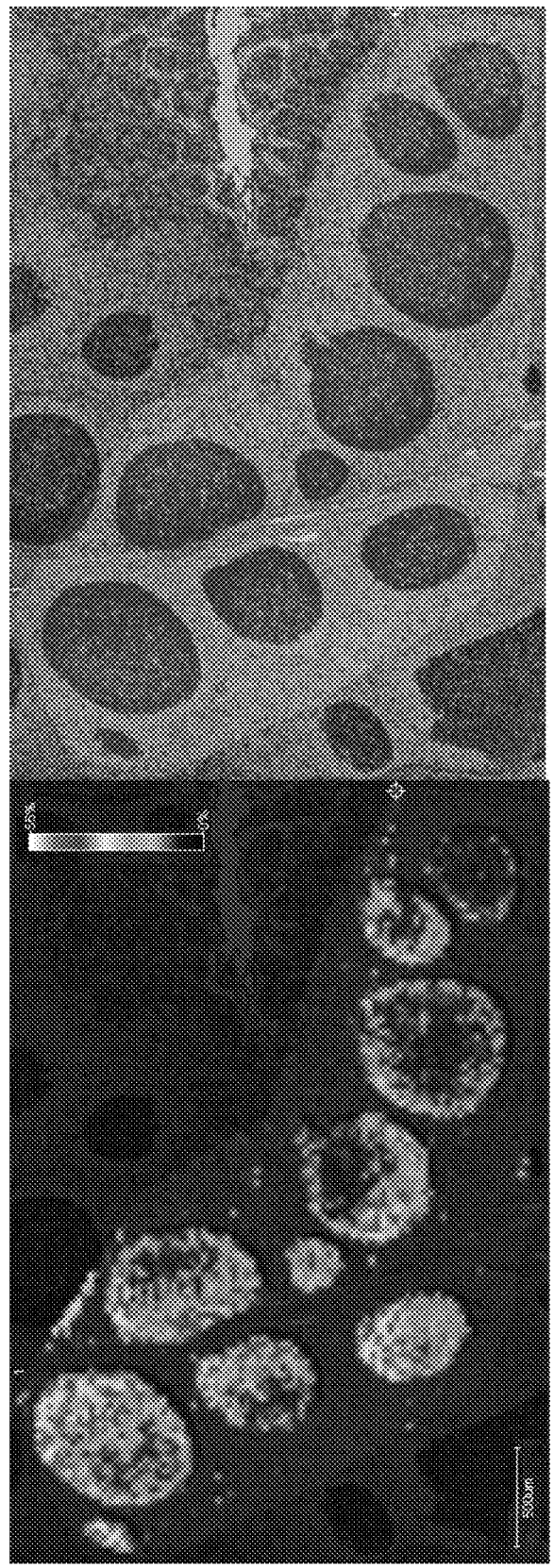

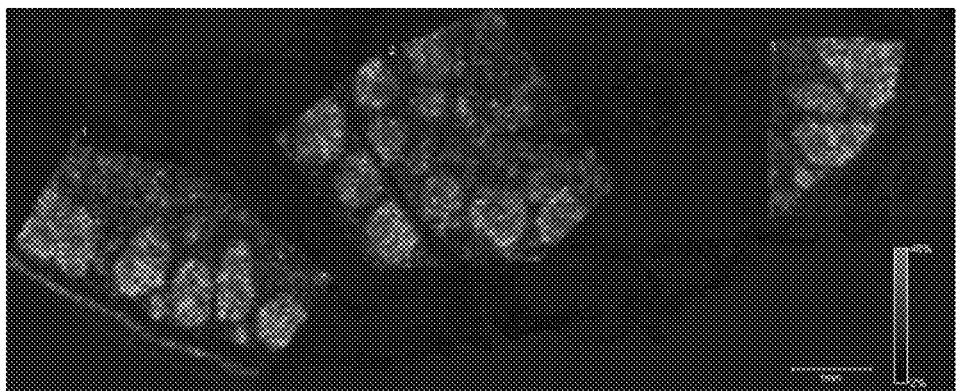
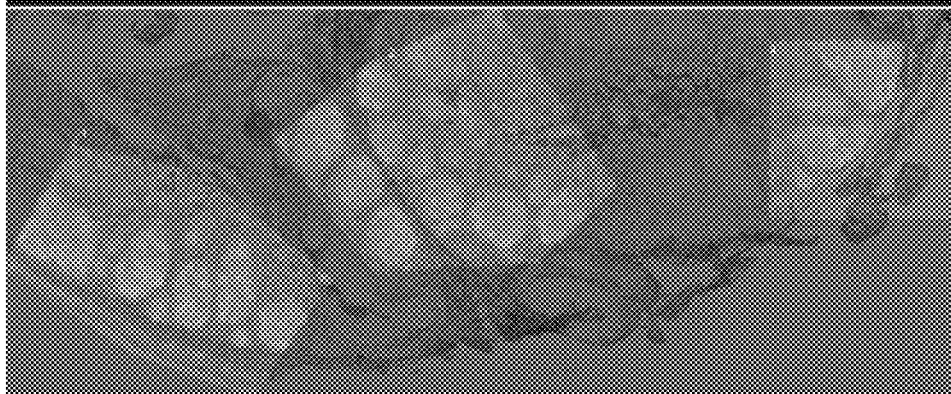
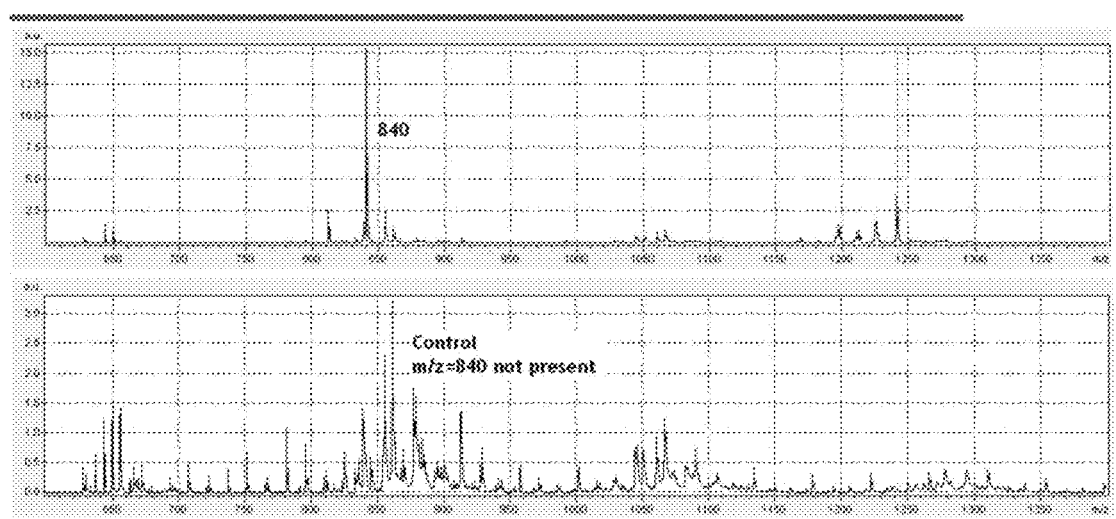
FIG. 65C

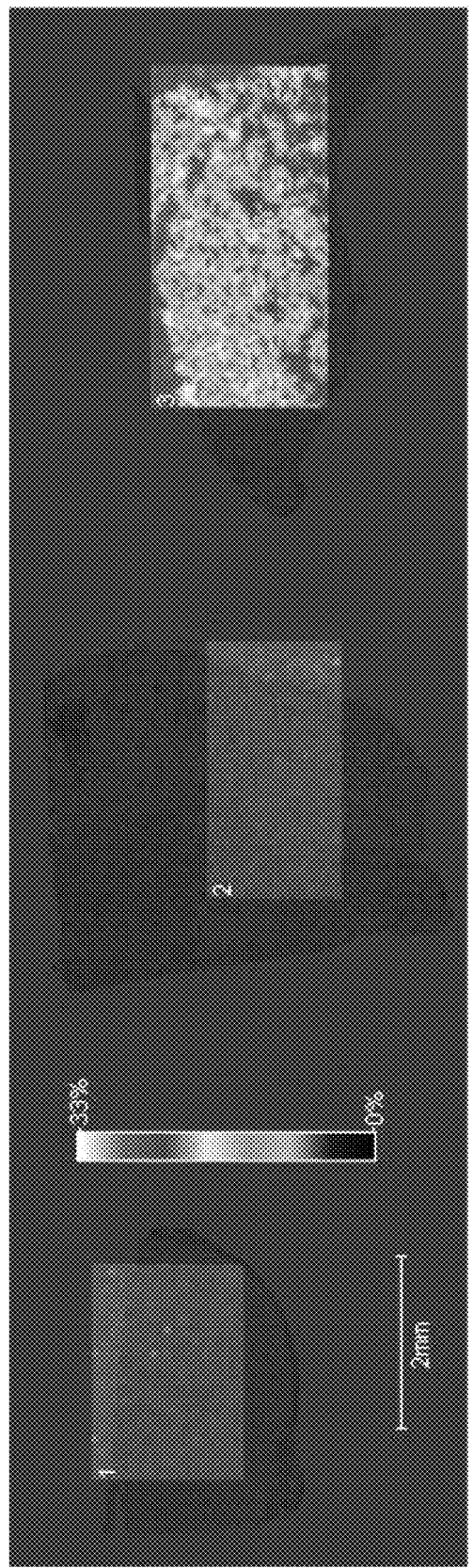

FIG. 72A
FIG. 72B
FIG. 72C
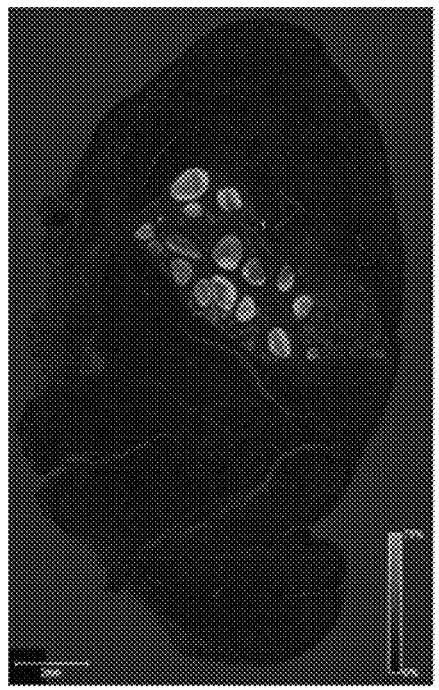
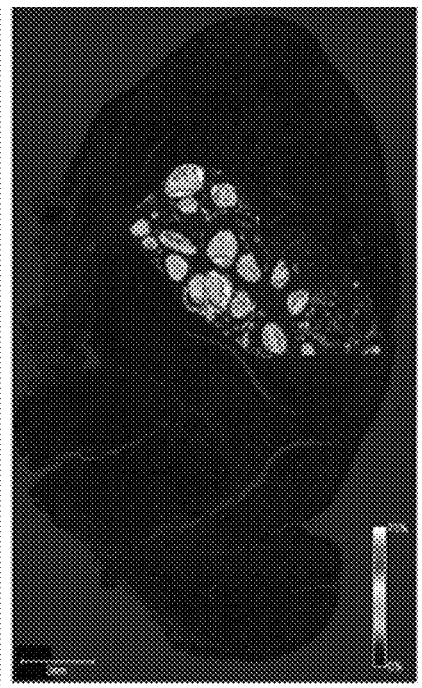
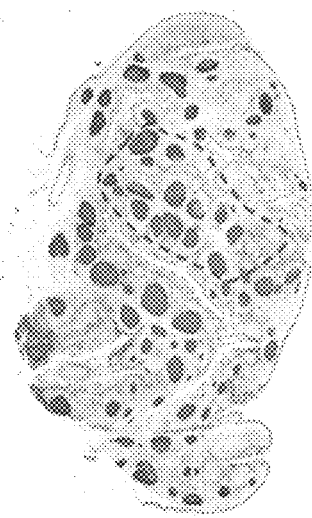
FIG. 72D
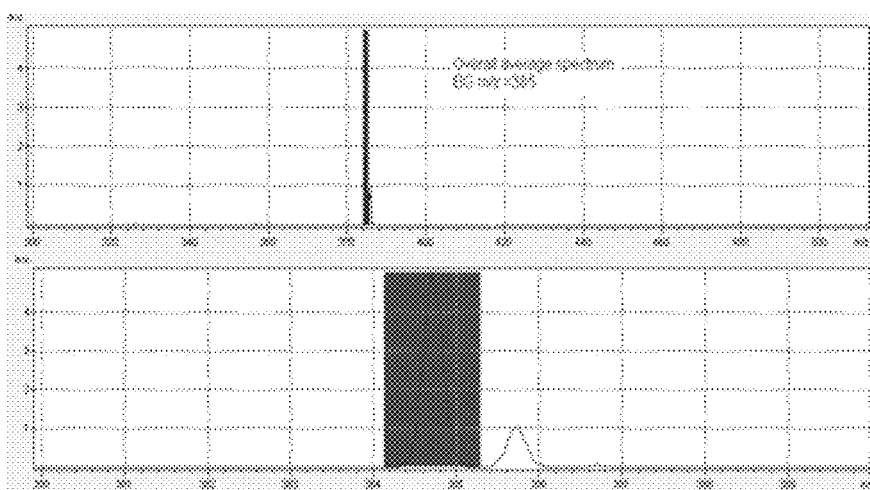

FIG. 73A
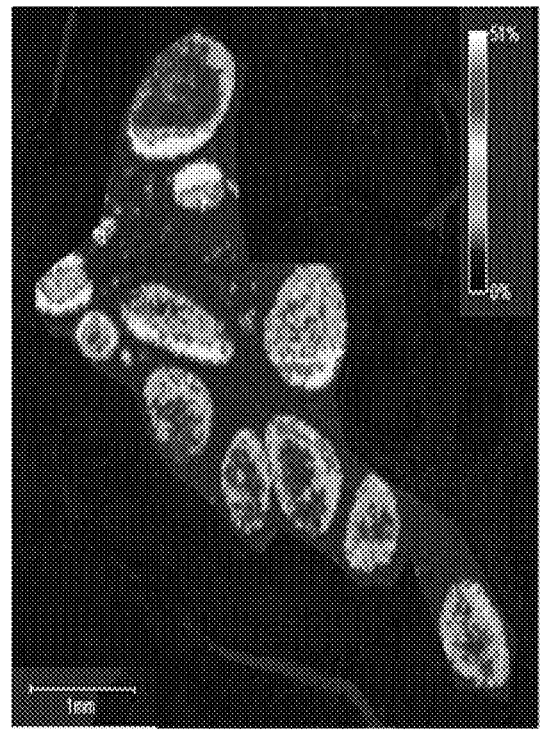
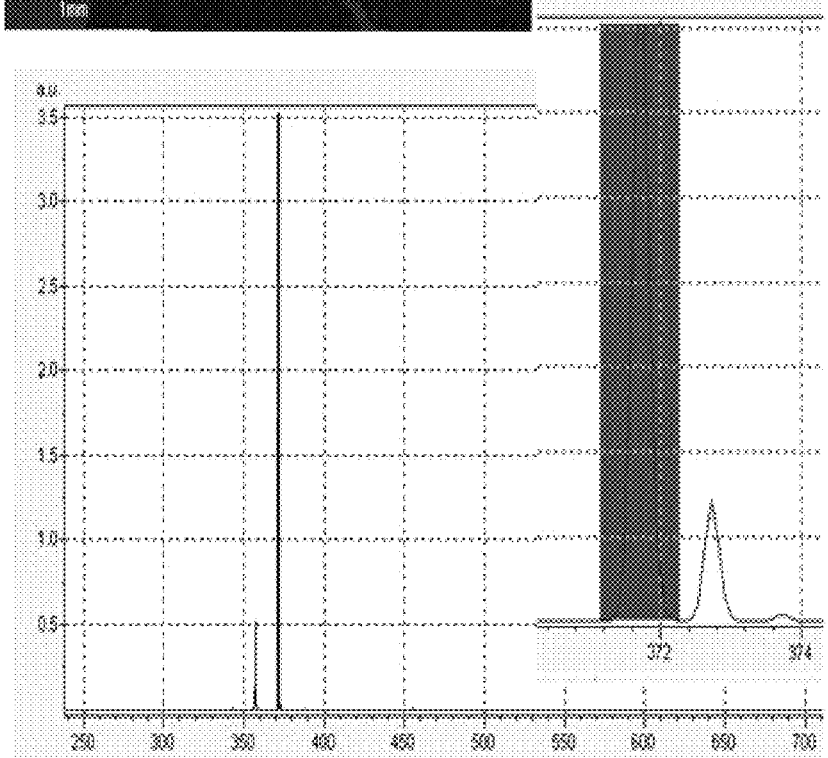
FIG. 73B

Her2 detected with Fast Blue BB (Scheme 25):
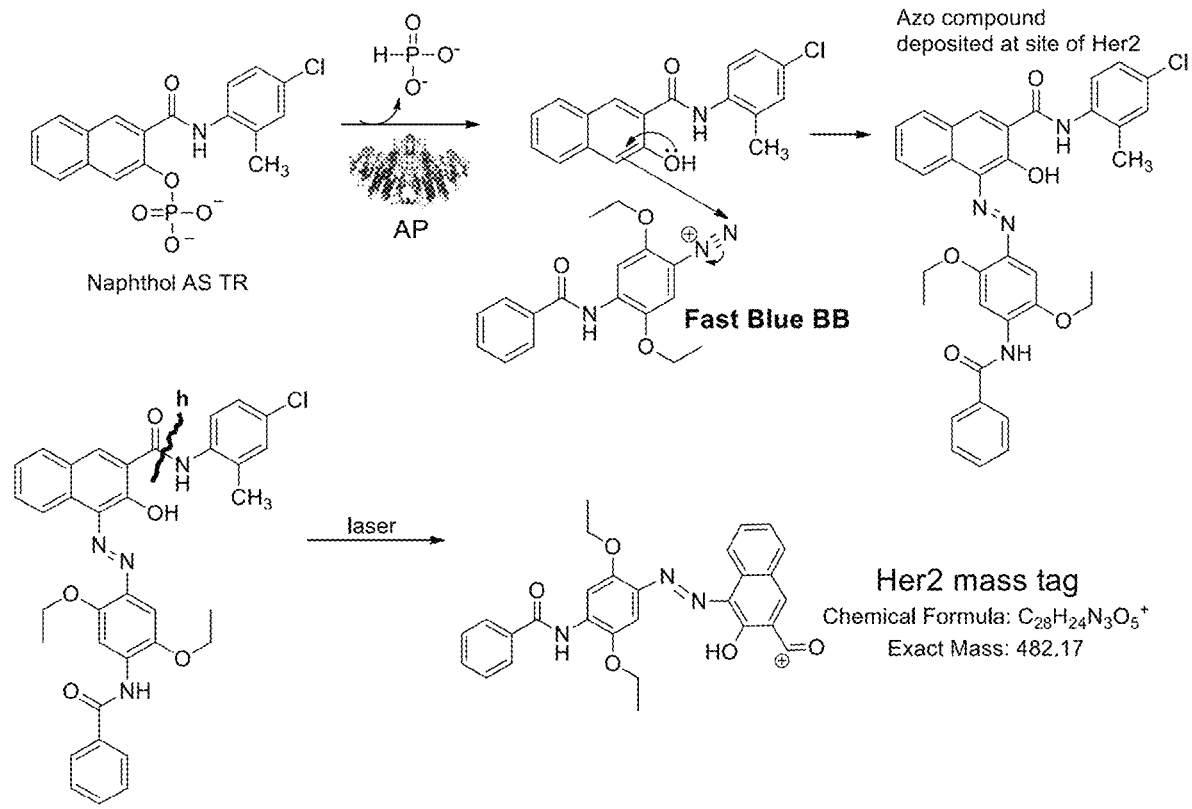
ER detected with Fast Blue RR
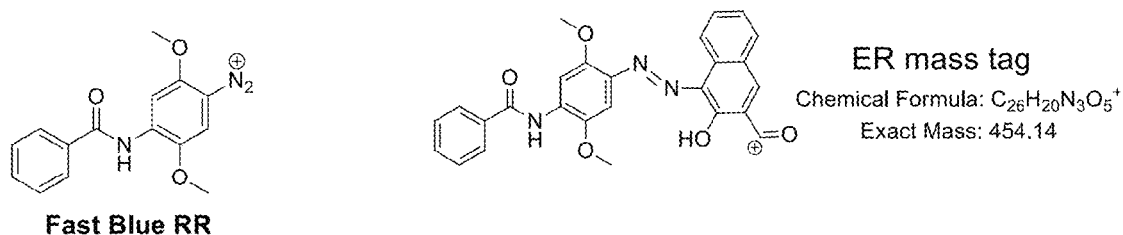
PR detected with Fast Violet B
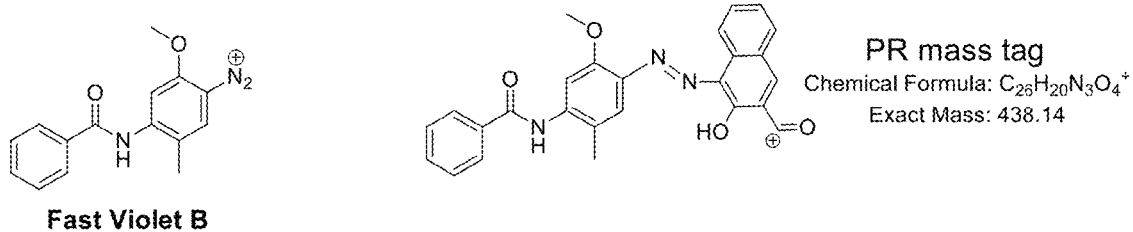
FIG. 76

SEQUENCE LISTING

<160> NUMBER OF SEQ ID NOS: 12

<210> SEQ ID NO 1
<211> LENGTH: 1210
<212> TYPE: PRT
<213> ORGANISM: Homo sapiens

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365
```

```
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
```

```
            785                 790                 795                 800
        Tyr Val Arg Glu His Lys Asp Asn Ile Gly Ser Gln Tyr Leu Leu Asn
                        805                 810                 815

Trp Cys Val Gln Ile Ala Lys Gly Met Asn Tyr Leu Glu Asp Arg Arg
                        820                 825                 830

Leu Val His Arg Asp Leu Ala Ala Arg Asn Val Leu Val Lys Thr Pro
                        835                 840                 845

Gln His Val Lys Ile Thr Asp Phe Gly Leu Ala Lys Leu Leu Gly Ala
        850                 855                 860

Glu Glu Lys Glu Tyr His Ala Glu Gly Gly Lys Val Pro Ile Lys Trp
        865                 870                 875                 880

Met Ala Leu Glu Ser Ile Leu His Arg Ile Tyr Thr His Gln Ser Asp
                        885                 890                 895

Val Trp Ser Tyr Gly Val Thr Val Trp Glu Leu Met Thr Phe Gly Ser
                        900                 905                 910

Lys Pro Tyr Asp Gly Ile Pro Ala Ser Glu Ile Ser Ser Ile Leu Glu
                        915                 920                 925

Lys Gly Glu Arg Leu Pro Gln Pro Pro Ile Cys Thr Ile Asp Val Tyr
                        930                 935                 940

Met Ile Met Val Lys Cys Trp Met Ile Asp Ala Asp Ser Arg Pro Lys
        945                 950                 955                 960

Phe Arg Glu Leu Ile Ile Glu Phe Ser Lys Met Ala Arg Asp Pro Gln
                        965                 970                 975

Arg Tyr Leu Val Ile Gln Gly Asp Glu Arg Met His Leu Pro Ser Pro
                        980                 985                 990

Thr Asp Ser Asn Phe Tyr Arg Ala Leu Met Asp Glu Glu Asp Met Asp
                        995                 1000                1005

Asp Val Val Asp Ala Asp Glu Tyr Leu Ile Pro Gln Gln Gly Phe
                        1010                1015                1020

Phe Ser Ser Pro Ser Thr Ser Arg Thr Pro Leu Leu Ser Ser Leu
                        1025                1030                1035

Ser Ala Thr Ser Asn Asn Ser Thr Val Ala Cys Ile Asp Arg Asn
                        1040                1045                1050

Gly Leu Gln Ser Cys Pro Ile Lys Glu Asp Ser Phe Leu Gln Arg
                        1055                1060                1065

Tyr Ser Ser Asp Pro Thr Gly Ala Leu Thr Glu Asp Ser Ile Asp
                        1070                1075                1080

Asp Thr Phe Leu Pro Val Pro Glu Tyr Ile Asn Gln Ser Val Pro
                        1085                1090                1095

Lys Arg Pro Ala Gly Ser Val Gln Asn Pro Val Tyr His Asn Gln
                        1100                1105                1110

Pro Leu Asn Pro Ala Pro Ser Arg Asp Pro His Tyr Gln Asp Pro
                        1115                1120                1125

His Ser Thr Ala Val Gly Asn Pro Glu Tyr Leu Asn Thr Val Gln
                        1130                1135                1140

Pro Thr Cys Val Asn Ser Thr Phe Asp Ser Pro Ala His Trp Ala
                        1145                1150                1155

Gln Lys Gly Ser His Gln Ile Ser Leu Asp Asn Pro Asp Tyr Gln
                        1160                1165                1170

Gln Asp Phe Phe Pro Lys Glu Ala Lys Pro Asn Gly Ile Phe Lys
                        1175                1180                1185

Gly Ser Thr Ala Glu Asn Ala Glu Tyr Leu Arg Val Ala Pro Gln
                        1190                1195                1200
```

Ser Ser Glu Phe Ile Gly Ala
    1205            1210

<210> SEQ ID NO 2
<211> LENGTH: 5616
<212> TYPE: DNA
<213> ORGANISM: Homo sapiens

<400> SEQUENCE: 2

| | | | | | |
|---|---|---|---|---|---|
| ccccggcgca | gcgcggccgc | agcagcctcc | gcccccgca | cggtgtgagc | gcccgacgcg | 60 |
| gccgaggcgg | ccggagtccc | gagctagccc | cggcggccgc | cgccgcccag | accgacgac | 120 |
| aggccacctc | gtcggcgtcc | gcccgagtcc | ccgcctcgcc | gccaacgcca | caaccaccgc | 180 |
| gcacggcccc | ctgactccgt | ccagtattga | tcgggagagc | cggagcgagc | tcttcgggga | 240 |
| gcagcgatgc | gaccctccgg | gacggccggg | gcagcgctcc | tggcgctgct | ggctgcgctc | 300 |
| tgcccggcga | gtcgggctct | ggaggaaaag | aaagtttgcc | aaggcacgag | taacaagctc | 360 |
| acgcagttgg | gcactttga | agatcatttt | ctcagcctcc | agaggatgtt | caataactgt | 420 |
| gaggtggtcc | ttgggaattt | ggaaattacc | tatgtgcaga | ggaattatga | tctttccttc | 480 |
| ttaaagacca | tccaggaggt | ggctggttat | gtcctcattg | ccctcaacac | agtggagcga | 540 |
| attcctttgg | aaaacctgca | gatcatcaga | ggaaatatgt | actacgaaaa | ttcctatgcc | 600 |
| ttagcagtct | tatctaacta | tgatgcaaat | aaaaccggac | tgaaggagct | gcccatgaga | 660 |
| aatttacagg | aaatcctgca | tggcgccgtg | cggttcagca | acaaccctgc | cctgtgcaac | 720 |
| gtggagagca | tccagtggcg | ggacatagtc | agcagtgact | ttctcagcaa | catgtcgatg | 780 |
| gacttccaga | accacctggg | cagctgccaa | agtgtgatc | caagctgtcc | caatgggagc | 840 |
| tgctggggtg | caggagagga | gaactgccag | aaactgacca | aaatcatctg | tgcccagcag | 900 |
| tgctccgggc | gctgccgtgg | caagtccccc | agtgactgct | gccacaacca | gtgtgctgca | 960 |
| ggctgcacag | gccccgga | gagcgactgc | ctggtctgcc | gcaaattccg | agacgaagcc | 1020 |
| acgtgcaagg | acacctgccc | cccactcatg | ctctacaacc | ccaccacgta | ccagatggat | 1080 |
| gtgaaccccg | agggcaaata | cagctttggt | gccacctgcg | tgaagaagtg | tccccgtaat | 1140 |
| tatgtggtga | cagatcacgg | ctcgtgcgtc | cgagcctgtg | gggccgacag | ctatgagatg | 1200 |
| gaggaagacg | gcgtccgcaa | gtgtaagaag | tgcgaagggc | cttgccgcaa | agtgtgtaac | 1260 |
| ggaataggta | ttggtgaatt | taaagactca | ctctccataa | atgctacgaa | tattaaacac | 1320 |
| ttcaaaaact | gcacctccat | cagtggcgat | ctccacatcc | tgccggtggc | atttaggggt | 1380 |
| gactccttca | cacatactcc | tcctctggat | ccacaggaac | tggatattct | gaaaaccgta | 1440 |
| aaggaaatca | cagggttttt | gctgattcag | gcttggcctg | aaaacaggac | ggacctccat | 1500 |
| gcctttgaga | acctagaaat | catacgcggc | aggaccaagc | aacatggtca | gttttctctt | 1560 |
| gcagtcgtca | gcctgaacat | aacatccttg | ggattacgct | ccctcaagga | gataagtgat | 1620 |
| ggagatgtga | taatttcagg | aaacaaaaat | ttgtgctatg | caaatacaat | aaactggaaa | 1680 |
| aaactgtttg | ggacctccgg | tcagaaaacc | aaaattataa | gcaacagagg | tgaaaacagc | 1740 |
| tgcaaggcca | caggccaggt | ctgccatgcc | ttgtgctccc | ccgagggctg | ctggggcccg | 1800 |
| gagcccaggg | actgcgtctc | ttgccggaat | gtcagccgag | cagggaatg | cgtggacaag | 1860 |
| tgcaaccttc | tggagggtga | gccaagggag | tttgtggaga | actctgagtg | catacagtgc | 1920 |
| cacccagagt | gcctgcctca | ggccatgaac | atcacctgca | caggacgggg | accagacaac | 1980 |
| tgtatccagt | gtgcccacta | cattgacggc | ccccactgcg | tcaagacctg | cccggcagga | 2040 |

```
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggggatga agaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt gcaacgtttt acaccgacta    4020
gccaggaagt acttccacct cgggcacatt ttgggaagtt gcattccttt gtcttcaaac    4080
tgtgaagcat ttacagaaac gcatccagca agaatattgt cccctttgagc agaaatttat    4140 ctttcaaaga ggtatatttg aaaaaaaaaa aagtatatg tgaggatttt tattgattgg    4200
ggatcttgga gttttcatt gtcgctattg attttacttt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
```

```
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca ataataact cggattccag cccacattgg attcatcagc     4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920
accccccaaa attagtttgt gttacttatg aagatagtt ttctcctttt acttcacttc     4980
aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccaccttt tttcctaatc tgtgtgtgcc ctgtaacctg    5340
actggttaac agcagtcctt tgtaaacagt gttttaaact ctcctagtca atatccaccc    5400
catccaattt atcaaggaag aaatggttca gaaaatattt tcagcctaca gttatgttca    5460
gtcacacaca catacaaaat gttccttttg cttttaaagt aatttttgac tcccagatca    5520
gtcagagccc ctacagcatt gttaagaaag tatttgattt ttgtctcaat gaaaataaaa    5580
ctatattcat ttccactcta aaaaaaaaaa aaaaaa                              5616
```

<210> SEQ ID NO 3
<211> LENGTH: 1255
<212> TYPE: PRT
<213> ORGANISM: Homo sapiens

<400> SEQUENCE: 3

```
Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
         115                 120                 125

Val Thr Gly Ala Ser Pro Gly Gly Leu Arg Glu Leu Gln Leu Arg Ser
     130                 135                 140

Leu Thr Glu Ile Leu Lys Gly Gly Val Leu Ile Gln Arg Asn Pro Gln
145                 150                 155                 160
```

```
Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575
```

-continued

```
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
        610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu  Asp Ser Thr Phe Tyr  Arg Ser Leu
```

```
               995                 1000                1005
Leu Glu  Asp Asp Asp Met  Gly Asp Leu Val  Asp Ala  Glu Glu Tyr
    1010             1015              1020

Leu Val  Pro Gln Gln Gly  Phe Phe Cys Pro  Asp Pro  Ala Pro Gly
    1025             1030              1035

Ala Gly  Gly Met Val His  His Arg His Arg  Ser Ser  Ser Thr Arg
    1040             1045              1050

Ser Gly  Gly Gly Asp Leu  Thr Leu Gly Leu  Glu Pro  Ser Glu Glu
    1055             1060              1065

Glu Ala  Pro Arg Ser Pro  Leu Ala Pro Ser  Glu Gly  Ala Gly Ser
    1070             1075              1080

Asp Val  Phe Asp Gly Asp  Leu Gly Met Gly  Ala Ala  Lys Gly Leu
    1085             1090              1095

Gln Ser  Leu Pro Thr His  Asp Pro Ser Pro  Leu Gln  Arg Tyr Ser
    1100             1105              1110

Glu Asp  Pro Thr Val Pro  Leu Pro Ser Glu  Thr Asp  Gly Tyr Val
    1115             1120              1125

Ala Pro  Leu Thr Cys Ser  Pro Gln Pro Glu  Tyr Val  Asn Gln Pro
    1130             1135              1140

Asp Val  Arg Pro Gln Pro  Pro Ser Pro Arg  Glu Gly  Pro Leu Pro
    1145             1150              1155

Ala Ala  Arg Pro Ala Gly  Ala Thr Leu Glu  Arg Pro  Lys Thr Leu
    1160             1165              1170

Ser Pro  Gly Lys Asn Gly  Val Val Lys Asp  Val Phe  Ala Phe Gly
    1175             1180              1185

Gly Ala  Val Glu Asn Pro  Glu Tyr Leu Thr  Pro Gln  Gly Gly Ala
    1190             1195              1200

Ala Pro  Gln Pro His Pro  Pro Pro Ala Phe  Ser Pro  Ala Phe Asp
    1205             1210              1215

Asn Leu  Tyr Tyr Trp Asp  Gln Asp Pro Pro  Glu Arg  Gly Ala Pro
    1220             1225              1230

Pro Ser  Thr Phe Lys Gly  Thr Pro Thr Ala  Glu Asn  Pro Glu Tyr
    1235             1240              1245

Leu Gly  Leu Asp Val Pro  Val
    1250             1255

<210> SEQ ID NO 4
<211> LENGTH: 4624
<212> TYPE: DNA
<213> ORGANISM: Homo sapiens

<400> SEQUENCE: 4
ggaggaggtg gaggaggagg gctgcttgag gaagtataag aatgaagttg tgaagctgag      60
attcccctcc attgggaccg gagaaaccag gggagccccc cgggcagccg cgcgcccctt     120
cccacggggc cctttactgc gccgcgcgcc cggcccccac ccctcgcagc accccgcgcc     180
ccgcgccctc ccagccgggt ccagccggag ccatggggcc ggagccgcag tgagcaccat     240
ggagctggcg gccttgtgcc gctgggggct cctcctcgcc ctcttgcccc ccggagccgc     300
gagcacccaa gtgtgcaccg gcacagacat gaagctgcgg ctccctgcca gtcccgagac     360
ccacctggac atgctccgcc acctctacca gggctgccag gtggtgcagg gaaacctgga     420
actcacctac ctgcccacca atgccagcct gtccttcctg caggatatcc aggaggtgca     480
gggctacgtg ctcatcgctc acaaccaagt gaggcaggtc ccactgcaga ggctgcggat     540
```

```
tgtgcgaggc acccagctct tgaggacaa ctatgccctg gccgtgctag acaatggaga    600
cccgctgaac ataccaccc ctgtcacagg ggcctcccca ggaggcctgc gggagctgca    660
gcttcgaagc ctcacagaga tcttgaaagg agggtcttg atccagcgga accccccagct   720
ctgctaccag gacacgattt tgtggaagga catcttccac aagaacaacc agctggctct   780
cacactgata gacaccaacc gctctcgggc ctgccacccc tgttctccga tgtgtaaggg   840
ctcccgctgc tggggagaga gttctgagga ttgtcagagc ctgacgcgca ctgtctgtgc   900
cggtggctgt gcccgctgca aggggccact gcccactgac tgctgccatg agcagtgtgc   960
tgccggctgc acgggcccca agcactctga ctgcctggcc tgcctccact tcaaccacag  1020
tggcatctgt gagctgcact gcccagccct ggtcacctac aacacagaca cgtttgagtc  1080
catgcccaat cccgagggcc ggtatacatt cggcgccagc tgtgtgactg cctgtcccta  1140
caactacctt tctacggacg tgggatcctg caccctcgtc tgcccctgc acaaccaaga   1200
ggtgacagca gaggatggaa cacagcggtg tgagaagtgc agcaagccct gtgcccgagt  1260
gtgctatggt ctgggcatgg agcacttgcg agaggtgagg gcagttacca gtgccaatat  1320
ccaggagttt gctggctgca agaagatctt tgggagcctg gcatttctgc cggagagctt  1380
tgatggggac ccagcctcca acactgcccc gctccagcca gagcagctcc aagtgtttga  1440
gactctggaa gagatcacag gttacctata catctcagca tggccggaca gcctgcctga  1500
cctcagcgtc ttccagaacc tgcaagtaat ccggggacga attctgcaca atggcgccta  1560
ctcgctgacc ctgcaagggc tgggcatcag ctggctgggg ctgcgctcac tgagggaact  1620
gggcagtgga ctgccctca tccaccataa cacccacctc tgcttcgtgc acacggtgcc   1680
ctgggaccag ctctttcgga acccgcacca agctctgctc cacactgcca accggccaga  1740
ggacgagtgt gtgggcgagg gcctggcctg ccaccagctg tgcgcccgag ggcactgctg  1800
gggtccaggg cccacccagt gtgtcaactg cagccagttc cttcggggcc aggagtgcgt  1860
ggaggaatgc cgagtactgc aggggctccc caggagtat gtgaatgcca ggcactgttt   1920
gccgtgccac cctgagtgtc agccccagaa tggctcagtg acctgttttg gaccggaggc  1980
tgaccagtgt gtggcctgtg cccactataa ggaccctccc ttctgcgtgg cccgctgccc  2040
cagcggtgtg aaacctgacc tctcctacat gcccatctgg aagtttccag atgaggaggg  2100
cgcatgccag ccttgcccca tcaactgcac ccactcctgt gtggacctgg atgacaaggg  2160
ctgccccgcc gagcagagag ccagccctct gacgtccatc atctctgcgg tggttggcat  2220
tctgctggtc gtggtcttgg gggtggtctt tgggatcctc atcaagcgac ggcagcagaa  2280
gatccggaag tacacgatgc ggagactgct gcaggaaacg gagctggtgg agccgctgac  2340
acctagcgga gcgatgccca accaggcgca gatgcggatc ctgaaagaga cggagctgag  2400
gaaggtgaag gtgcttggat ctggcgcttt tggcacagtc tacaagggca tctggatccc  2460
tgatggggag aatgtgaaaa ttccagtggc catcaaagtg ttgagggaaa acacatcccc  2520
caaagccaac aaagaaatct tagacgaagc atacgtgatg gctggtgtgg gctccccata  2580
tgtctcccgc cttctgggca tctgcctgac atccacggtg cagctggtga cacagcttat  2640
gccctatggc tgcctcttag accatgtccg gaaaaccgc ggacgcctgg gctcccagga   2700
cctgctgaac tggtgtatgc agattgccaa ggggatgagc tacctggagg atgtgcggct  2760
cgtacacagg gacttggccg ctcggaacgt gctggtcaag agtcccaacc atgtcaaaat  2820
tacagacttc gggctggctc ggctgctgga cattgacgag acagagtacc atgcagatgg  2880
gggcaaggtg cccatcaagt ggatggcgct ggagtccatt ctccgccggc ggttcaccca  2940
```

```
ccagagtgat gtgtggagtt atggtgtgac tgtgtgggag ctgatgactt tggggccaa      3000 accttacgat gggatcccag cccgggagat ccctgacctg ctggaaaagg gggagcggct      3060
gccccagccc cccatctgca ccattgatgt ctacatgatc atggtcaaat gttggatgat      3120
tgactctgaa tgtcggccaa gattccggga gttggtgtct gaattctccc gcatggccag      3180
ggacccccag cgctttgtgg tcatccagaa tgaggacttg gcccagcca gtcccttgga      3240 cagcaccttc taccgctcac tgctggagga cgatgacatg ggggacctgg tgatgctga      3300 ggagtatctg gtaccccagc agggcttctt ctgtccagac cctgccccgg gcgctggggg      3360
catggtccac cacaggcacc gcagctcatc taccaggagt ggcggtgggg acctgacact      3420
agggctggag ccctctgaag aggaggcccc caggtctcca ctggcaccct ccgaaggggc      3480
tggctccgat gtatttgatg gtgacctggg aatgggggca gccaaggggc tgcaaagcct      3540
ccccacacat gaccccagcc ctctacagcg gtacagtgag accccacag taccccctgcc      3600 ctctgagact gatggctacg ttgccccccct gacctgcagc cccagcctg aatatgtgaa      3660 ccagccagat gttcggcccc agcccccttc gccccgagag ggccctctgc ctgctgcccg      3720
acctgctggt gccactctgg aaaggcccaa gactctctcc ccagggaaga atggggtcgt      3780
caaagacgtt tttgcctttg ggggtgccgt ggagaacccc gagtacttga caccccaggg      3840
aggagctgcc cctcagcccc accctcctcc tgccttcagc ccagccttcg acaacctcta      3900
ttactgggac caggacccac cagagcgggg ggctccaccc agcaccttca agggacacc      3960 tacggcagag aacccagagt acctgggtct ggacgtgcca gtgtgaacca gaaggccaag      4020
tccgcagaag ccctgatgtg tcctcaggga gcagggaagg cctgacttct gctggcatca      4080
agaggtggga gggccctccg accacttcca ggggaacctg ccatgccagg aacctgtcct      4140
aaggaacctt ccttcctgct tgagttccca gatggctgga agggtccag cctcgttgga      4200 agaggaacag cactgggag tctttgtgga ttctgaggcc ctgcccaatg agactctagg      4260
gtccagtgga tgccacagcc cagcttggcc ctttccttcc agatcctggg tactgaaagc      4320
cttagggaag ctggcctgag aggggaagcg gccctaaggg agtgtctaag aacaaaagcg      4380
acccattcag agactgtccc tgaaacctag tactgccccc catgaggaag gaacagcaat      4440
ggtgtcagta tccaggcttt gtacagagtg ctttttctgtt tagttttac tttttttgtt      4500 ttgttttttt aaagatgaaa taaagaccca ggggagaat gggtgttgta tggggaggca      4560
agtgtggggg gtccttctcc acacccactt tgtccatttg caaatatatt ttggaaaaca      4620
gcta                                                                    4624
```

<210> SEQ ID NO 5
<211> LENGTH: 1342
<212> TYPE: PRT
<213> ORGANISM: Homo sapiens

<400> SEQUENCE: 5

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

-continued

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
            85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu

```
            485             490             495
Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910
```

```
Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
        965                 970                 975

Val Ile Lys Arg Glu Ser Gly Pro Gly Ile Ala Pro Gly Pro Glu Pro
        980                 985                 990

His Gly Leu Thr Asn Lys Lys Leu Glu Glu Val Glu Leu Glu Pro Glu
        995                 1000                1005

Leu Asp Leu Asp Leu Asp Leu Glu Ala Glu Glu Asp Asn Leu Ala
    1010            1015                1020

Thr Thr Thr Leu Gly Ser Ala Leu Ser Leu Pro Val Gly Thr Leu
    1025            1030                1035

Asn Arg Pro Arg Gly Ser Gln Ser Leu Leu Ser Pro Ser Ser Gly
    1040            1045                1050

Tyr Met Pro Met Asn Gln Gly Asn Leu Gly Glu Ser Cys Gln Glu
    1055            1060                1065

Ser Ala Val Ser Gly Ser Ser Glu Arg Cys Pro Arg Pro Val Ser
    1070            1075                1080

Leu His Pro Met Pro Arg Gly Cys Leu Ala Ser Glu Ser Ser Glu
    1085            1090                1095

Gly His Val Thr Gly Ser Glu Ala Glu Leu Gln Glu Lys Val Ser
    1100            1105                1110

Met Cys Arg Ser Arg Ser Arg Ser Arg Ser Pro Arg Pro Arg Gly
    1115            1120                1125

Asp Ser Ala Tyr His Ser Gln Arg His Ser Leu Leu Thr Pro Val
    1130            1135                1140

Thr Pro Leu Ser Pro Pro Gly Leu Glu Glu Glu Asp Val Asn Gly
    1145            1150                1155

Tyr Val Met Pro Asp Thr His Leu Lys Gly Thr Pro Ser Ser Arg
    1160            1165                1170

Glu Gly Thr Leu Ser Ser Val Gly Leu Ser Ser Val Leu Gly Thr
    1175            1180                1185

Glu Glu Glu Asp Glu Asp Glu Glu Tyr Glu Tyr Met Asn Arg Arg
    1190            1195                1200

Arg Arg His Ser Pro Pro His Pro Pro Arg Pro Ser Ser Leu Glu
    1205            1210                1215

Glu Leu Gly Tyr Glu Tyr Met Asp Val Gly Ser Asp Leu Ser Ala
    1220            1225                1230

Ser Leu Gly Ser Thr Gln Ser Cys Pro Leu His Pro Val Pro Ile
    1235            1240                1245

Met Pro Thr Ala Gly Thr Thr Pro Asp Glu Asp Tyr Glu Tyr Met
    1250            1255                1260

Asn Arg Gln Arg Asp Gly Gly Gly Pro Gly Gly Asp Tyr Ala Ala
    1265            1270                1275

Met Gly Ala Cys Pro Ala Ser Glu Gln Gly Tyr Glu Glu Met Arg
    1280            1285                1290

Ala Phe Gln Gly Pro Gly His Gln Ala Pro His Val His Tyr Ala
    1295            1300                1305
```

```
Arg Leu Lys Thr Leu Arg Ser  Leu Glu Ala Thr  Asp Ser Ala Phe
    1310             1315                 1320

Asp Asn  Pro Asp Tyr Trp His  Ser Arg Leu Phe  Pro Lys Ala Asn
    1325             1330                 1335

Ala Gln  Arg Thr
    1340

<210> SEQ ID NO 6
<211> LENGTH: 5765
<212> TYPE: DNA
<213> ORGANISM: Homo sapiens

<400> SEQUENCE: 6
actccagcct cgcgcgggag ggggcgcggc cgtgactcac ccccttccct ctgcgttcct      60
ccctccctct ctctctctct ctcacacaca cacacccctc ccctgccatc cctcccggca    120
ctccggctcc ggctccgatt gcaatttgca acctccgctg ccgtcgccgc agcagccacc    180
aattcgccag cggttcaggt ggctcttgcc tcgatgtcct agcctagggg ccccccgggcc   240 ggacttggct gggctcccct caccctctgc ggagtcatga gggcgaacga cgctctgcag    300
gtgctgggct tgcttttcag cctggcccgg ggctccgagg tgggcaactc tcaggcagtg    360
tgtcctggga ctctgaatgg cctgagtgtg accggcgatg ctgagaacca ataccagaca    420
ctgtacaagc tctacgagag gtgtgaggtg gtgatgggga accttgagat tgtgctcacg    480
ggacacaatg ccgacctctc cttcctgcag tggattcgag aagtgacagg ctatgtcctc    540
gtggccatga atgaattctc tactctacca ttgcccaacc tccgcgtggt gcgagggacc    600
caggtctacg atgggaagtt tgccatcttc gtcatgttga actataacac caactccagc    660
cacgctctgc gccagctccg cttgactcag ctcaccgaga ttctgtcagg ggtgtgttta    720
attgagaaga acgataagct ttgtcacatg gacacaattg actggaggga catcgtgagg    780
gaccgagatg ctgagatagt ggtgaaggac aatggcagaa gctgtccccc ctgtcatgag    840 gttttgcaagg ggcgatgctg gggtcctgga tcagaagact gccagacatt gaccaagacc    900
atctgtgctc ctcagtgtaa tggtcactgc tttgggccca ccccaaccat gtgctgccat    960
gatgagtgtg ccgggggctg ctcaggccct caggacacag actgctttgc ctgccggcac   1020
ttcaatgaca gtggagcctg tgtacctcgc tgtccacagc ctcttgtcta caacaagcta   1080
actttccagc tggaacccaa tccccacacc aagtatcagt atggaggagt ttgtgtagcc   1140
agctgtcccc ataactttgt ggtggatcaa acatcctgtg tcagggcctg tcctcctgac   1200
aagatggaag tagataaaaa tgggctcaag atgtgtgagc cttgtggggg actatgtccc   1260
aaagcctgtg agggaacagg ctctgggagc cgcttccaga ctgtggactc gagcaacatt   1320
gatggatttg tgaactgcac caagatcctg ggcaacctgg actttctgat caccggcctc   1380
aatggagacc cctggcacaa gatccctgcc ctggacccag agaagctcaa tgtcttccgg   1440
acagtacggg agatcacagg ttacctgaac atccagtcct ggccgcccca catgcacaac   1500
ttcagtgttt tttccaattt gacaaccatt ggaggcagaa gcctctacaa ccggggcttc   1560
tcattgttga tcatgaagaa cttgaatgtc acatctctgg gcttccgatc cctgaaggaa   1620
attagtgctg gcgtatctta taaagtgcc aataggcagc tctgctacca ccactctttg   1680
aactggacca aggtgcttcg ggggcctacg aagagcgac tagacatcaa gcataatcgg   1740
ccgcgcagag actgcgtggc agagggcaaa gtgtgtgacc cactgtgctc ctctgggga   1800 tgctggggcc caggccctgg tcagtgcttg tcctgtcgaa attatagccg aggaggtgtc   1860
```

```
tgtgtgaccc actgcaactt tctgaatggg gagcctcgag aatttgccca tgaggccgaa    1920
tgcttctcct gccacccgga atgccaaccc atggagggca ctgccacatg caatggctcg    1980
ggctctgata cttgtgctca atgtgcccat tttcgagatg gccccactg tgtgagcagc     2040 tgcccccatg gagtcctagg tgccaagggc ccaatctaca agtacccaga tgttcagaat    2100
gaatgtcggc cctgccatga gaactgcacc caggggtgta aggaccaga gcttcaagac     2160 tgtttaggac aaacactggt gctgatcggc aaaacccatc tgacaatggc tttgacagtg    2220
atagcaggat tggtagtgat tttcatgatg ctgggcggca ctttctcta ctggcgtggg     2280 cgccggattc agaataaaag gctatgagg cgatacttgg aacggggtga gagcatagag     2340
cctctggacc ccagtgagaa ggctaacaaa gtcttggcca gaatcttcaa agagacagag    2400
ctaaggaagc ttaaagtgct tggctcgggt gtctttggaa ctgtgcacaa aggagtgtgg    2460
atccctgagg gtgaatcaat caagattcca gtctgcatta aagtcattga ggacaagagt    2520
ggacggcaga gttttcaagc tgtgacagat catatgctgg ccattggcag cctggaccat    2580
gcccacattg taaggctgct gggactatgc ccagggtcat ctctgcagct tgtcactcaa    2640
tatttgcctc tgggttctct gctggatcat gtgagacaac accgggggc actgggccca    2700 cagctgctgc tcaactgggg agtacaaatt gccaaggaa tgtactacct tgaggaacat    2760
ggtatggtgc atagaaacct ggctgcccga aacgtgctac tcaagtcacc cagtcaggtt    2820
caggtggcag attttggtgt ggctgacctg ctgcctcctg atgataagca gctgctatac    2880
agtgaggcca agactccaat taagtggatg gcccttgaga gtatccactt tgggaaatac    2940
acacaccaga gtgatgtctg gagctatggt gtgacagttt gggagttgat gacccttcggg    3000 gcagagccct atgcagggct acgattggct gaagtaccag acctgctaga aaggggggag    3060
cggttggcac agccccagat ctgcacaatt gatgtctaca tggtgatggt caagtgttgg    3120
atgattgatg agaacattcg cccaaccttt aaagaactag ccaatgagtt caccaggatg    3180
gcccgagacc caccacggta tctggtcata aagagagaga gtgggcctgg aatagcccct    3240
gggccagagc ccatggtct gacaaacaag aagctagagg aagtagagct ggagccagaa     3300
ctagacctag acctagactt ggaagcagag aggacaacc tggcaaccac cacactgggc     3360
tccgccctca gcctaccagt tggaacactt aatcggccac gtgggagcca gagcctttta    3420
agtccatcat ctggatacat gcccatgaac caggtaatc ttggggagtc ttgccaggag     3480
tctgcagttt ctgggagcag tgaacggtgc ccccgtccag tctctctaca cccaatgcca    3540
cggggatgcc tggcatcaga gtcatcagag gggcatgtaa caggctctga ggctgagctc    3600
caggagaaag tgtcaatgtg taggagccgg agcaggagcc ggagcccacg gccacgcgga    3660
gatagcgcct accattccca gcgccacagt ctgctgactc ctgttacccc actctccca     3720 cccgggttag aggaagagga tgtcaacggt tatgtcatgc cagatacaca cctcaaaggt    3780
actccctcct cccgggaagg cacccttct tcagtgggtc tcagttctgt cctgggtact     3840
gaagaagaag atgaagatga ggagtatgaa tacatgaacc ggaggagaag gcacagtcca    3900
cctcatcccc ctaggccaag ttccttgag gagctgggtt atgagtacat ggatgtgggg     3960
tcagacctca gtgcctctct gggcagcaca cagagttgcc cactccaccc tgtacccatc    4020
atgcccactg caggcacaac tccagatgaa gactatgaat atatgaatcg caacgagat     4080 ggaggtggtc ctgggggtga ttatgcagcc atggggggcct gcccagcatc tgagcaaggg    4140
tatgaagaga tgagagcttt tcaggggcct ggacatcagg cccccatgt ccattatgcc      4200 cgcctaaaaa ctctacgtag cttagaggct acagactctg cctttgataa ccctgattac    4260
```

-continued

```
tggcatagca ggcttttccc caaggctaat gcccagagaa cgtaactcct gctccctgtg    4320
gcactcaggg agcatttaat ggcagctagt gcctttagag ggtaccgtct tctccctatt    4380
ccctctctct cccaggtccc agccccttttt ccccagtccc agacaattcc attcaatctt    4440
tggaggcttt taaacatttt gacacaaaat tcttatggta tgtagccagc tgtgcacttt    4500
cttctctttc ccaaccccag gaaaggtttt ccttatttttg tgtgctttcc cagtcccatt    4560
cctcagcttc ttcacaggca ctcctggaga tatgaaggat tactctccat atcccttcct    4620
ctcaggctct tgactacttg gaactaggct cttatgtgtg cctttgtttc ccatcagact    4680
gtcaagaaga ggaaagggag gaaacctagc agaggaaagt gtaattttgg tttatgactc    4740
ttaaccccct agaaagacag aagcttaaaa tctgtgaaga aagaggttag gagtagatat    4800
tgattactat cataattcag cacttaacta tgagccaggc atcatactaa acttcaccta    4860
cattatctca cttagtcctt tatcatcctt aaaacaattc tgtgacatac atattatctc    4920
attttacaca aagggaagtc gggcatggtg gctcatgcct gtaatctcag cactttggga    4980
ggctgaggca gaaggattac ctgaggcaag gagtttgaga ccagcttagc aacatagta    5040 agaccccat ctctttaaaa aaaaaaaaaa aaaaaaaaa aaaactttag aactgggtgc    5100
agtggctcat gcctgtaatc ccagccagca ctttgggagg ctgagatggg aagatcactt    5160
gagcccagaa ttagagataa gcctatgaa acatagcaag acactgtctc tacaggggaa    5220
aaaaaaaaaa gaaactgagc cttaaagaga tgaaataaat taagcagtag atccaggatg    5280
caaaatcctc ccaattcctg tgcatgtgct cttattgtaa ggtgccaaga aaaactgatt    5340
taagttacag cccttgttta aggggcactg tttcttgttt ttgcactgaa tcaagtctaa    5400
ccccaacagc cacatcctcc tatacctaga catctcatct caggaagtgg tggtgggggt    5460
agtcagaagg aaaaataact ggacatcttt gtgtaaacca taatccacat gtgccgtaaa    5520
tgatcttcac tccttatccg agggcaaatt cacaaggatc cccaagatcc acttttagaa    5580
gccattctca tccagcagtg agaagcttcc aggtaggaca gaaaaaagat ccagcttcag    5640
ctgcacacct ctgtcccctt ggatgggaa ctaagggaaa acgtctgttg tatcactgaa    5700
gttttttgtt ttgttttat acgtgtctga ataaaatgc caaagttttt tttcagcaaa    5760
aaaaa                                                                5765
```

<210> SEQ ID NO 7
<211> LENGTH: 1282
<212> TYPE: PRT
<213> ORGANISM: Homo sapiens

<400> SEQUENCE: 7

```
Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95
```

```
Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
```

```
                515                 520                 525
Gly Arg Ile Cys Ile Glu Ser Cys Asn Leu Tyr Asp Gly Glu Phe Arg
530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
                565                 570                 575
Cys Thr Lys Cys Ser His Phe Lys Asp Gly Pro Asn Cys Val Glu Lys
                580                 585                 590
Cys Pro Asp Gly Leu Gln Gly Ala Asn Ser Phe Ile Phe Lys Tyr Ala
                595                 600                 605
Asp Pro Asp Arg Glu Cys His Pro Cys His Pro Asn Cys Thr Gln Gly
                610                 615                 620
Cys Ile Gly Ser Ser Ile Glu Asp Cys Ile Gly Leu Met Asp Arg Thr
625                 630                 635                 640
Pro Leu Ile Ala Ala Gly Val Ile Gly Gly Leu Phe Ile Leu Val Ile
                645                 650                 655
Val Gly Leu Thr Phe Ala Val Tyr Val Arg Arg Lys Ser Ile Lys Lys
                660                 665                 670
Lys Arg Ala Leu Arg Arg Phe Leu Glu Thr Glu Leu Val Glu Pro Leu
                675                 680                 685
Thr Pro Ser Gly Thr Ala Pro Asn Gln Ala Gln Leu Arg Ile Leu Lys
690                 695                 700
Glu Thr Glu Leu Lys Arg Val Lys Val Leu Gly Ser Gly Ala Phe Gly
705                 710                 715                 720
Thr Val Tyr Lys Gly Ile Trp Val Pro Glu Gly Glu Thr Val Lys Ile
                725                 730                 735
Pro Val Ala Ile Lys Ile Leu Asn Glu Thr Thr Gly Pro Lys Ala Asn
                740                 745                 750
Val Glu Phe Met Asp Glu Ala Leu Ile Met Ala Ser Met Asp His Pro
                755                 760                 765
His Leu Val Arg Leu Leu Gly Val Cys Leu Ser Pro Thr Ile Gln Leu
                770                 775                 780
Val Thr Gln Leu Met Pro His Gly Cys Leu Leu Glu Tyr Val His Glu
785                 790                 795                 800
His Lys Asp Asn Ile Gly Ser Gln Leu Leu Leu Asn Trp Cys Val Gln
                805                 810                 815
Ile Ala Lys Gly Met Met Tyr Leu Glu Glu Arg Arg Leu Val His Arg
                820                 825                 830
Asp Leu Ala Ala Arg Asn Val Leu Val Lys Ser Pro Asn His Val Lys
                835                 840                 845
Ile Thr Asp Phe Gly Leu Ala Arg Leu Leu Glu Gly Asp Glu Lys Glu
                850                 855                 860
Tyr Asn Ala Asp Gly Gly Lys Met Pro Ile Lys Trp Met Ala Leu Glu
865                 870                 875                 880
Cys Ile His Tyr Arg Lys Phe Thr His Gln Ser Asp Val Trp Ser Tyr
                885                 890                 895
Gly Val Thr Ile Trp Glu Leu Met Thr Phe Gly Gly Lys Pro Tyr Asp
                900                 905                 910
Gly Ile Pro Thr Arg Glu Ile Pro Asp Leu Leu Glu Lys Gly Glu Arg
                915                 920                 925
Leu Pro Gln Pro Pro Ile Cys Thr Ile Asp Val Tyr Met Val Met Val
                930                 935                 940
```

Lys Cys Trp Met Ile Asp Ala Asp Ser Arg Pro Lys Phe Lys Glu Leu
945                 950                 955                 960

Ala Ala Glu Phe Ser Arg Met Ala Arg Asp Pro Gln Arg Tyr Leu Val
            965                 970                 975

Ile Gln Gly Asp Asp Arg Met Lys Leu Pro Ser Pro Asn Asp Ser Lys
        980                 985                 990

Phe Phe Gln Asn Leu Leu Asp Glu Glu Asp Leu Glu Asp Met Met Asp
    995                 1000                1005

Ala Glu Glu Tyr Leu Val Pro Gln Ala Phe Asn Ile Pro Pro Pro
1010                1015                1020

Ile Tyr Thr Ser Arg Ala Arg Ile Asp Ser Asn Arg Asn Gln Phe
1025                1030                1035

Val Tyr Arg Asp Gly Gly Phe Ala Ala Glu Gln Gly Val Ser Val
1040                1045                1050

Pro Tyr Arg Ala Pro Thr Ser Thr Ile Pro Glu Ala Pro Val Ala
1055                1060                1065

Gln Gly Ala Thr Ala Glu Ile Phe Asp Asp Ser Cys Cys Asn Gly
1070                1075                1080

Thr Leu Arg Lys Pro Val Ala Pro His Val Gln Glu Asp Ser Ser
1085                1090                1095

Thr Gln Arg Tyr Ser Ala Asp Pro Thr Val Phe Ala Pro Glu Arg
1100                1105                1110

Ser Pro Arg Gly Glu Leu Asp Glu Glu Gly Tyr Met Thr Pro Met
1115                1120                1125

Arg Asp Lys Pro Lys Gln Glu Tyr Leu Asn Pro Val Glu Glu Asn
1130                1135                1140

Pro Phe Val Ser Arg Arg Lys Asn Gly Asp Leu Gln Ala Leu Asp
1145                1150                1155

Asn Pro Glu Tyr His Asn Ala Ser Asn Gly Pro Pro Lys Ala Glu
1160                1165                1170

Asp Glu Tyr Val Asn Glu Pro Leu Tyr Leu Asn Thr Phe Ala Asn
1175                1180                1185

Thr Leu Gly Lys Ala Glu Tyr Leu Lys Asn Asn Ile Leu Ser Met
1190                1195                1200

Pro Glu Lys Ala Lys Lys Ala Phe Asp Asn Pro Asp Tyr Trp Asn
1205                1210                1215

His Ser Leu Pro Pro Arg Ser Thr Leu Gln His Pro Asp Tyr Leu
1220                1225                1230

Gln Glu Tyr Ser Thr Lys Tyr Phe Tyr Lys Gln Asn Gly Arg Ile
1235                1240                1245

Arg Pro Ile Val Ala Glu Asn Pro Glu Tyr Leu Ser Glu Phe Ser
1250                1255                1260

Leu Lys Pro Gly Thr Val Leu Pro Pro Pro Tyr Arg His Arg
1265                1270                1275

Asn Thr Val Val
    1280

<210> SEQ ID NO 8
<211> LENGTH: 3931
<212> TYPE: DNA
<213> ORGANISM: Homo sapiens

<400> SEQUENCE: 8
cagcacggga tctgagactt ccaaaaaatg aagccggcga caggactttg ggtctgggtg      60

```
agccttctcg tggcggcggg gaccgtccag cccagcgatt ctcagtcagt gtgtgcagga    120
acggagaata aactgagctc tctctctgac ctggaacagc agtaccgagc cttgcgcaag    180
tactatgaaa actgtgaggt tgtcatgggc aacctggaga taaccagcat tgagcacaac    240
cgggacctct ccttcctgcg gtctgttcga gaagtcacag gctacgtgtt agtggctctt    300
aatcagtttc gttacctgcc tctggagaat ttacgcatta ttcgtgggac aaaactttat    360
gaggatcgat atgccttggc aatattttta aactacagaa agatggaaa  ctttggactt    420 caagaacttg gattaaagaa cttgacagaa atcctaaatg gtggagtcta tgtagaccag    480
aacaaattcc tttgttatgc agacaccatt cattggcaag atattgttcg gaacccatgg    540
ccttccaact tgactcttgt gtcaacaaat ggtagttcag gatgtggacg ttgccataag    600
tcctgtactg gccgttgctg gggacccaca gaaaatcatt gccagacttt gacaaggacg    660
gtgtgtgcag aacaatgtga cggcagatgc tacggacctt acgtcagtga ctgctgccat    720
cgagaatgtg ctggaggctg ctcaggacct aaggacacag actgctttgc ctgcatgaat    780
ttcaatgaca gtggagcatg tgttactcag tgtccccaaa cctttgtcta caatccaacc    840
acctttcaac tggagcacaa tttcaatgca agtacacat  atggagcatt ctgtgtcaag    900
aaatgtccac ataactttgt ggtagattcc agttcttgtg tgcgtgcctg ccctagttcc    960 aagatgaag  tagaagaaaa tgggattaaa atgtgtaaac cttgcactga catttgccca   1020
aaagcttgtg atggcattgg cacaggatca ttgatgtcag ctcagactgt ggattccagt   1080
aacattgaca aattcataaa ctgtaccaag atcaatggga atttgatctt tctagtcact   1140
ggtattcatg gggacccta  caatgcaatt gaagccatag acccagagaa actgaacgtc   1200
tttcggacag tcagagagat aacaggtttc ctgaacatac agtcatggcc accaaacatg   1260
actgacttca gtgttttttc taacctggtg accattggtg gaagagtact ctatagtggc   1320
ctgtccttgc ttatcctcaa gcaacagggc atcacctctc tacagttcca gtccctgaag   1380
gaaatcagcg caggaaacat ctatattact gacaacagca acctgtgtta ttatcatacc   1440
attaactgga caaacactctt cagcacaatc aaccagagaa tagtaatccg ggacaacaga   1500
aaagctgaaa attgtactgc tgaaggaatg gtgtgcaacc atctgtgttc cagtgatggc   1560
tgttggggac ctgggccaga ccaatgtctg tcgtgtcgcc gcttcagtag aggaaggatc   1620
tgcatagagt cttgtaacct ctatgatggt gaatttcggg agtttgagaa tggctccatc   1680
tgtgtggagt gtgaccccca gtgtgagaag atggaagatg gcctcctcac atgccatgga   1740
ccgggtcctg acaactgtac aaagtgctct cattttaaag atggcccaaa ctgtgtggaa   1800
aaatgtccag atggcttaca gggggcaaac agtttcattt tcaagtatgc tgatccagat   1860
cgggagtgcc acccatgcca tccaaactgc acccaagggt gcataggctc aagtattgaa   1920
gactgcatcg gcctgatgga tagaactccc ctgattgcag ctggagtaat tggtgggctc   1980
ttcattctgg tcattgtggg tctgacattt gctgtttatg ttagaaggaa gagcatcaaa   2040
aagaaaagag ccttgagaag attcttggaa acagagttgg tggaaccatt aactcccagt   2100
ggcacagcac ccaatcaagc tcaacttcgt attttgaaag aaactgagct gaagagggta   2160
aaagtccttg gctcaggtgc ttttggaacg gtttataagg gtatttgggt acctgaagga   2220
gaaactgtga agattcctgt ggctattaag attcttaatg agacaactgg tcccaaggca   2280
aatgtggagt tcatggatga agctctgatc atggcaagta tggatcatcc acacctagtc   2340
cggttgctgg gtgtgtgtct gagcccaacc atccagctgg ttactcaact tatgcccat   2400
```

```
ggctgcctgt tggagtatgt ccacgagcac aaggataaca ttggatcaca actgctgctt    2460
aactggtgtg tccagatagc taagggaatg atgtacctgg aagaaagacg actcgttcat    2520
cgggatttgg cagcccgtaa tgtcttagtg aaatctccaa accatgtgaa atcacagat     2580 tttgggctag ccagactctt ggaaggagag gaaaaagagt acaatgctga tggaggaaag    2640
atgccaatta aatggatggc tctggagtgt atacattaca ggaaattcac ccatcagagt    2700
gacgtttgga gctatggagt tactatatgg gaactgatga cctttggagg aaaaccctat    2760
gatggaattc caacgcgaga aatccctgat ttattagaga aaggagaacg tttgcctcag    2820
cctcccatct gcactattga cgtttacatg gtcatggtca aatgttggat gattgatgct    2880
gacagtagac ctaaatttaa ggaactggct gctgagtttt caaggatggc tcgagaccct    2940
caaagatacc tagttattca gggtgatgat cgtatgaagc ttcccagtcc aaatgacagc    3000
aagttctttc agaatctctt ggatgaagag gatttggaag atatgatgga tgctgaggag    3060
tacttggtcc ctcaggcttt caacatccca cctcccatct atacttccag agcaagaatt    3120
gactcgaata ggaaccagtt tgtgtaccga gatggaggtt ttgctgctga caaggagtg    3180 tctgtgccct acagagcccc aactagcaca attccagaag ctcctgtggc acagggtgct    3240
actgctgaga ttttgatga ctcctgctgt aatggcaccc tacgcaagcc agtggcaccc    3300
catgtccaag aggacagtag cacccagagg tacagtgctg accccaccgt gtttgcccca    3360
gaacggagcc cacgaggaga gctggatgag gaaggttaca tgactcctat gcgagacaaa    3420
cccaaacaag aatacctgaa tccagtggag gagaaccctt tgtttctcg gagaaaaat    3480 ggagaccttc aagcattgga taatcccgaa tatcacaatg catccaatgg tccacccaag    3540
gccgaggatg agtatgtgaa tgagccactg tacctcaaca cctttgccaa caccttggga    3600
aaagctgagt acctgaagaa caacatactg tcaatgccag agaaggccaa gaaagcgttt    3660
gacaaccctg actactggaa ccacagcctg ccacctcgga gcacccttca gcacccagac    3720
tacctgcagg agtacagcac aaaatatttt tataaacaga atgggcggat ccggcctatt    3780
gtggcagaga atcctgaata cctctctgag ttctccctga gccaggcac tgtgctgccg    3840 cctccacctt acagacaccg gaatactgtg gtgtaagctc agttgtggtt ttttaggtgg    3900
agagacacac ctgctccaat ttccccaccc c                                   3931
```

<210> SEQ ID NO 9
<211> LENGTH: 595
<212> TYPE: PRT
<213> ORGANISM: Homo sapiens

<400> SEQUENCE: 9

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
```

-continued

```
                100                 105                 110
    Pro Pro Pro Gln Leu Ser Pro Phe Leu Gln Pro His Gly Gln Gln Val
            115                 120                 125
    Pro Tyr Tyr Leu Glu Asn Glu Pro Ser Gly Tyr Thr Val Arg Glu Ala
            130                 135                 140
    Gly Pro Pro Ala Phe Tyr Arg Pro Asn Ser Asp Asn Arg Arg Gln Gly
    145                 150                 155                 160
    Gly Arg Glu Arg Leu Ala Ser Thr Asn Asp Lys Gly Ser Met Ala Met
                        165                 170                 175
    Glu Ser Ala Lys Glu Thr Arg Tyr Cys Ala Val Cys Asn Asp Tyr Ala
                            180                 185                 190
    Ser Gly Tyr His Tyr Gly Val Trp Ser Cys Glu Gly Cys Lys Ala Phe
                    195                 200                 205
    Phe Lys Arg Ser Ile Gln Gly His Asn Asp Tyr Met Cys Pro Ala Thr
            210                 215                 220
    Asn Gln Cys Thr Ile Asp Lys Asn Arg Arg Lys Ser Cys Gln Ala Cys
    225                 230                 235                 240
    Arg Leu Arg Lys Cys Tyr Glu Val Gly Met Met Lys Gly Gly Ile Arg
                        245                 250                 255
    Lys Asp Arg Arg Gly Gly Arg Met Leu Lys His Lys Arg Gln Arg Asp
                            260                 265                 270
    Asp Gly Glu Gly Arg Gly Glu Val Gly Ser Ala Gly Asp Met Arg Ala
                    275                 280                 285
    Ala Asn Leu Trp Pro Ser Pro Leu Met Ile Lys Arg Ser Lys Lys Asn
            290                 295                 300
    Ser Leu Ala Leu Ser Leu Thr Ala Asp Gln Met Val Ser Ala Leu Leu
    305                 310                 315                 320
    Asp Ala Glu Pro Pro Ile Leu Tyr Ser Glu Tyr Asp Pro Thr Arg Pro
                        325                 330                 335
    Phe Ser Glu Ala Ser Met Met Gly Leu Leu Thr Asn Leu Ala Asp Arg
                            340                 345                 350
    Glu Leu Val His Met Ile Asn Trp Ala Lys Arg Val Pro Gly Phe Val
                    355                 360                 365
    Asp Leu Thr Leu His Asp Gln Val His Leu Leu Glu Cys Ala Trp Leu
            370                 375                 380
    Glu Ile Leu Met Ile Gly Leu Val Trp Arg Ser Met Glu His Pro Gly
    385                 390                 395                 400
    Lys Leu Leu Phe Ala Pro Asn Leu Leu Leu Asp Arg Asn Gln Gly Lys
                        405                 410                 415
    Cys Val Glu Gly Met Val Glu Ile Phe Asp Met Leu Leu Ala Thr Ser
                            420                 425                 430
    Ser Arg Phe Arg Met Met Asn Leu Gln Gly Glu Glu Phe Val Cys Leu
                    435                 440                 445
    Lys Ser Ile Ile Leu Leu Asn Ser Gly Val Tyr Thr Phe Leu Ser Ser
            450                 455                 460
    Thr Leu Lys Ser Leu Glu Glu Lys Asp His Ile His Arg Val Leu Asp
    465                 470                 475                 480
    Lys Ile Thr Asp Thr Leu Ile His Leu Met Ala Lys Ala Gly Leu Thr
                        485                 490                 495
    Leu Gln Gln Gln His Gln Arg Leu Ala Gln Leu Leu Leu Ile Leu Ser
                            500                 505                 510
    His Ile Arg His Met Ser Asn Lys Gly Met Glu His Leu Tyr Ser Met
                    515                 520                 525
```

```
Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595

<210> SEQ ID NO 10
<211> LENGTH: 6330
<212> TYPE: DNA
<213> ORGANISM: Homo sapiens

<400> SEQUENCE: 10
aggagctggc ggagggcgtt cgtcctggga ctgcacttgc tcccgtcggg tcgcccggct      60
tcaccggacc cgcaggctcc cggggcaggg ccggggccag agctcgcgtg tcggcgggac     120
atgcgctgcg tcgcctctaa cctcgggctg tgctcttttt ccaggtggcc cgccggtttc     180
tgagccttct gccctgcggg gacacggtct gcaccctgcc cgcggccacg gaccatgacc     240
atgaccctcc acaccaaagc atctgggatg ccctactgc atcagatcca agggaacgag      300
ctggagcccc tgaaccgtcc gcagctcaag atcccctgg agcggcccct gggcgaggtg      360
tacctggaca gcagcaagcc cgccgtgtac aactaccccg agggcgccgc ctacgagttc     420
aacgccgcgg ccgccgccaa cgcgcaggtc tacggtcaga ccggcctccc ctacggcccc     480
gggtctgagg ctgcggcgtt cggctccaac ggcctggggg gtttcccccc actcaacagc     540
gtgtctccga gcccgctgat gctactgcac ccgccgccgc agctgtcgcc tttcctgcag     600
ccccacggcc agcaggtgcc ctactacctg agaacgagc ccagcggcta cacggtgcgc     660
gaggccggcc cgccggcatt ctacaggcca aattcagata tcgacgcca gggtggcaga      720 gaaagattgg ccagtaccaa tgacaaggga agtatggcta tggaatctgc caaggagact     780
cgctactgtg cagtgtgcaa tgactatgct tcaggctacc attatggagt ctggtcctgt     840
gagggctgca aggccttctt caagagaagt attcaaggac ataacgacta tatgtgtcca     900
gccaccaacc agtgcaccat tgataaaaac aggaggaaga gctgccaggc ctgccggctc     960
cgcaaatgct acgaagtggg aatgatgaaa ggtgggatac gaaaagaccg aagaggaggg    1020
agaatgttga acacaagcg ccagagagat gatggggagg gcaggggtga agtggggtct     1080
gctggagaca tgagagctgc caaccttttgg ccaagcccgc tcatgatcaa cgctctaag    1140 aagaacagcc tggccttgtc cctgacggcc gaccagatgg tcagtgcctt gttggatgct    1200
gagcccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgaccctc catgatcagg tccaccttct agaatgtgcc    1380
tggctagaga tcctgatgat tggtctcgtc tggcgctcca tggagcaccc agggaagcta    1440
ctgtttgctc ctaacttgct cttggacagg aaccaggaa aatgtgtaga gggcatggtg     1500
gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
```

```
acagacactt tgatccacct gatggccaag gcaggcctga ccctgcagca gcagcaccag   1740
cggctggccc agctcctcct catcctctcc cacatcaggc acatgagtaa caaaggcatg   1800
gagcatctgt acagcatgaa gtgcaagaac gtggtgcccc tctatgacct gctgctggag   1860
atgctggacg cccaccgcct acatgcgccc actagccgtg gaggggcatc cgtggaggag   1920
acggaccaaa gccacttggc cactgcgggc tctacttcat cgcattcctt gcaaaagtat   1980
tacatcacgg gggaggcaga gggtttccct gccacggtct gagagctccc tggctcccac   2040
acggttcaga taatccctgc tgcattttac cctcatcatg caccacttta gccaaattct   2100
gtctcctgca tacactccgg catgcatcca acaccaatgg ctttctagat gagtggccat   2160
tcatttgctt gctcagttct tagtggcaca tcttctgtct tctgttggga acagccaaag   2220
ggattccaag gctaaatctt gtaacagctc tctttccccc cttgctatgt tactaagcgt   2280
gaggattccc gtagctcttc acagctgaac tcagtctatg ggttggggct cagataactc   2340
tgtgcattta agctacttgt agagacccag gcctggagag tagacatttt gcctctgata   2400 agcactttt aaatggctct aagaataagc cacagcaaag aatttaaagt ggctccttta   2460
attggtgact tggagaaagc taggtcaagg gtttattata gcaccctctt gtattcctat   2520
ggcaatgcat cctttatga aagtggtaca ccttaaagct tttatatgac tgtagcagag   2580
tatctggtga ttgtcaattc attcccccta taggaataca aggggcacac agggaaggca   2640
gatcccctag ttggcaagac tatttttaact tgatacactg cagattcaga tgtgctgaaa   2700
gctctgcctc tggcttttccg gtcatggggtt ccagttaatt catgcctccc atggacctat   2760
ggagagcagc aagttgatct tagttaagtc tccctatatg agggataagt tcctgatttt   2820 tgttttatt tttgtgttac aaaagaaagc cctccctccc tgaacttgca gtaaggtcag   2880
cttcaggacc tgttccagtg ggcactgtac ttggatcttc ccggcgtgtg tgtgccttac   2940 acagggtga actgttcact gtggtgatgc atgatgaggg taaatggtag ttgaaaggag   3000
caggggccct ggtgttgcat ttagccctgg ggcatggagc tgaacagtac ttgtgcagga   3060
ttgttgtggc tactagagaa caagagggaa agtagggcag aaactggata cagttctgag   3120
gcacagccag acttgctcag ggtggccctg ccacaggctg cagctaccta ggaacattcc   3180
ttgcagaccc cgcattgccc ttgggggtg ccctgggatc cctggggtag tccagctctt   3240
cttcatttcc cagcgtggcc ctggttggaa gaagcagctg tcacagctgc tgtagacagc   3300
tgtgttccta caattggccc agcaccctgg ggcacgggag aagggtgggg accgttgctg   3360
tcactactca ggctgactgg ggcctggtca gattacgtat gcccttggtg gtttagagat   3420
aatccaaaat cagggtttgg tttggggaag aaaatcctcc cccttcctcc cccgccccgt   3480
tccctaccgc ctccactcct gccagctcat ttccttcaat ttcctttgac ctataggcta   3540
aaaaagaaag gctcattcca gccacagggc agccttccct gggcctttgc ttctctagca   3600
caattatggg ttacttcctt tttcttaaca aaaagaatg tttgatttcc tctgggtgac   3660
cttattgtct gtaattgaaa cccctattgag aggtgatgtc tgtgttagcc aatgacccag   3720
gtgagctgct cgggcttctc ttggtatgtc ttgtttggaa aagtggattt cattcatttc   3780
tgattgtcca gttaagtgat caccaaagga ctgagaatct gggagggcaa aaaaaaaaa   3840 aaagttttta tgtgcactta aatttgggga caattttatg tatctgtgtt aaggatatgt   3900
ttaagaacat aattctttg ttgctgtttg tttaagaagc accttagttt gtttaagaag   3960
caccttatat agtataatat atatttttt gaaattacat tgcttgttta tcagacaatt   4020
```

```
gaatgtagta attctgttct ggatttaatt tgactgggtt aacatgcaaa aaccaaggaa   4080
aaatatttag ttttttttt  tttttttgta tacttttcaa gctaccttgt catgtataca    4140
gtcatttatg cctaaagcct ggtgattatt catttaaatg aagatcacat ttcatatcaa   4200
cttttgtatc cacagtagac aaaatagcac taatccagat gcctattgtt ggatactgaa   4260
tgacagacaa tcttatgtag caaagattat gcctgaaaag gaaaattatt cagggcagct   4320
aattttgctt ttaccaaaat atcagtagta atattttgg  acagtagcta atgggtcagt   4380
gggttctttt taatgtttat acttagattt tcttttaaaa aaattaaaat aaaacaaaaa   4440
aaaatttcta ggactagacg atgtaatacc agctaaagcc aaacaattat acagtggaag   4500
gttttacatt attcatccaa tgtgtttcta ttcatgttaa gatactacta catttgaagt   4560
gggcagagaa catcagatga ttgaaatgtt cgcccagggg tctccagcaa ctttggaaat   4620
ctctttgtat ttttacttga agtgccacta atggacagca gatattttct ggctgatgtt   4680
ggtattgggt gtaggaacat gatttaaaaa aaaactcttg cctctgcttt cccccactct   4740
gaggcaagtt aaaatgtaaa agatgtgatt tatctggggg gctcaggtat ggtggggaag   4800
tggattcagg aatctgggga atggcaaata tattaagaag agtattgaaa gtatttggag   4860
gaaaatggtt aattctgggt gtgcaccagg gttcagtaga gtccacttct gccctggaga   4920
ccacaaatca actagctcca tttacagcca tttctaaaat ggcagcttca gttctagaga   4980
agaaagaaca acatcagcag taaagtccat ggaatagcta gtggtctgtg tttcttttcg   5040
ccattgccta gcttgccgta atgattctat aatgccatca tgcagcaatt atgagaggct   5100
aggtcatcca aagagaagac cctatcaatg taggttgcaa aatctaaccc ctaaggaagt   5160
gcagtctttg atttgatttc cctagtaacc ttgcagatat gtttaaccaa gccatagccc   5220
atgccttttg agggctgaac aaataaggga cttactgata atttacttt  gatcacatta   5280
aggtgttctc accttgaaat cttatacact gaaatggcca ttgatttagg ccactggctt   5340
agagtactcc ttcccctgca tgacactgat tacaaatact ttcctattca tactttccaa   5400
ttatgagatg gactgtgggt actgggagtg atcactaaca ccatagtaat gtctaatatt   5460
cacaggcaga tctgcttggg gaagctagtt atgtgaaagg caaatagagt catacagtag   5520
ctcaaaaggc aaccataatt ctctttggtg caggtcttgg gagcgtgatc tagattacac   5580
tgcaccattc ccaagttaat cccctgaaaa cttactctca actggagcaa atgaactttg   5640
gtcccaaata tccatctttt cagtagcgtt aattatgctc tgtttccaac tgcatttcct   5700
ttccaattga attaaagtgt ggcctcgttt ttagtcattt aaaattgttt tctaagtaat   5760
tgctgcctct attatggcac ttcaatttg  cactgtcttt tgagattcaa gaaaaatttc   5820
tattcttttt tttgcatcca attgtgcctg aacttttaaa atatgtaaat gctgccatgt   5880
tccaaaccca tcgtcagtgt gtgtgtttag agctgtgcac cctagaaaca acatattgtc   5940
ccatgagcag gtgcctgaga cacagacccc tttgcattca cagagaggtc attggttata   6000
gagacttgaa ttaataagtg acattatgcc agtttctgtt ctctcacagg tgataaacaa   6060
tgcttttgt  gcactacata ctcttcagtg tagagctctt gttttatggg aaaaggctca   6120
aatgccaaat tgtgtttgat ggattaatat gcccttttgc cgatgcatac tattactgat   6180
gtgactcggt tttgtcgcag ctttgctttg tttaatgaaa cacacttgta aacctctttt   6240
gcactttgaa aaagaatcca gcgggatgct cgagcacctg taaacaattt tctcaaccta   6300
tttgatgttc aaataaagaa ttaaactaaa                                    6330
```

-continued

```
<210> SEQ ID NO 11
<211> LENGTH: 933
<212> TYPE: PRT
<213> ORGANISM: Homo sapiens

<400> SEQUENCE: 11

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
            115                 120                 125

Pro Ser Pro Pro Ala Cys Glu Val Thr Ser Ser Trp Cys Leu Phe Gly
130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Gly Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Val
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380
```

```
Leu Lys Ile Lys Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
            405                 410                 415

Phe Pro Leu Gly Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
            435                 440                 445

Ser Ser Ala Ser Ser Ser Gly Ser Thr Leu Glu Cys Ile Leu Tyr Lys
450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
            485                 490                 495

Ser Thr Ser Ala Ser Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
            515                 520                 525

Val Leu Lys Glu Gly Leu Pro Gln Val Tyr Pro Pro Tyr Leu Asn Tyr
530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
            565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
            595                 600                 605

Cys Ile Val Asp Lys Ile Arg Arg Lys Asn Cys Pro Ala Cys Arg Leu
610                 615                 620

Arg Lys Cys Cys Gln Ala Gly Met Val Leu Gly Gly Arg Lys Phe Lys
625                 630                 635                 640

Lys Phe Asn Lys Val Arg Val Arg Ala Leu Asp Ala Val Ala Leu
            645                 650                 655

Pro Gln Pro Leu Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
            675                 680                 685

Asn Leu Leu Met Ser Ile Glu Pro Asp Val Ile Tyr Ala Gly His Asp
            690                 695                 700

Asn Thr Lys Pro Asp Thr Ser Ser Leu Leu Thr Ser Leu Asn Gln
705                 710                 715                 720

Leu Gly Glu Arg Gln Leu Leu Ser Val Val Lys Trp Ser Lys Ser Leu
            725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
            755                 760                 765

Lys His Val Ser Gly Gln Met Leu Tyr Phe Ala Pro Asp Leu Ile Leu
            770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
```

```
                 805                 810                 815
Glu Phe Leu Cys Met Lys Val Leu Leu Leu Asn Thr Ile Pro Leu
            820                 825                 830

Glu Gly Leu Arg Ser Gln Thr Gln Phe Glu Glu Met Arg Ser Ser Tyr
            835                 840                 845

Ile Arg Glu Leu Ile Lys Ala Ile Gly Leu Arg Gln Lys Gly Val Val
        850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
    930
```

<210> SEQ ID NO 12
<211> LENGTH: 3014
<212> TYPE: DNA
<213> ORGANISM: Homo sapiens

<400> SEQUENCE: 12

```
ctgaccagcg ccgccctccc ccgccccga  cccaggaggt ggagatccct ccggtccagc      60
cacattcaac acccactttc tcctccctct gccctatat tcccgaaacc ccctcctcct     120
tcccttttcc ctcctccctg gagacggggg aggagaaaag gggagtccag tcgtcatgac     180
tgagctgaag gcaaagggtc cccgggctcc cacgtggcg gcggcccgc cctccccga      240
ggtcggatcc ccactgctgt gtcgcccagc cgcaggtccg ttcccgggga ccagacctc     300
ggacaccttg cctgaagttt cggccatacc tatctccctg acgggctac tcttccctcg    360
gccctgccag ggacaggacc cctccgacga aaagacgcag accagcagt cgctgtcgga    420
cgtggagggc gcatattcca gagctgaagc tacaaggggt gctggaggca gcagttctag    480
tccccccagaa aaggacagcg gactgctgga cagtgtcttg gacactctgt ggcgccctc    540
aggtcccggg cagagccaac ccagccctcc cgcctgcgag gtcaccagct cttggtgcct    600
gtttggcccc gaacttcccg aagatccacc ggctgcccc gccacccagc gggtgttgtc    660
cccgctcatg agccggtccg ggtgcaaggt tggagacagc tccggacgg cagctgccca    720
taaagtgctg cccgggggcc tgtcaccagc ccggcagctg ctgctcccgg cctctgagag    780
ccctcactgg tccggggccc cagtgaagcc gtctccgcag gccgctgcgg tggaggttga    840
ggaggaggat ggctctgagt ccgaggagtc tgcgggtccg cttctgaagg gcaaacctcg    900
ggctctgggt ggcgcggcgg ctggaggagg agccgcggct gtcccgcgg gggcggcagc    960
aggaggcgtc gccctggtcc ccaaggaaga ttccgcttc tcagcgccca gggtcgccct   1020
ggtggagcag gacgcgccga tggcgcccgg gcgctcccg ctgccacca cggtgatgga    1080
tttcatccac gtgcctatcc tgcctctcaa tcacgcctta ttggcagccc gcactcggca    1140
gctgctggaa gacgaaagtt acgacggcgg ggccggggct gccagcgcct ttgcccgcc    1200
gcggagttca ccctgtgcct cgtccacccc ggtgctgta ggcgacttcc ccgactgcgc    1260
gtacccgccc gacgccgagc ccaaggacga cgcgtaccct ctctatagcg acttccagcc    1320
gcccgctcta aagataaagg aggaggagga aggcgcggag gcctccgcgc gctccccgcg    1380
```

```
ttcctacctt gtggccggtg ccaacccgc agccttcccg gatttcccgt tggggccacc    1440
gcccccgctg ccgccgcgag cgaccccatc cagacccggg gaagcggcgg tgacggccgc    1500
acccgccagt gcctcagtct cgtctgcgtc ctcctcgggg tcgaccctgg agtgcatcct    1560
gtacaaagcg gagggcgcgc cgccccagca gggcccgttc gcgccgccgc cctgcaaggc    1620
gccgggcgcg agcggctgcc tgctcccgcg ggacggcctg ccctccacct ccgcctctgc    1680
cgccgccgcc ggggcggccc ccgcgctcta ccctgcactc ggcctcaacg ggctcccgca    1740
gctcggctac caggccgccg tgctcaagga gggcctgccg caggtctacc cgccctatct    1800
caactacctg aggccggatt cagaagccag ccagagccca caatacagct tcgagtcatt    1860
acctcagaag atttgtttaa tctgtgggga tgaagcatca ggctgtcatt atggtgtcct    1920
tacctgtggg agctgtaagg tcttctttaa gagggcaatg gaagggcagc acaactactt    1980
atgtgctgga agaaatgact gcatcgttga taaaatccgc agaaaaaact gcccagcatg    2040
tcgccttaga aagtgctgtc aggctggcat ggtccttgga ggtcgaaaat ttaaaaagtt    2100
caataaagtc agagttgtga gagcactgga tgctgttgct ctcccacagc cattgggcgt    2160
tccaaatgaa agccaagccc taagccagag attcactttt tcaccaggtc aagacataca    2220
gttgattcca ccactgatca acctgttaat gagcattgaa ccagatgtga tctatgcagg    2280
acatgacaac acaaaacctg acacctccag ttctttgctg acaagtctta atcaactagg    2340
cgagaggcaa cttctttcag tagtcaagtg gtctaaatca ttgccaggtt ttcgaaactt    2400
acatattgat gaccagataa ctctcattca gtattcttgg atgagcttaa tggtgtttgg    2460
tctaggatgg agatcctaca aacatgtcag tgggcagatg ctgtattttg cacctgatct    2520
aatactaaat gaacagcgga tgaaagaatc atcattctat tcattatgcc ttaccatgtg    2580
gcagatccca caggagtttg tcaagcttca agttagccaa gaagagttcc tctgtatgaa    2640
agtattgtta cttcttaata caattccttt ggaagggcta cgaagtcaaa cccagtttga    2700
ggagatgagg tcaagctaca ttagagagct catcaaggca attggtttga ggcaaaaagg    2760
agttgtgtcg agctcacagc gtttctatca acttacaaaa cttcttgata acttgcatga    2820
tcttgtcaaa caacttcatc tgtactgctt gaatacattt atccagtccc gggcactgag    2880
tgttgaattt ccagaaatga tgtctgaagt tattgctgca caattaccca agatattggc    2940
agggatggtg aaacccctc tctttcataa aaagtgaatg tcatcttttt cttttaaaga    3000
attaaatttt gtgg                                                      3014
```

DETECTING TARGETS USING MASS TAGS AND MASS SPECTROMETRY

CROSS REFERENCES TO RELATED APPLICATIONS

The present application is a continuation of U.S. patent application Ser. No. 16/055,046, filed on Aug. 4, 2018, which is a continuation of U.S. patent application Ser. No. 14/981,181, filed on Dec. 28, 2015, which is a continuation of U.S. patent application Ser. No. 13/805,983, filed Jan. 25, 2013, which is the National Stage of International Application No. PCT/US2011/042853, filed Jul. 1, 2011, which claims the benefit of the earlier filing date under 35 U.S.C. § 119 (e) of U.S. provisional patent application No. 61/398,944, filed Jul. 2, 2010, U.S. provisional patent application No. 61/398,942, filed Jul. 2, 2010, U.S. provisional patent application No. 61/464,937, filed Mar. 11, 2011, and U.S. provisional patent application No. 61/464,977, filed Mar. 11, 2011, the disclosures of which are hereby incorporated by reference herein in their entirety.

FIELD

The present disclosure concerns embodiments of compounds, compositions comprising such compounds, and methods for using such compounds and compositions for imaging a target and/or multiple targets in a sample, and kits for performing the methods. In particular, the present disclosure concerns using enzymatic reactions to localize mass tags proximal to or at one or more targets in a tissue sample, and detecting mass codes enzymatically deposited at the target(s) using mass spectrophotometric techniques.

BACKGROUND

Cancer is one of the most common diseases worldwide. Biomarkers play a key role in cancer diagnosis and prognosis. Determining the presence of and/or quantities (relative amounts and/or absolute amounts) of multiple biomarkers are useful for accurate prediction and prognosis of cancers, and survival rate may depend at least in part on targeted therapy based upon accurate detection and quantification, wherein quantification comprises determining the size of a mass peak and correlating it with the amount of particular biomarkers. For example, in breast cancer, the relative abundances of estrogen receptor (ER), progesterone receptor (PR), and human epidermal growth factor receptor 2 (Her2) biomarkers correlates to the patient's chances of surviving five or more years.

Immunohistochemistry (IHC) has been a major diagnostic tool to identify therapeutic biomarkers and to subclassify cancer patients. Conventional IHC methods using optical imaging are suitable for detecting one or more targets within a sample (e.g., a tissue sample). However, IHC methods cannot provide accurate quantitative results for the detected targets. Typically, only certified medical personnel are sufficiently skilled to evaluate a subject's diagnosis and prognosis based upon IHC optical imaging results. Currently, there is no suitable IHC platform for quantitative multiplexed assays useful for assessing cancers and determining personalized cancer therapy.

A number of methods have been developed for detecting and imaging biomolecules, such as nucleic acids and proteins. Nucleic acids, for example, may be analyzed using labeled probe molecules. The labels are detected to determine whether specific binding or hybridization has taken place. Various probe labeling methods are known, including radioactive atoms, fluorescent dyes, luminescent reagents, electron capture reagents and light absorbing dyes. Each of these methods has features suitable for certain applications, but there also are inherent limitations to each such method.

Mass spectrometry has been increasingly used for bioanalytical analyses. Mass spectrometry his well suited for multiplexing because mass differentiation allows many simultaneous detection channels. However, complex biomolecules, such as DNA, have complex mass spectra and may be difficult to detect in a matrix due to relatively poor sensitivity.

SUMMARY

A need exists in the art for additional tissue analysis and imaging techniques. Certain embodiments address many of the drawbacks associated with prior techniques, and allows for the use of more durable tissue samples, rather than fresh, frozen tissue samples used in other techniques. Matrix-assisted mass spectrometry may not be required with the disclosed method, which allows sample detection without the background interference, and eliminates "hot spots" that may result from using a matrix, crystal formation, or laser power limitations associated with the use of MALDI mass spectrometry. Other embodiments also allow substantial signal amplification, which provides much more sensitive detection and improved spatial resolution than techniques that do not involve signal amplification. All methods result in substantial signal amplification, allowing detection and imaging for both protein and nucleic acid.

A need also exists for a method to quantify, particularly in a single sample, multiple targets, e.g., cancer biomarkers, on formalin-fixed, paraffin-embedded (FFPE) tissue for diagnosis and prognosis. Certain disclosed embodiments address these and other needs.

Disclosed herein are embodiments of a conjugate, comprising a mass tag precursor, an enzyme substrate or a tyramine moiety or a tyramine derivative, and an optional linker. In particular disclosed embodiments, the mass tag precursor may be isotopically labeled. Also disclosed are embodiments of a method for detecting a target in a sample, and embodiments of a kit comprising the disclosed mass tag precursors.

Other embodiments utilize several classes of mass tag precursors including, by way of example and without limitation, triarylmethane derivatives, such as substituted triarylmethane compounds, triarylmethane dyes, triarylmethane-diazonium species, azo-naphthol carbonyl compounds, ultra small metal clusters, oligomers of peroxidase (e.g. horseradish peroxidase) substrates, such as aniline and phenol derivatives, certain cationic dyes, nitrophenyl compounds, heteraryl compounds, metal-heteraryl complexes, nanoparticle-based compounds, and any isotopically-labeled derivative thereof.

Other embodiments of the disclosed mass tag precursors concern azo dyes that are formed by the addition of various phenol, aniline, or naphthol derivatives, which are generated as a product of an enzymatic reaction (e.g. cleavage using a phosphatase, or glycosidase catalyzed hydrolysis), with various diazonium salts. The naphthol/azo dye is usually of deep color and specifically precipitates at the target. Laser-mediated cation formation can be facilitated by the presence of electron donating groups in the aromatic conjugated systems of the naphthol/azo mass tag.

Another class of mass tag precursors that are disclosed includes various substrates for a peroxidase (e.g. horseradish peroxidase [HRP]), including substituted aryl and heteroaryl compounds. This class of mass tag precursors encompasses substituted aryl and heteroaryl compounds that are capable of oligomerization, such as diaminobenzidine, diaminonaphthalenes, and aminoquinolines. Tissue targets labeled with a peroxidase, such as HRP, can be treated with these compounds and LDI mass spectrometry can be used to ionize the oligomeric mass tags formed through enzymatic reactions, followed by detecting the mass codes.

Still other disclosed embodiments concern heteroaryl mass tag precursors that undergo fragmentation upon exposure to an energy source. Disclosed embodiments may comprise azine moieties (having only one nitrogen atom in the aromatic ring), diazine moieties (having two nitrogen atoms in the aromatic ring), triazine moieties (having three nitrogen atoms in the aromatic ring), and tetrazine (having four nitrogen atoms in the aromatic ring) moieties. Particular disclosed embodiments utilize a tetrazine mass tag precursor, which readily undergoes fragmentation upon exposure to an energy source.

Naphthol derivatives can be used with cationic dyes to comprise another class of effective mass tag precursors. In a particular embodiment, naphthol derivatives precipitate at the desired site by catalyzed oxidation and can be further stained with various cationic dyes. These dyes are mostly cationic and have high absorbance at the wavelength of the laser used in LDI mass spectrometry, and are therefore useful candidates for mass tag precursors.

Another class of mass tag precursors concern nitrophenyl moieties, which undergo photolysis to release a corresponding mass code. In certain disclosed embodiments, the mass code comprises a linker (such as a polyethylene glycol linker), a charged moiety (such as arginine, lysine, histidine, or phosphate), and/or a chromophore (such as a hapten or dye).

In some disclosed embodiments, a metal-heteroaryl mass tag precursor may be used. Embodiments of these mass tag precursors can be selected from metal-monoheteroaryl complexes, metal-biheteroaryl complexes, and metal-terheteroaryl complexes. More typically these metal-heteroaryl mass tag precursors are selected from metal-monopyridine complexes, metal-bipyridine complexes, and metal-terpyridine complexes. Other metal-complexed mass tag precursors are disclosed, wherein the mass tag precursor is a metal-peptide complex. These complexes can be ionized to form detectable mass codes. In particular embodiments, these mass tag precursors comprise a nickel complex which is bound to two or more equivalent or different amino acids. Exemplary amino acids include any amino acid (e.g. histidine) capable of chelating with a metal.

In some disclosed embodiments, a nanoparticle functionalized with mass tag ligands may be used as a mass tag precursor. The mass tag ligands are bound to the nanoparticle via a binding moiety. The mass tag-functionalized nanoparticles are also coupled to one or more tyramine moieties and/or tyramine derivatives. In other disclosed embodiments, the conjugates include the nanoparticle, itself, as a mass tag precursor, which produces small cluster metal ions upon exposure to an energy source. These small cluster metal ions act as a mass code. These disclosed embodiments use metals or a semiconductor, wherein the metals can be selected from Groups 3-15 of the periodic table. Typically, metals are selected from Y, La, Ag, Au, Pt, Ni, Pd, Rh, Jr, Co, Cu, Bi, or a combination thereof.

Illustrative embodiments include mass tag precursors conjugated to enzyme substrate moieties, such as phosphates, galactosides, and lactams. These disclosed embodiments of the disclosed conjugate typically are water soluble, but are deposited on a desired target by enzymatic cleavage to form water insoluble mass tags.

In certain disclosed embodiments, the mass tag precursor is coupled to a tyramine or tyramine derivative via a linker, such as an aliphatic, heteroaliphatic, or a heterobifunctional linker. Particular disclosed embodiments concern heteroaliphatic linkers, such as polyethylene glycol units having a formula $PEG_n$ where n ranges from 1 to about 50, 1 to about 30, 1 to about 25, 1 to about 10, and 4 or 8. Other embodiments use heterobifunctional linkers to form mass tag precursor-tyramine conjugates or mass tag precursor-tyramine derivative conjugates.

In some embodiments, multiple mass tag precursors, tyramine moieties, and/or tyramine derivatives are conjugated to multivalent carriers. These carriers include polymers, biomolecules, liposomes, micelles, and nanoparticles. Polymers can be linear (such as a polyacid, polyamine, polysaccharide, polyhydrazine, or co-polymer) or hyperbranched (such as polyethyleneimine or dendrimers). A biomolecule carrier can also be used, and may be selected from a protein, a polypeptide, an oligopeptide, a peptide, a nucleic acid, DNA, RNA, an oligosaccharide, a polysaccharide, and monomers thereof. Nanoparticles are comprised of a semiconductor, metal or multiple metals, selected from Group 3-15 of the periodic table. Particular embodiments utilize nanoparticles comprising Y, La, Ag, Au, Pt, Ni, Pd, Rh, Jr, Co, Cu, and Bi, or a combination thereof.

Particular disclosed embodiments of the disclosed conjugate can be formed using any of the disclosed mass tag precursors, optional linkers or carriers, tyramine moieties, or tyramine derivatives. Particular disclosed embodiments of the disclosed conjugate comprising a triarylmethane mass tag precursor in conjunction with a tyramine or tyramine derivative, either conjugated directly or through a linker or carrier; a nitrophenyl mass tag precursor in conjunction with a tyramine or tyramine derivative, either conjugated directly or through a linker or carrier; a heteroaryl mass tag precursor in conjunction with a tyramine or tyramine derivative, either conjugated directly or through a linker or carrier; a naphtholazo mass tag precursor in conjunction with a tyramine or tyramine derivative, either conjugated directly or through a linker or carrier; a metal-heteroaryl chelate mass tag precursor in conjunction with a tyramine or tyramine derivative, either conjugated directly or through a linker or carrier; a ligand mass tag precursor in conjunction with a tyramine or tyramine derivative, either conjugated directly or through a linker or carrier; and a nanoparticle as a mass tag precursor in conjunction with a tyramine or tyramine derivative, either conjugated directly or through a linker or carrier. Any of these disclosed embodiments can be used in disclosed embodiments of the disclosed method. These disclosed embodiments can also be utilized for multiplexing in order to detect multiple targets in a sample.

Also contemplated in the disclosed embodiments of the disclosed conjugate are isotopically-labeled derivatives of any of the disclosed mass tag precursors.

A method for detecting a target in a sample concerns contacting a sample with an enzyme-specific binding moiety conjugate selected to recognize the target. The sample then is contacted with a mass tag precursor conjugate, comprising a mass tag precursor and an enzyme substrate, a tyramine moiety, or a tyramine derivative, and an optional linker. The mass tag precursor conjugate undergoes reaction with the enzyme or with the product of the enzymatic reaction to produce precipitated mass tags, covalently bound mass tags, or non-covalently bound mass tags. The sample is exposed to an energy source, which provides sufficient energy to produce a mass code from the mass tag. After ionization, the mass code can be detected using a detection method, such as mass spectrometry. In some embodiments, the sample is exposed to a first solution comprising the enzyme-specific binding moiety conjugate and a second solution comprising the mass tag precursor conjugate. Enzyme moieties of the enzyme-specific binding moiety can be selected from oxidoreductase enzymes (e.g. peroxidases), phosphatases (e.g. alkaline phosphatase), lactamases (e.g. β-lactamase), and galactosidases (e.g. β-D-galactosidase, β-galactosidase). Specific binding moieties can be selected from a protein, a polypeptide, an oligopeptide, a peptide, a nucleic acid, DNA, RNA, an oligosaccharide, a polysaccharide, and monomers thereof. Particular disclosed embodiments concern using alkaline phosphatase-antibody conjugates and horseradish peroxidase-antibody conjugates. In some disclosed embodiments, a specific binding moiety recognizes the target. In other disclosed embodiments, the specific binding moiety recognizes a primary antibody bound to the target.

In addition, certain disclosed embodiments utilize an active species, generated as the product of an enzymatic reaction, to deposit a mass tag at the target. The reactions between the active species and the mass tag precursor include, but are not limited to, redox reactions, addition reactions, elimination reactions and substitution reactions. For example, metal ions can be reduced in the presence of various reductants, such as hydroquinone, in the presence of hydrogen peroxide and horseradish peroxidase. This redox process causes the reduced metal to precipitate at a particular target site, followed by subsequent detection of the metal cluster mass codes using LDI-TOF mass spectrometry.

Certain disclosed embodiments concern a method for imaging and quantifying multiple targets in a sample, such as a tissue sample, using stable-isotope-labeled mass tag precursors and mass spectrometric (MS) techniques, such as laser desorption/ionization, including matrix-assisted laser desorption/ionization time-of-flight mass spectrometry (MALDI-TOF MS). The targets may be proteins, peptides, nucleic acid sequences, or any combination thereof. In some embodiments, the targets are cancer biomarkers, and mass tag precursors are used to identify and/or quantify each target. For example, the cancer biomarkers may be breast cancer biomarkers, such as ER, PR, Her2, and/or Ki67. In particular embodiments, the targets are different forms of the same cancer biomarker, e.g., intact and truncated forms, such as intact and truncated forms of Her2. In certain embodiments, the sample is formalin-fixed, paraffin-embedded (FFPE) tissue. The mass tag precursors used to identify and/or quantify multiple targets within a single tissue sample are labeled with stable isotopes (e.g., $^2H$, $^{13}C$, $^{15}N$, etc.) to produce mass tag precursors having the same chemical structure but different masses. In particular embodiments, the mass tag precursors are stable-isotope-labeled chromogens useful for IHC tissue staining.

One advantage of the disclosed method is that it can be used for multiplexed detection of multiple targets in a particular sample. For example, consecutive enzymatic reactions can be used to distribute several mass tags at several different target locations in a sample. Many embodiments provide new methods for tissue analysis through the use of a wide class of mass tag precursors that provide effective and efficient methods for detection of particular target sites. The mass tag precursors, mass tags, mass codes, and method of using the mass tag precursors conjugates described in the current method are intended for the use in tissue mass imaging applications, especially for FFPE tissue samples. However, certain embodiments can also be utilized for enzyme-linked immunoassays in general. The adoption of these methods in enzyme-linked immunoassays offers enhanced sensitivity and quantifiability in a multiplexing fashion.

In some embodiments, the method comprises depositing a first mass tag at a first target in a tissue sample and depositing a second mass tag at a second target in the tissue sample, ionizing each mass tag to produce a mass code corresponding to a target at which the mass tag was deposited, detecting each mass code, and quantifying each target by quantifying an amount of the mass code deposited at each target. The first mass tag and the second mass tag have the same chemical structure, but at least one of the first mass tag and the second mass tag is isotopically labeled such that they differ in mass, thereby producing respective mass codes having the same chemical structure but differing in mass. In certain embodiments, the method further includes depositing additional mass tags at one or more subsequent targets in the tissue sample, wherein each additional mass tag has the same chemical structure as the first and second mass tags and is isotopically labeled such that its mass differs from any other mass tag used to identify and quantify any other target in the tissue sample. In particular embodiments, detecting each mass code is performed using mass spectrometry, and each mass code corresponding to a target differs in mass from any other mass code corresponding to any other target by a sufficient mass amount to prevent overlap of mass spectrometric peaks from two or more mass codes.

In some embodiments, an amount of a mass code is quantified by measuring a mass spectrometric peak having a m/z ratio corresponding to an expected m/z ratio of the mass code. In other embodiments, a plurality of mass spectrometric peaks is measured and the measurements are combined to quantify the amount of the mass code. The plurality of peaks includes a primary peak having a m/z ratio of x corresponding to the expected m/z ratio of the mass code and at least one secondary peak having a m/z ratio of x+n where n is an integer≥1 and x+n is less than a m/z ratio corresponding to an expected m/z ratio of any other mass code present.

In some embodiments, depositing a mass tag includes immobilizing an enzyme at a target, and contacting the tissue sample with an enzyme substrate moiety and a mass tag precursor. The enzyme substrate moiety reacts with the enzyme and the mass tag precursor to produce and deposit a mass tag at the target. When two or more targets are present in the tissue sample, mass tags are deposited sequentially at each target as described above. After a mass tag is deposited, the corresponding enzyme is deactivated prior to depositing a subsequent mass tag at a subsequent target. In other disclosed embodiments, the enzyme reacts with a mass tag precursor-tyramine conjugate or a mass tag precursor-tyramine derivative conjugate to deposit, typically covalently, the mass tag proximal to the target.

In some embodiments, immobilizing an enzyme at a target includes contacting the tissue sample with a conjugate comprising a specific binding moiety and an enzyme. In certain embodiments, the specific binding moiety is an antibody. The specific binding moiety is capable of recognizing and binding directly to the target or to another specific binding moiety previously bound to the target. In particular embodiments, the first enzyme, the second enzyme, and any additional enzyme are the same.

In some embodiments, the target is a protein or a peptide, and the specific binding moiety previously bound to the target is an antibody. In some embodiments, the target is a nucleic acid sequence, and the specific binding moiety previously bound to the target is a labeled probe capable of hybridizing to the nucleic acid sequence or a portion thereof.

In some embodiments, the mass tags are ionized by exposing one or more mass tags to laser-initiated ionization/desorption to produce a mass code. The one or more mass codes are detected and quantified. The first target is quantified by quantifying the first mass code, and the second target is quantified by quantifying the second mass code. In certain embodiments, the laser ionizes mass tags in a section of the tissue sample. In particular embodiments, the tissue sample and/or laser subsequently is moved such that the laser is positioned to ionize mass tags in a subsequent section of the tissue sample, and mass codes from the subsequent section are detected and quantified. The steps of moving the sample and the laser relative to one another, ionizing mass tags, and detecting and quantifying the mass codes can be performed in a plurality of subsequent sections of the tissue sample.

In some embodiments, a representative map of the sample is constructed. Certain disclosed embodiments concern a map that includes a plurality of sections corresponding to the tissue sample sections, and each map section includes data correlating to mass code quantification wherein quantification comprises determining the size of a mass peak and correlating it with the amount the target for the corresponding tissue sample section. In certain embodiments, the data is presented in representative form, whereby a data representative such as a color, symbol, etc. is provided that corresponds to a numerical value for the data correlating to the mass code quantification. In particular embodiments, the data correlates to a ratio of two mass codes quantified for two targets in the corresponding tissue sample section.

In some embodiments, first and second mass tags are deposited at first and second targets, and the diazonium salts used to react with a naphthol moiety, thus forming a first mass tag precursor and second mass tag precursor, have the structures

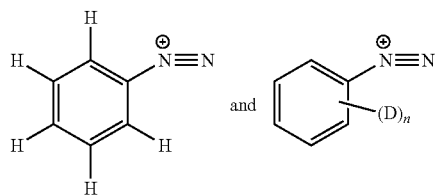

where n is 1, 2, 3, 4, or 5. Preferably n is 2-5, with disclosed working examples having n=5 as shown below.

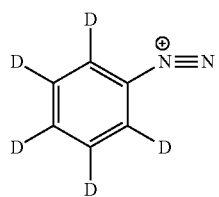 [SMILES: [2H]c1c([2H])c([2H])c([N+]#N)c([2H])c1[2H]]

In certain embodiments, the tissue sample includes two to four targets, and the diazonium salts selected to ultimately produce the first mass tag precursor, the second mass tag precursor, and any additional mass tag precursors are selected from

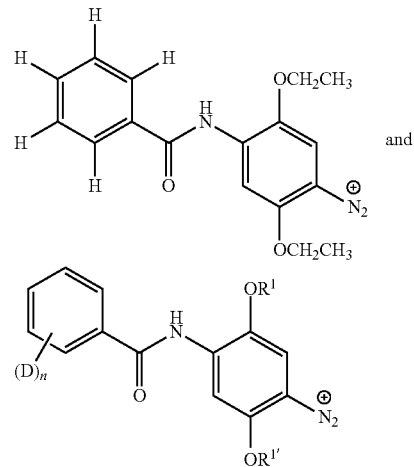

where n is 0-5, and $R^1$ and $R^{1'}$ are independently lower alkyl optionally substituted with one or more isotopes, e.g., —$CD_3$, —$CD_2CD_3$, etc. In some examples, the diazonium salts are selected from

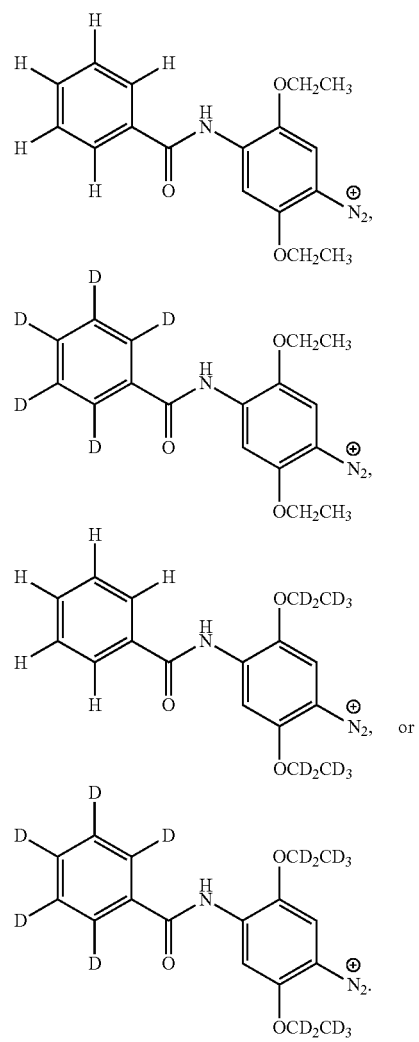

Embodiments of a kit for detecting plural targets by mass spectrometry include at least a first mass tag precursor and a second mass tag precursor and at least one conjugate comprising an enzyme and a specific binding moiety capable of recognizing and binding to a target in a tissue sample or to another specific binding moiety previously bound to a target in a tissue sample. The first and second mass tag precursors have the same chemical structure, except that at least one of the precursors is isotopically labeled such that the first and second mass tag precursors differ in mass from one another.

In some embodiments, the kit also includes an enzyme substrate moiety capable of reacting with the enzyme and the first mass tag precursor to produce and deposit a first mass tag at a first target in the tissue sample. The enzyme substrate moiety further is capable of reacting with the enzyme and the second mass tag precursor to produce and deposit a second mass tag at a second target in the tissue sample.

In certain embodiments, the kit includes one or more additional mass tag precursors, wherein each additional mass tag precursor has the same chemical structure as the first and second mass tag precursors, except that each additional mass tag precursor is isotopically labeled such that each additional mass tag precursor differs in mass from the mass of the first mass tag precursor, the second mass tag precursor, and any other additional mass tag precursor. In such embodiments, the enzyme substrate moiety is capable of reacting with the enzyme and each additional mass tag precursor to produce and deposit an additional mass tag at an additional target in the tissue sample.

In some embodiments, the kits include one or more mass tag precursor conjugates, comprising a mass tag precursor, an enzyme substrate, or a tyramine or a tyramine derivative, an optional linker, and an optional carrier. Each conjugate is capable of reacting with the enzyme to deposit a mass tag at a particular target tin the tissue sample.

The foregoing and other objects, features, and advantages of the invention will become more apparent from the following detailed description, which proceeds with reference to the accompanying figures.

BRIEF DESCRIPTION OF THE DRAWINGS

FIG. 6A, is presented and FIG. 6B is an image where $Ag_2^+$ was detected as mass code. FIG. 6D is an image where $Ag_3^+$ was detected as mass code, and FIG. 6C is an overlapped image of $Ag_2^+$ and $Ag_3^+$ mass codes.

FIG. 16 depicts ER/PR ratios ranging from 0.2-4.0; FIG. 17 depicts ER/PR ratios ranging from 0.66 to 1.5; FIG. 18 depicts ER/PR ratios ranging from 2.0 to 4.0.

FIGS. 21A-21C are images illustrating exemplary results. FIG. 21A illustrates a heat map of a malachite green (MG) mass code used in Example 4 using color scale imaging for indicating intensity of the peak; FIG. 21B is an ion map in one color, as discussed in Example 4; and FIG. 21C is an optical image of a control slide (a serial sectioned slide) stained with BCIP/NBT, which illustrates the specificity of mass tag staining and imaging.

FIGS. 24A-24C are images illustrating exemplary results using a disclosed mass tag precursor wherein FIGS. 24A and 24B are MS images illustrating 8-AQ oligomers formed by HRP-catalyzed oxidation, followed by imaging under LDI conditions, according to Example 7, and FIG. 24C is a mass spectrum of the 8-AQ oligomers.

FIGS. 25A-25E are images illustrating exemplary results obtained by using an embodiment of the disclosed method.

FIGS. 25A and 25B are heat maps obtained using the method according to Example 8 for FFPE human prostate V161-G13; FIG. 25C is a BCIP/NBT control slide; FIG. 25D is a DAB control slide (red dots encircle cancer region); and FIG. 25E is an overall average mass spectrum obtained for entire measured region.

FIGS. 26A-26C are optical images of a MCF-7 xenograft (FIG. 26A), a ZR-751 xenograft (FIG. 26B), and a Calu-3 xenograft (FIG. 26C) stained with a SISH protocol according to Example 9.

FIGS. 27A-27C are images of heat maps of $Ag_2^+$ ion in MCF-7 xenografts (FIG. 27A), ZR-751 xenografts (FIG. 27B), and Calu-3 xenografts (FIG. 27C) for detection of Her2 gene.

FIGS. 29A-29C are optical images of MCF-7 xenograft negative control (no Her2 gene probe) (FIG. 29A), ZR-751 xenograft negative control (no Her2 gene probe) (FIG. 29B), and Calu-3 xenograft negative control (no Her2 gene probe) (FIG. 29C).

FIGS. 30A-30C are images of the heat maps of $Ag_2^+$ ion in negative control slide (no Her2 gene probe) for MCF-7 (FIG. 30A), ZR-751 (FIG. 30B), and for Calu-3 (FIG. 30C).

FIGS. 32A-32F are 40× microscope images of sample Her2 slides imaged in MS for MCF-7 (FIG. 32A), ZR-751 (FIG. 32B), and Calu-3 (FIG. 32C); and 40× microscope images of negative control Her2 slides imaged in MS for MCF-7 (FIG. 32D), ZR-751 (FIG. 32E), and Calu-3 (FIG. 32F).

FIGS. 34A-34D are optical images of C-33A xenografts (FIG. 34A), SiHa xenografts (FIG. 34B), Hela xenografts (FIG. 34C), and CaSki xenografts (FIG. 34D), with SISH detection of HIV genes.

FIGS. 35A-35D are images of heat maps of $Ag_2^+$ ion in C-33A xenografts (FIG. 35A), SiHa xenografts (FIG. 35B), HeLa xenografts (FIG. 35C), and CaSki xenografts (FIG. 35D) for detection of HPV gene.

FIGS. 37A-37D are optical images of C-33A xenograft (FIG. 37A), SiHa xenograft (FIG. 37B), HeLa xenograft (FIG. 37C), and CaSki xenograft (FIG. 37D) negative control slides (no HPV gene probe).

FIGS. 38A-38D are images of the heat maps of $Ag_2^+$ ion in C-33A (FIG. 38A), SiHa (FIG. 38B), HeLa (FIG. 38C), and CaSki (FIG. 38D) negative control slides (no HPV gene probe).

FIGS. 40A-40H are 40× microscope images of sample HPV slides imaged in MS for C-33A xenograft (FIG. 40A), SiHa xenograft (FIG. 40B), HeLa xenograft (FIG. 40C), and CaSki xenograft (FIG. 40D); and the 40× microscope images of negative control HPV slides imaged in MS for C-33A xenograft (FIG. 40E), SiHa xenograft (FIG. 40F), HeLa xenograft (FIG. 40G), and CaSki xenograft (FIG. 40H).

FIG. 42A is an image of the xenografts; FIG. 42B illustrates heat maps for the xenografts employing the Her2 mass tag precursor (mass code has m/z=~482), FIG. 42C illustrates heat maps for the xenografts employing the ER mass tag mass tag precursor (mass code has m/z=~454), FIG. 42D illustrates the heat maps for the xenografts employing the PR mass tag mass tag precursor (mass code has m/z=~438), and FIG. 42E illustrates the heat maps for the xenografts wherein images from all three mass tags are overlayed.

FIGS. 43A-43C are images of mass spectra from individual raster points, taken from the MCF7 xenograft (FIG. 43A), a ZR751 xenograft (FIG. 43B), and a Calu3 xenograft (FIG. 43C).

FIGS. 44A-4C are images of overall average mass spectra obtained for MCF7 (FIG. 44A), ZR751 (FIG. 44B), and Calu3 (FIG. 44C) measured regions, showing mass codes detected for Her2 (m/z=482), ER (m/z=454) and PR (m/z=438).

FIGS. 45A-45C are images illustrating the exemplary results obtained by using multiplexing: FIG. 45A illustrates heat maps produced by exemplary embodiments; FIG. 45B illustrates intensity histograms (arbitrary units [au, x-axis] versus frequency [y-axis]) of exemplary mass codes produced in the exemplary working embodiment; and FIG. 45C illustrates a density map (mass charge [m/z, x-axis] versus arbitrary units [au, y-axis]) and an overall mass spectra (mass charge [m/z, x-axis] versus arbitrary units [au, y-axis]) of exemplary mass codes detecting particular xenografts.

FIGS. 52A and 52B are mass spectral images of the results obtained from exemplary working embodiments with an exemplary protein in tonsil tissue stained with DAB and $NiCl_2$.

FIGS. 57A and 57B show ER and PR antigens, respectively, stained using an alkaline phosphatase red detection kit.

FIG. 57C shows both ER and PR antigens stained according to one embodiment of the disclosed method for multiplex staining with stable-isotope-labeled mass tags; in this example, the mass tags were azo dyes.

FIGS. 65A-65C are images illustrating the following: FIG. 65A is an image of the heat maps of ions detected in analysis of Ki-67 in tonsil tissue for both a sample of interest and FIG. 65B is an image of a control sample; and FIG. 65C is the corresponding overall mass spectra of the sample of interest and the control sample.

FIGS. 66A-66C are images illustrating heat maps of a Her2 3-in1 xenograft; with results shown for MCF7 (FIG. 66A), ZR-75-1 (FIG. 66B) and Calu 3 (FIG. 66C).

FIGS. 72A-72D are images illustrating the following: FIG. 72A is an ion map in one color for the BG mass code, according to Example 4; FIG. 72B is an image of a heat map of the Brilliant Green (BG) mass code, imaging with color scale for indicating intensity of the peak; FIG. 72C is an optical image of a control slide (a serial sectioned slide) stained with BCIP/NBT under identical conditions used in Example 4 to show the specificity of mass tag staining and imaging; and FIG. 72D is a mass spectrum of BG (m/z=~385) as a mass code, as discussed in Example 4 including a blown up region of the mass spectrum.

FIGS. 73A and 73B are images illustrating the representative MSI of Ki-67 staining with crystal violet (CV, m/z=~372) as a mass code (FIG. 73A), as discussed in Example 4 and a mass spectrum of crystal violet (CV, m/z=~372) as a mass code (FIG. 73B), as discussed in Example 4.

FIG. 76 illustrates the chemistry of the alkaline phosphatase catalyzed mass tag deposition.

SEQUENCE LISTING

Figure 1:
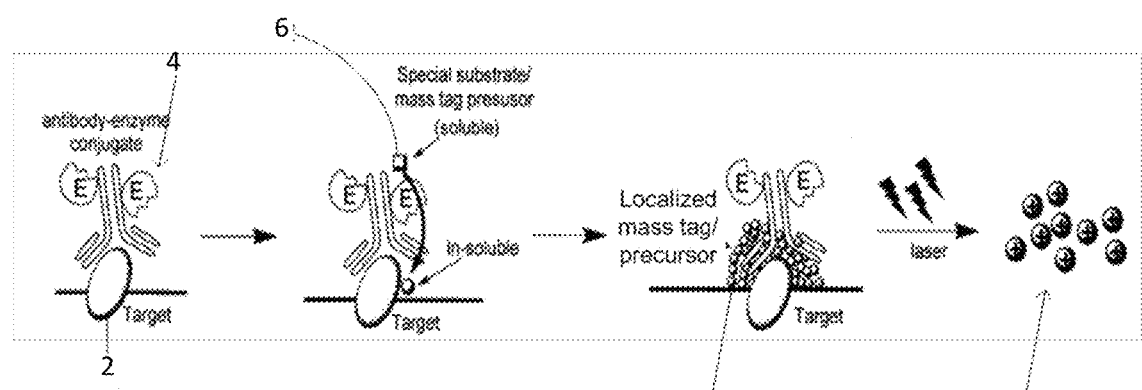
FIG. 1 is a schematic diagram illustrating the use of an antibody-enzyme conjugate to deposit mass tags at a target, followed by ionization and desorption to produce detectable ions.

The nucleic and amino acid sequences provided herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing is submitted as an ASCII text file, named "87482-01 ST25," created on Dec. 17, 2015, 97KB, which is incorporated by reference herein.

SEQ ID NO: 1 is a Her1 amino acid sequence (NCBI Reference Sequence No. NP_005219.2).

SEQ ID NO: 2 is an exemplary cDNA sequence encoding Her1 (NCBI Reference Sequence No. NM_005228.3).

SEQ ID NO: 3 is a Her2 amino acid sequence (NCBI Reference Sequence No. NP_004439.2).

SEQ ID NO: 4 is an exemplary cDNA sequence encoding Her2 (NCBI Reference Sequence No. NM_004448.2).

SEQ ID NO: 5 is a Her3 amino acid sequence (NCBI Reference Sequence No. NP_001973.2).

SEQ ID NO: 6 is an exemplary cDNA sequence encoding Her3 (NCBI Reference Sequence No. NM_001982.3).

SEQ ID NO: 7 is a Her4 amino acid sequence (Genbank Accession No. AAI43750).

SEQ ID NO: 8 is an exemplary cDNA sequence encoding Her4 (GenBank Accession No. BC143749.1).

SEQ ID NO: 9 is an Estrogen Receptor amino acid sequence (NCBI Reference Sequence No. NP_000116.2).

SEQ ID NO: 10 is an exemplary cDNA sequence encoding an Estrogen Receptor (NCBI Reference Sequence No. NM_000125.3).

SEQ ID NO: 11 is a Progesterone Receptor amino acid sequence (Genbank Accession No. AAD01587.1).

SEQ ID NO: 12 is an exemplary cDNA sequence encoding a Progesterone Receptor (GenBank Accession No. AF016381.1).

DETAILED DESCRIPTION

I. Terms And Abbreviations

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), The *Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting. All sequences referred to by GenBank Accession numbers herein are incorporated by reference as they appeared in the database on Jun. 30, 2011.

In order to facilitate review of the various examples of this disclosure, the following explanations of specific terms and abbreviations are provided:

Aliphatic: Any open or closed chain molecule, excluding aromatic compounds, containing only carbon and hydrogen atoms which are joined by single bonds (alkanes), double bonds (alkenes), or triple bonds (alkynes). This term encompasses saturated and unsaturated aliphatic compounds.

Amplification: Certain embodiments of the present invention allow a single target to be detected using plural visualization complexes, where the complexes can be the same or different, to facilitate identification and/or quantification wherein quantification comprises determining the size of a mass peak and correlating it with the amount of a particular target.

Analog or Derivative: An analog is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant, or binding affinity, for the molecule of interest that is at least $10^3$ $M^{-1}$ greater, at least $10^4$ $M^{-1}$ greater or at least $10^5$ $M^{-1}$ greater than a binding constant for other molecules in a biological sample. In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antigen: A compound, composition, or substance that may be specifically bound by the products of specific humoral or cellular immunity, such as an antibody molecule. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids, proteins, and peptides. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

Aromatic: A term describing conjugated rings having unsaturated bonds, lone pairs, or empty orbitals, which exhibit a stabilization stronger than would be expected by the stabilization of conjugation alone. It can also be considered a manifestation of cyclic delocalization and of resonance.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc.

Aryl alkyl: A compound, or a radical thereof ($C_7H_7$ for toluene) as a substituent bonded to another group, particularly other organic groups, containing both aliphatic and aromatic structures.

Biomarker: A biological marker or indicator of a biological state that may be measured or evaluated to indicate a particular disease state or other physiological state of an organism. Biomarkers can indicate a change in expression or state of a protein that correlates with a disease risk or progression. Biomarkers can be used to measure the progression of a disease. Biomarkers also can be used to predict or measure the efficacy of a particular treatment for a disease. Biomarkers can be, for example, specific cells, molecules, genes, gene products, enzymes, or hormones.

Carrier: A molecule to which another molecule can be bound, such as a hapten, a mass tag, a mass tag precursor, or an antigen. Carrier molecules include immunogenic carriers and specific-binding carriers. When bound to an immunogenic carrier, the bound molecule may become immunogenic.

Immunogenic carriers may be chosen to increase the immunogenicity of the bound molecule and/or to elicit antibodies against the carrier, which are diagnostically, analytically, and/or therapeutically beneficial. Covalent linking of a molecule to a carrier can confer enhanced immunogenicity and T-cell dependence. Useful carriers include polymeric carriers, which can be natural (for example, proteins from bacteria or viruses), semi-synthetic or synthetic materials containing one or more functional groups to which a reactant moiety can be attached. Specific binding carriers can be any type of specific binding moiety, including an antibody, a nucleic acid, an avidin, a protein-nucleic acid. The carrier can be water soluble or insoluble, and in some embodiments is a protein or polypeptide.

Chromogen: An aromatic compound comprising a chemical grouping, or chromophore, that gives color to the compound by causing displacement of, or appearance of, absorbent bands in the visible spectrum. Exemplary chromophores include, but are not limited to, —NO (e.g., nitroso dyes), —$NO_2$ (e.g., nitro dyes), and —N═N— (e.g., azo dyes).

Conjugate: A molecule comprising two independent molecules, which have been joined through a bond (typically a covalent or ionic bond), such as a mass tag precursor joined with an enzyme substrate.

Conjugating, joining, bonding or linking: Covalently linking one molecule to another molecule to make a larger molecule. For example, making two polypeptides into one contiguous polypeptide molecule, or covalently attaching a mass tag precursor, hapten or other molecule to a polypeptide, such as an scFv antibody.

Coupled: A first atom and/or molecule being attached to a second atom and/or molecule. Coupling generally refers to attaching the atoms or molecules by non-covalent means. The term "coupled" refers to both directly coupled and indirectly coupled. A secondary antibody provides an example of indirect coupling. One specific example of indirect coupling is a rabbit anti-hapten primary antibody that is bound by a mouse anti-rabbit IgG antibody, that is in turn bound by a goat anti-mouse IgG antibody that is covalently linked to a detectable label; thus, the detectable label is "coupled" indirectly to the mouse anti-rabbit IgG antibody and to the rabbit anti-hapten primary antibody.

Deactivat(e/ion): Deactivate and deactivation generally refer to inhibiting an enzyme or making an enzyme inactive. Examples of deactivating and deactivation include the following: mechanically removing an enzyme after it has reacted with the enzyme substrate-mass tag conjugate, such as by washing away the enzyme via elution of the secondary antibody, to which the enzyme is conjugated, as well as the primary antibody (if present); chemically deactivating the enzyme after it has reacted with the enzyme substrate-mass tag conjugate, such as by exposing the sample comprising the enzyme to an oxidant, such as hydrogen peroxide; and/or chemically inhibiting the enzyme after it has reacted with the enzyme substrate-mass tag conjugate with an agent capable of inhibiting a particular enzymatic action. Deactivation encompasses any of these techniques, any combination thereof, and any other technique now known or hereafter developed that achieves the stated purpose.

Detectable Label: A detectable compound or composition that is attached directly or indirectly to another molecule, such as an antibody or a protein, to facilitate detection of that molecule. Specific, non-limiting examples of labels include fluorescent tags, enzymes, and radioactive isotopes.

Derivative: In chemistry, a derivative is a compound that is derived from a similar compound or a compound that can be imagined to arise from another compound, for example, if one atom is replaced with another atom or group of atoms. The latter definition is common in organic chemistry. In biochemistry, derivative refers to compounds that at least theoretically can be formed from the precursor compound.

Effective amount: As used herein, an effective amount is an amount sufficient to produce a desired effect, e.g., an amount sufficient to enable detection of a target or analyte.

Epitope: An antigenic determinant. These are particular chemical groups or contiguous or non-contiguous peptide sequences on a molecule that are antigenic, that is, that elicit a specific immune response. An antibody binds a particular antigenic epitope.

ER: Estrogen receptor.

FFPE: Formalin-fixed, paraffin-embedded.

Hapten: A molecule, typically a small molecule that can combine specifically with an antibody, but typically is substantially incapable of being immunogenic except in combination with a carrier molecule.

Human epidermal growth factor receptor (Her) family: A family of structurally related proteins, including at least Her1, Her2, Her3 and Her4 (aka EGFR1, EGFR2, EGFR3 and EGFR4, respectively, or ErbB-1, ErbB-2, ErbB-3 and ErbB-4, respectively). Her1, Her2 and Her4 are receptor tyrosine kinases; although Her3 shares homology with Her1, Her2 and Her4, Her3 is kinase inactive. Included in the Her family is p95, a truncated form of Her2 lacking portions of the Her2 extracellular domain (see, e.g., Arribas et al., *Cancer Res.*, 71:1515-1519, 2011; Molina et al., *Cancer Res.*, 61:4744-4749, 2001).

The human epidermal growth factor family of receptors mediate cell growth and are disregulated in many types of cancer. For example Her1 and Her2 are upregulated in many human cancers, and their excessive signaling may be critical factors in the development and malignancy of these tumors. See, e.g., Herbst, *Int. J. Radiat. Oncol. Biol. Phys.*, 59:21-6, 2004; Zhang et al., *J. Clin. Invest.* 117 (8): 2051-8, 2007. Receptor dimerization is essential for Her pathway activation leading to receptor phosphorylation and downstream signal transduction. Unlike Her1, -3 and -4, Her2 has no known ligand and assumes an open conformation, with its dimerization domain exposed for interaction with other ligand-activated Her receptors.

Approximately 30% of breast cancers have an amplification of the Her2 gene or overexpression of its protein product. Her2 overexpression also occurs in other cancer types, such as ovarian cancer, stomach cancer, and biologically aggressive forms of uterine cancer, such as uterine serous endometrial carcinoma. See, e.g., Santin et al., *Int. J. Gynaecol. Obstet.*, 102 (2): 128-31, 2008. Her2-containing homo- and hetero-dimers are transformation competent protein complexes. Trastuzumab, a humanized antibody that prevents Her2 homodimerization is used to treat certain Her2 overexpressing cancers, including breast cancer. Additionally, the level of Her2 expression in cancer tissue is predictive of patient response to Her2 therapeutic antibodies (e.g., Trastuzumab). Because of its prognostic role as well as its ability to predict response to Trastuzumab, tumors (e.g., tumors associated with breast cancer) are routinely checked for overexpression of Her2.

The Her pathway is also involved in ovarian cancer pathogenesis. Many ovarian tumor samples express all members of the Her family. Co-expression of Her1 and Her2 is seen more frequently in ovarian cancer than in normal ovarian epithelium, and overexpression of both receptors correlates with poor prognosis. Preferred dimerization with Her2 (Her1/Her2, Her2/Her3) and subsequent pathway activation via receptor phosphorylation have also been shown to drive ovarian tumor cell proliferation, even in the absence of Her2 overexpression. Pertuzumab, a humanized antibody that prevents Her2 dimerization (with itself and with Her3) has been shown to provide therapeutic benefit to patients with Her2 and/orHer3 expressing ovarian cancer.

Examples of Her1 amino acid sequence include NCBI/Genbank accession Nos. NP_005219.2, CAA25240.1, AAT52212.1, AAZ66620.1, BAF83041.1, BAH11869.1, ADZ75461.1, ADL28125.1, BAD92679.1, AAH94761.1. Examples of, Her2, amino acid sequences include NCBI/Genbank accession BAJ17684.1, P04626.1, AAI67147.1, NP_001005862.1, NP_004439.2, AAA75493.1, AAO18082.1. Examples of Her3 amino acid sequences include NCBI/Genbank accession Nos. NP_001973.3, P21860.1, AAH82992.1, AAH02706.1, AAA35979.1. Examples of Her4 amino acid sequences include NCBI/Genbank accession Nos., AAI43750, Q15303.1, NP_005226.1, NP_001036064.1, AAI43748.1.

Heteroaliphatic: An aliphatic group, which contains one or more atoms other than carbon and hydrogen, such as, but not limited to, oxygen, sulfur, nitrogen, phosphorus, chlorine, fluorine, bromine, iodine, and selenium.

Heterobifunctional: A molecule or group of atoms that contains at least two different reactive groups (typically one reactive group at each end), which are reactive towards particular functional groups, including but not limited to sulfhydryls and amines. For example, a heterobifunctional molecule can be used to create chemical covalent bonds between two or more molecules.

IHC: Immunohistochemistry.

Ionization: The process of converting an atom or molecule into an ion by adding or removing charged particles such as electrons, protons, or other polyatomic ions.

Immunogenic Conjugate or Composition: A composition useful for stimulating or eliciting a specific immune response (or immunogenic response) in a vertebrate. In some embodiments, the immunogenic response is protective or provides protective immunity by enabling the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" component has been substantially separated or purified from other components, e.g., other components of a solution, a mixture, or a cell. An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Isotope: One of two or more forms of an element that have the same atomic number, but different masses. The mass differences are due to the presence of one or more extra neutrons in the nucleus. For example, deuterium and tritium are isotopes of hydrogen. Hydrogen has one proton, one electron, and no neutrons, and has a mass of 1 dalton. Deuterium has one proton, one electron, and one neutron, and has a mass of 2 daltons. Tritium has one proton, one electron, and two neutrons, and has a mass of 3 daltons.

Linker: As used herein, a linker is a molecule or group of atoms positioned between two moieties. For example, a mass tag precursor conjugate may include a linker between the mass tag and the enzyme substrate moiety. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

Linker peptide: A peptide positioned between two moieties. One example of a linker peptide is an antibody binding fragment (such as an Fv fragment) that indirectly bonds the variable heavy chain to the variable light chain. "Linker" can also refer to a peptide serving to link a targeting moiety, such as a scFv, to an effector molecule, such as a cytotoxin or a detectable label.

Lower alkyl: Any aliphatic chain that contains 1-10 carbon atoms.

Mass Code/Reporter Ion: An ion that is produced from a mass tag during an ionization step that can be detected, such as by a mass spectrometer. For example, a photolabile moiety, having at least one photolabile bond may be desorbed and ionized to form a mass code. The mass code, or reporter ion, can be an ionized form of the mass tag (e.g. soft ionization) or can be an ionized fragment.

Mass Tag: A moiety that is capable of producing a mass code upon ionization. Mass tag moieties may comprise one or more labile bonds, such as photolabile bonds, that will cleave, ionize, or dissociate upon photolysis. In some embodiments, the mass tag is equivalent to a mass code, such as when the mass tag comprises a charged moiety. Mass tags may be selected according to the properties that make them useful for ionization and/or the properties that make them useful for deposition proximal to the enzyme. Stability of the mass tag or its dominant fragments as ions, susceptibility to laser ablation, and dissociation from the matrix may all distinguish mass tags from other compounds.

Mass tag precursor: A moiety that is capable of undergoing a reaction to form a mass tag. For example, a mass tag precursor may be capable of being enzymatically converted into a mass tag. The mass tag precursor may be part of a conjugate, a portion of which is a substrate for an enzyme. The mass tag precursor conjugate is typically converted by an enzyme in a manner so that the resulting mass tag is localized in the vicinity of the enzyme. For example, the mass tag precursor may be water-soluble, wherein the enzyme catalyzes the formation of a water-insoluble mass tag which is deposited (e.g. precipitates) in the vicinity of the enzyme. The mass tag precursor may also include a substrate that is activatable by the enzyme to form a reactive species. Illustratively, the reactive species may be a short-lived reactive species that covalently binds to proximal to the enzyme. The mass tag precursor may also form a mass tag upon reaction with a reactive intermediate, for example a reactive intermediate enzymatically formed.

Metal Heteroaryl Chelate: A complex comprising a metal having two or more separate binding interactions with one or more aryl groups containing at least one or more atoms other than carbon. Examples include mono-heteroaryl chelates in which none of A, A', B, B', C or C' are bonded to another ring, biheteroaryl chelates, in which rings A and A' are bonded together, with rings C and B being bonded together, and C' and B' bonded together, or terheteroaryl chelates, in which rings A, B, and C, are bonded together, and A', B', and C' are bonded together.

Micelle: A micelle is a colloidal aggregate of large molecules, e.g., surfactant molecules.

Molecule of interest or Target: A molecule for which the presence, location and/or concentration is to be determined. Examples of molecules of interest include proteins, peptides, and nucleic acid sequences. In certain examples, the molecule of interest, or target, is a biomarker.

Monoclonal antibody: An antibody produced by a single clone of B-lymphocytes or by a cell into which the light and heavy chain genes of a single antibody have been transfected. Monoclonal antibodies are produced by methods known to those of ordinary skill in the art, for instance by making hybrid antibody-forming cells from a fusion of myeloma cells with immune spleen cells. Monoclonal antibodies include humanized monoclonal antibodies.

MS: Mass spectrometry; mass spectrometric.

MSI: Mass spectrometric imaging.

Multiplex, -ed, -ing: Embodiments of the present invention allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Nanoparticle: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Neoplasia and Tumor: The process of abnormal and uncontrolled growth of cells. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Photolabile Moiety: A moiety which is labile upon effective exposure to light. Photolabile moieties contain one or more bonds that are broken by exposure to light.

Photolysis: A chemical process in which a chemical compound is broken down by photons.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" refers to an amino acid that is incorporated into a protein, polypeptide, or peptide.

PR: Progesterone receptor.

Protein: A molecule, particularly a polypeptide, comprised of amino acids.

Proximal, -ly: The term "proximal" means being situated at or near the point of attachment or origin. Typically, attachment refers to coupling one moiety to another moiety. In some instances, "proximal" refers to the ability to distinguish single copies of target DNA with ISH. However, actual spatial resolution may be limited by the resolution achievable by the techniques used, such as spectrometric techniques. As used herein, proximal means within about 100 nm, within about 50 nm, within about 10 nm, or within about 5 nm. Proximal also may indicate within a range of about 10 angstroms to about 100 nm, about 10 angstroms to about 50 nm, about 10 angstroms to about 10 nm, or about 10 angstroms to about 5 nm.

Purified: The term "purified" does not require absolute purity; rather, it is intended as a relative term. Thus, for example, a purified peptide, protein, conjugate, or other active compound is one that is isolated in whole or in part from proteins or other contaminants. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Reactive Groups or functional groups: Formulas throughout this application refer to "reactive groups" or "functional groups," which can be any of a variety of groups suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, mannich condensation products, iodination reaction products, and combinations thereof. Photoreactive chemical functional groups include aryl azides, halogenated aryl azides, benzophonones, diazo compounds, diazirine derivatives, and combinations thereof.

Resonance: The appearance of delocalized electrons within certain molecules or polyatomic ions, so that the bonding cannot be expressed by one single Lewis formula. Typically used in reference to electron delocalization of molecules.

Sample: A biological specimen, typically containing DNA, RNA (including mRNA), protein, peptides, carbohydrates, or combinations thereof, obtained from a subject. Examples include, but are not limited to, peripheral blood, urine, saliva, tissue biopsy, surgical specimen, amniocentesis samples and autopsy material. In one example, a sample includes a biopsy of an adenocarcinoma, a sample of non-cancerous tissue, a sample of normal tissue (from a subject not afflicted with a known disease or disorder).

SILMSI: Stable isotope label-based mass spectrometry imaging.

Specific binding moiety: A member of a specific-binding pair. Specific binding pairs are pairs of molecules that are characterized in that they bind each other to the substantial exclusion of binding to other molecules (for example, specific binding pairs can have a binding constant that is at least $10^3$ M$^{-1}$ greater, $10^4$ M$^{-1}$ greater or $10^5$ M$^{-1}$ greater than a binding constant for either of the two members of the binding pair with other molecules in a biological sample). Particular examples of specific binding moieties include specific binding proteins (for example, antibodies, lectins, avidins such as streptavidins, glycoproteins, and protein A), nucleic acid sequences (for example, nucleic acid oligomers), and protein-nucleic acids. Specific binding moieties can also include the molecules (or portions thereof) that are specifically bound by such specific binding proteins.

A substituent is an atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group. Unless otherwise stated, any compound or functional group disclosed herein may be substituted or unsubstituted.

Tertiary Carbon: An spa-hybridized (bound to four other atoms) carbon atom which is bound to three other carbon atoms and a fourth atom that is not carbon.

TOF: Time-of-flight; refers to time-of-flight mass spectroscopy in which ions' mass-to-charge ratio is determined via a time measurement.

Tyramine: A compound having the formula $C_8H_{11}NO$, also known as 4-(2-aminoethyl)phenol.

II. Introduction

Disclosed embodiments herein concern a method for imaging and/or quantifying one or more targets in a sample, e.g., a tissue sample such as a formalin-fixed, paraffin-embedded tissue sample, using mass tags and mass spectrometry (MS), such as laser desorption/ionization (LDI), including matrix-assisted laser desorption/ionization (MALDI). Some embodiments use an enzyme substrate and a separate mass tag precursor. The enzyme converts the substrate into an active species that can react with the mass tag precursor to deposit a mass tag, such as by precipitation, at the target site. Other embodiments use conjugates comprising a mass tag coupled directly or indirectly to an enzyme substrate moiety. The mass tag may be bonded to the enzyme substrate moiety by one or more covalent bonds, one or more ionic bonds, any other bonding association sufficiently robust to produce a conjugate suitable for use in the method, and combinations of bonds. The mass tag and the enzyme substrate moiety can be coupled directly together, or can be coupled using a linker.

In illustrative embodiments, a sample having a target of interest is first contacted with an enzyme, which may be coupled to a specific binding moiety that recognizes a particular target, or region of a target, such as an epitope. The sample is then exposed to the conjugate, or multiple conjugates. A mass tag is deposited at the site of a target in a sample at the target for subsequent detection by MS in the form of a mass code (an ion). The mass tags may be deposited (covalently, non-covalently, precipitated) at a target location, or multiple target locations, where they are exposed to ionization source to produce mass codes. The mass codes may be detected using mass spectrometry. For example, laser desorption ionization, matrix assisted laser desorption ionization, flowing atmospheric pressure afterglow ionization, laser ablation flowing atmospheric pressure afterglow ionization, desorption electrospray ionization, secondary ion, and laser ablation inductively coupled plasma mass spectrometry are technologies known in the art that could be adapted for use in tissue target identification using the mass tag conjugates. As such, disclosed embodiments herein are not limited to the method of mass spectrometry utilized for detection purposes.

The use of mass spectrometry and mass spectral imaging coupled to an enzymatic reaction enables identification, quantification, and imaging previously unavailable. In particular, the sensitivity, selectivity, quantifiability, and multiplexability of mass spectrometry is enhanced within the scope of the present disclosure by coupling with an amplification step. For example, the amplification step may include the use of an enzyme to create a large number of mass tags for a single recognition event. Furthermore, the selection of disclosed mass tags enhances the mass spectral analysis to enhance imaging and quantification. The current approach enables essentially limitless multiplexing. The use of isotopically labeled mass tags, which would be enzymatically amplified according to essentially the same kinetics, enables multiplexing that is also capable of providing relative quantitative information. This information is not only now uniquely available, but linked to contextual information through imaging which has heretofore be unavailable.

With respect to multiplexing, samples having multiple targets can be treated in a manner so that each target is identified and detected using a different mass. The mass tags may have the same chemical structure but include different isotopes and/or different amounts of a particular isotope such that mass tags are differtiable according to their spectra. As described herein, because the kinetic relationship between various isotopes of a mass tag and the enzyme remains consistent, the amplification of the various isotopes will be consistent between targets. Accordingly, the methods described herein which use mass tags with the same chemical structure facilitate identification and at least relative target quantization.

III. Mass Tag Precursors

While mass spectrometry can be applied to a wide range of chemical species, the present disclosure provides examples of compounds with particular utility as mass tag precursors. While several examples of useful mass tags precursors are disclosed herein, one of ordinary skill will appreciate that these are merely examples selected to provide insight so that others may appreciate the entire genus of compounds useful within the scope of the present application. In particular, those compounds with closely related structures, properties, and functions are within the scope of the present disclosure.

One group of mass tag precursors useful within the scope of the present disclosure includes triarylmethane derivatives. Illustrative triarylmethane embodiments satisfy general Formulas 1A and 1B below.

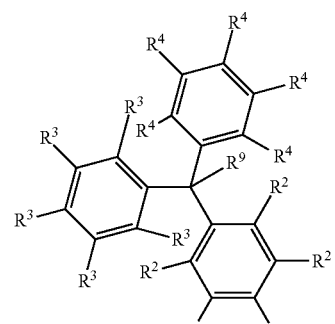

Formula 1A

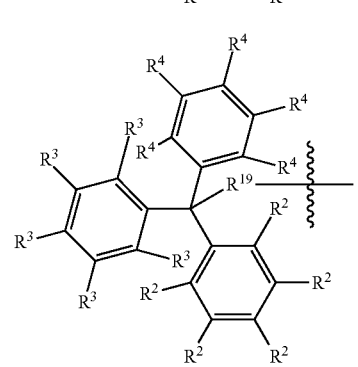

Formula 1B

With reference to general Formulas 1A, each $R^2$, $R^4$, and $R^3$ may also comprise a linker, such as to link to an enzyme substrate moiety (e.g. a phosphate group, a lactam or a galactoside) to the triarylmethane. Each of the aryl groups can have various different substituents. For example, each of the $R^4$ substituents can be the same or different. And each of $R^2$-$R^4$ independently can be the same or different. Many of the triarylmethane derivatives include substituents at the para position relative to the tertiary carbon bearing $R^9$. Substituents at the para position help stabilize carbocation formation, either inductively through the introduction of alkyl groups, or by resonance through the introduction of electron-donating groups. Certain amine-substituted compounds satisfy general Formulas 2A and 2B, below.

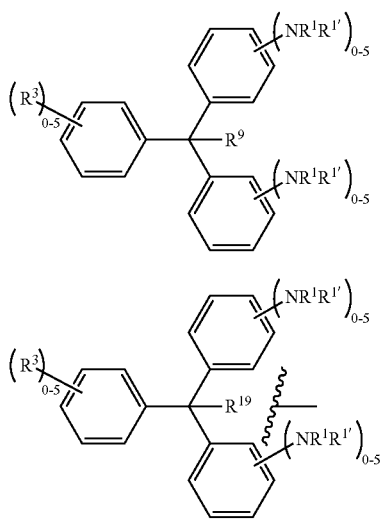

Formula 2A

Formula 2B

With reference to Formulas 2A and 2B, $R^1$ and $R^{1'}$ independently can be hydrogen, deuterium, alkyl, particularly lower alkyl, such as methyl, ethyl, propyl, butyl, etc., and aryl. The amine substituent can be located at any one or more of the ring positions. Thus, there can be multiple ring functionalizations with anywhere from zero to five substituents placed on each ring. Particular compounds include methyl at $R^1$ and/or $R^{1'}$, but a person of ordinary skill in the art will recognize that $R^1$ and $R^{1'}$ may be the same or different. In particular disclosed embodiments, $R^3$ can be selected from hydrogen and alkylene oxy. In certain disclosed embodiments, $R^3$ is at the para position and comprises an ethylene oxy subunit, or polyethylene glycol.

Scheme 1 illustrates a particular embodiment of the disclosed conjugate wherein triarylmethane mass tags 2 or 6 are exposed to a radiation source (e.g. a laser) to produce mass codes 4 or 8. A person of ordinary skill in the art will recognize that any compounds having either one of Formula 2A and 2B may undergo the process shown in Scheme 1.

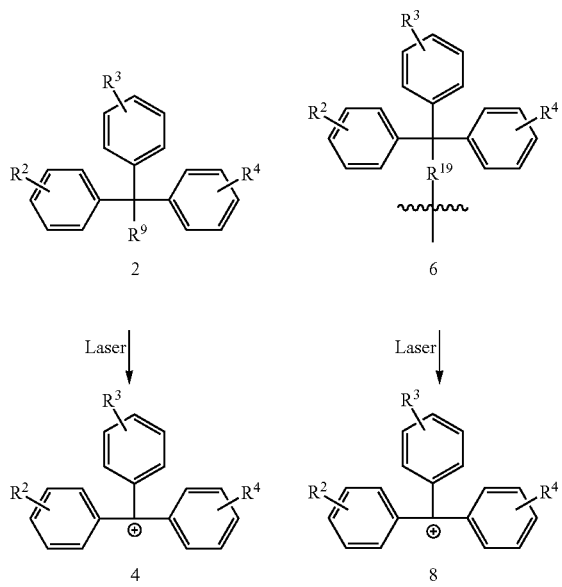

Scheme 1

In one embodiment, the mass tag precursor may have the following structure.

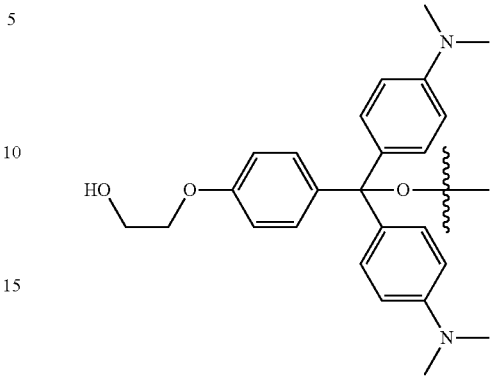

Another group of mass tag precursors classifiable as triarylmethane derivitives includes triarylmethane dyes. An exemplary triarylmethane dye satisfies general Formula 3.

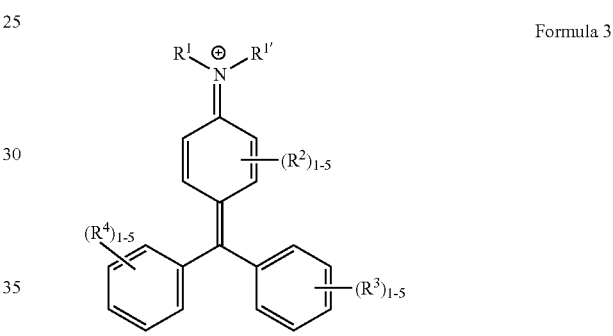

Formula 3

With reference to Formula 3, $R^2$, $R^3$ and $R^4$ also can be atoms, typically carbon atoms, in a ring bonded or fused to the illustrated rings. Each of the aryl groups can have various different substituents. For example, each of the $R^1$ substituents can be the same or different. And each of $R^1$, $R^{1'}$, $R^2$, $R^3$, and $R^4$ independently can be the same or different.

Compounds according to Formula 3 can be used in combination with a reducing agent, such as 5-bromo-4-chloro-3-indole generated from an AP catalyzed cleavage of 5-bromo-4-chloro-3-indole phosphate (BCIP), as illustrated in Scheme 2, to produce a mass tag for use according to disclosed embodiments. According to the embodiment of Scheme 2, an enzyme substrate 10, such as 5-bromo-4-chloro-indolyl-phosphate (BCIP), is contacted with an enzyme 12, such as alkaline phosphatase. This results in active species 14. In this particular example, species 14 is a reducing agent. Species 14 is contemplated to reduce a number of compounds, such as triarylmethane dye 18, during which, species 14 dimerizes to produce dimer 16. The reduction affords a colorless mass tag precipitate 20. Scheme 2 depicts using brilliant green. Precipitate 20 is converted into a mass code 22, such as by using a laser. A person of ordinary skill in the art will appreciate that dyes in addition to the brilliant green dye also can be used. When BCIP is used, a dimerized blue precipitate forms during the reaction of -5-bromo-4-chloro-3-indole with a triarylmethane compound having a structure as described in Formula 3. Laser-initiated ionization forms the corresponding mass code cation.

Scheme 2

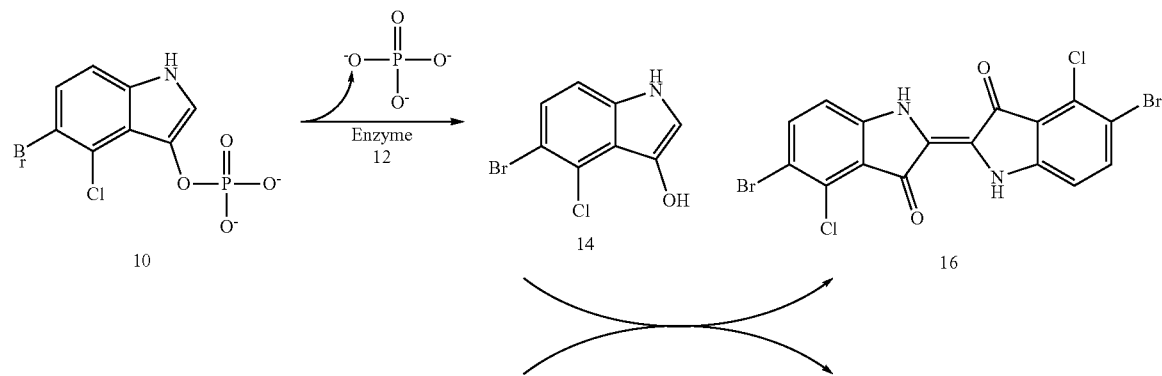

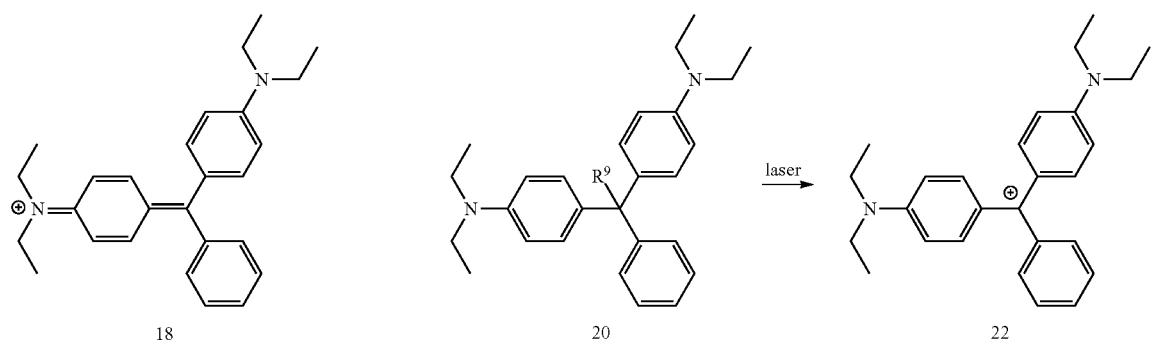

Such compounds typically satisfy the following Formula 4 as well.

Formula 4

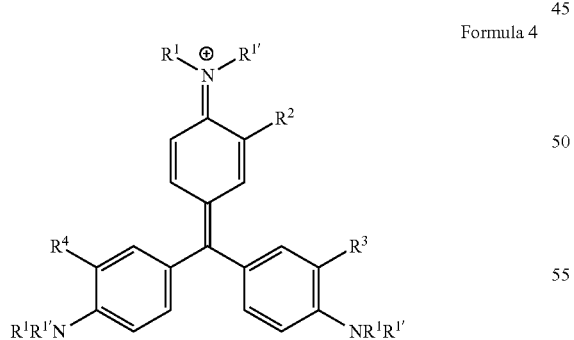

With reference to this Formula 4, $R^1$-$R^4$ typically are hydrogen, lower alkyl, particularly methyl, ethyl, butyl, etc., aryl, aryl aliphatic, more typically aryl alkyl, more typically hydrogen, deuterium, methyl, ethyl, or phenyl. Exemplary compounds having such substitution patterns include, but are not limited to, the following compounds.

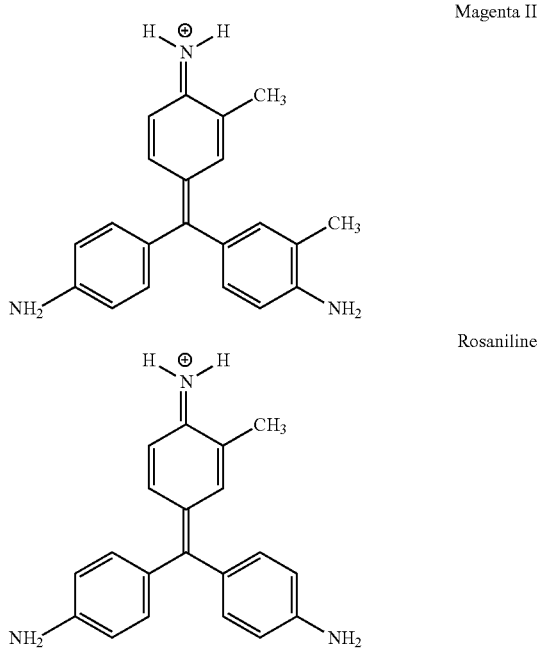

Crystal Violet

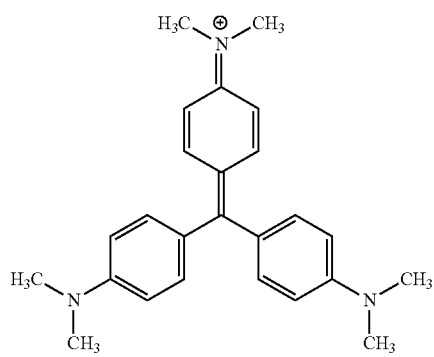

New Fuchsine

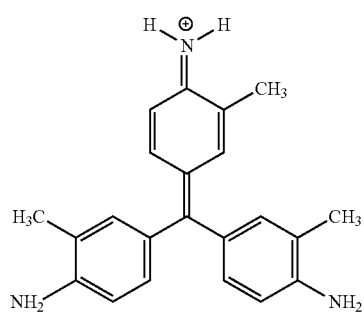

Malachite Green

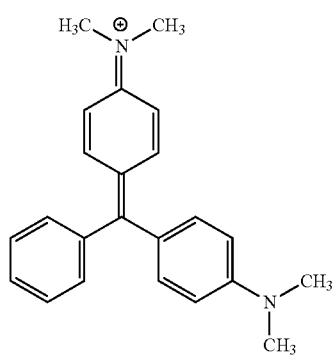

Brilliant Green

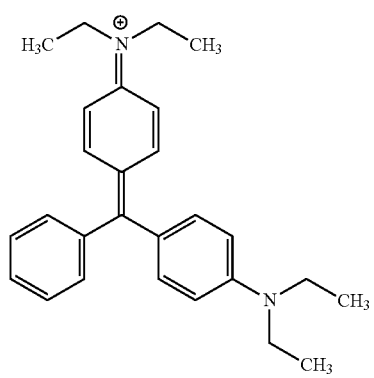

Methyl Violet

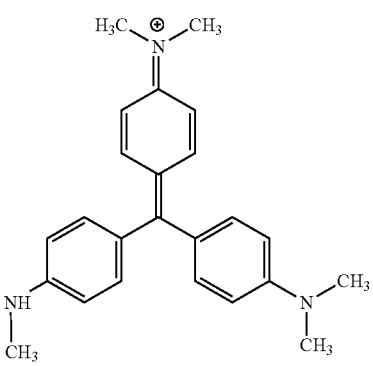

For certain disclosed embodiments, with reference to Formulas 3 and/or 4, $R^2$-$R^4$ can be substituents, typically comprising carbon atoms, but potentially heteroatoms too, such as nitrogen and/or oxygen, in a ring system. Particular disclosed embodiments may also have the following structures.

Victoria Blue 4R

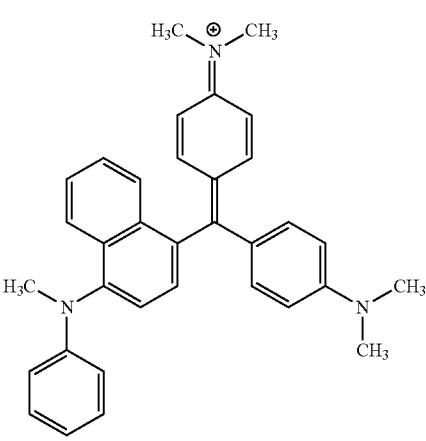

Victoria Blue B

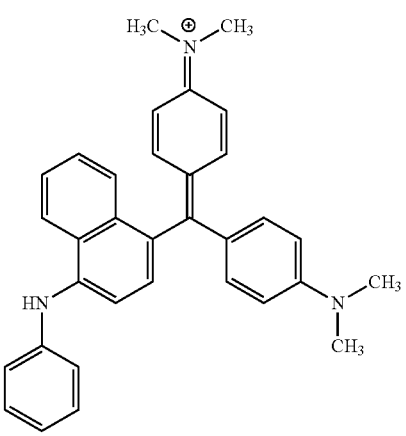

Another triarylmethane derivative useful within the present disclosure includes mass tag precursor conjugates including a naphthol moiety and a triarylmethane-diazo derivatives. Such compounds typically have the following general Formulas 5 and 6.

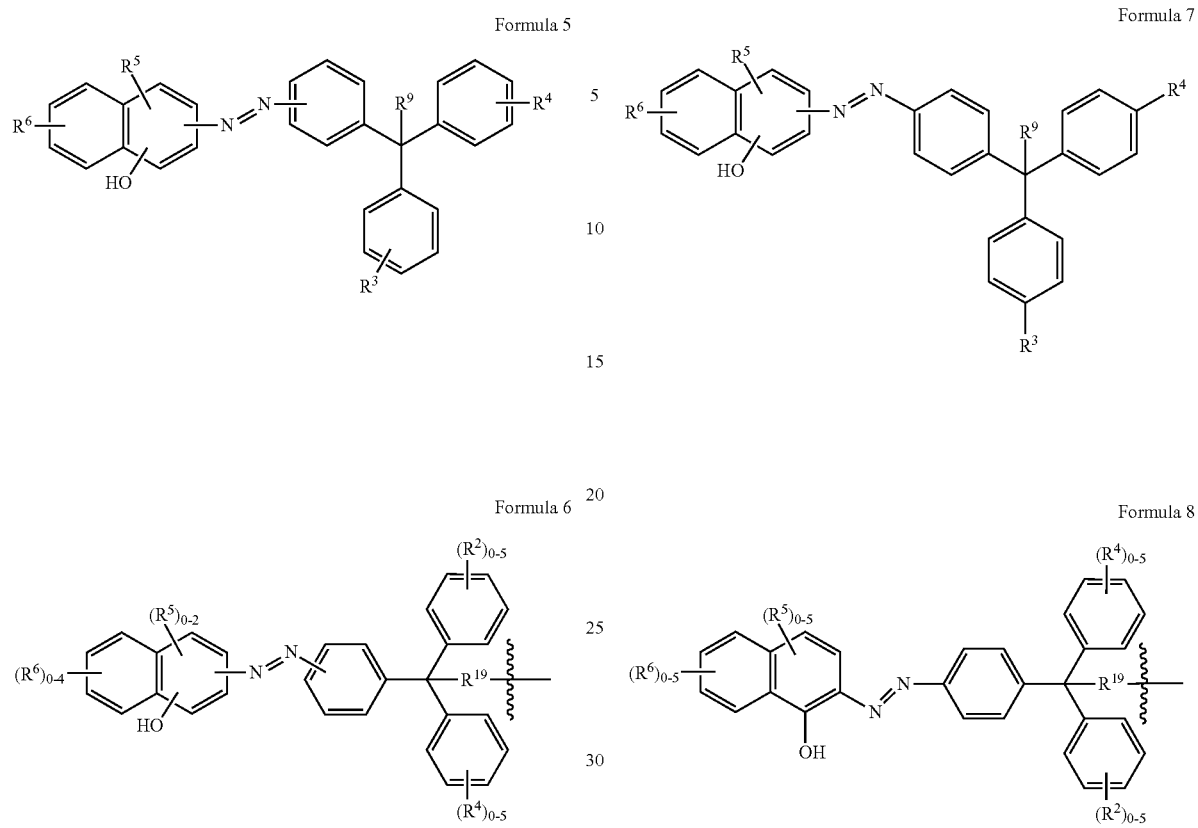

The hydroxyl and diazo moieties can be attached to the naphthalene ring at any position. The diazo moiety can be located at any position of the triarylmethane.

For certain disclosed embodiments, substituents on the triarylmethane rings are located at the para position relative to the tertiary carbon atom. Without being limited to a particular theory of operation, it is currently believed that having the substituents in this position may facilitate stabilizing the carbocation formed during analysis with mass spectrometry, such as by resonance or inductive effects. The hydroxyl group and diazo moieties can be attached to the naphthalene ring at any reasonable position, and any combination thereof. Particular embodiments have the general Formulas 7 or 8.

Naphthol-triarylmethane diazo compounds can be used to image a target in a sample. One disclosed embodiment of a method for using naphthol-triarylmethane diazo compounds is shown below in Scheme 3. According to this disclosed embodiment, a naphthol derivative 24 having a substrate moiety, such as a phosphate group, a galactoside, a lactam, etc., is reacted with an enzyme localized at a desired epitope using a specific binding moiety, such as an antibody. This produces a free naphthol 26, which can react with a water-soluble diazonium salt 34 that is produced by, for example, reacting an amine-triarylmethane compound 32 with an oxidizing agent, such as $NaNO_2$. The triarylmethane-naphthol conjugate 28 is not water soluble, and precipitates at the target site. Specific embodiments of this type of conjugate include conjugates 36 and 38. Laser-initiated ionization produces detectable mass codes 30.

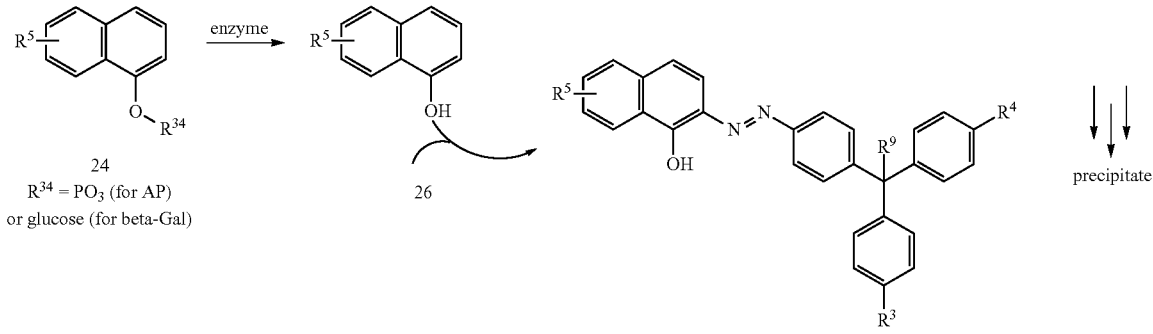

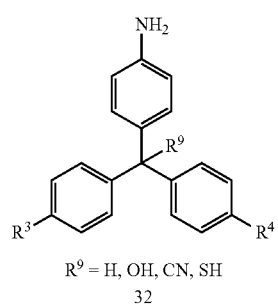
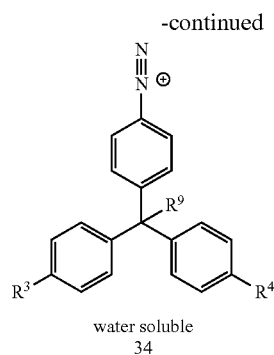
-continued
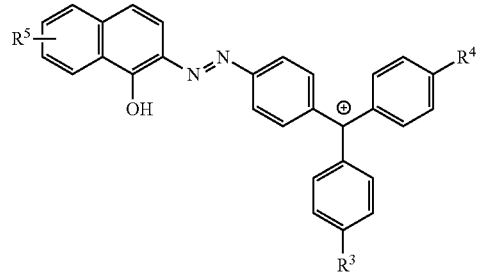
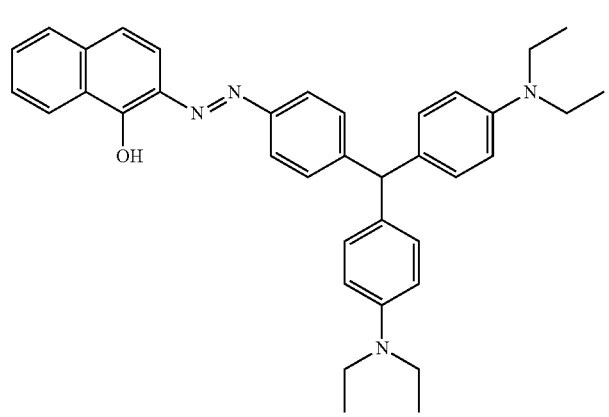
Exact Mass: 556.320
36
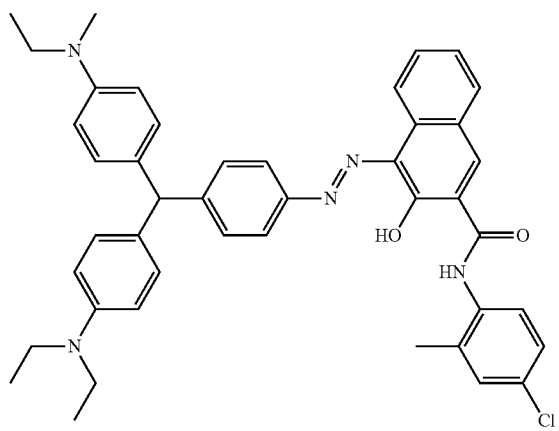
Exact Mass: 723.334
38
Specific Examples of Naphthol-Trityl Diazo Mass Tags Naphthol-azo mass tag moieties can also be used in conjunction with a triaryl methane derivative to produce another class of photolabile mass tags. These mass tags can produce a mass code upon ionization of the mass tag precursor conjugate. The mass code produced from these mass tags is a naphthol-azo triaryl methane species having a tertiary carbocation. This mass code can be detected, such as by using mass spectrometry. In some embodiments, a naphthol azo moiety is bonded to an aryl ring of a triaryl methane derivative, as illustrated below.

A particular embodiment of this class of mass tags has the following structure.

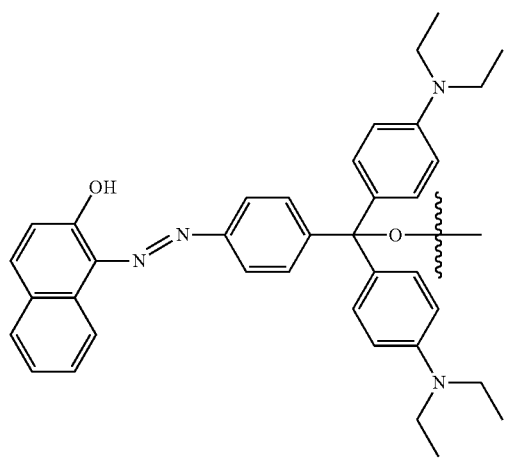 [SMILES: *OC(c1ccc(/N=N/c2c(O)ccc3ccccc23)cc1)(c1ccc(N(CC)CC)cc1)c1ccc(N(CC)CC)cc1]

Triarylmethane groups also can be used to form thio-based mass tag precursors. Particular disclosed embodiments have the following general Formula 9.

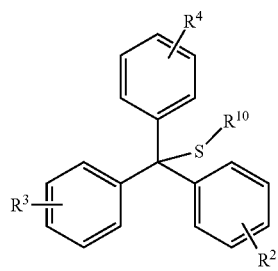

Formula 9

With reference to Formula 9, $R^{10}$ can be aliphatic, such as alkyl, alkenyl, alkynyl, aryl, aryl aliphatic, more typically aryl alkyl, or any peptide containing a cysteine, such as glutathione.

In one embodiment, the mass tag precursor has the following structure:

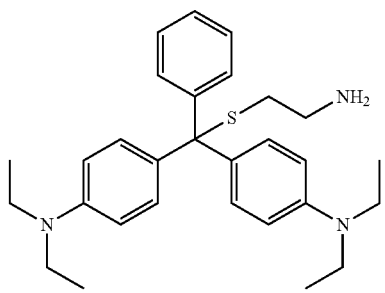 [SMILES: CCN(CC)c1ccc(C(SCCN)(c2ccccc2)c2ccc(N(CC)CC)cc2)cc1]

Particular disclosed embodiments of the disclosed conjugate comprising thiophosphate-derived triarylmethane mass tag precursors can be made in any way known to a person of ordinary skill in the art, for example, the synthetic methods illustrated in Scheme 2.

Scheme 4

AP-thiophosphate/trityl dyes based MT

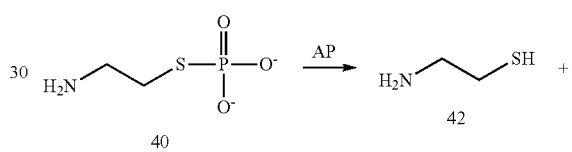

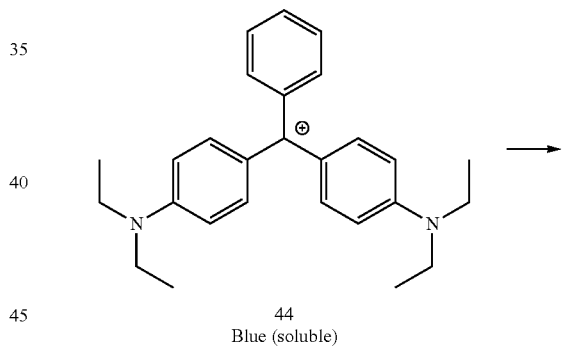

44
Blue (soluble)

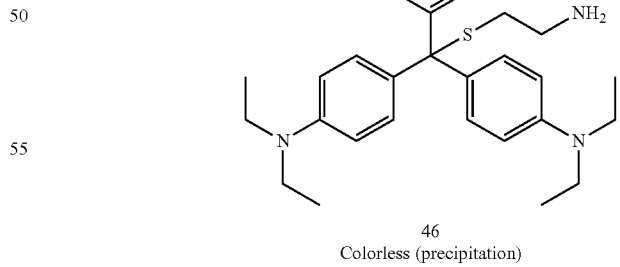

46
Colorless (precipitation)

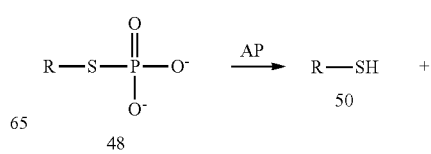

48

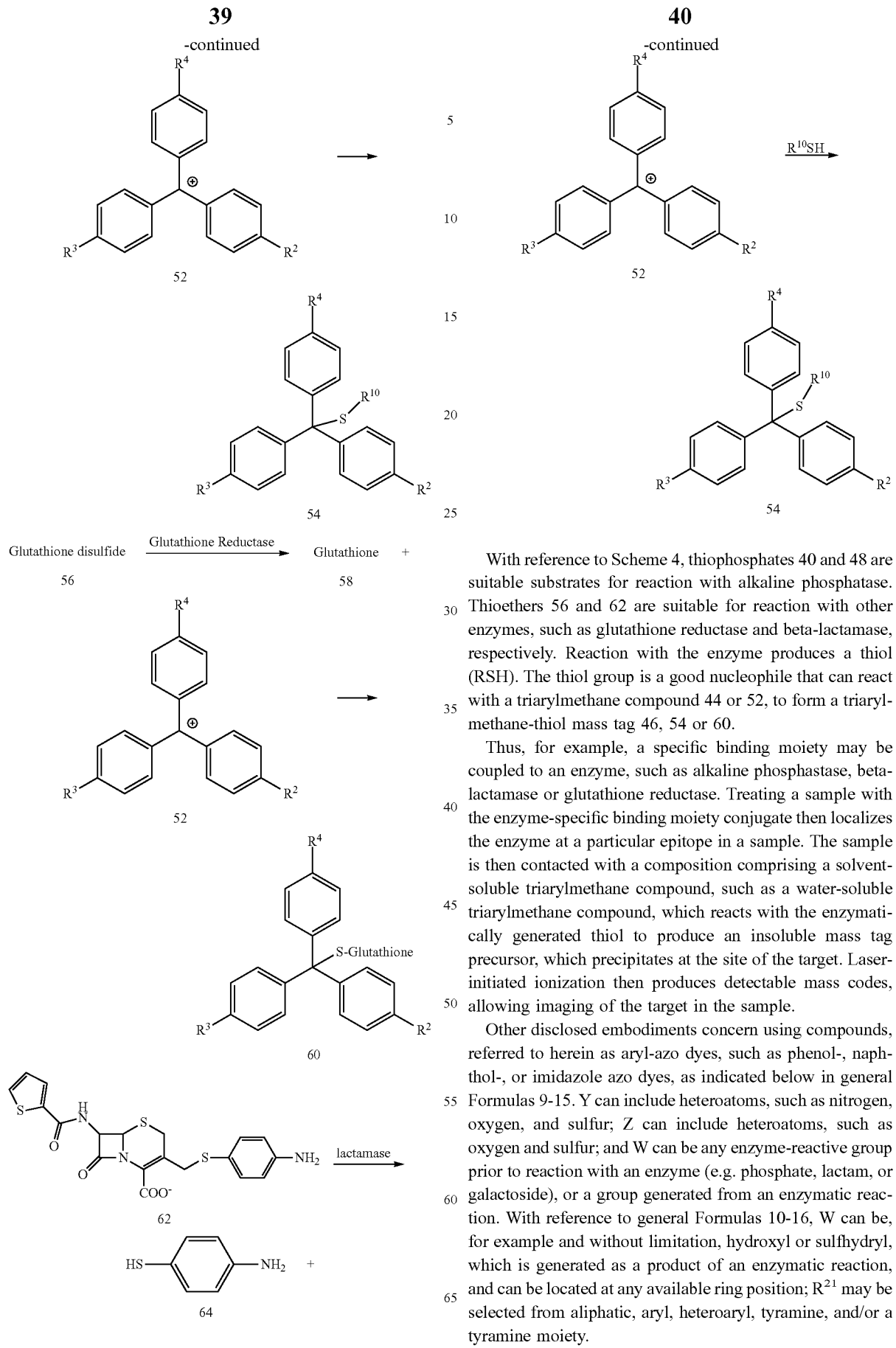

With reference to Scheme 4, thiophosphates 40 and 48 are suitable substrates for reaction with alkaline phosphatase. Thioethers 56 and 62 are suitable for reaction with other enzymes, such as glutathione reductase and beta-lactamase, respectively. Reaction with the enzyme produces a thiol (RSH). The thiol group is a good nucleophile that can react with a triarylmethane compound 44 or 52, to form a triarylmethane-thiol mass tag 46, 54 or 60.

Thus, for example, a specific binding moiety may be coupled to an enzyme, such as alkaline phosphastase, beta-lactamase or glutathione reductase. Treating a sample with the enzyme-specific binding moiety conjugate then localizes the enzyme at a particular epitope in a sample. The sample is then contacted with a composition comprising a solvent-soluble triarylmethane compound, such as a water-soluble triarylmethane compound, which reacts with the enzymatically generated thiol to produce an insoluble mass tag precursor, which precipitates at the site of the target. Laser-initiated ionization then produces detectable mass codes, allowing imaging of the target in the sample.

Other disclosed embodiments concern using compounds, referred to herein as aryl-azo dyes, such as phenol-, naphthol-, or imidazole azo dyes, as indicated below in general Formulas 9-15. Y can include heteroatoms, such as nitrogen, oxygen, and sulfur; Z can include heteroatoms, such as oxygen and sulfur; and W can be any enzyme-reactive group prior to reaction with an enzyme (e.g. phosphate, lactam, or galactoside), or a group generated from an enzymatic reaction. With reference to general Formulas 10-16, W can be, for example and without limitation, hydroxyl or sulfhydryl, which is generated as a product of an enzymatic reaction, and can be located at any available ring position; $R^{21}$ may be selected from aliphatic, aryl, heteroaryl, tyramine, and/or a tyramine moiety.

Formula 10
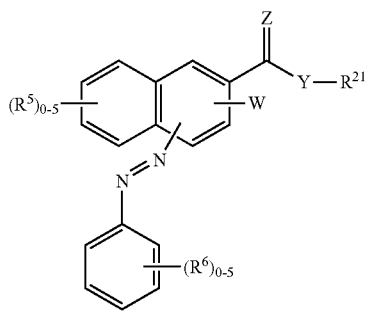
Formula 11
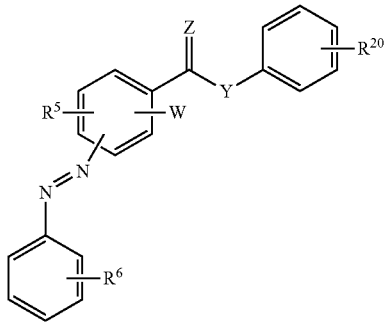
Formula 12
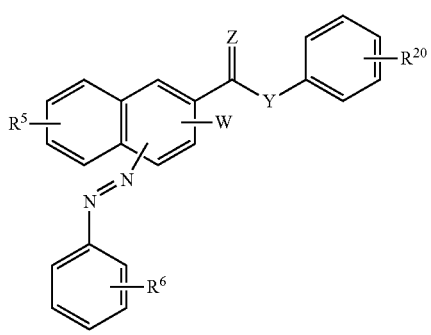
Formula 13
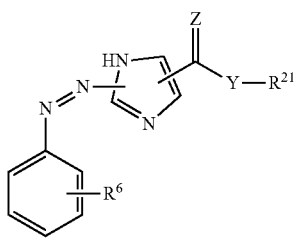
Formula 14
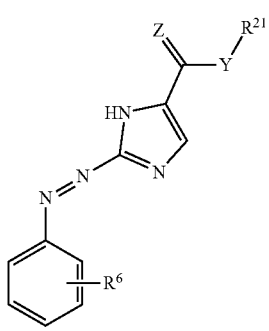
Formula 15
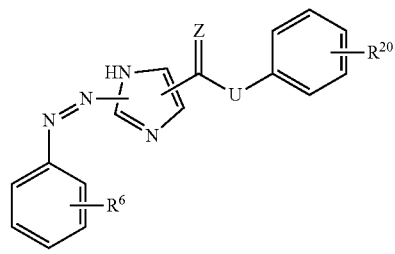
Formula 16
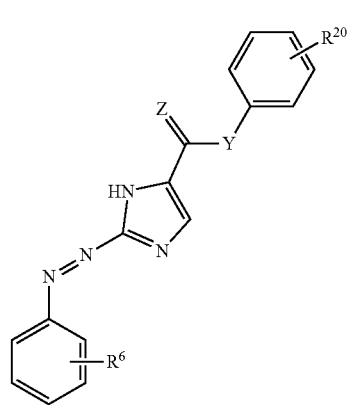
Certain disclosed embodiments also have the following general Formulas 17-19.
Formula 17
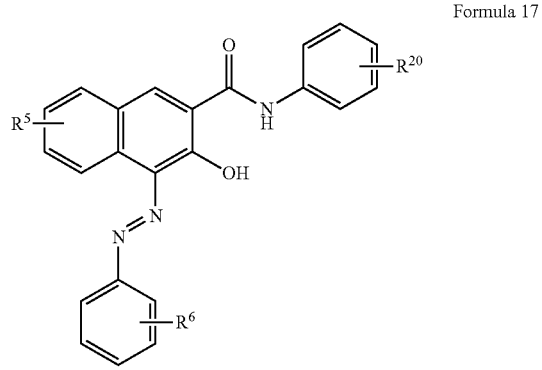
Formula 18
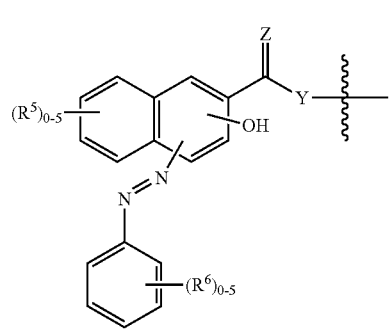

Formula 19

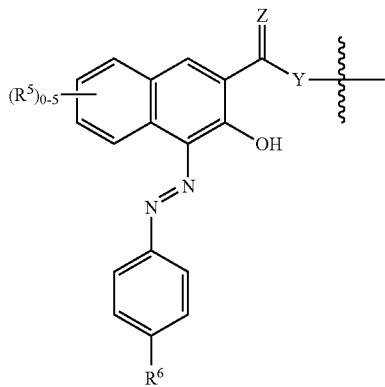

Certain disclosed embodiments use naphthol derivatives having the following general Formula 20 wherein the enzyme substrate moiety typically is at either $C_1$ or $C_2$.

Formula 20

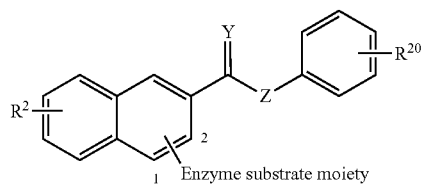

Particular disclosed embodiments concern naphthol-azo mass codes produced from naphthol mass tag precursors having the following structures.

Exemplary AP substrates

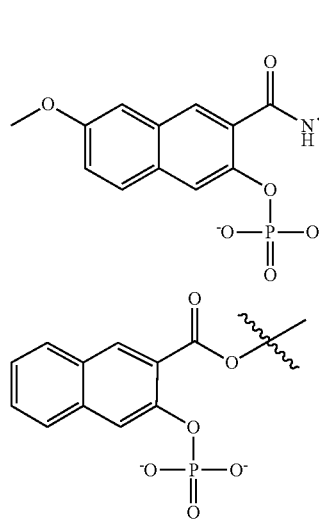

These particular disclosed embodiments of a mass tag precursosr are dephosphorylated with an enzyme, such as alkaline phosphatase, and then reacted with a diazo-containing compound (e.g. methoxy naphthol AS-TR) to produce the desired mass tag. The mass tag is ionized upon exposure to an energy source to produce the corresponding mass code.

Particular embodiments of naphthol-azo mass tags have the following structures.

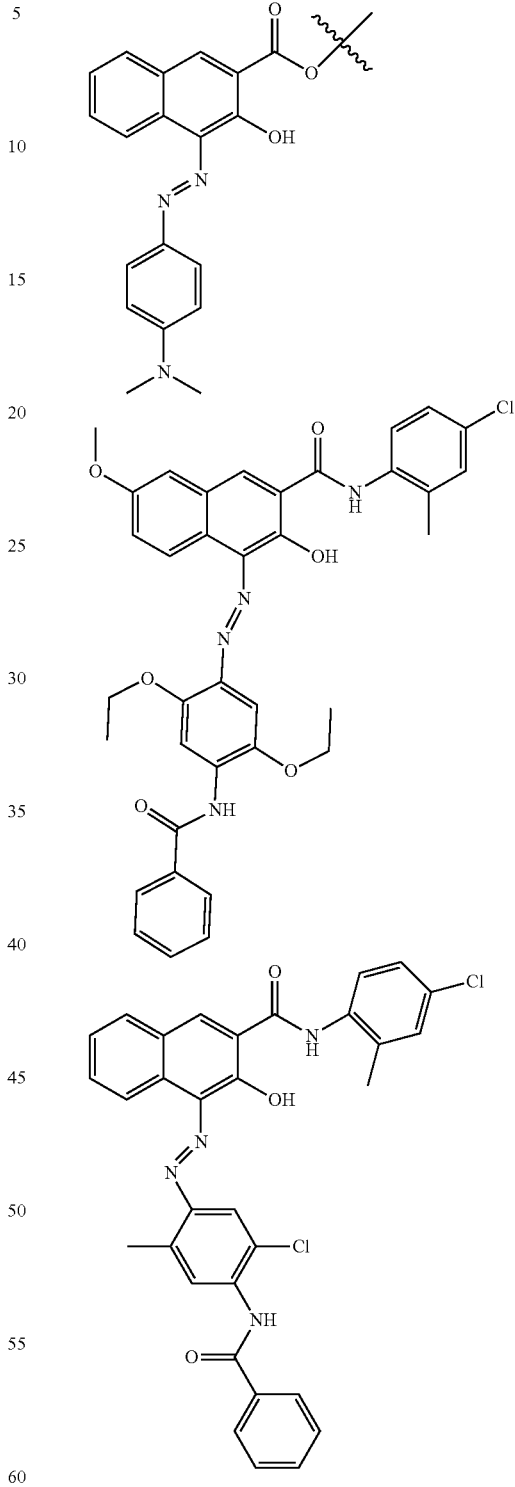

As further illustrated in Scheme 5, certain embodiments have $R^5$ being hydrogen, deuterium, or an electron donating group, $R^4$ being hydrogen, deuterium, or an electron-withdrawing group, and $R^6$ being hydrogen, deuterium, or an electron donating group. Scheme 5 illustrates using compound 66 comprising a naphthol portion and an azo portion derived from, for example, fast red. The naphthol-azo dye mass code 68 is produced via laser-initiated ionization.
Scheme 5
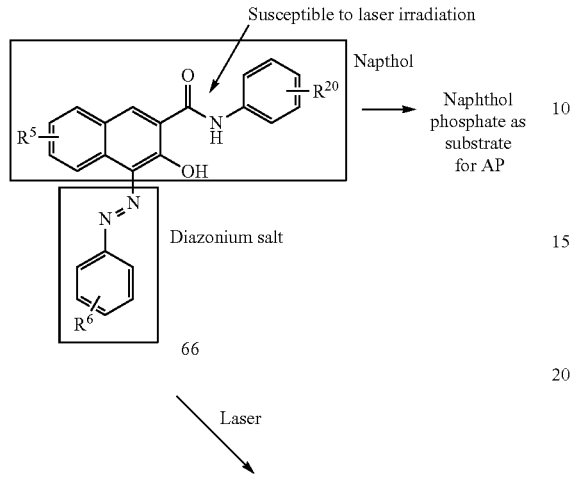
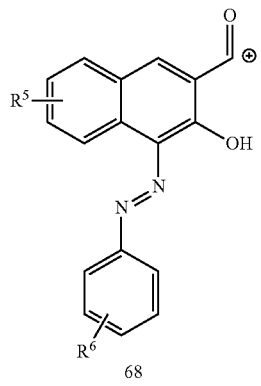
$R^4$: electron withdrawing group
$R^5$: electron donating group
$R^6$: electron donating group
Scheme 6 illustrates one embodiment of a naphthol-azo dye mass tag method.
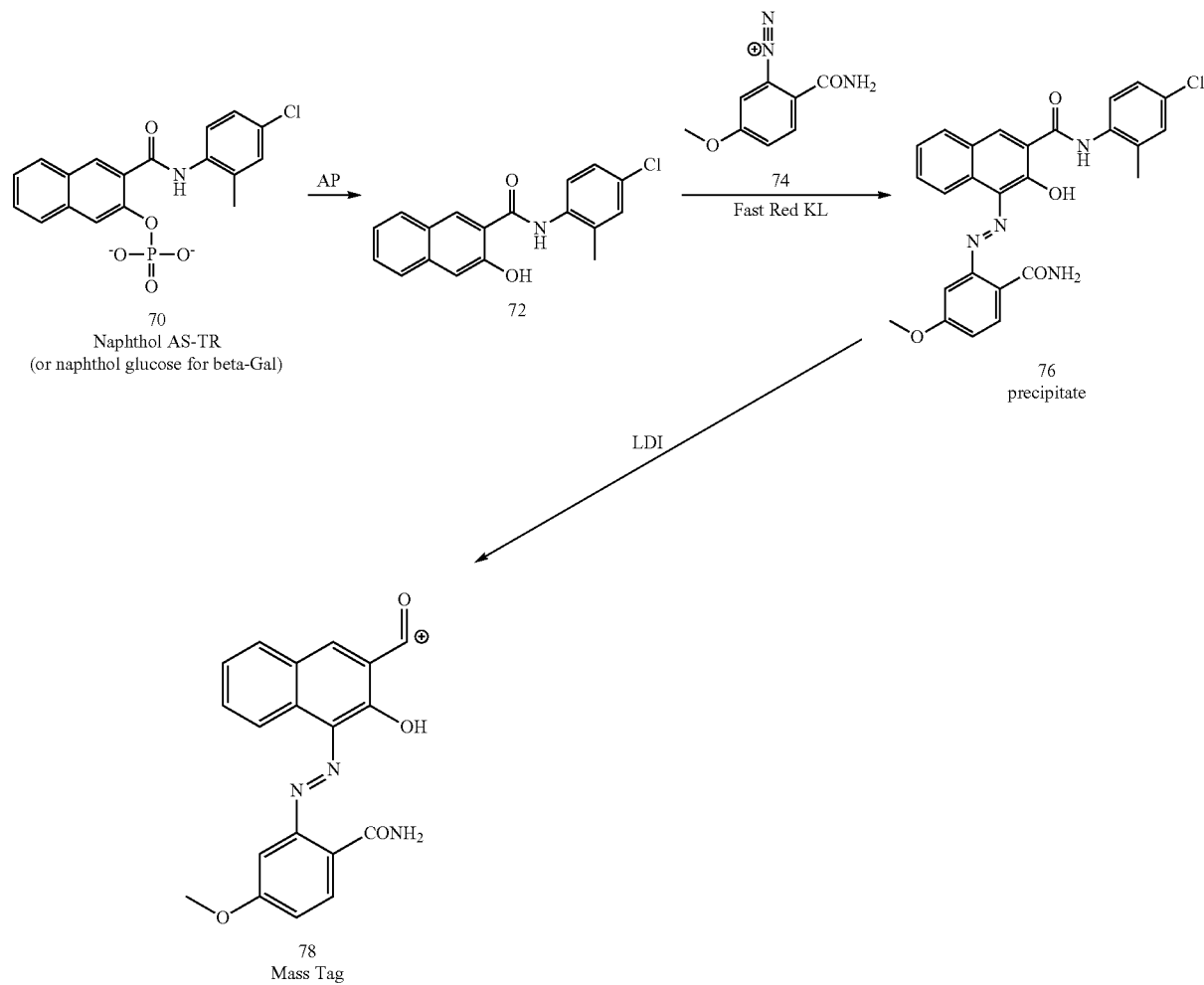

A naphthol derivative 70, such as naphthol AS-TR, for use with alkaline phosphatase or naphthol-glucose for use with Beta-galactosidase, is provided. These derivatives are used in combination with the appropriate enzyme to cleave the enzyme substrate moiety and provide a naphthol derivative for reaction with a diazonium salt species. Scheme 6 illustrates the process using Fast Red KL as the diazonium salt. Diazonium salt 74 reacts with naphthol 72 to produce azo compound 76 suitable for laser-initiated ionization to form the detectable tag, 78. A person of ordinary skill in the art will appreciate that the structure of the naphthol derivative can vary, as can the diazonium salt structure.

Yet other embodiments utilize a photolabile nitrophenyl moiety, comprising at least one photolabile bond, as a mass tag precursor. These embodiments utilize a nitrophenyl moiety in the disclosed conjugate, particularly in a conjugate comprising tyramine or a tyramine derivative, and an optional linker or carrier, comprising a nitrophenyl linker and a mass code. A general formula illustrating these types of mass tag precursors is shown below.

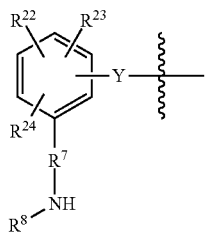

Formula 21

With reference to Formula 21, $R^{22}$-$R^{24}$ independently are selected from aliphatic, heteroaliphatic, aryl, heteroaryl, carbonyl, halogen, hydrogen, hydroxyl, isothiocyanate, isocyanate, nitrile, nitro, thiol, or any combination thereof, with at least one of $R^{22}$-$R^{24}$ being nitro. More typically, $R^{23}$ is nitro and is located at a carbon atom on the aromatic ring adjacent to the carbon atom bearing an $R^7$ substituent. $R^7$ is selected from aliphatic, or heteroaliphatic, more typically aliphatic, particularly —[CH(Me)]—. $R^8$ is a linker, a charged species, a chromophore, or any combination thereof. More typically, $R^8$ is a charged amino acid moiety, such as arginine, lysine, or histidine, or a tetra-alkyl ammonium species, such as tetramethyl ammonium, which is bound directly or via a linker to a chromophore, typically a dye or a hapten. In some embodiments, the $R^8$ substituent has a m/z value in a range from about 100 to about 5000, more typically from about 500 to about 2000.

The mass code produced by nitrophenyl mass tags after exposure to an energy source typically has a formula $[H_2NR^8]^+$. This mass code is produced either by photo-induced cleavage of a covalent bond between —[N(H)—$R^8$] and the $R^7$ substituent, or cleavage and subsequent ionization. The mass code is released from the mass tag and subsequently detected, such as by a mass spectrometer. Scheme 7 illustrates a particular disclosed embodiment wherein mas tag 80 is converted to mass code 82. Using a charged species as an $R^8$ moiety, such as arginine, provides a cationic molecule at neutral pH. The cationic molecule is an MS detectable ion even in the absence of any matrix, thus illustrating the capacity of this mass tag to be used in conjunction with LDI, not specifically MALDI. In other embodiments, where $R^8$ is not a charged moiety, the ionized mass code is produced by ionization, which takes place after bond cleavage.

Scheme 7

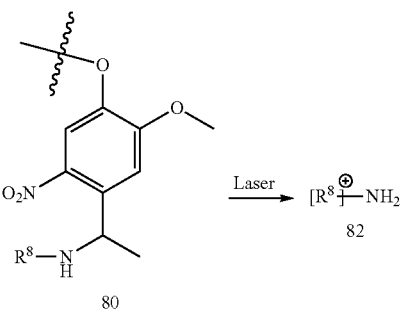

Certain embodiments have a Formula 22, illustrated below. With reference to Formula 22, $R^{22}$-$R^{24}$, and $R^7$ and $R^8$ are as recited above.

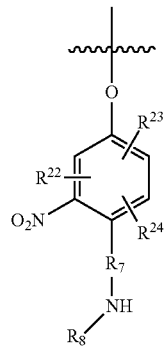

Formula 22

Particular embodiments utilize nitrophenyl mass tags having the following structures.

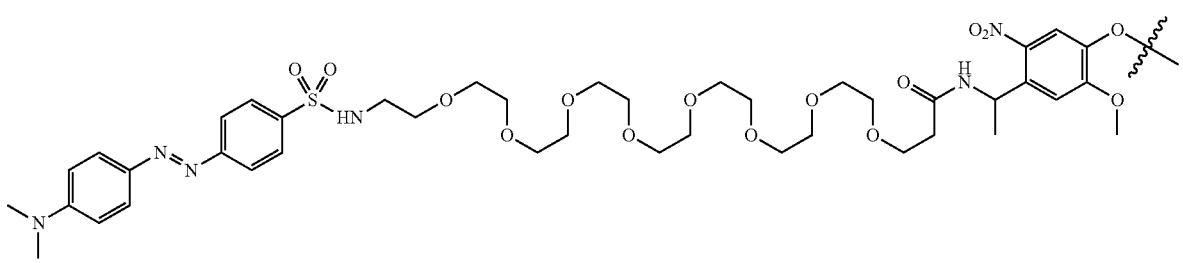

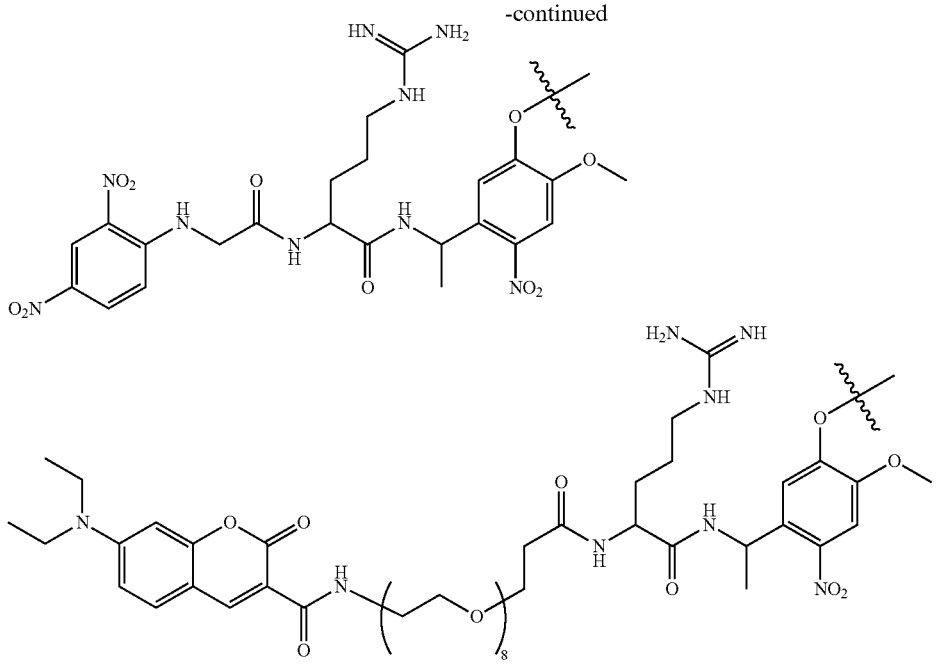

In further illustrative embodiments concern photolabile a mass tag precursor conjugate comprising a heteroaryl moiety as the mass tag precursor. The photolabile characteristics of these moieties is described by Smith (*Angew. Chem. Int. Ed.* (2010)49:3612). These mass tag precursors have a general Formula 23, illustrated below.

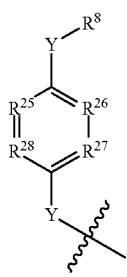

Formula 23

With reference to Formula 23, $R^{25}$-$R^{28}$ independently are carbon or nitrogen, with at least one of $R^{25}$-$R^{28}$ being nitrogen; more typically $R^{25}$-$R^{28}$ are all nitrogen, thus comprising a tetrazine. A person of ordinary skill in the art will recognize that it is also possible for the heteroaryl moiety to comprise an azine, a diazine, or a triazine. $R^8$ is a linker, a charged species, a chromophore, or any combination thereof. $R^8$ can be selected from any of the recitations for $R^8$ presented in reference to nitrophenyl mass tags. In particular embodiments, Y is sulfur. Scheme 8 illustrates a particular disclosed embodiment wherein mass tag 84 is exposed to a radiation source (e.g. a laser) and produces mass code 86.

Scheme 8

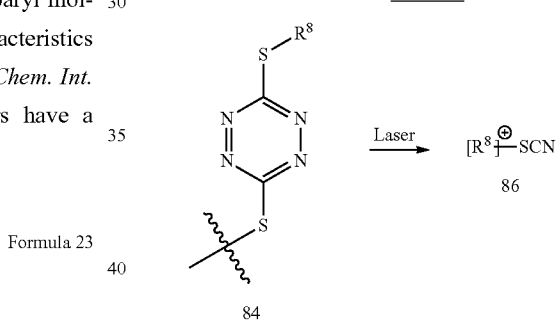

Certain embodiments have a Formula 24, illustrated below. With reference to Formula 24, $R^8$ can be selected from any of the recitations for $R^8$ presented in reference to nitrophenyl mass tag precursors.

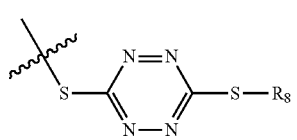

Formula 24

Particular embodiments have the following structure.

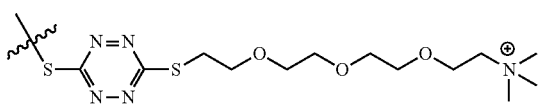 [SMILES: *Sc1nnc(SCCOCCOCCOCC[N+](C)(C)C)nn1]

Certain disclosed embodiments of the substituted aryl and heteroaryl compounds satisfy general Formulas 25 and 26 below.

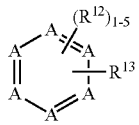

Formula 25

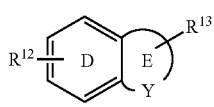

Formula 26

With reference to general Formulas 25 and 26, A in Formula 24 is selected from carbon and heteroatoms, such as oxygen and nitrogen. $R^{12}$ is an amine ($NH_2$, or $NR^1R^{1'}$), ether, thiol (SH), thioether, hydroxyl (OH), or combinations thereof. $R^{13}$ is independently selected from aliphatic, such as alkyl, alkenyl, and alkynyl, aryl, aryl aliphatic, more typically aryl alkyl, more typically alkyl, and even more typically lower alkyl, such as methyl and ethyl, aryl, hydrogen, and combinations thereof. $R^{13}$ also can be atoms in a ring connected with the first ring. With reference to Formula 26, the E ring is an aromatic or heteroaromatic ring having any suitable number of atoms in the ring, most typically 5, 6 or 7 atoms in the ring, and Y is a carbon or a heteroatom, such as nitrogen, oxygen or sulfur. For disclosed embodiments having a single ring, the amine substituents typically are either ortho or para to each other. Examples of dyes satisfying general Formula 25 for the heteroaryl compounds include, ortho and para phenylenediamine and diaminobenzidine (DAB).

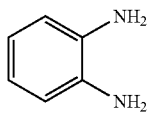 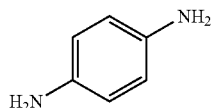

oPD         pPD

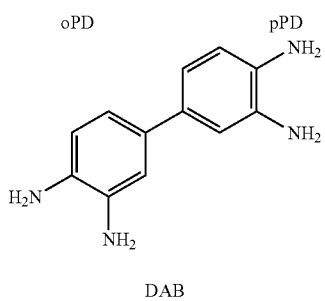

DAB

Examples of disclosed embodiments having a second aromatic ring attached to the first include, without limitation, diaminonaphthalenes (DAN), such as those shown below.

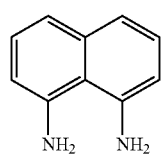 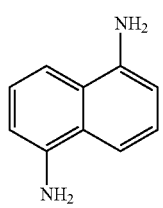

1,8-diaminonaphthalene     1,5-diaminonaphthalene

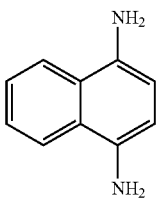

1,4-diaminonaphthalene

A person of ordinary skill in the art will appreciate that heteroatoms, such as nitrogen, oxygen and sulfur, can be substituted for one or more carbon atoms in the aryl rings. Examples of such compounds include the aminoquinolines, as shown below.

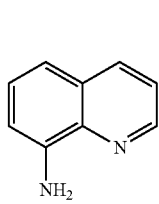 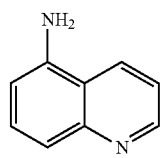

8-aminoquionoline     5-aminoquionoline

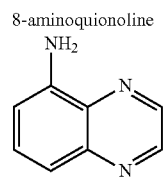

8-aminoquionoxaline

Moreover, the aryl rings and the nitrogen atoms can include substituents other than hydrogen, including aliphatic and aryl groups, with lower alkyl groups being examples of suitable substituents.

Certain disclosed embodiments concern using oligomers generated by a peroxidase-catalyzed oxidative reaction detectable by MS. For example, DAB-stained tissue showed detectable signal (DAB dimer) but the background was high in some cases. 1,8-DAN gave a peak at m/z=297 and 8-AQ gave peaks at m/z=426 and m/z=567.

Tissue has also been stained with 1,8-DAN and 8-AQ. 8-AQ gave similar staining as DAB (Ki-67 on tonsil). A tissue sample stained by 8-AQ demonstrated that the oligomers (mostly trimers and tetramers) of 8-AQ can be readily detected on tissue samples without the need for using a matrix. Therefore, certain disclosed embodiments concern using oligomers of quinoline derivatives formed in an HRP-catalyzed reaction. These oligomers are highly colored and therefore absorb laser energy efficiently. In this sense, they serve as an in-situ matrix for their own ionization and desorption. In addition, the presence of multiple amines and nitrogen-containing aromatics facilitates protonation or the formation of radical cations, and therefore these oligomers can be readily ionized for use in MS.

The above-mentioned peroxidase substrates can also be used in conjunction with a metal ion. Examples of ions include $Ni^{2+}$, $Pd^{2+}$, $Zn^{2+}$, $Cu^{2+}$, $Fe^{2+}$, $Mn^{2+}$, $Co^{2+}$, and others. A soluble metal salt solution, for example $NiCl_2$ was pre-mixed with a peroxidase substrate solution, such as DAB or 1,8 DAN, and was applied to a tissue sample labeled with peroxidase on the target. Enhanced ionization of the mass tags are usually observed.

One advantage HRP offers is the irreversible inhibition of the enzyme by high concentrations of $H_2O_2$. Irreversible inhibition provides multiplexing capability by sequential deposition and inhibition steps.

Figure 74:
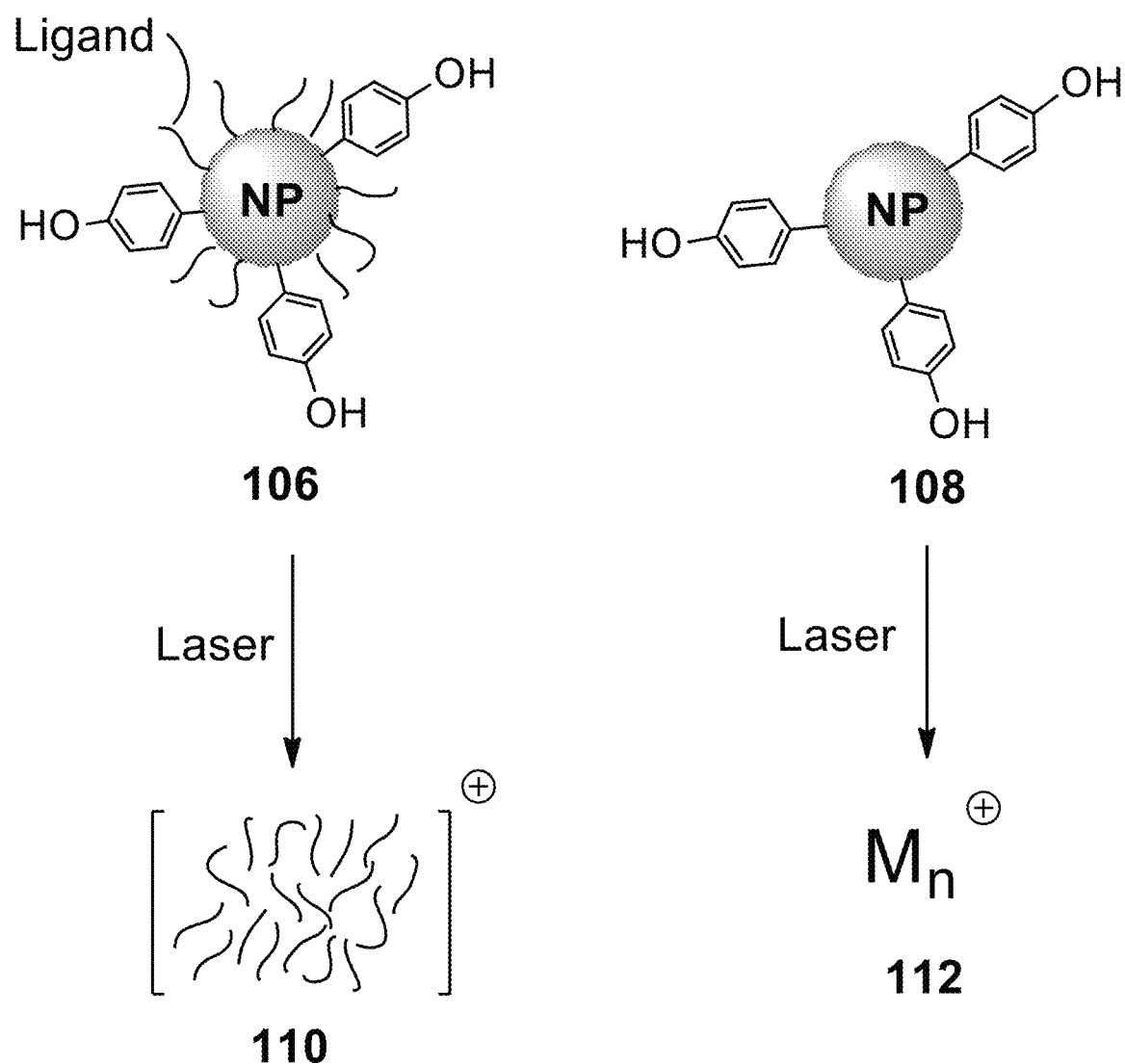
FIG. 74 illustrates an embodiment wherein mass tags 88 (bipyridyl) and 100 (terpyridyl) are ionized by a radiation source (e.g. a laser) to produce mass codes 102 and 104, respectively.

In illustrative embodiments, photolabile, metal-complexed mass tags are sources of detectable mass codes, which can be used to determine the location of a particular target in a sample. Upon ionization of the mass tag precursor conjugate, a detectable mass code is produced. A person of ordinary skill in the art will recognize that ionization can involve cleavage of a covalent bond to produce a charged moiety or the release of a metal from a coordination complex to produce a charged moiety. In certain disclosed embodiments, a mass tag produces a detectable mass code upon ionization of a metal-heteroaryl chelate. In particular disclosed embodiments, metal-heteroaryl chelate mass tags produce mass codes in which a metal-biheteroaryl chelate is released from a mass tag precursor conjugate. Exemplary embodiments include formation of mass codes in which a metal is chelated to a bipyridine. Other embodiments include metal-heteroaryl chelate mass tags, which can produce mass codes in which a metal-terheteroaryl chelate is released from the mass tag precursor conjugate. These metal complexes can also contain one or more non-aryl ligands, such as, but not limited to nitrile, thiocyanate, hydroxyl, thiol, amine, carbonyl, phosphonyl, halide, phosphine, or heteroaliphatic. In particular examples, these chelates include mass codes in which a metal is chelated to a terpyridine. Scheme 10 illustrates a disclosed embodiment wherein mass tags 88 (bipyridyl) and 100 (terpyridyl) are ionized by a radiation source (e.g. a laser) to produce mass codes 102 and 104, respectively (see FIG. 74).

Scheme 9

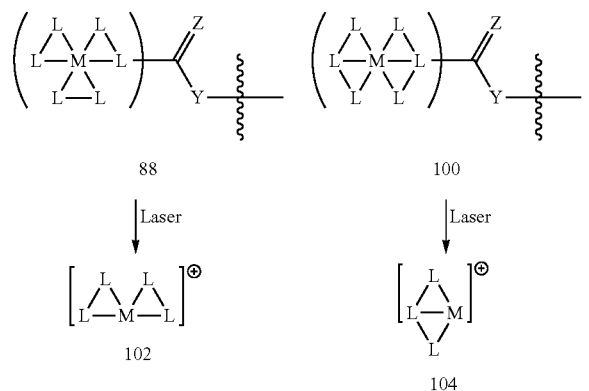

A person of ordinary skill in the art will recognize that mass codes also can comprise metal-monopyridine chelates. Certain embodiments have mass tags with general Formulas 27-31, illustrated below.

Formula 27

-continued

Formula 28

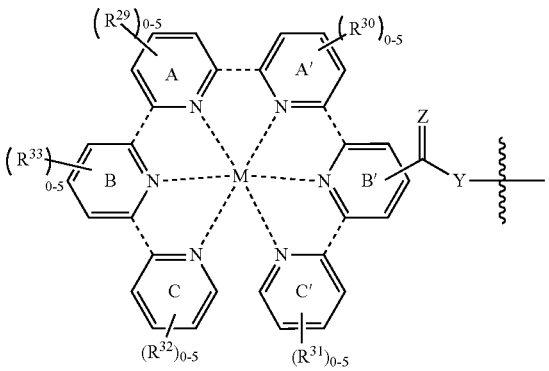

Formula 29

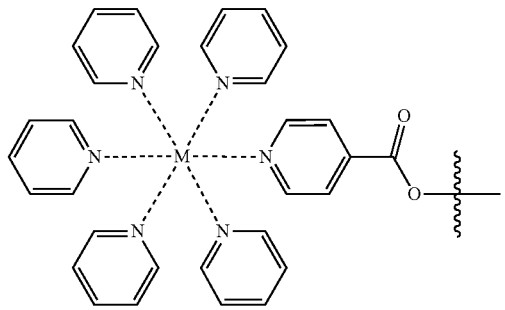

Formula 30

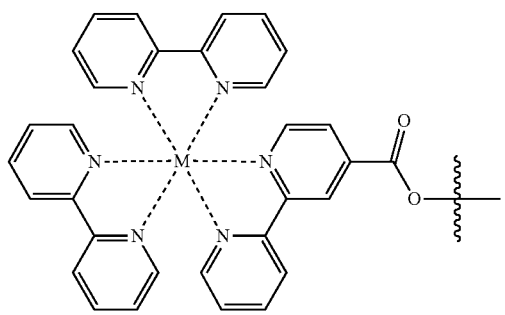

Formula 31

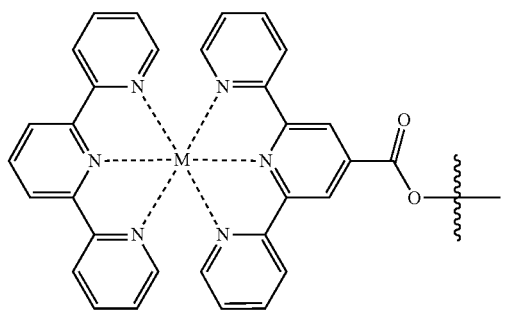

With reference to Formula 27, L is selected from nitrile, thiocyanate, hydroxyl, thiol, amine, carbonyl, phosphonyl, halide, phosphine, or heteroaliphatic. Y and Z independently are selected from oxygen, sulfur, and -(nitrogen-$R^{11}$)—. With reference to Formula 28, $R^{29}$-$R^{33}$ independently are selected from aliphatic, heteroaliphatic, aryl, heteroaryl, carbonyl, halogen, hydrogen, hydroxyl, isothiocyanate, isocyanate, nitrile, nitro, thiol, and any combination thereof. With reference to Formulas 27-31, M is a metal selected from Groups 3-12 of the periodic table, which is capable of forming a chelate structure; in some embodiments, M is Zn, Ni, Co, Ru, Cd, Pt, and Fe. M is selected to coordinate to rings A, A', B, B', C, C'. These rings can form a monoheteroaryl chelate, in which rings A, A', B, B', C, C' are only chelated to M and not bonded to each other, a biheteroaryl chelate, in which rings A and A' are bonded together, B and C are bonded together, and B' and C' are bonded together, or a terheteroaryl chelate, in which rings A, B, and C are bonded together and rings A', B', and C' are bonded together. Y and Z independently are selected from oxygen, sulfur, and -(nitrogen-$R^{11}$)—.

Other embodiments utilize peptide dimers as mass tags. These mass tags are produced from ionization of mass tag precursor conjugate comprising peptide dimers chelated to metal complexes. In certain embodiments, a tyramine or tyramine derivative is bound to a chelating reagent, such as nitrilotriacetic acid (NTA), which coordinates to a metal. The metal also coordinates to a peptide dimer mass tag comprising an amino acid capable of coordinating to a metal, such as histidine. Upon ionization, the peptide dimer is released and detected, such as by using mass spectrometry. Peptide dimer mass tags have a general formula (Formula 32) wherein $R^{14}$ is selected from ether, hydroxyl, and -(nitrogen-$R^{11}$)—, Y is selected from oxygen, sulfur, and -(nitrogen-$R^{11}$)—, and $R^8$ is as recited for nitrophenyl mass tag precursors and heteroaryl mass tag precursors.

forming a conjugate with an enzyme substrate, such as tyramine or tyramine derivatives. The nanoparticle typically comprises a semiconductor, a metal, or multiple metals selected from Groups 3-15, such as, but not limited to, Y, La, Ag, Au, Pt, Ni, Pd, Rh, Jr, Co, Cu, and Bi, or a combination thereof. Tyramine or tyramine derivatives can effectively couple to the metal of the nanoparticle. Upon ionization of the mass tag precursor conjugate, the metal cluster ions serve as the mass code, which can be detected using mass spectrometry.

In other embodiments, a nanoparticle is used in conjunction with a mass tag moiety and a tyramine or tyramine derivative moiety. In these particular embodiments, the nanoparticle serves as a carrier, which carries a mass tag and tyramine or tyramine derivative, or multiple such moieties, to the target. Certain embodiments utilize from 1 to about a few thousand ligands, more typically from 1 to about 1000 ligands, even more typically greater than 1 to several hundred, such as greater than 1 to about 500, greater than 1 to about 250, greater than 1 to about 200, greater than 1 to about 150, greater than 1 to about 100, and greater than 1 to about 50. In some embodiments, 1 to about 20 tyramine or tyramine derivatives are bound to the nanoparticle. Particular embodiments utilize ligands comprising an $R^{15}$ moiety, a linker, a binding moiety, and any combination thereof. In certain embodiments, these ligands have a general Formula 33.

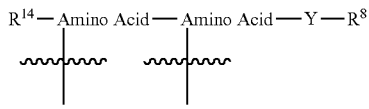

Formula 32

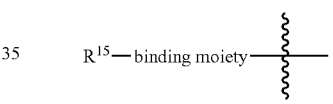

Formula 33

Particular embodiments have the following structure.

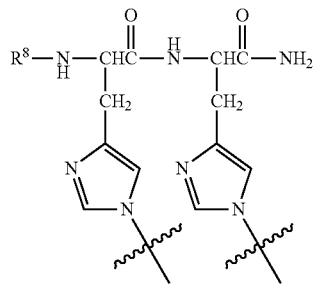

Another class of mass tags that can be employed in the current method includes nanoparticles that are capable of With reference to Formula 33, the $R^{15}$ moiety is effectively coupled to a binding moiety. $R^{15}$ is selected from any previously described mass tag moiety, a hapten, or a peptide, such as an oligo-peptide. $R^{15}$ can be directly bonded to the binding moiety, or can be bound to the binding moiety with a linker. The linker can be aliphatic, heteroaliphatic, or heterobifunctional. The binding moiety is selected to effectively couple to the nanoparticle, and typically comprises a hydroxyl group, an amine group, a thiol group, or a phosphine group. Scheme 10 (FIG. 74) illustrates a particular disclosed embodiment wherein a nanoparticle comprising mass tag ligands (106) and a nanoparticle mass tag 108 are exposed to a radiation source (e.g. a laser) to produce ligand mass codes 110 and a nanoparticle mass code 112, respectively. Particular embodiments use the following mass tag ligands.

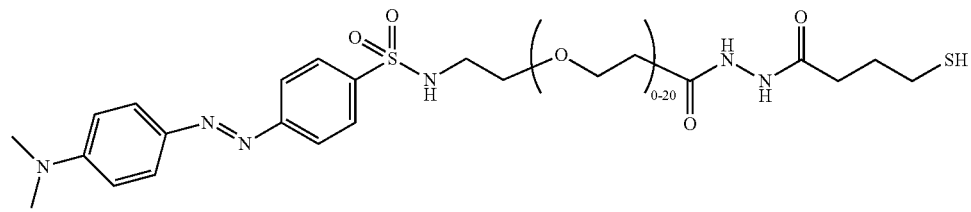

-continued

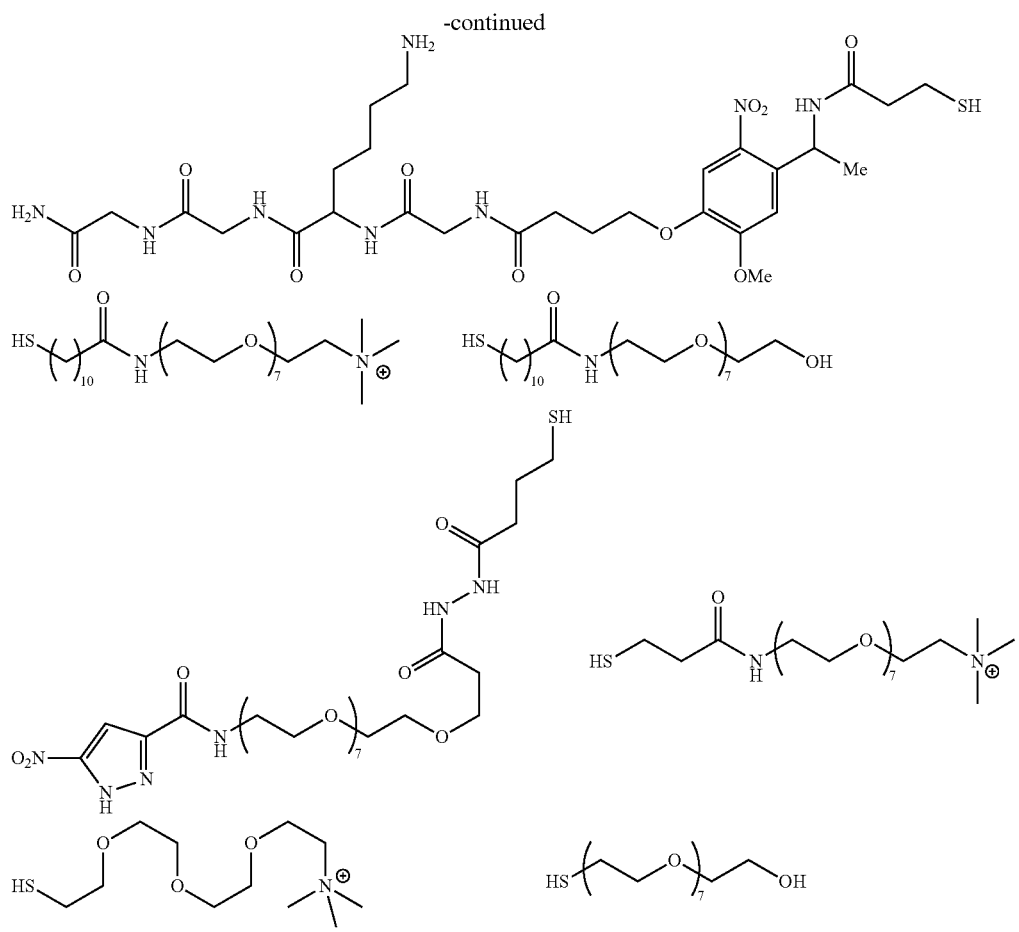

Another class of mass tags useful for certain disclosed embodiments is metal ions that can be reduced to form metals, that precipitate at a particular target site. Typically, such metals are used in combination with a reducing agent to reduce a metal ion from a non-ground oxidation state (e.g. 1+, 2+, 3+, etc. oxidation state) to a ground state (oxidation state) for precipitation at a specified target. The metal can be irradiated with a laser to form ultra-small cluster ions (where ultra-small refers to the number of atoms in the cluster, which typically is from about 2 to about 10) and subsequently be detected by a suitable mass spectrometric technique. Solely by way of example, and without limiting the application to a particular theory of operation, the metals considered useful for this technique include bismuth, cobalt, copper, gold, indium, mercury, nickel, platinum, ruthenium, silver and tin. Further information regarding this subject matter can be found in U.S. Pat. No. 7,691,598, which is incorporated herein by reference. In addition, the description of enzymatic metal deposition disclosed in U.S. Pat. No. 6,670,113 and U.S. Patent Publication No. US-2008-0213783-A1 are incorporated herein by reference.

This embodiment can be illustrated with reference to using a horseradish peroxidase-silver ion reduction protocol in which silver nitrate is reduced to $Ag^0$, which precipitates at the site of formation. In a particular embodiment, silver nitrate is reduced to $Ag^0$ in the presence of hydroquinone (HQ), hydrogen peroxide ($H_2O_2$) and horseradish peroxidase (HRP). Other reducing agents include n-propyl gallate, 4-methylaminophenol sulfate, 1,4 phenylenediamine, o-phenylenediamine, chloroquinone, bromoquinone, 2-methoxyhydroquinone, hydrazine, and 1-phenyl-3-pyrazolidinone (phenidone aminophenol). Further information concerning this subject matter can be found in U.S. Pat. No. 7,183,072, which is incorporated herein by reference. Additional enzymes that can be used include catalase and/or lactoperoxidase. Further information concerning enzyme species can be found in U.S. Pat. No. 7,592,153, which is incorporated herein by reference. The reduction of $Ag^0$ by HQ is detailed in U.S. Pat. No. 7,632,652 (Column 9, line 20-50), which is incorporated herein by reference.

Figure 6A:
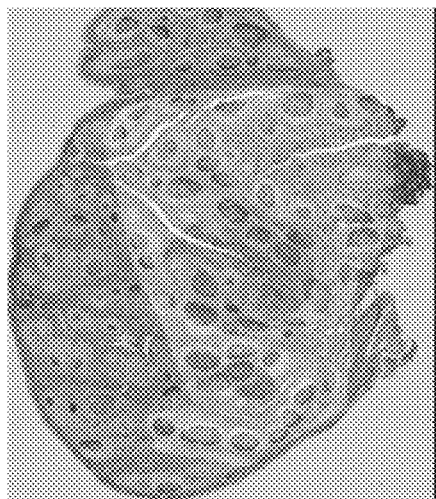
FIGS. 6A-6D are images illustrating HRP-Ag-based detection where Ag was deposited on tissue using HRP, HQ and $H_2O_2$. An image of the control sample.
Figure 6B:
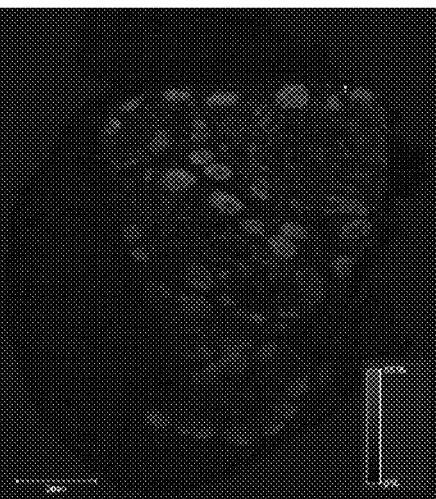
Figure 6D:
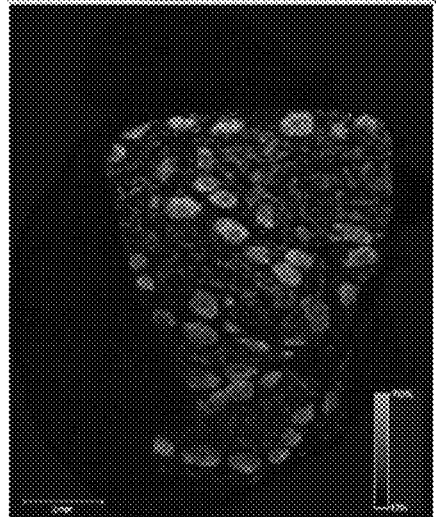
Figure 6C:
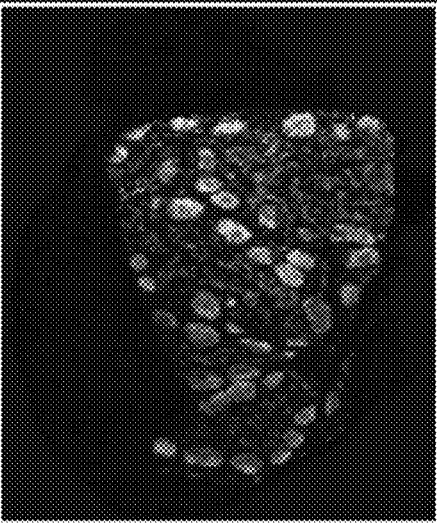

$Ag_2^+$ and $Ag_3^+$ ions are predominately detected from the deposited silver under LDI conditions. Silver deposited on a tissue sample can be imaged using MS. FIGS. 6A-6C illustrate successful detection of Ki-67 on tonsil tissue based on HRP-silver IHC staining and subsequent mass imaging. Thus, HRP may be used with a new type of mass tag, namely, ultra-small metal cluster ions ($M_n^+$, n equal 2 to 10, more typically 2 to 5). In the case of silver, $Ag_2^+$ and $Ag_3^+$ were the predominant ions detected. A person of ordinary skill in the art will appreciate that other metals and alloys can be employed, such as Au. Metal-cluster-ion-based mass tags are very easily ionized and thus reduce the number of laser shots required per spot. For example, typical imaging efforts without using metal-cluster-ion-based mass tags have used 100 laser shots per spot. However, with the silver-based system, the number of shots can be greatly reduced, which speeds up the scanning rate.

Another example of a metal-based approach comprises using an alkaline phosphatase/5-bromo-4-chloro-3-indolylphosphate (AP-BCIP) reduction protocol. This method is illustrated below in Scheme 11. Similar imaging results can be achieved using this method. U.S. Pat. No. 7,087,379 teaches the use of a nitro blue tetrazolium (NBT)/BCIP method, which has been shown to result in an "increase in sensitivity for detection of nucleic acid sequences using alkaline phosphatase catalyzed detection techniques." Page 5, lines 4-5 of U.S. Pat. No. 7,087,379.

Scheme 11

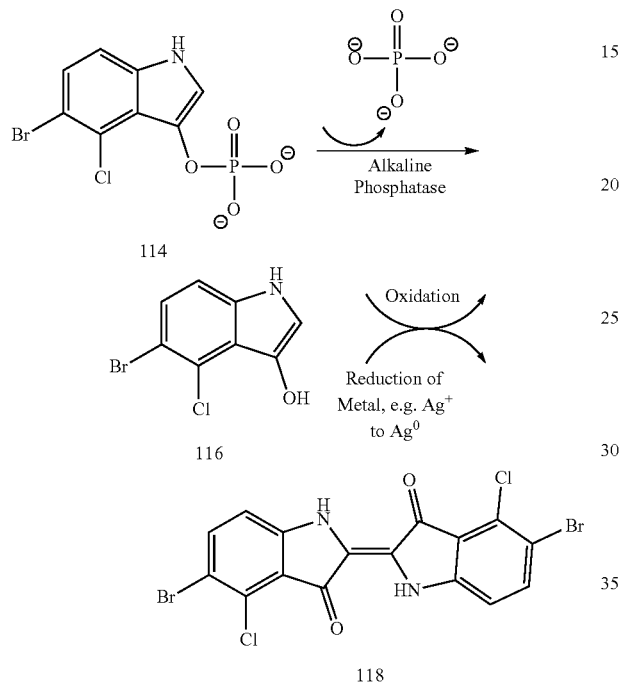

Naphthols, 4-chloro-1-naphthol (4-CN) as an example, are known but not widely used substrates for HRP-based detection. For example, 1-naphthol has been used as the substrate for HRP, but without using MS techniques. See, for example, *Histochemistry* (1985) 83:97-102. The naphthol precipitate is further stained with various basic dyes (cationic), such as azure A, methylene blue, cresyl violet, crystal violet, methyl green, acridine orange, and basic fuchsin. Certain embodiments concern using the dyes absorbed to naphthol precipitates in mass tag applications.

Basic Dyes Adsorbing to 1-Naphthol Precipitate
(Histochemistry, 1985, 83:97-102)

Azure A

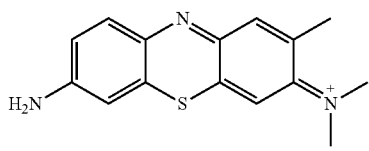

Chemical Formula: $C_{15}H_{16}N_3S^+$
Exact Mass: 270.11

-continued

Cresyl Violet

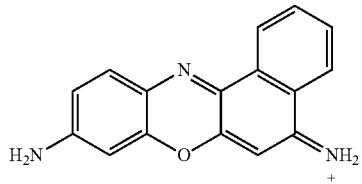

Chemical Formula: $C_{16}H_{12}N_3O^+$
Exact Mass: 262.097

Methylene Blue

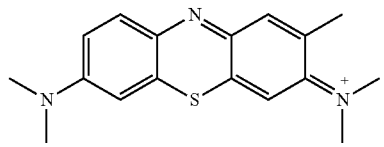

Chemical Formula: $C_{17}H_{20}N_3S^+$
Exact Mass: 298.137

Acridine Orange

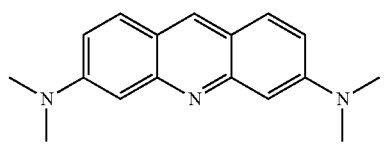

Chemical Formula: $C_{17}H_{19}N_3$
Exact Mass: 265.158

Thionin

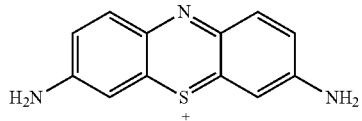

Chemical Formula: $C_{12}H_{10}N_3S^+$
Exact Mass: 228.059

Basic fuchsin

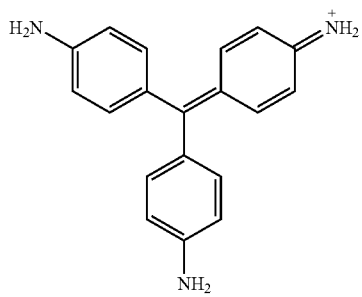

Chemical Formula: $C_{19}H_{18}N_3^+$
Exact Mass: 288.150

Safranin

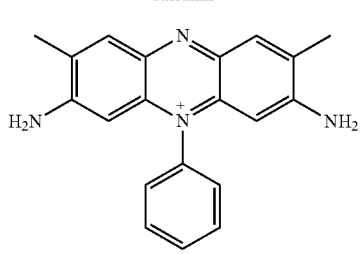

Chemical Formula: $C_{20}H_{19}N_4^+$
Exact Mass: 315.160

Thioflavin T

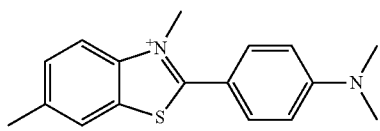

Chemical Formula:
$C_{17}H_{19}N_2S^+$
Exact Mass: 283.126

These dyes are mostly positively charged and have high absorbance at the wavelength of the laser. Therefore they are useful candidates for use as mass tags. Crystal violet has been used in AP-BCIP based systems. These dyes presumably physically adsorb to the naphthol precipitate instead of becoming chemically conjugated to the naphthol precipitate. However, they have been shown to be stable and specific. A tissue sample stained by such a method may be imaged using mass spectrometry.

Figure 75:
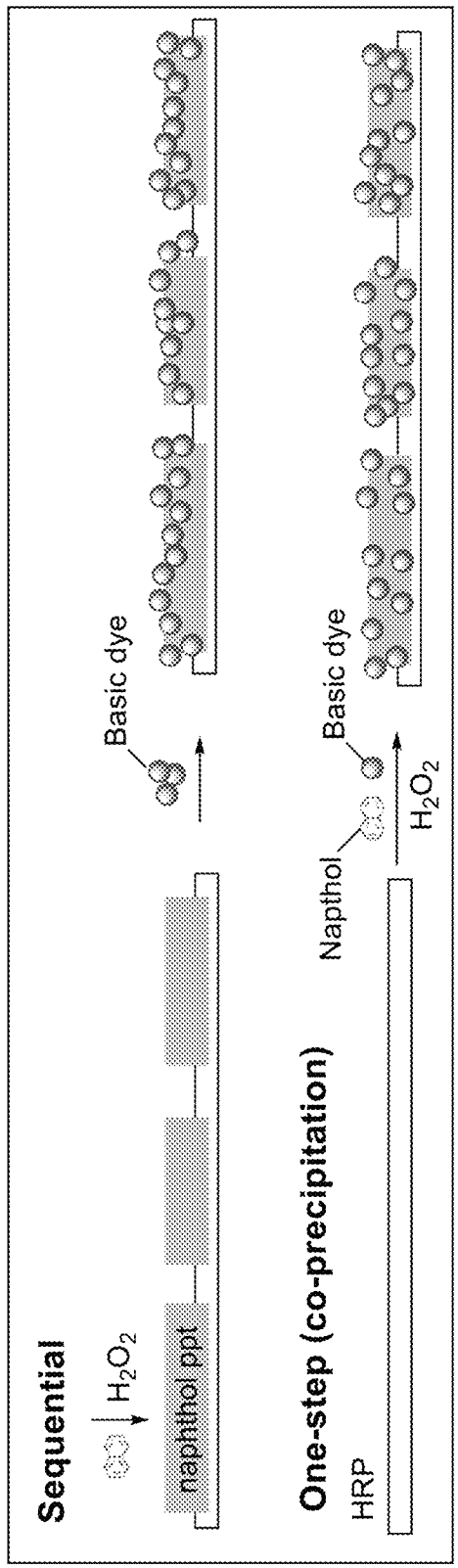
FIG. 75 illustrates that that naphthol and a first dye may be added in a one-step (co-precipitate) method to a tissue sample or by sequential addition to tissue.

This approach can be used either sequentially, or in a one-step method. The one-step method involves mixing naphthol and the dye first before adding to a tissue sample. In this way, the dye would precipitate together with naphthol as the enzymatic reaction proceeds, as shown below in Scheme 12 (FIG. 75).

The adsorbed mass tag, for example crystal violet, can be readily detected by LDI MS, even on normal glass slides (non-ITO slide). In this approach, many non-triarylmethane molecules can be used as mass tags.

In further illustrative embodiments, one or more atoms of any mass tag precursor, mass tag, and/or mass code disclosed herein, or hereafter discovered that is useful for practicing the disclosed method, may be replaced with stable isotopes (e.g., $^2H$, $^3H$, $^{13}C$, $^{14}C$, $^{15}N$, $^{18}O$ etc.). Replacing atoms with stable isotopes can be used, for example, to provide a homologous series of mass tags having the same chemical structure but differing molecular weights. For example, one or more hydrogen atoms on one or more rings of a triarylmethane-containing compound, an aryl azo dye, a basic dye, or a heteroaryl compound as described herein can be replaced by deuterium or tritium atoms. Similarly one or more carbon atoms can be replaced by one or more carbon-13 atoms. In some embodiments, one or more isotopes may be present in an enzyme substrate, e.g., a naphthol (such as a naphthol phosphate), that reacts with an enzyme and a mass tag precursor to form a mass tag. Desirably, the isotopes are in the portion of the mass tag that forms the mass code after ionization, thereby providing mass codes having the same chemical structure but differing masses.

Additional species of triaryl methane derivatives are disclosed in U.S. Pat. No. 6,780,981 and types of mass spectrometry techniques are disclosed in U.S. Pat. No. 7,198,893, where are incorporated by reference herein. Compounds disclosed herein include reference to substituents by "R" groups or substituents, such as "$R^1$". Unless otherwise indicated, $R^1$ and $R^{1'}$ may be selected from aliphatic, such as alkyl, more typically lower alkyl, such as methyl, ethyl, propyl, butyl, etc., alkenyl, alkynyl, aryl, aryl aliphatic, such as aryl alkyl, hydrogen, and deuterium; $R^2$, $R^3$, $R^4$, $R^5$ and $R^6$ may be selected from aliphatic, such as alkyl, more typically lower alkyl, such as methyl, ethyl, propyl, butyl, etc., alkenyl, alkynyl, aryl, aryl aliphatic, such as aryl alkyl, and electron-donating heteroatom-containing moieties selected from, but not limited to, ether ($R^aOR^b$), hydroxyl ($R^aOH$), silyl ether ($R^aR^bR^cSiOR^d$), phosphine ($PR^aR^bR^c$), thiol ($R^aSH$), thioether/sulfide ($R^aSR^b$), disulfide ($R^aSSR^b$), isothiocyanate ($R^aNCS$), isocyanate ($R^aNCO$), amine ($NH_2$, $NHR^a$, $NR^aR^b$), amide ($R^aNR^bC(O)R^c$, ester ($R^aOC(O)R^b$); $R^{20}$ is an electron withdrawing group, and may be selected from heteroatom-containing moieties selected from halogen (I, Br, Cl, F), carbonate ($R^aOC(O)OR^b$), carboxyl ($R^aC(O)OH$), carboxylate ($R^a$-$COO^-$), ester ($R^aC(O)OR^b$), ketone ($R^aC(O)R^b$), phosphate ($R^aOP(O)OH_2$), phosphoryl ($R^aP(O)(OH)_2$), sulfinyl ($R^aS(O)R^b$), sulfonyl ($R^aSO_2R^b$), carbonothioyl ($R^aC(S)R^b$ or $R^aC(S)H$), sulfino ($RaS(O)OH$), sulfo ($R^aSO_3H$), amide ($R^aC(O)NR^bR^c$), azide ($N_3$), nitrile ($R^aCN$), isonitrile ($R^aN^+C^-$), and nitro ($R^aNO_2$). With reference to all the heteroatom-containing moieties disclosed herein, $R^a$ represents one or more of the aryl rings of the triarylmethane, the naphthol, or the diazo mass tag precursors/mass tags/mass codes described herein; and $R^b$, $R^c$, and $R^d$ independently are hydrogen, aliphatic, aryl, heteroaliphatic, heteroaryl, and any combination thereof. Unless otherwise stated, $R^9$ can be any group that can form, or that can be removed, to form, an ion, typically a carbocation. Exemplary $R^9$ groups can include halogens (fluorine, chlorine, bromine and iodine), nitriles (CN), sulfonyl groups, such as mesyl (Ms), tosyl (Ts), trifluoromethyl (Tf), hydroxyl, ether, amine, thiol, thioether, and salts thereof. Unless otherwise stated, $R^{19}$ is any group that can form, or that can be removed to form, a carbocation. Typically, $R^{19}$ is selected from oxygen, sulfur, and -(nitrogen-$R^{11}$)—.

Any one or more of $R^1$, $R^{1'}$, $R^2$, $R^3$, $R^4$, $R^5$, and $R^6$, particularly $R^2$, $R^3$, $R^4$, $R^5$, and $R^6$, may be varied to produce a compound of a particular selected molecular weight. For example, $R^1$, $R^{1'}$, $R^2$, $R^3$, $R^4$, $R^5$, and/or $R^6$ may be a species, such as halogen or a stable isotope, such as deuterium, and may be used to provide a homologous series of tags of differing molecular weights. In some embodiments, one or more ring carbon atoms may be replaced with one or more $^{13}C$ and/or $^{14}C$ isotopes to provide a homologous series of tags of differing molecular weights. Unless otherwise indicated, $R^{16}$ is selected from ether, hydroxyl, -(nitrogen-$R^{11}$)—; $R^{17}$ is selected from aliphatic, heteroaliphatic, aryl, and heteroaryl; Y is selected from oxygen, sulfur, and -(nitrogen-$R^{11}$)—; and $R^{11}$ is selected from aliphatic, heteroaliphatic, aryl, heteroaryl, and hydrogen.

IV. Tyramine And Tyramine Derivatives

In some embodiments, mass tag precursors are conjugated to a tyramine or a tyramine derivative. Particular embodiments utilize tyramine for the formation conjugates. A mass tag precursor conjugate comprising a tyramine or tyramine derivative typically have the following general Formula 34.

Formula 34

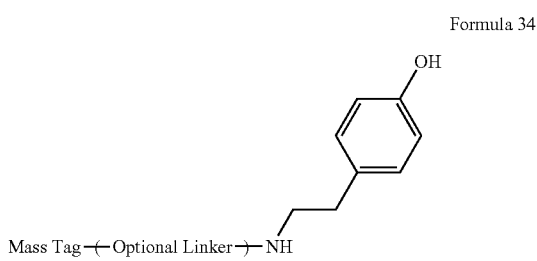

Some embodiments utilize tyramine derivatives for mass tag precursor conjugate. These tyramine derivatives have the following general Formula 35, wherein n is from 1 to 20.

Formula 35

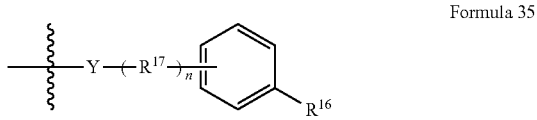

V. Optional Linkers

Certain embodiments include the use of a linker, which is used to couple one moiety to a second moiety. For example, linkers may be used to couple, such as to covalently or electro-statically bind, a mass tag precursor to a tyramine or a tyramine derivative. These linkers can be selected from any moiety capable of effectively coupling two moieties, such as a mass tag precursor and a tyramine or tyramine derivative, including aliphatic, heteroaliphatic, or heterobifunctional linkers.

In particular embodiments, the optional linker can have the following Formula 36.

Formula 36

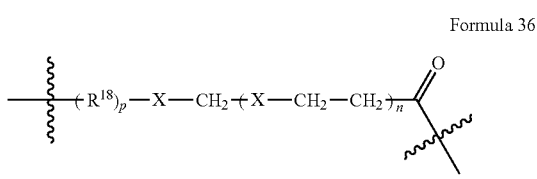

With reference to Formula 36, each X independently is selected from $CH_2$, oxygen, sulfur, and -(nitrogen-$R^{11}$)—. $R^{18}$ is carbonyl or sulfoxyl; n is 1-20; and p is 0 or 1.

Other embodiments utilize polyethylene glycol linkers, having a general formula $PEG_n$, where in n is 1-20, typically 4 to 12.

VI. Carriers

Certain embodiments utilize carriers as a way to deliver multiple mass tags, tyramine moieties, or tyramine derivatives to the target. Carrier moieties can facilitate the deposition of the mass tag precursor proximal to the target. In particular disclosed embodiments, a carrier may be used to facilitate formation of covalent bonds of mass tag precursor conjugates comprising tyramine or a tyramine derivative to the target, providing a potential increased signal produced by the mass code upon cleavage and ionization.

Carriers can be selected from polymers, biomolecules, liposomes, micelles, or nanoparticles. Exemplary polymers include linear polymers, such as polyacid (more typically polyacrylic acid), polyamine (more typically poly-L-lysine), polysaccharide (more typically dextran, or chitosan), polyhydrazine, or a co-polymer. Other exemplary polymers are hyperbranched polymers, such as polyethyleneimine or a dendrimer. Exemplary biomolecules include proteins, polypeptides, oligopeptides, peptides, nucleic acids, DNA, RNA, oligosaccharides, polysaccharides, and monomers thereof. These carriers are selected to bind individual or multiple mass tag moieties, tyramine moieties, and/or tyramine derivative moieties. Typically binding occurs via thiol, amine, carboxylic acid, hydroxyl, halide, anhydride, or hydrazine moieties located on the polymer and/or biomolecule.

Nanoparticle carriers typically comprise a semiconductor material, a metal, or multiple metals. Metals are selected from Groups 3-15 of the periodic table, such as, but not limited to, Y, La, Ag, Au, Pt, Ni, Pd, Rh, Jr, Co, Cu, and Bi, or a combination thereof. Nanoparticles are typically bound to a mass tag ligand, tyramine and/or tyramine derivative, or multiple such moieties, through a binding moiety, such as a thiol group, an amine group, a hydroxyl group, or a phosphine group located on the mass tag, tyramine or tyramine derivative.

VII. Embodiments of a Mass Tag Precursor Conjugate

Certain embodiments concern a mass tag precursor conjugate comprising an enzyme substrate moiety, a mass tag precursor, and an optional linker. For example, an enzyme substrate moiety can be either conjugated to mass tag precursor disclosed herein or hereafter developed, or an enzyme substrate moiety may be conjugated to the mass tag precursor using a linker. Certain disclosed conjugates satisfy general Formula 37 below.

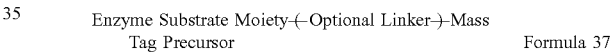

Formula 37

With reference to general Formula 37, the mass tag precursor can be any tag useful for imaging targets as disclosed herein, and that is readily ionizable and detectable under LDI conditions. The enzyme substrate moiety can be any group capable of being transformed by an enzyme. The optional linker can be any structure that does not interfere with the conjugate for use in disclosed embodiments of the process for imaging targets. In some embodiments, the linker is hydrophobic. In more particular embodiment, the linker is an alkylene oxy moiety, such as an ethylene oxy subunit, or polyethylene glycol group.

Certain disclosed embodiments concern a mass tag precursor conjugate comprising a mass tag precursor, tyramine or a tyramine derivative, and an optional linker or carrier. These conjugates have the following general Formula 38.

Formula 38

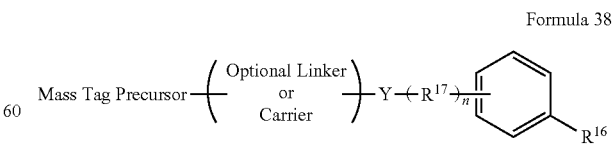

With reference to Formula 38, n is 1-20. The optional linker is selected from aliphatic, heteroaliphatic, or heterobifunctional. The mass tag is a moiety that produces a mass code upon ionization of the conjugate.

Figure 7:
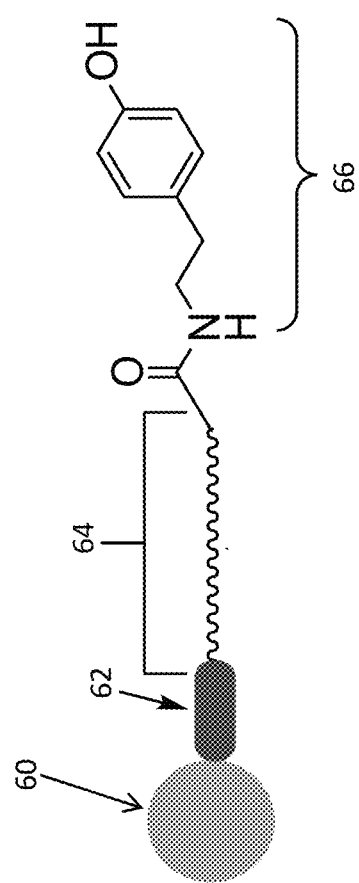
FIG. 7 is a schematic diagram illustrating one embodiment of a mass tag precursor conjugate.

The previously disclosed mass tags and tyramine or tyramine derivatives can be used to form conjugates, which can be used in embodiments of the disclosed method. FIG. 7 illustrates a general mass tag precursor conjugate. A mass tag 60, which can be ionized to form mass codes are bound to an optional linker 64 via a photolabile moiety 62, comprising one or more photolabile bonds. The optional linker 64 binds the mass tag 60 to a tyramine 66, forming a conjugate. Particular embodiments of the mass tag precursor conjugate are described below.

In illustrative embodiments, the conjugate comprises a triarylmethane group mass tag precursor, and have a general Formula 39. The optional linker may be selected from aliphatic, aryl, heteroaliphatic, and combinations thereof. In particular disclosed embodiments, the linker is an alkylene oxy linker, which provides a pendent hydroxyl group for attaching an enzyme substrate moiety, such as a phosphate group. A person of ordinary skill in the art will appreciate that these particular linkers can include heteroatoms other than oxygen, such as sulfur. Sulfur is particularly suitable for coupling beta-lactams, such as cephalosporin, to a triarylmethane mass tag. Other linkers that can be used include any short, hydrophobic linker.

Formula 39

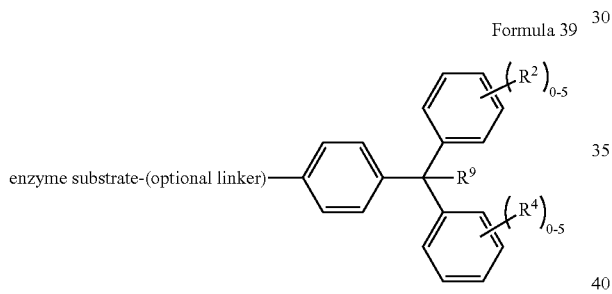

With reference to Formula 39, a person of ordinary skill in the art will appreciate that an enzyme substrate moiety can be attached to the desired linker or directly to the aryl ring. The triarylmethane can be selected to provide a first-water soluble tag coupled to an enzyme substrate moiety. For example, certain disclosed compounds include a phosphate group or a galactoside, as an enzyme substrate moiety coupled to an aryl ring, such as through a pendent hydroxyl group. The phosphate and/or galactoside is water soluble. In addition the triarylmethane derivatives can be coupled to a substrate suitable for reaction with a lactamase, such as a lactam. Removing the phosphate, galactoside, and/or lactam group, such as by an enzymatic reaction using an appropriate enzyme (e.g. a phosphatase cleaves phosphates, a galactosidase cleaves galactosides, and a lactomase cleaves lactams), forms an insoluble compound that precipitates at the site of the target. Laser-initiated ionization forms the mass code. Particular disclosed embodiments have Formulas 40-42

Formula 40

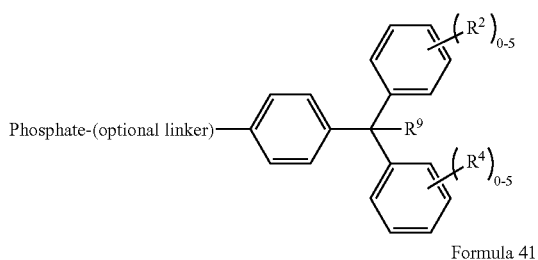

Formula 41

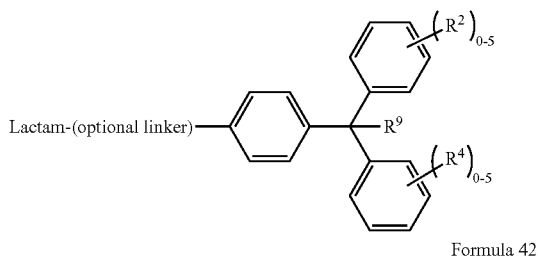

Formula 42

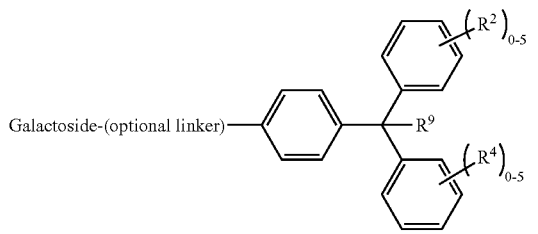

Certain disclosed embodiments concern using a mass tag precursor conjugate having the following Formulas 43-45, wherein n ranges from 1 to about 10.

Formula 43

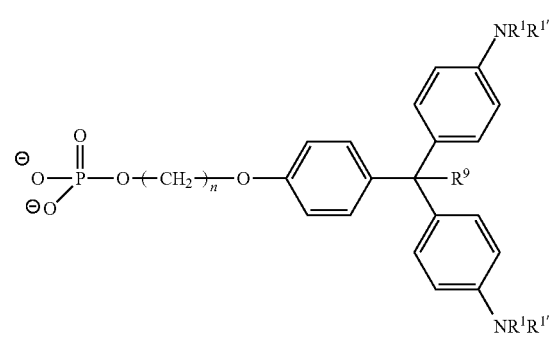

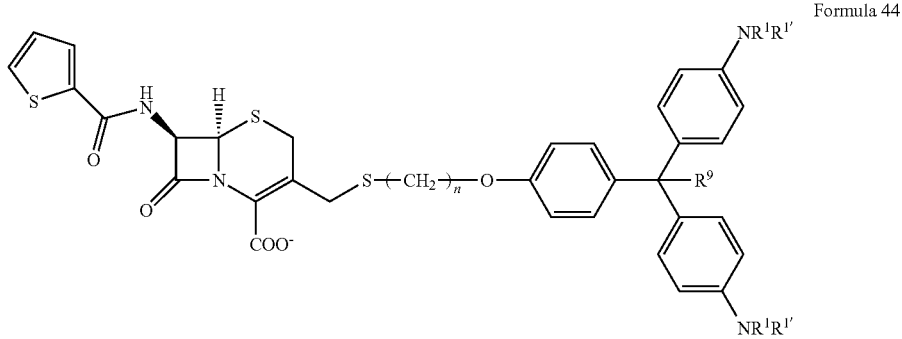

Formula 44

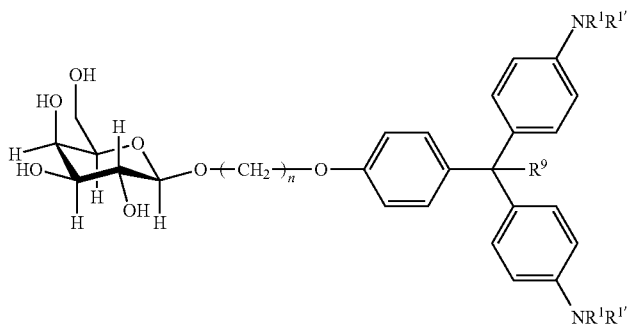

Formula 45

Scheme 13 provides an example of a conjugate comprising a mass tag precursor and an enzyme substrate and a method for making the conjugate. According to Scheme 13, a protected monosaccharide 120, is reacted with triarylmethane derivative 122, in the presence of 0.5 equivalent of indium bromide (InBr$_3$), to form ether 124. Ether 124 is then deprotected in 20% hydrazine/methanol to form deprotected conjugate 126 comprising both a triarylmethane mass tag and a substrate for a galactosidase. The conjugate 126 is an exemplary conjugate that may be a substrate for β-D-galactosidase, which catalyzes the hydrolysis of galactosides into monosaccharides. If the galactoside is an α-galactoside, the enzyme is α-galactosidase, and if the galactoside is a β-galactoside, the enzyme is β-galactosidase. Thus, as shown in Scheme 13, contacting conjugate 126 with a enzyme (e.g. galactosidase) produces a monosaccharide, such as D-galactose 130, and a water insoluble mass tag 128 that can be ionized for detection by a suitable MS technique.

Scheme 13

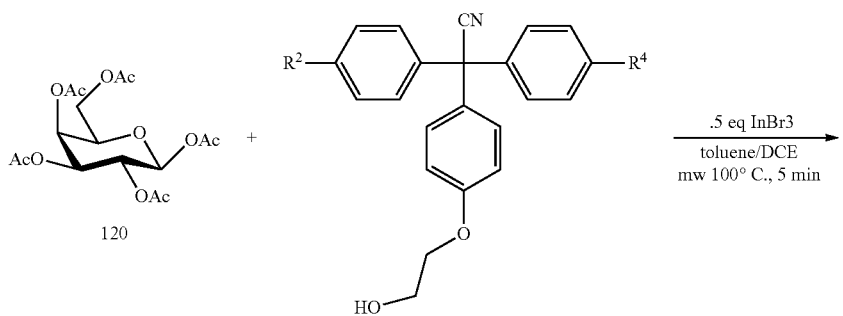

-continued
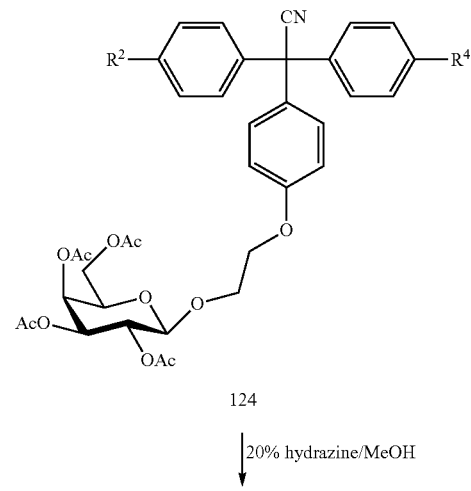
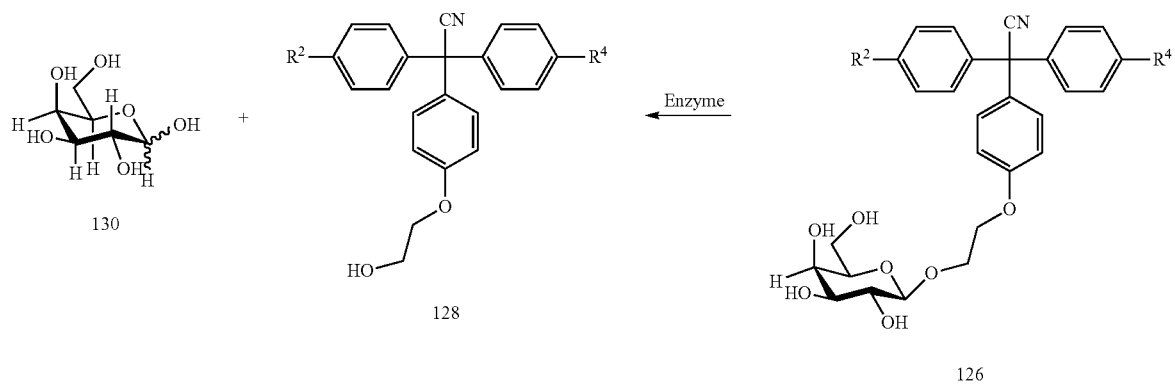

Scheme 14 also provides an example of a conjugate comprising a mass tag precursor and an enzyme substrate. Conjugate 132 comprises a mass tag precursor and a β-lactam moiety, such as cephalosporin, as a substrate for β-lactamase. β-lactams have a common element in their molecular structure: the four-atom β-lactam ring. Additional examples of β-lactams include penicillins, cephamycins, and carbapenems (ertapenem). The lactamase enzyme cleaves the conjugate to form the water insoluble mass tag 134, which upon ionization produces a mass code detected by a suitable MS technique.

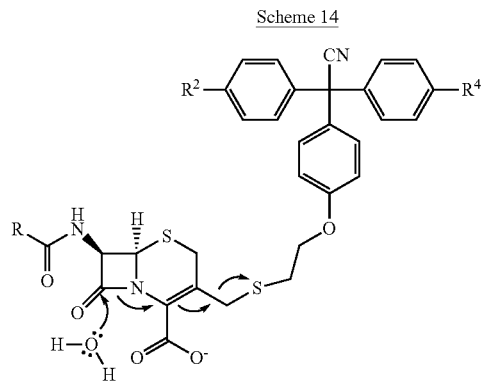

132

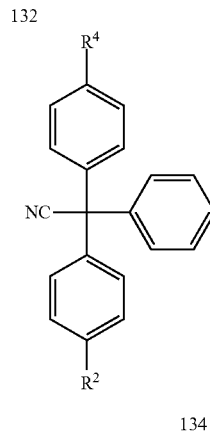

134

Some disclosed embodiments use triarylmethane derivatives as mass tag precursors to construct the mass tag precursor conjugate. Certain embodiments of the conjugate have a general Formula 46, illustrated below.

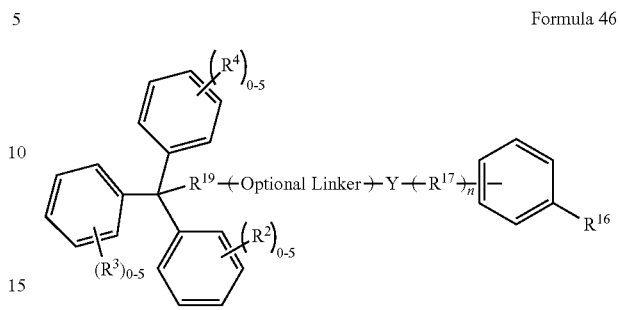

Formula 46

With reference to Formula 46, optional linkers include aliphatic, heteroaliphatic, or heterobifunctional linkers; and n ranges from 1 to about 20. In some embodiments, mass tag precursor conjugates are formed with a carrier, which allows for one or more mass tags, tyramine and/or tyramine derivatives to be deposited at a target. Carriers are selected from polymers, biomolecules, and nanoparticles.

Particular embodiments of triarylmethane mass tags have the following Formula 47.

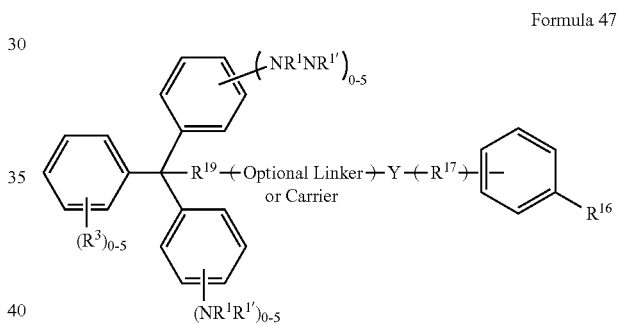

Formula 47

With reference to Formula 47, $R_7$, n, and the optional linker are as recited above. $R^4$ and $R^5$ independently are selected from aliphatic, heteroaliphatic, aryl, heteroaryl, and hydrogen.

Particular embodiments concern using a mass tag precursor conjugate having the following structure.

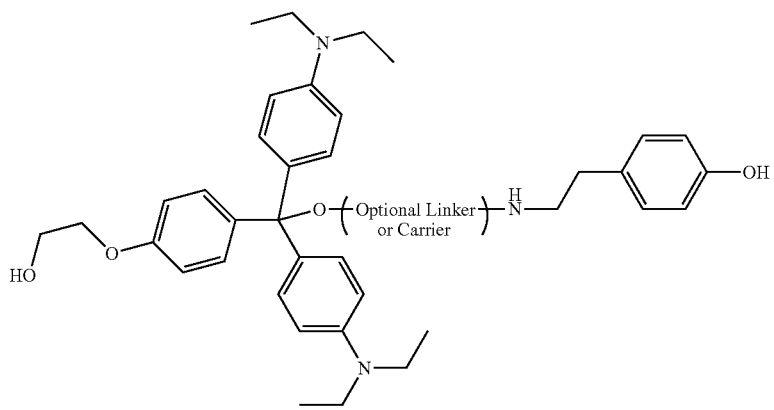

Further illustrative embodiments concern a conjugate comprising an enzyme substrate moiety that is either covalently bound to an azo-naphthol mass tag precursor or bound through a linker. Certain disclosed embodiments satisfy general Formula 48 below.

Formula 48

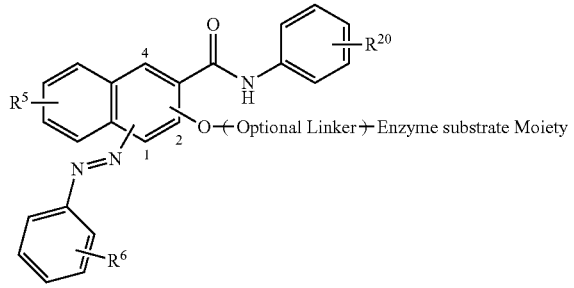

With reference to general Formula 48, the enzyme substrate moiety can be any group capable of being cleaved by an enzyme. The optional linker can be any hydrophobic, ethylene oxy subunit, or polyethylene glycol group capable of binding the enzyme substrate moiety. The diazo species and the ether containing the enzyme substrate moiety can be located at positions 1, 2, and/or 4, or any combination thereof. Certain disclosed embodiments of naphthol azo dye conjugates have the Formulas 49-51 indicated below.

Formula 49

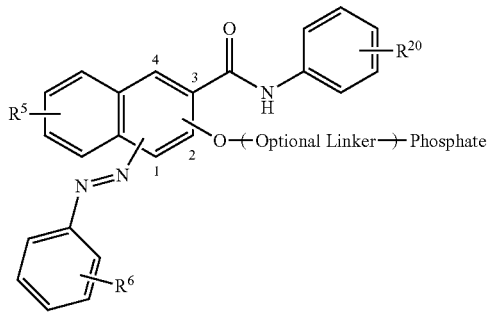

Formula 50

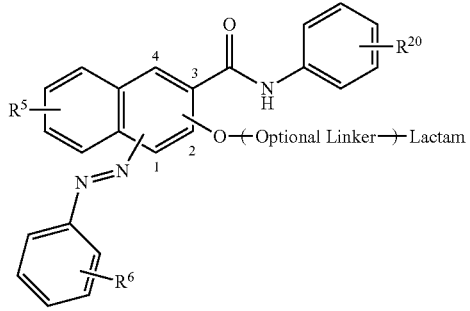

Formula 51

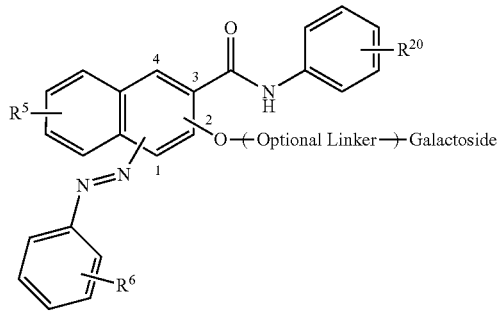

Particular disclosed embodiments have the following Formulas 52-54.

Formula 52

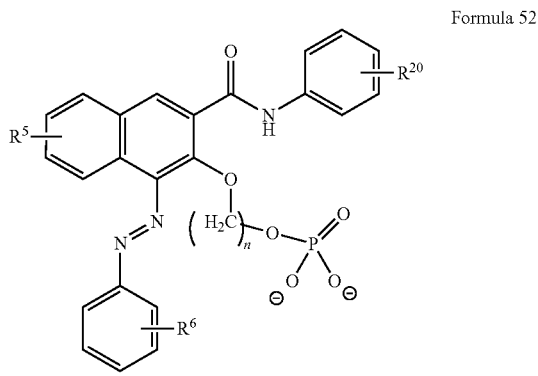

Formula 53

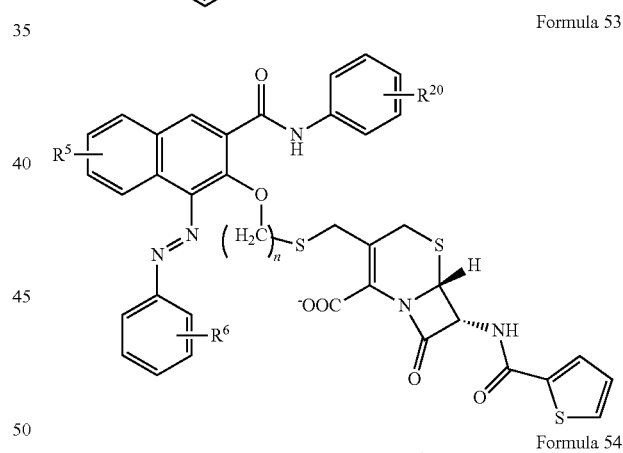

Formula 54

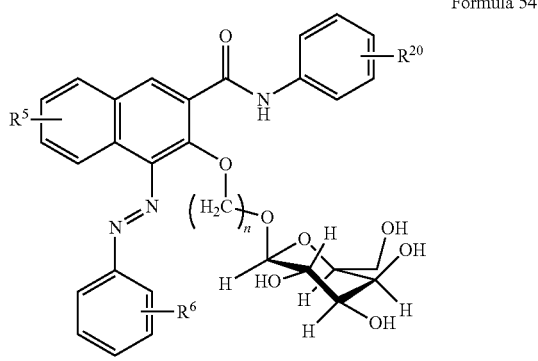

Another genus of the disclosed mass tag precursor conjugate includes those in which the mass tag precursor is a naphthol-azo moiety. These embodiments of the disclosed conjugate have a general Formula 55, illustrated below.

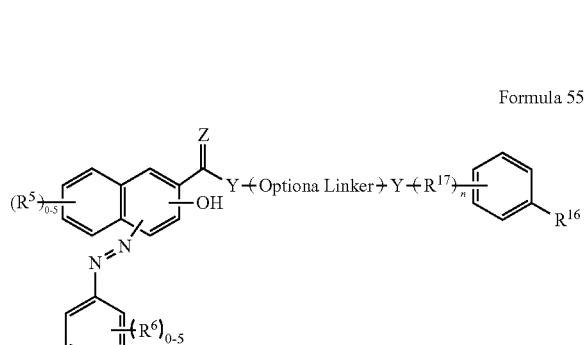

Formula 55

With reference to Formula 55, Z is selected from oxygen sulfur, and -(nitrogen-$R^{11}$)—. In particular embodiments, Z is oxygen.

A particular embodiment of the mass tag precursor conjugate is illustrated below.

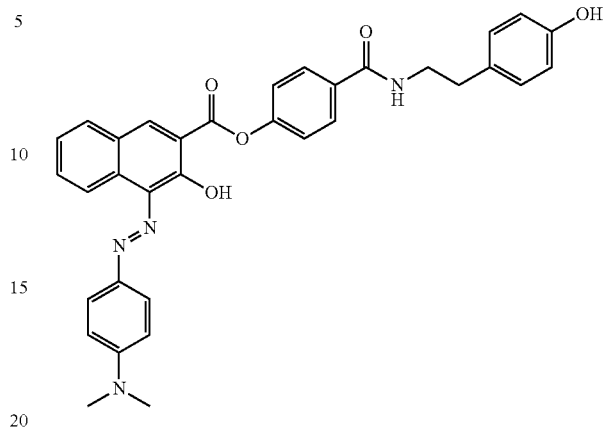

In some embodiments, naphthol-azo mass tag moieties are used in conjunction with a triaryl methane derivative to produce another class of photolabile conjugates. In these examples, a naphthol azo moiety is bonded to an aryl ring of a triaryl methane derivative, as illustrated below.

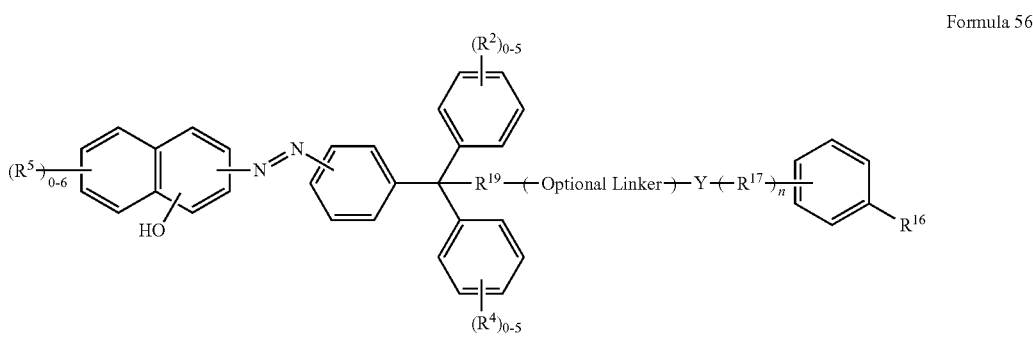

Formula 56

The mass tag precursor conjugate may deposit a mass tag, which forms a mass code comprising a naphthol-azo-triaryl-methane cation. This cationic mass code is then detected, typically using mass spectrometry. A particular embodiment of these conjugates is illustrated below.

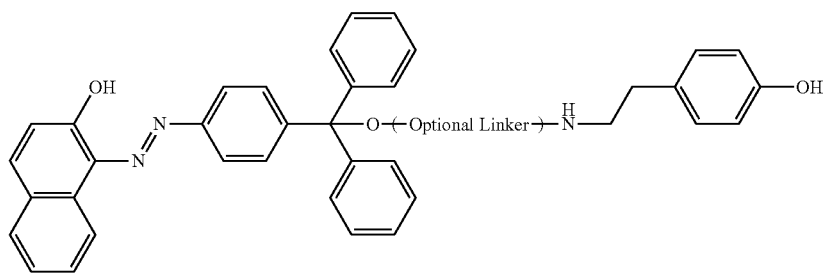

In illustrative embodiments, a conjugate comprises a photolabile nitrophenyl moiety as a mass tag precursor. These embodiments utilize a nitrophenyl mass tag moiety as a linker to effectively couple a mass code precursor to the mass tag precursor conjugate. A general formula illustrating these types of conjugates is shown below.

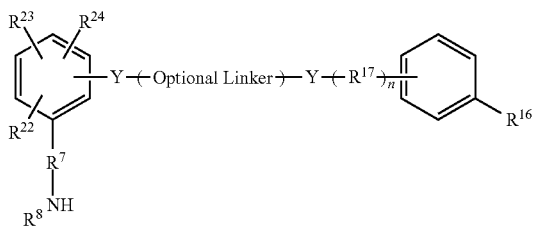

Formula 57

With reference to Formula 57, the optional linker typically is selected from aliphatic, heteroaliphatic, or heterobifunctional linkers and n ranges from 1 to about 20. $R^{22}$-$R^{24}$ independently are selected from aliphatic, heteroaliphatic aryl, heteroaryl, carbonyl, halogen, hydrogen, hydroxyl, isothiocyanate, isocyanate, nitrile, nitro, thiol, and any combination thereof, with at least one of $R^{22}$-$R^{24}$ being nitro; $R^7$ is aliphatic, or heteroaliphatic. $R^8$ is selected from a linker (typically aliphatic or heteroaliphatic) a charged species (typically selected from charged amino acids, such as arginine, lysine, or histidine), a tetra-alkyl ammonium species (such as tetramethyl ammonium), a chromophore (typically selected from a dye or a hapten) and any combination thereof. In particular embodiments, $R^8$ moieties have a m/z value in a range from about 100 to about 5000, or from about 500 to about 2000.

Certain embodiments have a Formula 58, illustrated below, where the variables are as recited for Formula 57.

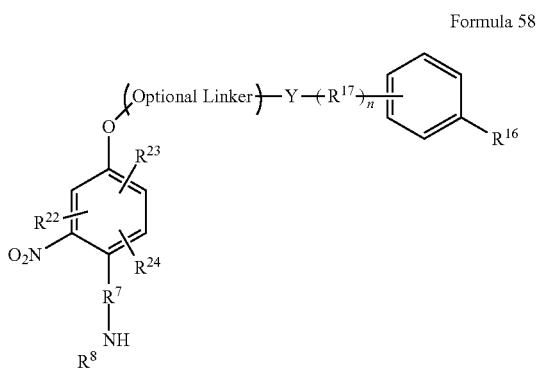

Formula 58

Particular embodiments of these conjugates are illustrated below.

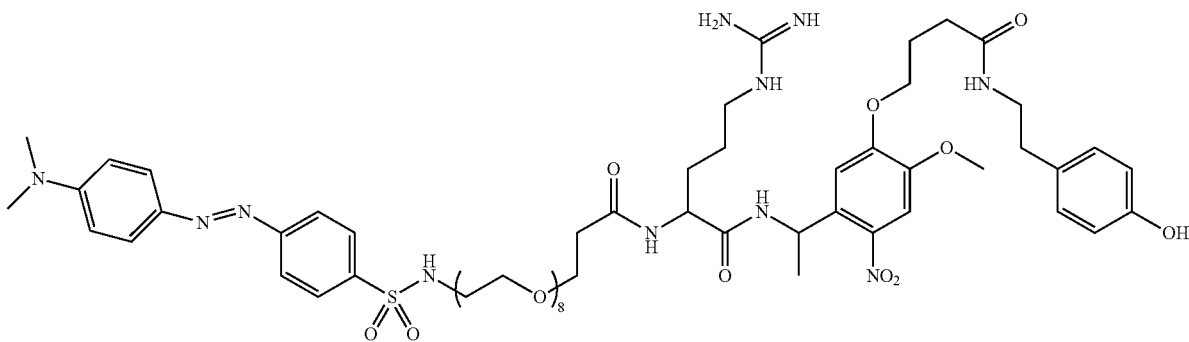

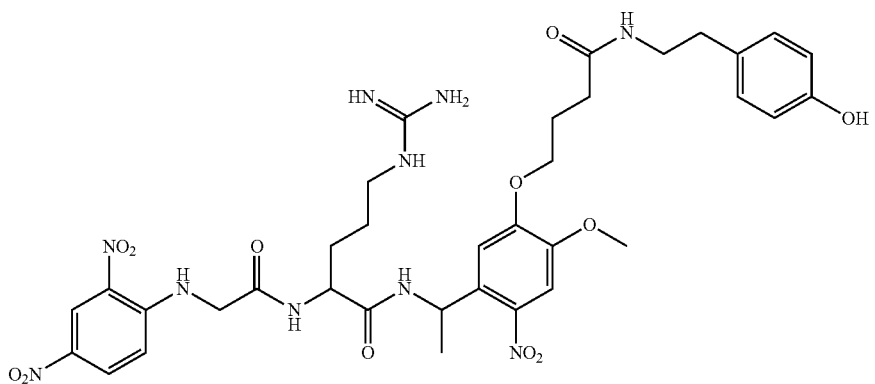

-continued

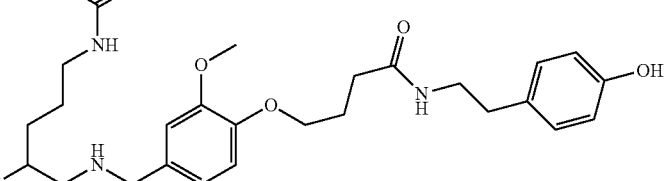

Some photolabile mass tag precursor conjugates comprising a tyramine or tyramine derivative include heteroaryl moieties as mass tag precursors. These conjugates have a general Formula 59, illustrated below.

Formula 59

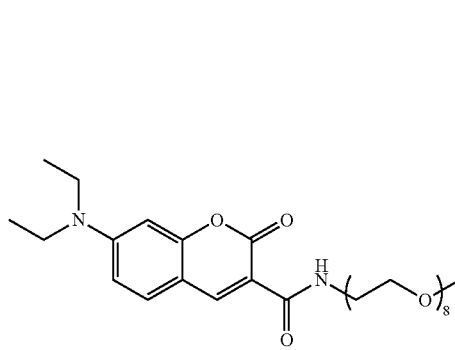

With reference to Formula 59, the optional linker typically is selected from aliphatic, heteroaliphatic, or heterobifunctional. $R^{25}$-$R^{28}$ independently are selected from carbon or nitrogen, with at least one of $R^{25}$-$R^{28}$ being nitrogen. In certain embodiments, $R^{25}$-$R^{28}$ are nitrogen. A person of ordinary skill in the art will recognize that when $R^{25}$-$R^{28}$ are nitrogen, the heteroaryl moiety is a tetrazine. A person of ordinary skill in the art also will appreciate that the heteroaryl moiety can be an azine (where one of $R^{25}$-$R^{28}$ comprises nitrogen), a diazine (where two of $R^{25}$-$R^{28}$ comprises nitrogen), or a triazine (where three of $R^{25}$-$R^{28}$ comprises nitrogen). $R^8$ is selected from a linker (typically aliphatic or heteroaliphatic) a charged species (typically selected from charged amino acids, such as arginine, lysine, or histidine; or a tetra-alkyl ammonium species, such as tetramethyl ammonium) a chromophore (typically selected from a dye or a hapten) and any combination thereof. In particular embodiments, $R^8$ moieties have a m/z value in a range from about 100 to about 5000, or from about 500 to about 2000.

The mass codes produced from these embodiments of the disclosed conjugate, after exposure to an energy source, typically have a formula NCS—$R^8$, wherein $R^8$ can be a charged moiety. In cases where $R^8$ is not a charged moiety, the mass code is obtained by bond cleavage, which first produces a neutral NCS—$R^8$ fragment, and subsequent ionization produces a charged mass code. This mass code results from photo-induced degradation of the heteroaryl moiety. The mass code subsequently is detected, such as by a mass spectrometer.

Particular embodiments have a structure illustrated below.

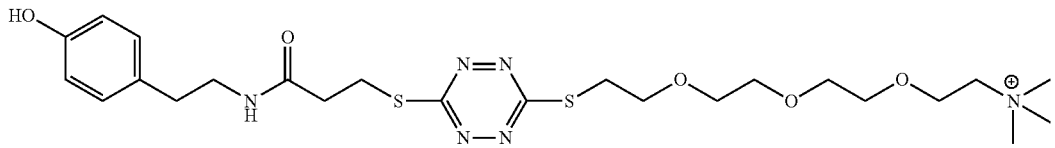 [SMILES: C[N+](C)(C)CCOCCOCCOCCSc1nnc(SCCC(=O)NCCc2ccc(O)cc2)nn1]

In some embodiments, photolabile the metal-complexed mass tag precursor conjugate is a source of a detectable mass code, which can be used to determine the location of a particular target in a sample. Exemplary embodiments utilize metal complexes as mass tags. Upon ionization of the conjugate, a detectable mass code is produced. A person of ordinary skill in the art will recognize that ionization can involve cleavage of a covalent bond to produce a charged moiety or the release of a metal from a coordination complex to produce a charged moiety.

Certain embodiments have a mass tag precursor conjugate with a general Formulas 60 and 61, illustrated below.

Formula 60

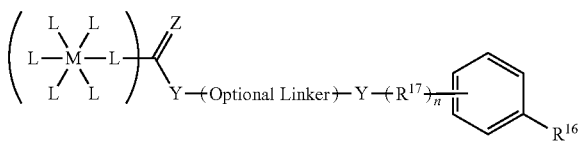

With reference to Formulas 60 and 61, the optional linker typically is selected from aliphatic, heteroaliphatic, or heterobifunctional linkers. With reference to Formula 60, L is a non-aryl ligand, such as, but not limited to nitrile, thionitrile, hydroxyl, thiol, amine, carbonyl, phosphonyl, halide, phosphine, or heteroaliphatic.

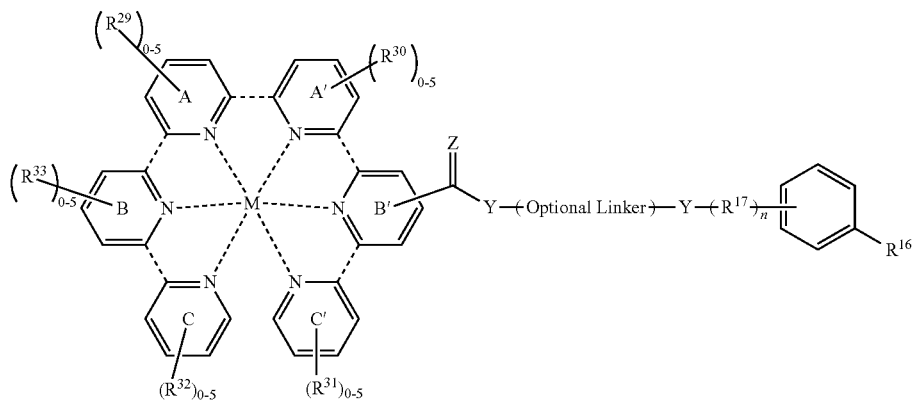

Formula 61

With reference to Formula 61, $R^{29}$-$R^{33}$ independently are selected from aliphatic, heteroaliphatic, aryl, heteroaryl, carbonyl, halogen, hydrogen, hydroxyl, isothiocyanate, isocyanate, nitrile, nitro, thiol, and any combination thereof. For both Formulas 60 and 61, M is a metal selected from Groups 3-12 of the periodic table capable of forming a chelate structure; in some embodiments, M is Zn, Ni, Co, Ru, Cd, Pt, and Fe. M is coordinated to rings A, A', B, B', C, C'. These rings can form a monoheteroaryl chelate, in which rings A, A', B, B', C, C' are only chelated to M and not bonded to each other; a biheteroaryl chelate, in which rings A and A' are bonded together, B and C are bonded together, and B' and C' are bonded together; or a terheteroaryl chelate, in which rings A, B, and C are bonded together and rings A', B', and C' are bonded together. Z is selected from oxygen, sulfur, and -(nitrogen-$R^{11}$)—.

Particular embodiments of this genus of mass tag precursor conjugate are illustrated below.

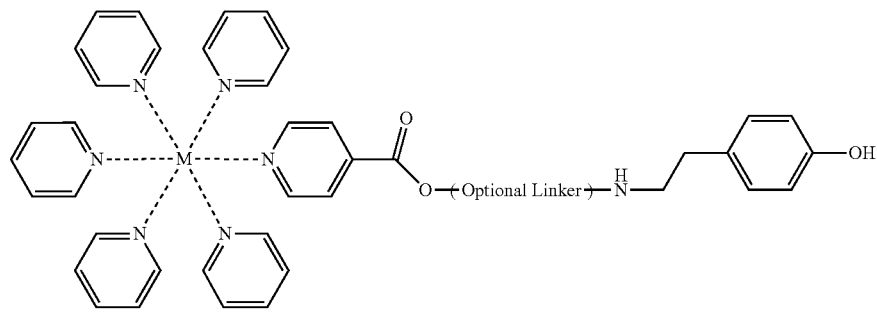

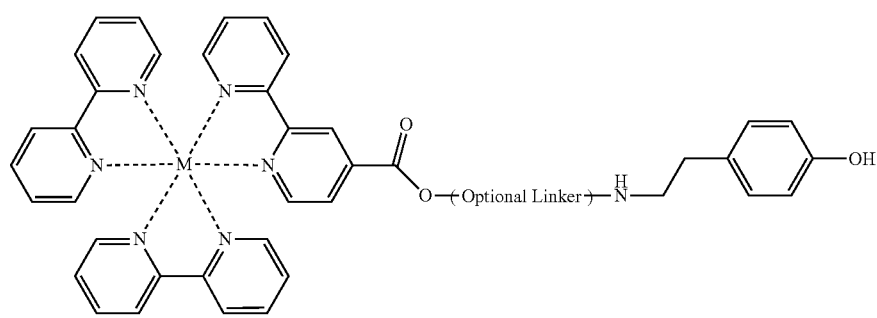

-continued

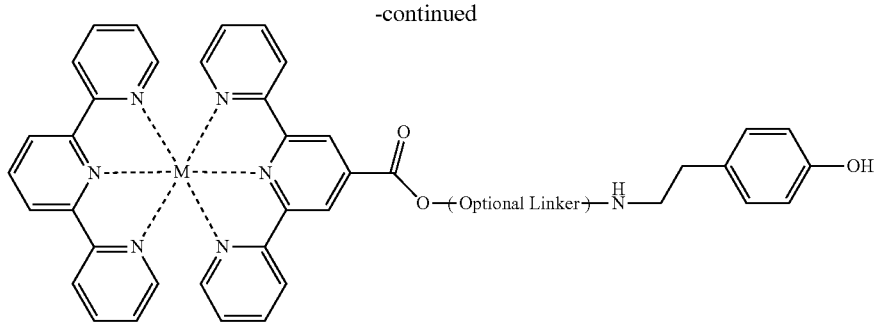

In other embodiments utilizing a metal-heteroaryl chelate mass tag precursor conjugate, a tyramine or tyramine derivative is bound to a chelating reagent, such as nitrilotriacetic acid (NTA), which coordinates to a metal. The metal also coordinates to a peptide dimer comprising an amino acid capable of coordinating to a metal, such as histidine. Upon ionization, the peptide dimer is released and detected, such as by using mass spectrometry. Particular embodiments have the following general formula.

Formula 62

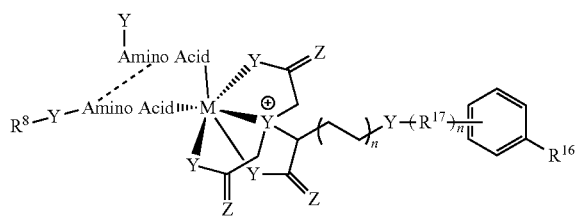

With reference to Formula 62, M and Z are as recited above. The amino acid moieties can be an amino acid capable of forming a covalent or ionic bond with a metal (such as, but not limited to histidine), and $R^8$ is selected from a linker (typically aliphatic or heteroaliphatic), a charged species (typically selected from charged amino acids, such as arginine, lysine, or histidine; or a tetra-alkyl ammonium species, such as tetramethyl ammonium), a chromophore (typically selected from a dye or a hapten) and any combination thereof. In particular embodiments, $R^8$ moieties have a m/z value in a range from about 100 to about 5000, or from about 500 to about 2000.

In other illustrative embodiments, the mass tag precursor is a nanoparticle-based mass tag precursor conjugate. In particular disclosed embodiments, the mass tag precursor comprises an enzyme substrate, such as a tyramine or tyramine derivative. In these embodiments, the nanoparticle may be used as a carrier to carry a mass tag and tyramine or tyramine derivative, or multiples of such moieties to the target. Alternatively, the nanoparticle, itself, can be used as a mass tag. When a conjugate utilizes a nanoparticle as a carrier, the mass tag typically is a ligand, which produces a mass code upon ionization. Disclosed embodiments of these genus of the conjugate have a Formula 63, illustrated below.

Formula 63

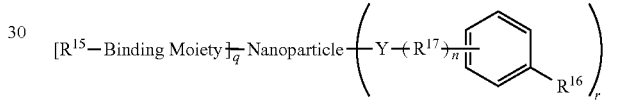

With reference to Formula 63, a ligand typically comprises a $R^{15}$ moiety, a linker, and a binding moiety. $R^{15}$ can be selected from any of the previously disclosed mass tags, a hapten, or a peptide. Linkers are selected from aliphatic, heteroaliphatic, and heterobifunctional linkers; and n ranges from 1 to about 20. Binding moieties are groups that are selected to bind to the nanoparticle, and typically are selected from a hydroxyl moiety, an amine moiety, and a thiol moiety and q is 1 to about 2000 (more typically 1 to about 500). The nanoparticle is selected to contain a semiconductor, a metal or multiple metals. Metals are typically selected from Groups 3-15 of the periodic table, more typically, Y, La, Ag, Au, Pt, Ni, Pd, Rh, Jr, Co, Cu, and Bi, and a combination thereof. Tyramine is represented when $R^{16}$ is hydroxyl, $R^{17}$ is aliphatic, n is 2 and Y is NH.

In particular embodiments, a nanoparticle-based mass tag precursor conjugate has any one of Formulas 64 and 65. The variable "q" is 1 to about 2000 (more typically 1 to about 500); and r is 1 to about 20.

Formula 64

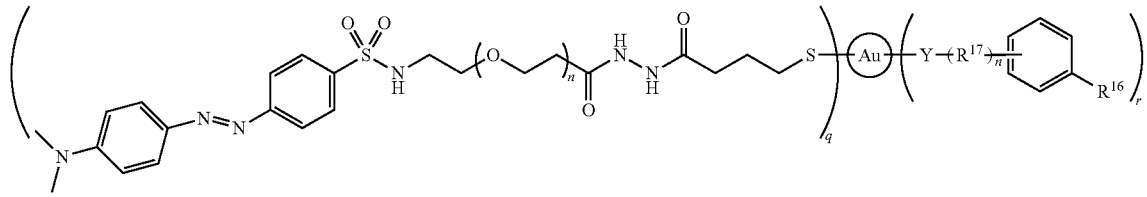

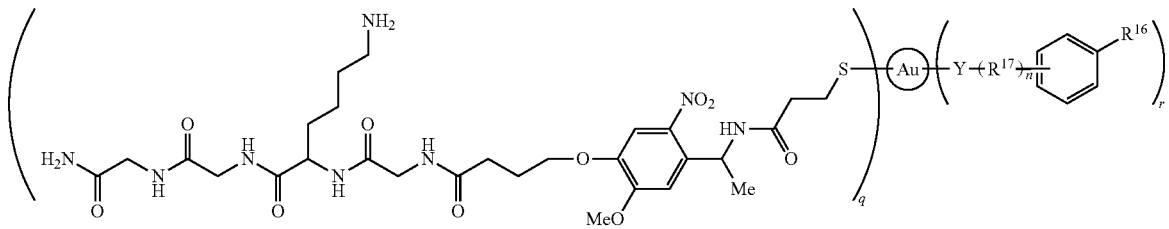

Formula 65

Nanoparticles also can be used as mass tags in disclosed embodiments. When a nanoparticle is used as a mass tag, the metal cluster ions generated upon irradiation act as a mass code, which is detected, such as by mass spectrometry. A nanoparticle mass tag typically is conjugated to a tyramine or a tyramine derivative to provide a conjugate such as that illustrated in Formula 66. With reference to Formula 66, n and r are as recited in Formulas 64 and 65.

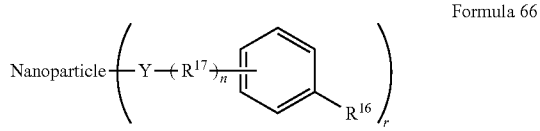

Formula 66

VIII. Mass Tags Produced from Disclosed Embodiments of the Mass Tag Precursor Conjugate In particular disclosed embodiments, the mass tag precursor conjugate reacts with an enzyme to produce a mass tag that is deposited proximal to the target. In particular embodiments, the enzyme reacts with the enzyme substrate to cleave a particular moiety from the mass tag precursor conjugate to form the mass tag. In other disclosed embodiments, the enzyme reacts with the mass tag precursor conjugate to form an active species, such as a radical, which allows the mass tag to deposit proximal to the target.

IX. Specific Binding Moiety/Enzyme Conjugates

Particular embodiments also concern conjugates comprising an enzyme coupled, typically being covalently bound, to a specific binding moiety, as shown in general Formula 67. The enzyme can be any enzyme capable of recognizing an enzyme substrate moiety connected to a mass tag or other species. The specific binding moiety can be any species capable of binding to a target or an epitope.

Enzyme-Specific Binding Moiety  Formula 67

The specific binding moiety can be a protein, a peptide, an antibody, an oligomer, a lectin, and/or a nucleic acid, such as DNA or RNA, as indicated below.

Enzyme-Protein   Enzyme-DNA

Enzyme-Antibody   Enzyme-RNA

The enzyme is bound to any specific binding moiety capable of specifically recognizing a target. Certain particular embodiments concern alkaline phosphatase, galactosidases, and lactamases conjugated to specific binding moieties, as shown below.

Alkaline Phosphatase-Specific Binding Moiety

Galactosidase-Specific Binding Moiety

β-lactamase-Specific Binding Moiety

Certain disclosed embodiments of specific binding moiety/enzyme conjugates include an antibody covalently bound to alkaline phosphatase, shown in Formula 68. This conjugate can be used to enzymatically cleave an enzyme substrate moiety, which will subsequently react with a mass tag.

Alkaline Phosphatase-Antibody  Formula 68

X. Synthetic Methods

Certain disclosed embodiments of mass tags, such as triarylmethane-base compounds are commercially available. Other embodiments can be made as will be recognized by a person of ordinary skill in the art. Scheme 15 illustrates one embodiment of a method for making particular triarylmethane compounds that are useful as mass tags according to certain disclosed embodiments. As illustrated in Scheme 15, starting compound 136, 2-(4-bromophenoxy)ethanol, is commercially available, such as from Aldrich Chemical Co. Compound 136 is converted to the lithiated derivative 138 by reaction with n-butyl lithium. Compound 138 is a good nucleophile for reaction with carbonyl derivatives, e.g. compound 140, such as 4,4'-(dimethylamino)benzophenonone. A person of ordinary skill in the art will recognize that any commercially available benzophenone derivatives may be used, such as, but not limited to, 4,4'-bis(dimethylamino)benzophenone, 4,4'-bis(diethylamino)benzophenone, 4,4'-dimethoxybenzophenone, 4-benzoylbenzoic acid, bBenzophenone-4-isothiocyanate, and 4-aminobenzophenone. Reaction with compound 140 produces hydroxylated triarylmethane derivative 142, which can be converted into the corresponding nitrile compound 144 by reaction with potassium cyanide (KCN). Compound 144 is then converted to conjugate 146, which is suitable for an enzymatic reaction, using phosphorous oxychloride ($POCl_3$).

Scheme 15

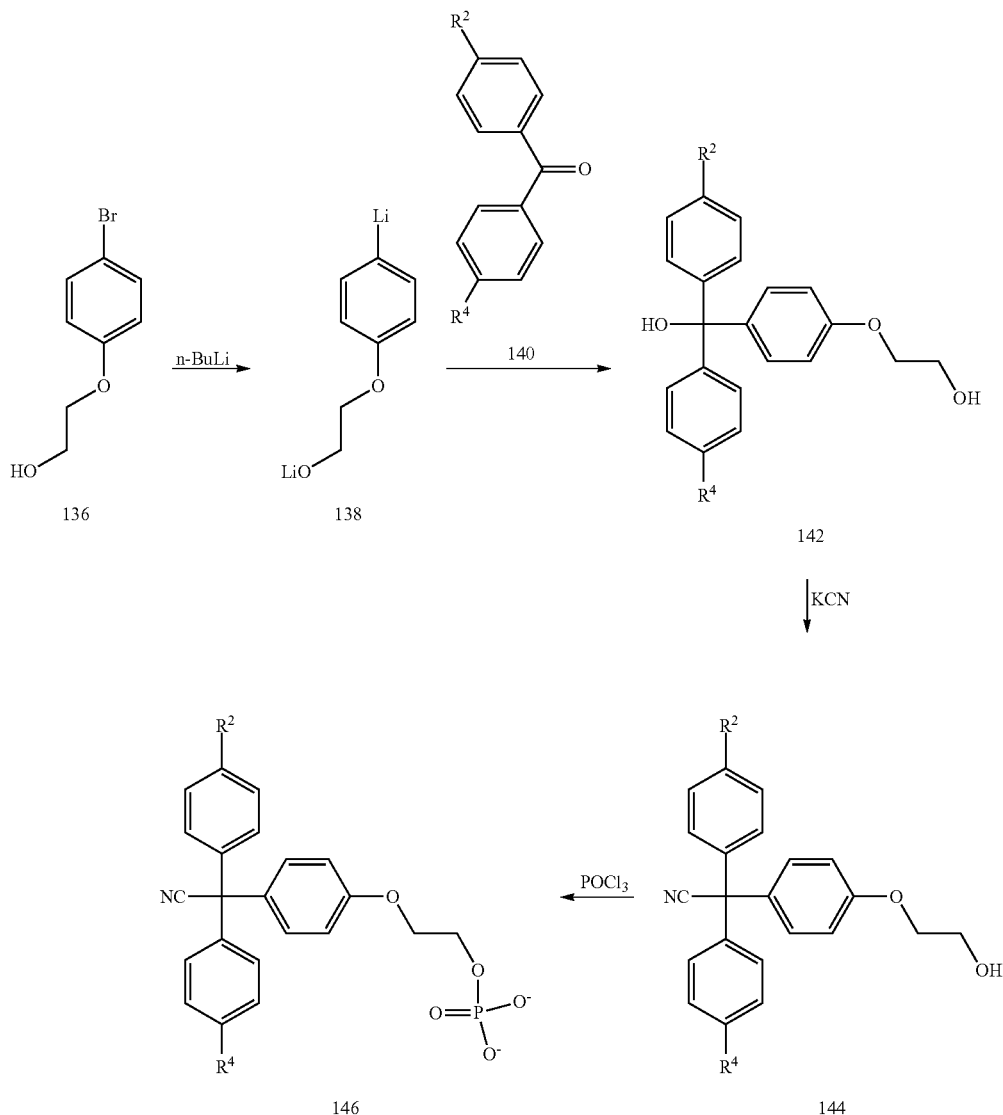

Scheme 16 illustrates one embodiment for a method for making a substrate both for horseradish peroxidase (HRP) and for alkaline phosphatase. Compound 148, 2-methylbenzothiazole, commercially available from Aldrich, is reacted with para-anisaldehyde 150 (4-methoxybenzaldehyde, which also is commercially available from Aldrich), to form olefin 152. Olefin 152 is then reacted with hydroiodic acid (HI) to form phenol 154. Phenol 154 is a suitable substrate for HRP. Phenol 154 also can be converted into a substrate suitable for alkaline phosphatase by reacting phenol 154 with phosphorous oxychloride ($POCl_3$) to produce phosphate 156.

Scheme 16

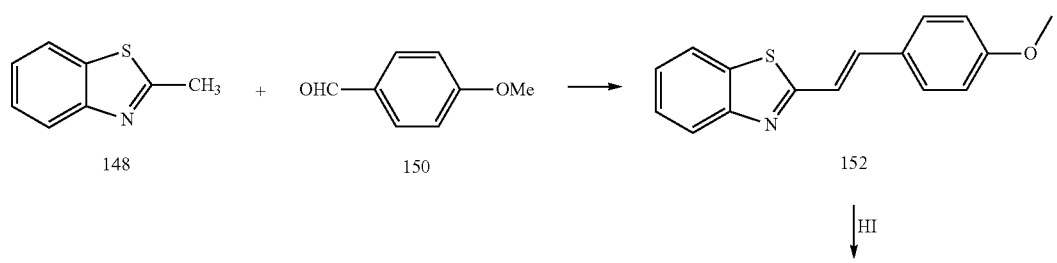

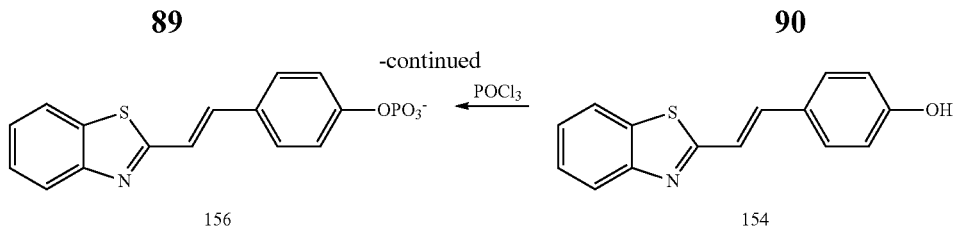

Scheme 17 illustrates one embodiment of a method for making a substrate for ☐-lactamase. In this example, a cephalosporin derivative 158 is reacted with compound 160 to produce a substrate suitable for ☐-lactamase 162.

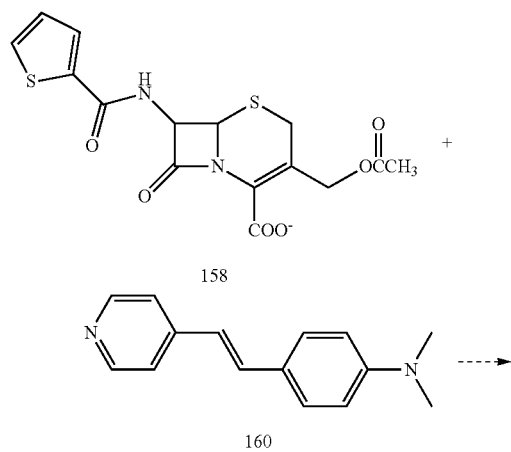

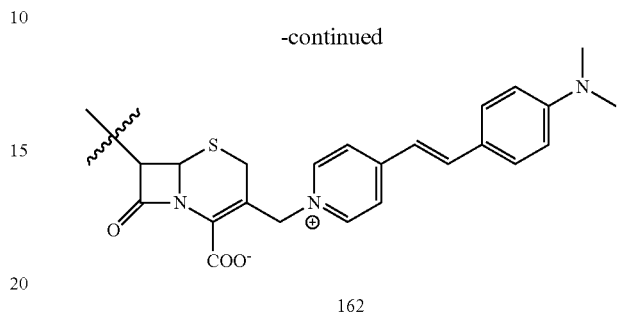

Scheme 18 illustrates one embodiment for synthesizing nitrophenyl mass tag precursors. As shown in Scheme 18, nitrophenyl mass tag compounds can be synthesized using solid phase synthesis. A nitrophenyl compound 166 is loaded onto a trityl chloride resin 164. The Fmoc protecting group of protected amine 168 is removed under basic conditions to provide an amine 170, which is further coupled using peptide coupling conditions to give rise to an amino acid-coupled amine 172. This step can be repeated to conjugate as many amino acids or linkers as desired, in particular to give rise to peptide 174. The desired mass tag precursor 176 is liberated from the resin under acidic conditions.

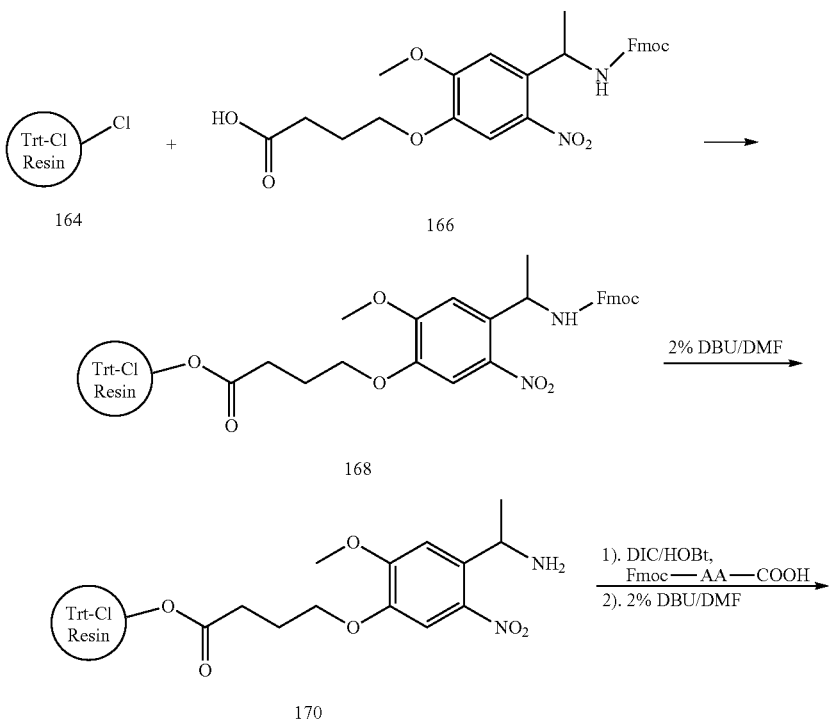

-continued

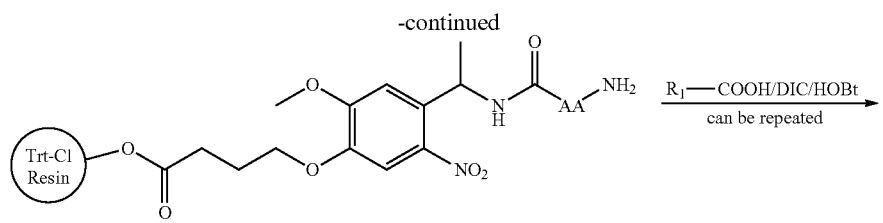

172

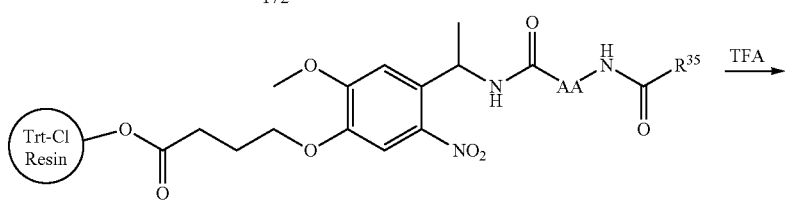

174

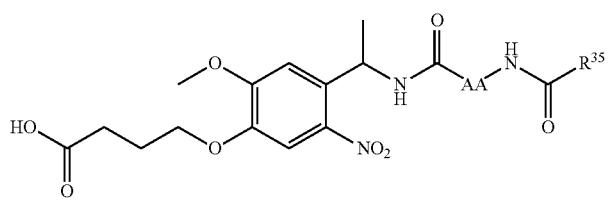

176

Scheme 19 illustrates one embodiment of a method for making a particular mass tag precursor conjugate. In this scheme, a nitrophenyl mass tag is coupled to a tyramine through a coupling sequence. Carboxylic acid 176 is subjected to an esterification reaction using dicyclohexylcarbodiimide (DCC) and N-hydroxysuccinimide to provide activated ester 178. Ester 178 can then be converted to the mass tag precursor conjugate 180 using tyramine.

Scheme 19

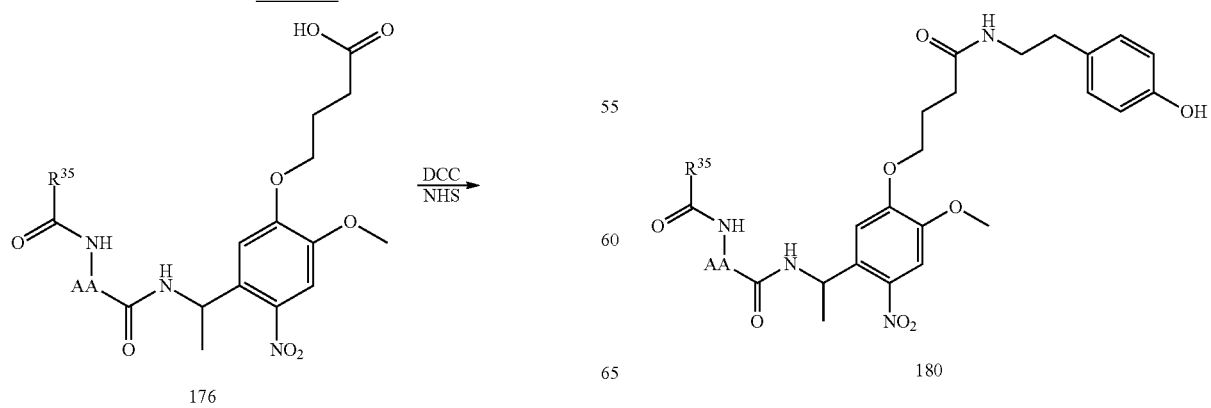

-continued

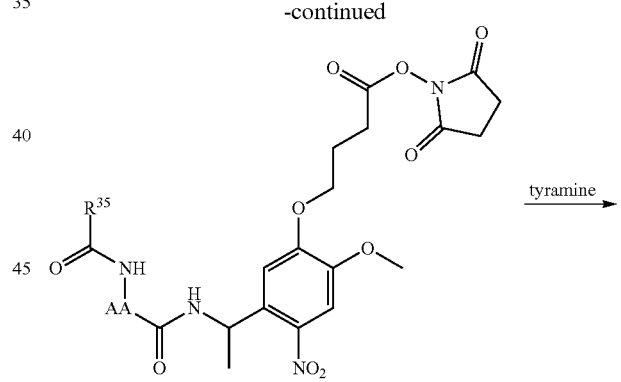

178

180

Scheme 20 illustrates one embodiment of a method for making a particular mass tag precursor conjugate. In Scheme 20, a commercially available carboxylic acid 182 is coupled to an esterified tyramine moiety 184. The resulting amide 186 is chelated with nickel to provide chelate 188, followed by chelation of the nickel to a histidine dimer 190 to give mass tag 192.
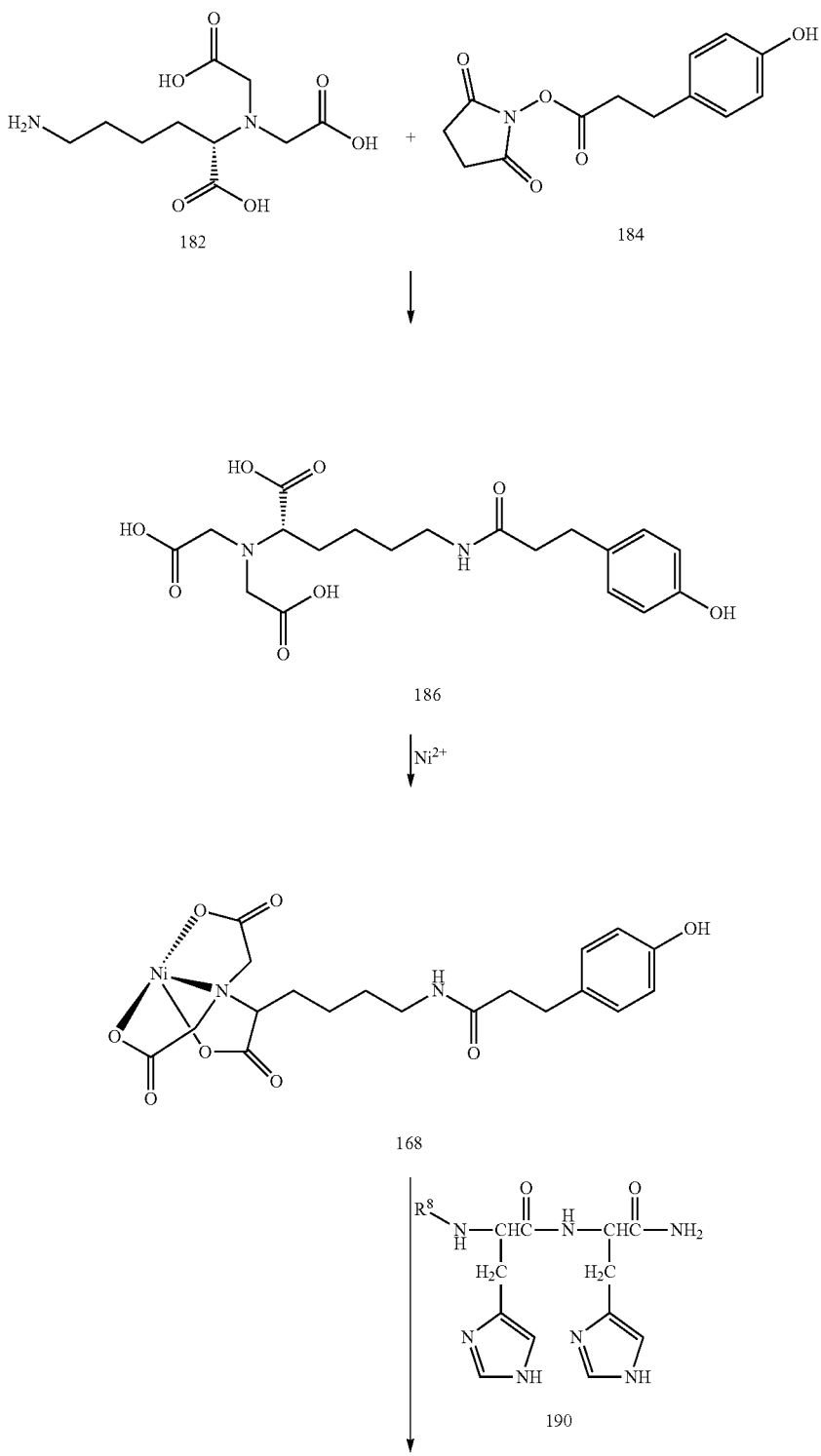

-continued

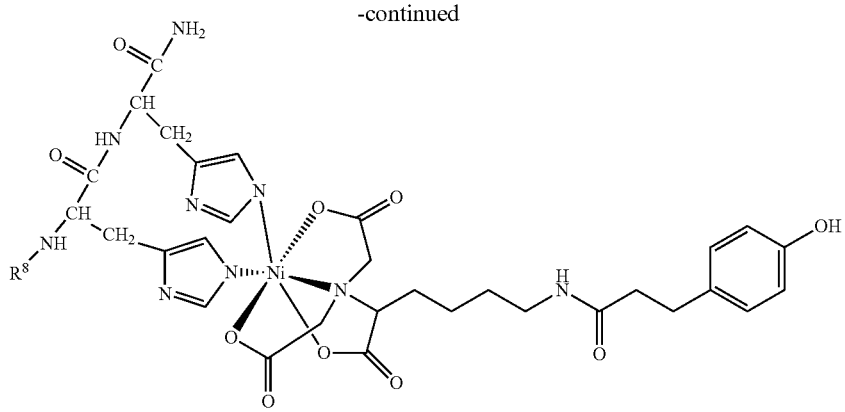

192

One embodiment of a method for making a stable-isotope-labeled mass tag precursor pair capable of reacting with naphthol phosphate in the presence of a phosphatase, e.g., alkaline phosphatase, to produce aryl azo dyes is illustrated below in Scheme 21. The mass tag precursor pair is suitable for use in a multiplexed assay, such as a duplexed assay, to detect and quantify two biomarkers, or two forms of a single biomarker, in a tissue sample. An isotopically-labeled mass tag precursor pair can be used, for example, to detect relative amounts of ER and PR breast cancer biomarkers in a tissue sample. In some embodiments, the isotopically-labeled mass tag precursor pair can be used to detect two forms of a biomarker, such as intact Her2 and truncated Her2.

Aniline 194 and deuterated aniline analogs, such as aniline-d5 198, are converted to benzene diazonium cations 196 and 200, respectively, by reaction with sodium nitrite and acid (e.g., tetrafluoroboric acid) to produce a "light" diazonium salt that may be used to produce a "light" mass tag precursor and a "heavy" diazonium salt that may be used to produce a "heavy" mass tag precursor:

Scheme 21

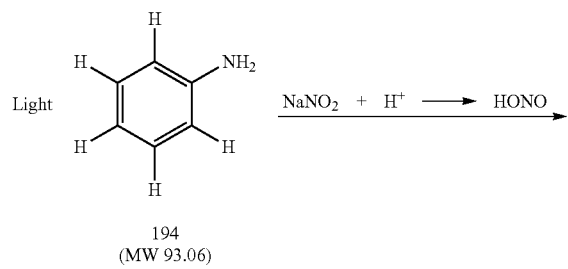

194
(MW 93.06)

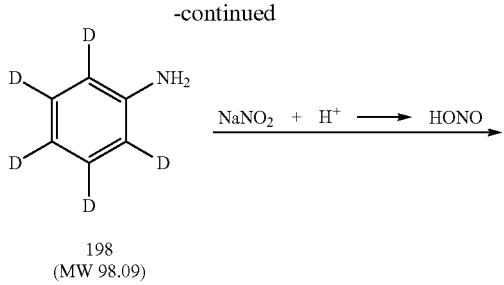

198
(MW 98.09)

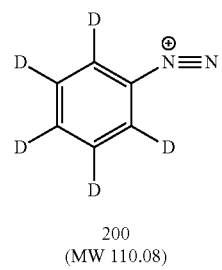

200
(MW 110.08)

The diazonium salts react with a naphthol phosphate in the presence of a phosphatase enzyme to produce an azo dye mass tag precursor, which precipitates as a mass tag, which is ionizable to produce reporter ions, or mass codes, with the same chemical structure but having molecular weights that differ by as little as 1 Dalton, and perhaps 2-5 daltons (Scheme 22).

Scheme 22

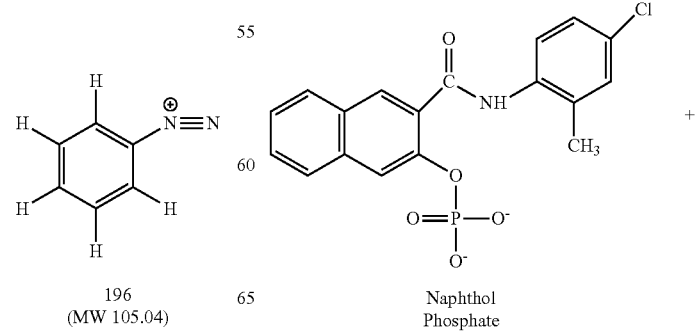

196
(MW 105.04)

Naphthol
Phosphate

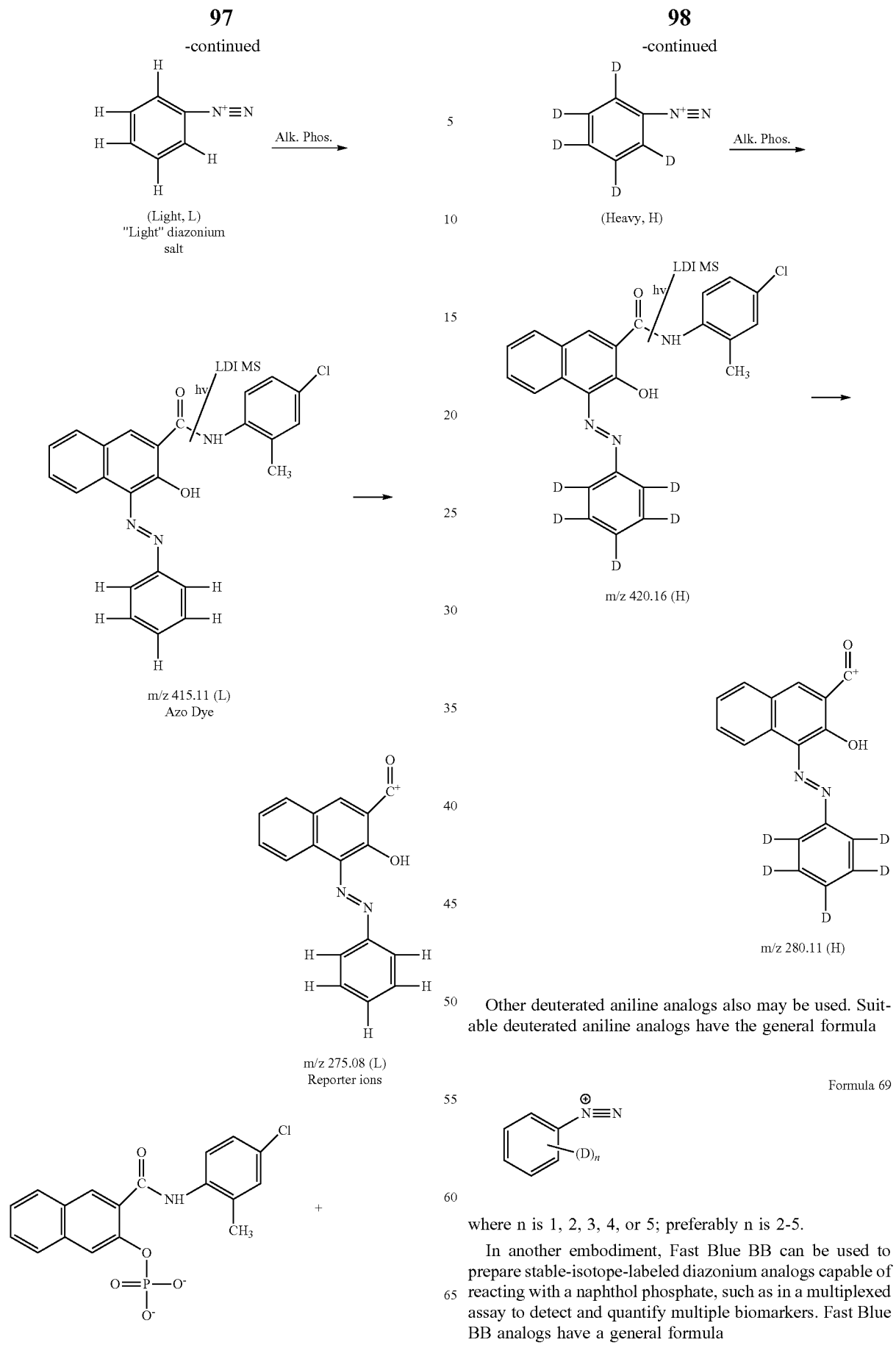

Other deuterated aniline analogs also may be used. Suitable deuterated aniline analogs have the general formula Formula 69 where n is 1, 2, 3, 4, or 5; preferably n is 2-5.

In another embodiment, Fast Blue BB can be used to prepare stable-isotope-labeled diazonium analogs capable of reacting with a naphthol phosphate, such as in a multiplexed assay to detect and quantify multiple biomarkers. Fast Blue BB analogs have a general formula

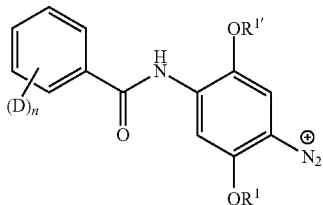

Formula 70 where n is 0, 1, 2, 3, 4, or 5. $R^1$ and $R^{1'}$ are independently alkyl, preferably lower alkyl, and may include one or more isotopes. Suitable $R^1$ and $R^{1'}$ groups include, for example, $-CD_3$ and $-CD_2CD_3$.

In a particular embodiments, a set of diazonium salt analogs are capable of reacting with a naphthol phosphate in a quadruplexed assay to detect and quantify up to four biomarkers, such as an assay for the breast cancer markers ER, PR, Her2, and Ki67. In this example, the diazonium salts increase in molecular weight by increments of 5 daltons.

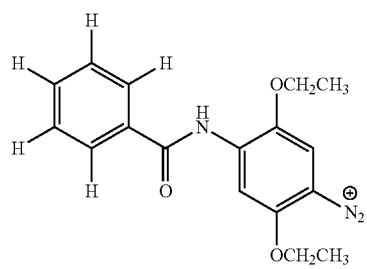

Fast Blue BB
m/z 312.13

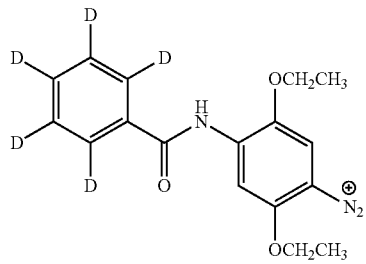

m/z 317.17

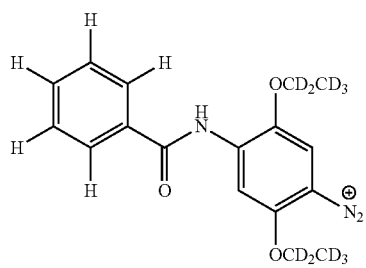

m/z 322.2

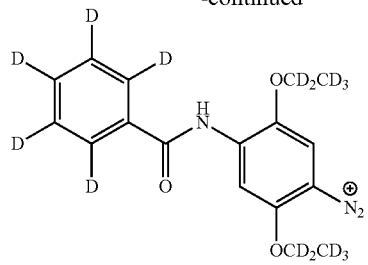

m/z 327.23

Although the preceding examples illustrate isotopic labeling with deuterium, other stable isotopes can be used. For example, hydrogen atoms can be replaced by tritium atoms, carbon atoms can be replaced by $^{13}C$ isotopes, nitrogen atoms can be replaced by $^{15}N$ isotopes, and/or oxygen atoms can be replaced by $^{17}O$ isotopes. It also is contemplated that a mixture of isotopes, e.g., $^2H$ and $^{13}C$, can be used to create a greater variety of stable-isotope-labeled mass tag precursors.

In some embodiments, isotopically labeled precursors, e.g., aniline-d5, may be commercially available. In other embodiments, mass tags can be synthesized or labeled with isotopes using methods known to those of ordinary skill in the art of organic synthesis. Isotopic labeling can be performed with any mass tag, mass tag precursor, mass tag, mass code, and/or enzyme substrate moiety disclosed herein to produce a series of two or more mass tags, mass tag precursors, mass codes, and/or enzyme substrate moieties suitable for use in multiplexed assays to yield two or more mass codes having the same chemical structure but different molecular weights.

Suitable isotope-labeled mass tags differ in mass sufficiently to produce mass codes that can be distinguished from one another during mass spectrometric detection. A mass spectrometer may be capable of distinguishing mass codes that differ in mass by only 1 dalton. Accordingly, useful isotope-labeled mass tags differ in mass by at least one dalton. In some embodiments, isotope-labeled mass tags differ from one another in mass by at least 1 dalton to at least 50 daltons, more typically at least 1 dalton to about 20 daltons, even more typically at least 1 dalton to about 10 daltons, with working embodiments being exemplified by a mass difference of 1-5 daltons, such as by 1, 2, 3, 4, or 5 daltons. In particular working examples, isotope-labeled mass tags differ from one another in mass by 5 daltons.

Figure 8:
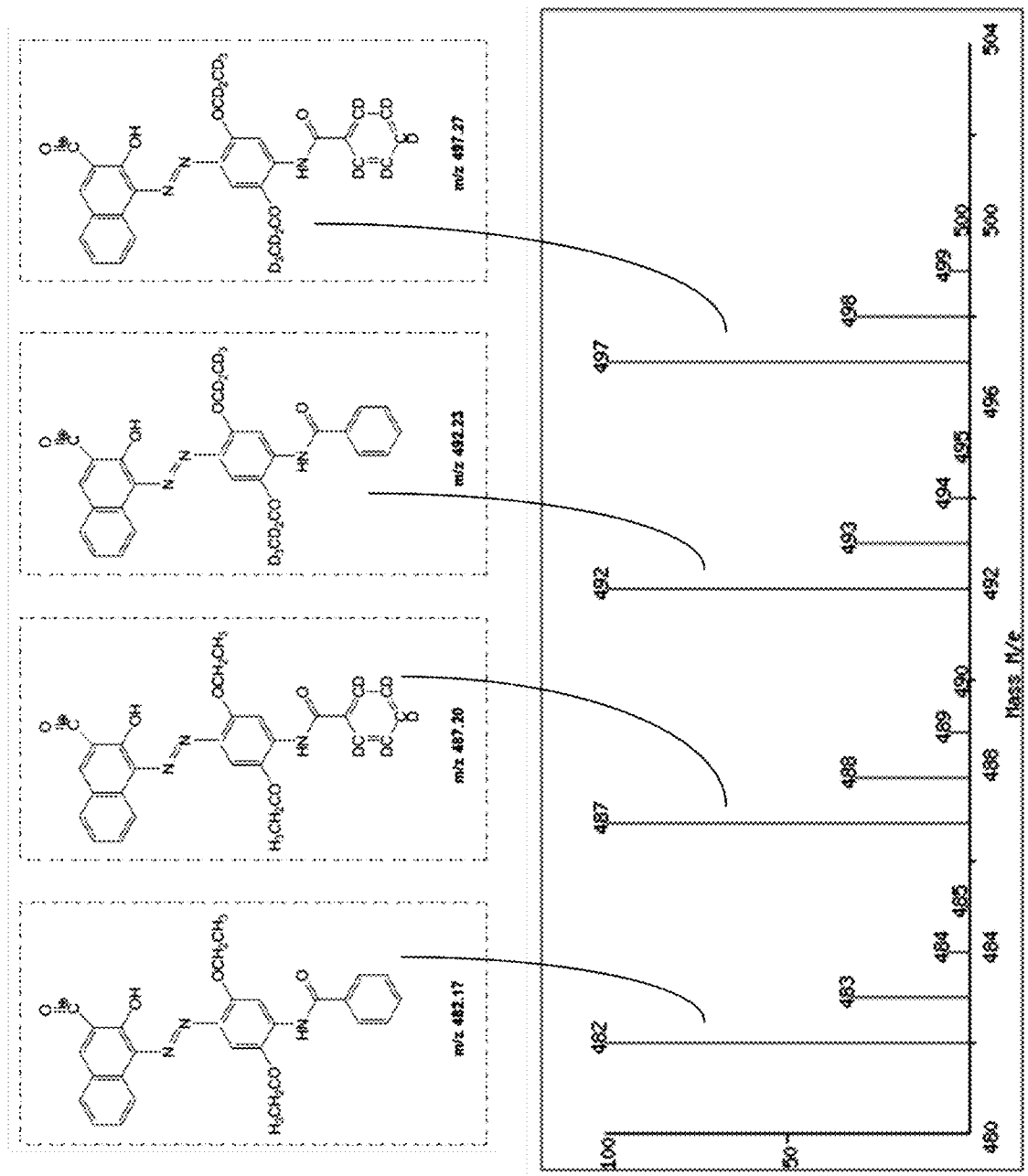
FIG. 8 illustrates the expected reporter ions (mass codes) and mass spectrum produced by one embodiment of a method for detecting four antigens with four stable-isotope-labeled mass tags.

Due to naturally occurring isotopes, it is expected that any given mass tag, and its corresponding mass code, will have some variability in its molecular weight. For example, some molecules may contain one or more "naturally occurring" deuterium atoms, tritium atoms, $^{13}C$ atoms, $^{14}C$ atoms, $^{15}N$ atoms, etc. Thus, a given mass code may produce MS peaks at the expected m/z value, x, as well as progressively smaller peaks having m/z values of x+n where n is an integer. In particular embodiments, n ranges from 1 to 3 or 1 to 4. Typically, peaks are not seen at x+4 or greater. For example, a reporter ion with an expected m/z of 482 typically will generate progressively smaller peaks at 483, 484, and 485. Although mass codes having a m/z difference of just 1 dalton can be detected separately, if isotope-labeled pairs have a mass difference of less than 4 daltons, there may be at least some overlap between the MS peaks produced by the two mass codes. Any significant overlap can reduce accuracy when quantifying the amount of mass codes corresponding to each target within the tissue sample. A mass difference of at least 4 daltons, or at least 5 daltons, provides insignificant or no overlap between MS peaks produced by the mass codes. Thus, in some embodiments, the mass difference between any given pair of stable-isotope-labeled mass tags, mass tag precursors, or mass codes having the same chemical structure is at least 4 daltons. In particular embodiments, the mass difference is at least 5 daltons. FIG. 8 depicts the mass spectrum expected from the four reporter ions produced from mass tags formed when the four Fast Blue BB mass tag precursors shown above react with naphthol phosphate in the presence of a phosphatase enzyme, and the mass tags subsequently are ionized in a mass spectrometer.

XI. Targets

Particular embodiments concern using nucleic acid sequences or proteins (e.g. Her1, Her2, Her3, Her4, ER, PR, and p95Her2), or combinations of nucleic acids or proteins, as targets in multiplexing analysis, particularly where such detection provides better diagnostic capabilities for a particular malady. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. As another example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof. In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample. In one example, the genomic target nucleic acid sequence is selected to include a gene (e.g., an oncogene) that is reduplicated in one or more malignancies (e.g., a human malignancy). For example, Her2, also known as c-erbB2 or Her2/neu, is a gene that plays a role in the regulation of cell growth (a representative human Her2 genomic sequence is provided at GENBANK™ Accession No. NC_000017, nucleotides 35097919-35138441). The gene codes for a 185 kd transmembrane cell surface receptor that is a member of the tyrosine kinase family. Her2 is amplified in human breast, ovarian, and other cancers. Therefore, a Her2 gene (or a region of chromosome 17 that includes the Her2 gene) can be used as a genomic target nucleic acid sequence, or its protein product can be used as a target protein. Other breast cancer relevant proteins include ER, PR, and Ki67.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with maladies, such as neoplastic transformation and/or growth are known to those of ordinary skill in the art, or shall be hereafter discovered. Target proteins that are produced by nucleic acid sequences (e.g., genomic target nucleic acid sequences), which have been correlated with neoplastic transformation are useful in the disclosed methods.

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum, Entamoeba histolytica,* and *Giardia lamblia,* as well as *Toxoplasma, Eimeria, Theileria,* and *Babesia* species). In some examples, the target protein is produced from a nucleic acid sequence (e.g., genomic target nucleic acid sequence) from a viral genome.

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

XII. Method of Using Disclosed Embodiments of the Mass Tag Precursor Conjugate

Disclosed embodiments herein concern a method for imaging and/or quantifying one or more targets in a sample, e.g., a tissue sample such as a formalin-fixed, paraffin-embedded tissue sample, using mass tag precursors, mass tags, mass codes, and mass spectrometric (MS) techniques, such as laser desorption/ionization, including laser desorption/ionization (LDI). Some embodiments use an enzyme substrate and a separate mass tag precursor. The enzyme converts the substrate into an active species that can react with the mass tag precursor to deposit a mass tag, such as by precipitation, at the target site. Other embodiments use a conjugate comprising a mass tag precursor coupled directly or indirectly to an enzyme substrate moiety. The mass tag precursor may be bonded to the enzyme substrate moiety by one or more covalent bonds, one or more ionic bonds, any other bonding association sufficiently robust to produce a conjugate suitable for use in the method, and combinations of bonds. The mass tag precursor and the enzyme substrate moiety can be coupled directly together, or can be coupled using a linker.

Other particular embodiments concern using an enzyme substrate and a mass tag precursor conjugate. The enzyme converts the mass tag precursor conjugate into an activated species that is effectively coupled (e.g. covalently bound) to tyrosine moieties proximal to the target, such as at tyrosine moieties on the enzyme, on the specific binding moiety, or on the target.

In certain embodiments concerning samples having multiple targets, each target is identified and detected using a mass tag, typically a different mass tag. For certain disclosed embodiments, the mass tags have the same chemical structure but include different isotopes and/or different amounts of a particular isotope such that each mass tag has a different mass. Using mass tags with the same chemical structure facilitates accurate target quantification, wherein quantification comprises determining the size of a mass peak and correlating it with the amount of the target.

A sample having a target of interest is first contacted with an enzyme, which may be coupled to a specific binding moiety that recognizes a particular target, or region of a target, such as an epitope. The sample is then exposed to the conjugate, or plural such conjugates. A mass tag is deposited at the site of a target in a sample, such as by precipitation, at the target for subsequent detection by MS in the form of a mass code (an ion).

The mass tags as described herein are deposited (covalently or non-covalently) or precipitated at a target location, or multiple target locations, where they are exposed to laser-initiated ionization, producing mass codes, which are detected using LDI mass spectrometry. However, it is contemplated that additional mass spectrometry technologies are adaptable and amenable to the disclosed compositions for tissue target identification. For example, desorption electrospray ionization (DESI; Wiseman et al., 2008, Proc. Natl. Acad. Sci. 105:18120-18125) mass spectrometry, secondary ion mass spectroscopy (SIMS; Boxer et al., 2009, Annu. Rev. Biophys. 38:53-74), laser ablation inductively coupled plasma mass spectrometry (LA-ICP; Becker et al., 2010, Mass. Spectrom. Rev. 29:156-175), and laser ablation flowing atmospheric pressure afterglow ambient pressure mass spectrometry (LA-FAPA; Shelley et al., Anal. Chem. 2008, 80, 8308-8313) are technologies known in the art that could be adapted for use in tissue target identification using the disclosed mass tag precursor conjugate. As such, disclosed embodiments herein are not limited to the method of mass spectrometry utilized for detection purposes.

A general depiction of one embodiment of a method for using deposition of mass tags is provided in FIG. 1. FIG. 1 illustrates a target 2, which is first labeled with an antibody-enzyme conjugate 4 such that the antibody specifically binds to a target epitope or a probe hybridized to a nucleic acid target sequence. Conjugate 4 is added at a concentration and in a manner effective to allow the antibody (or other specific binding moiety) to detect the target 2. The sample is then exposed to an enzyme substrate solution or a mixture of substrate and mass tag precursors 6 simultaneously or sequentially so that, after the enzymatic reaction, mass tags 8 deposit at the site of the target 2 to produce a precipitate of mass tags 8 localized at the target 2. These mass tags 8 are readily ionized to mass codes 10 and desorbed from the sample by laser irradiation, and further detected in a mass detector (TOF, for example).

Figure 2:
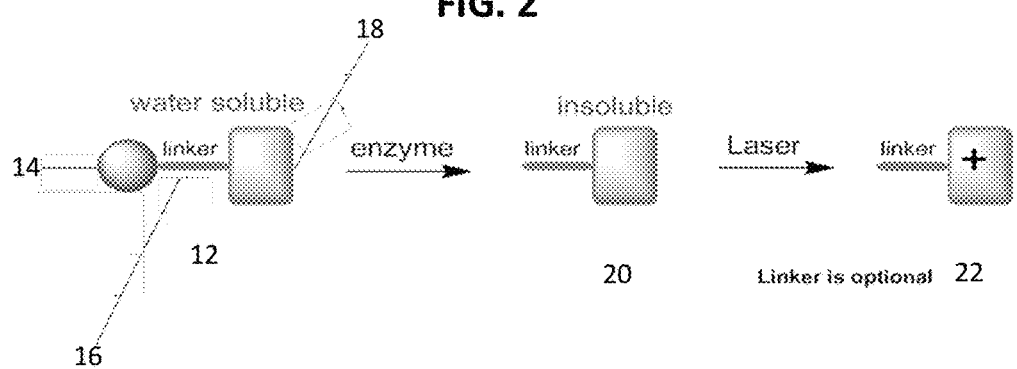
FIG. 2 is a schematic diagram illustrating the general concept of a method for directly depositing a mass tag comprising a linker through enzymatic reaction.

FIG. 2 illustrates a particular disclosed embodiment of the disclosed method. Conjugate 12 comprising an enzyme substrate 14 (typically a hydrophilic substrate) is coupled to a mass tag precursor 18. The enzyme substrate 14 may be coupled directly to the mass tag precursor 18, or optionally coupled to the mass tag precursor by a linker 16. In the presence of an enzyme, the enzyme substrate 14 is separated from the conjugate 12 to produce a water-insoluble mass tag 20 at a desired target location, such as by precipitation. A mass code 22 is formed, such as by laser-initiated ionization, to produce a MS detectable signal.

Figure 3:
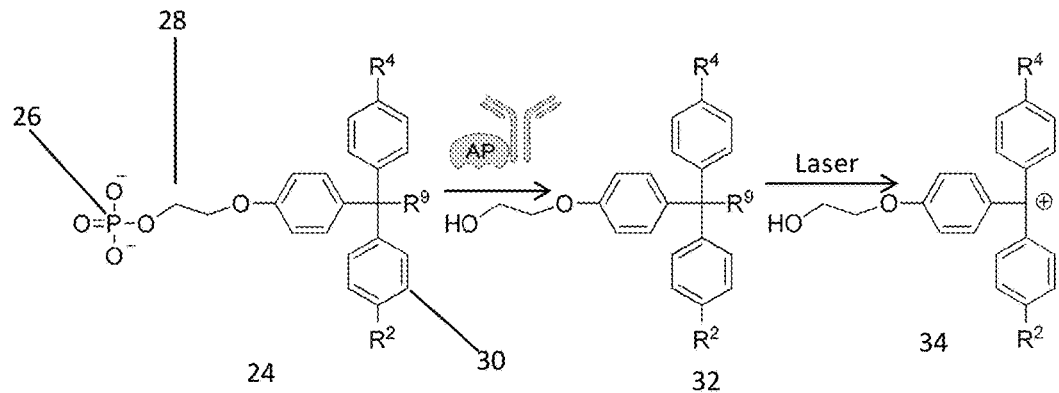
FIG. 3 is a schematic diagram illustrating one embodiment of a method whereby the enzyme substrate moiety of the mass tag precursor conjugate is cleaved by an enzyme to generate an insoluble mass tag, which is readily ionized and detected under UV laser irradiation as a mass code.

FIG. 3 is a schematic diagram illustrating detection of a target in a sample using a conjugate 24. Conjugate 24 comprises an enzyme substrate 26 (e.g., an enzyme substrate) coupled to a mass tag precursor 30 by an ethylene oxy linker 28. An enzyme, e.g., alkaline phosphatase (AP), cleaves the enzyme substrate 26 from the conjugate 24 to produce a water-insoluble mass tag 32. Mass code 34 is formed from the water-insoluble mass tag 32, such as by laser-initiated ionization. However, a person of ordinary skill in the art will appreciate that other types of enzymes and hence enzyme substrate moieties can be used to practice particular embodiments.

Figure 4:
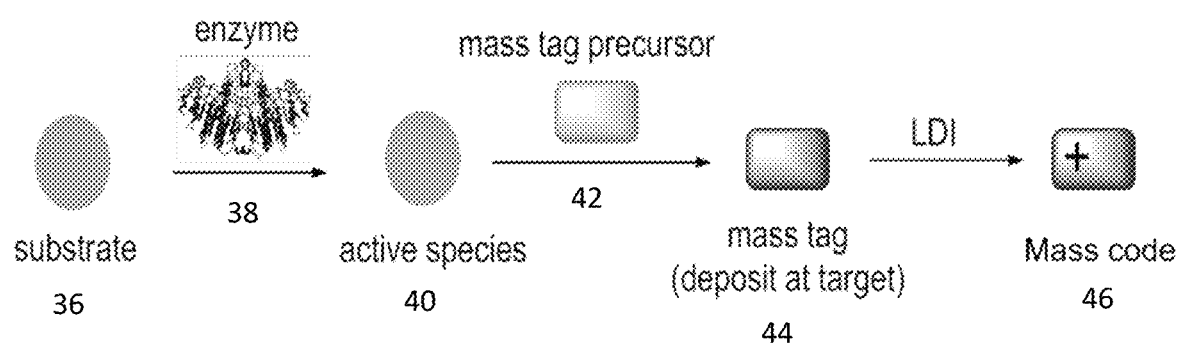
FIG. 4 is a generalized schematic diagram illustrating a method comprising forming an active species and converting a mass tag precursor to a mass tag.

FIG. 4 is a schematic representation of another disclosed embodiment of the current method. FIG. 4 illustrates using an enzyme 38 to convert a substrate 36 into an "active" species 40. The term "active" in this context refers to a compound that can react or interact with a mass tag precursor 42 to deposit a mass tag 44, such as by precipitation, at a desired target site. For example, the active species 40 might be a reducing agent that donates one or more electrons to the water-soluble mass tag precursor 42 to produce a water-insoluble mass tag 44 at the desired target location. The precipitate is then converted to a mass code 46, such as by using an LDI laser.

Figure 5:
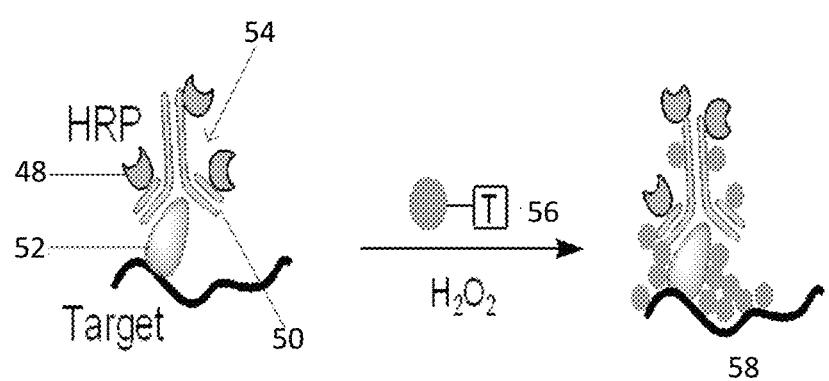
FIG. 5 is a schematic diagram illustrating one embodiment of a method for binding mass tag precursor conjugate comprising tyramine, or a derivative thereof, proximal to the target using an enzyme-specific binding moiety conjugate.

A general depiction of one embodiment of a method for using a mass tag precursor conjugate is provided in FIG. 5. An enzyme-specific binding moiety conjugate 54, comprising an enzyme 48 and an antibody 50 is bound to a target 52 in a sample. A mass tag precursor conjugate 56, comprising a tyramine or a tyramine derivative, is then added to the sample. The enzyme 48 acts to effectively couple conjugate 54 proximal to the target 52, the enzyme 48, or the antibody 50 to produce complex 58.

Figure 9:
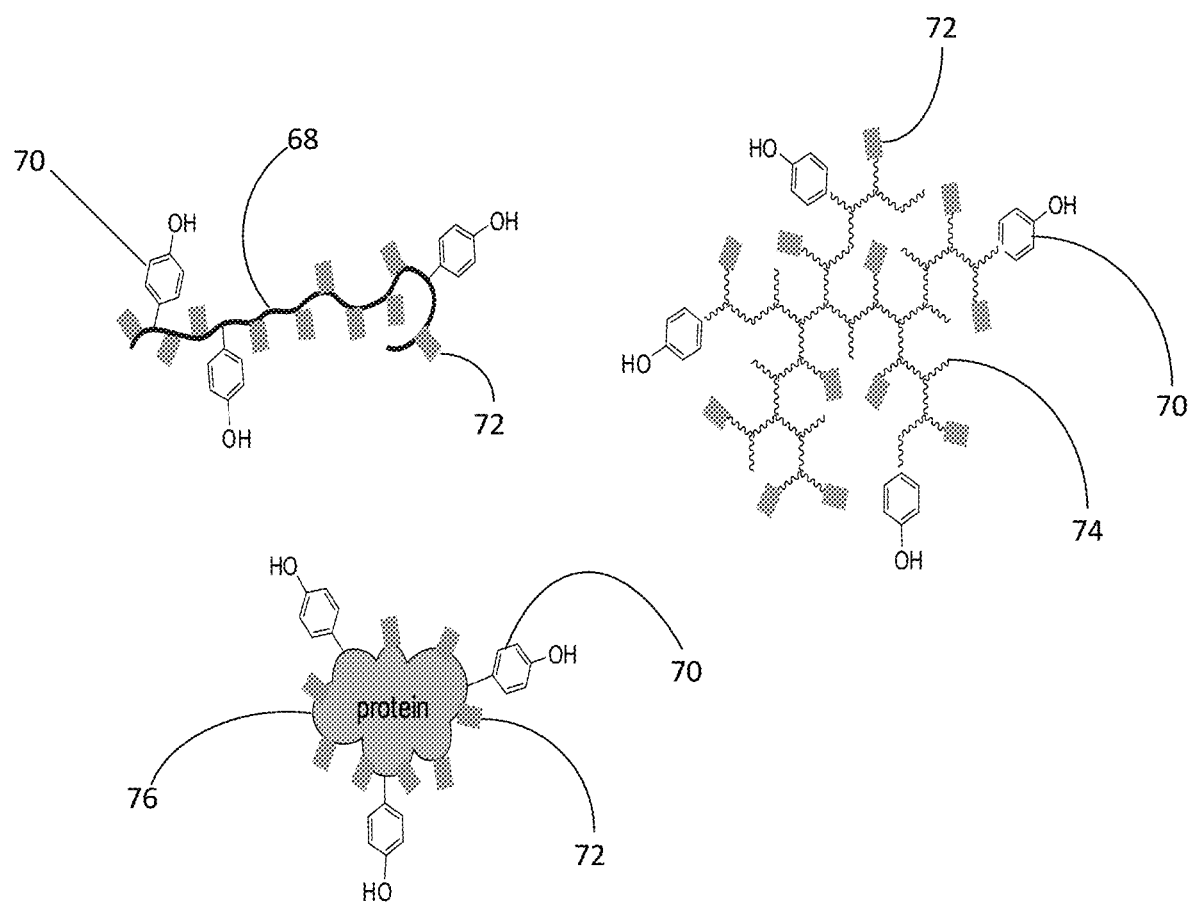
FIG. 9 illustrates embodiments of carriers, such as polymers and biomolecules, which can bind multiple mass tag precursor and tyramine.

The mass tag precursor, and tyramine or tyramine derivative, or multiple such moieties, also can be used in conjunction with polymers, biomolecules, and/or nanoparticles to achieve deposition of multiple tyramine, tyramine derivatives, and mass tags, thus increasing the chances of reliable detection. FIG. 9 illustrates embodiments of the carriers, such as polymers and biomolecules, which can bind multiple mass tag precursors, tyramine moieties, and/or tyramine derivatives. A linear polymer carrier 68 can be used to bind multiple tyramine moieties 70 and effectively couple the tyramine moieties with a mass tag precursor 72. Hyperbranched polymers 74 can be used in the same manner, as can biomolecules, such as protein 76.

Figure 10:
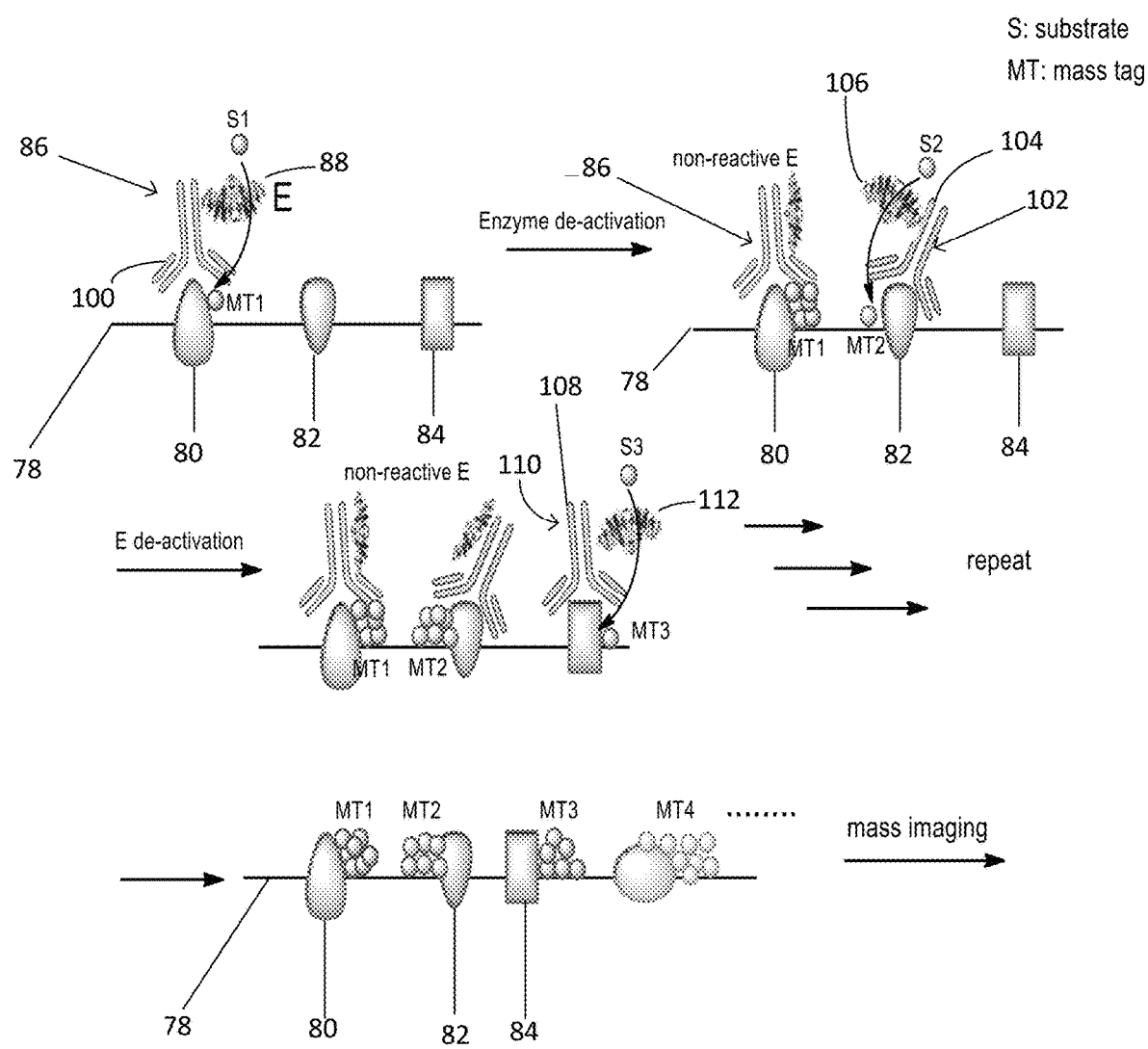
FIG. 10 is a schematic diagram illustrating one disclosed embodiment of a multiplexed detection scheme for detecting multiple targets in a sample using enzymatic mass tag detection protocols.

In illustrative embodiments, a multiplexed analysis of a sample is disclosed. One such multiplexed embodiment is illustrated in FIG. 10. A sample 78 includes plural different targets 80, 82 and 84. Sample 78 is contacted with a first conjugate 86 comprising a specific binding moiety 100, such as an antibody, and an enzyme 88 in a manner effective to allow the specific binding moiety to bind to target 80. The resulting complex is then treated with a substrate 51 suitable for the particular enzyme 88 to precipitate a mass tag MT1 at target 80. FIG. 10 illustrates using alkaline phosphatase and an enzyme deactivation step to deactivate enzyme 88 of conjugate 86 prior to contacting sample 78 with a second conjugate 102. A person of ordinary skill in the art will appreciate that the enzymes need not be the same. In embodiments where different enzymes are used, there may be no need for an enzyme deactivation step. Conjugate 102 comprises a specific binding moiety 104, such as an antibody, and an enzyme 106, such as HRP. The sample is then contacted with a substrate S2 for the enzyme 106 to precipitate a mass tag MT2 at target 82. A deactivation step is performed to deactivate the second enzyme. FIG. 10 illustrates a third target 84 and a third conjugate 110 comprising specific binding moiety 108 and enzyme 112. The sample 78 is then treated with substrate S3 suitable for reaction with enzyme 112, thereby precipitating a mass tag MT3 at target 84. Once all desired targets are detected with a suitable conjugate having an appropriate specific binding moiety, the sample is irradiated, such as by using an LDI laser, to produce mass codes at the targets that can be detected using a suitable MS technique.

Certain disclosed examples of multiplexed analysis include using a first enzyme to produce a first mass tag to detect a first target, and then using a second enzyme to detect a second target. For example, a first target in a sample can be detected using an alkaline phosphatase-catalyzed mass tag deposition approach, as discussed above. A second target can be detected using a second enzyme, such as horseradish peroxidase. A person of ordinary skill in the art will appreciate that even additional targets can be detected using yet a third, or even more, enzymatic reactions to deposit a mass tag at a target in sample. Thus, this detection approach is referred to as a plural enzyme, such as a dual enzyme, system.

Figure 11:
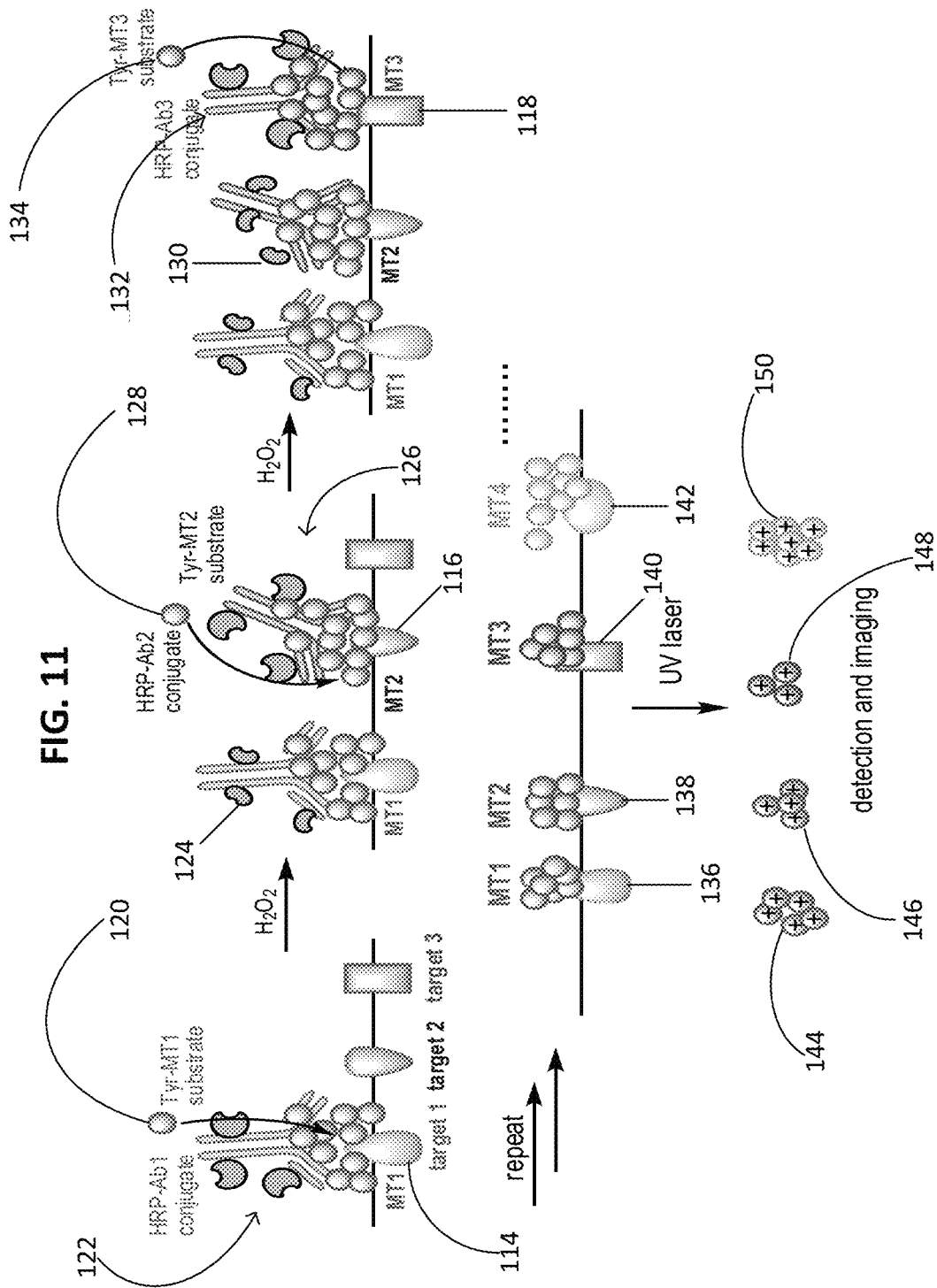
FIG. 11 is a schematic diagram illustrating one embodiment in which a mass tag precursor conjugate comprising tyramine, or a derivative thereof, is used in a multiplexing technique.

Plural enzymes need not be used. Instead, a single enzyme, with plural intervening enzyme deactivation steps can be used. For example, a first target may be detected by a first enzymatic reaction. Residual enzyme from the first aliquot then is deactivated. For example, horseradish peroxidase can be used, and after a first mass tag is deposited at a first target, residual horseradish peroxidase can be deactivated using excess hydrogen peroxide. The second target is then detected using a second mass tag deposited using a second horse radish peroxidase reaction. Particular embodiments of a multiplexing method concern using a mass tag precursor conjugate. One such multiplexed embodiment is illustrated in FIG. 11 for detecting a plurality of targets 114, 116, and 118. A mass tag precursor conjugate 120, comprising a tyramine or tyramine derivative, is bound to a target 114 proximal to the first enzyme-specific binding moiety conjugate 122, to form complex MT1. Once complex MT1 has been formed, deactivated enzyme 124 of the first enzyme-specific binding moiety is obtained by addition of an excess of a peroxide reagent, in this case hydrogen peroxide ($H_2O_2$) or a combination of peroxide and EDTA. After this deactivation step, the sample is washed to remove the excess peroxide reagent. A second enzyme-specific binding moiety conjugate 126 is then added and bound to the target 116. A second mass tag precursor conjugate 128 is deposited onto a second target site 116 to form complex MT2. Once complex MT2 has been formed, deactivated enzyme 130 of the second enzyme-specific binding moiety is obtained by addition of an excess of a peroxide reagent, in this case hydrogen peroxide ($H2O_2$) or a combination of peroxide and EDTA. After this deactivation step, the sample is washed to remove the excess peroxide reagent. A third enzyme-specific binding moiety conjugate 132 is then added and bound to the target 118. A third mass tag precursor conjugate 134 is deposited onto a third target site 118 to form complex MT3. This sequence can be repeated any number of times to provide multiple mass tag-target complexes, 136, 138, 140 and 142. Upon ionization of the mass tags, a plurality of mass codes, 144, 146, 148, and 150 are produced, which can then be detected using mass spectrometry. This multiplexing technique provides detection of multiple targets of interest on the same tissue sample, which may be of significant medical value.

Embodiments of the disclosed stable-isotope-labeled mass tag precursors, mass tags, and mass codes are suitable for multiplexed assays, wherein multiple targets in a sample, such as a tissue sample, are imaged and quantified using mass tags and MS techniques. Suitable targets include proteins, peptides, and nucleic acid sequences such as DNA and/or RNA sequences of interest. In some embodiments, the targets are cancer biomarkers. In certain embodiments, an enzyme is immobilized on the target. The enzyme is exposed to a mass tag precursor and an enzyme substrate moiety with which the enzyme is capable of reacting. The reaction forms a mass tag precursor conjugate comprising the enzyme substrate moiety and mass tag precursor, and the mass tag is deposited proximal to the target. A mass code, or reporter ion, is subsequently cleaved from the mass tag and detected by mass spectrometry.

When multiple targets are present, an enzyme is immobilized at each of the targets. Each enzyme is exposed to a mass tag precursor and an enzyme substrate moiety with which the enzyme is capable of reacting, thereby forming mass tags proximal each target. A mass code, or reporter ion, is subsequently cleaved from each mass tag and detected by MS. In some embodiments, the targets are cancer biomarkers. In certain embodiments, the sample is formalin-fixed, paraffin-embedded (FFPE) tissue.

Stable isotope label-based mass spectrometry imaging (SILMSI) has several advantages compared to conventional IHC tissue analysis. In some embodiments, SILMSI provides accurate detection for simultaneous quantification wherein quantification comprises determining the size of a mass peak and correlating it with the amount of multiple cancer biomarkers on FFPE tissue. In certain embodiments, SILMSI techniques demonstrate good linearity (e.g., $0.96 \leq R^2 \leq 0.99$) within a dynamic range of $10^3$ in the mass spectrometric peak intensity measurement. SILMSI provides objective, quantitative information for multiple biomarkers, whereas IHC images typically are evaluated subjectively by trained medical personnel. SILMSI can provide a medical practitioner with more accurate information for a patient's cancer diagnosis and prognosis, thereby enabling the practitioner to devise a personalized treatment plan for the patient.

In one embodiment, a first target is contacted with a first enzyme, which may be coupled to a specific binding moiety that recognizes the first target, or a region of the first target, such as an epitope, within the tissue sample. The tissue sample then is exposed to the enzyme substrate moiety and a first mass tag precursor. The enzyme substrate moiety reacts with the enzyme and the mass tag precursor, thereby depositing a mass tag at the site of the target in a sample, such as by precipitation. A subsequent target is contacted with a subsequent enzyme, which may be coupled to a specific binding moiety that recognizes the subsequent target, or a region of the subsequent target. The subsequent enzyme may the same or different, than the first enzyme. The sample then is exposed to the enzyme substrate moiety and a subsequent mass tag precursor. A mass tag is deposited at the site of the subsequent target in the sample. The first mass tag and the subsequent mass tag have substantially the same chemical structure, but differ in molecular weight. The molecular weight is varied by replacing particular atoms in the chemical structure of the mass tag precursor and/or the enzyme substrate moiety with isotopes of those atoms. For example, hydrogen atoms may be replaced with deuterium atoms. The mass codes are subsequently cleaved from the tags and detected by MS. The amounts of the mass codes are quantified to determine the relative amounts of each target in the sample.

With reference to FIGS. 10 and 11, in some embodiments, each mass tag (MT1, MT2, and MT3) has the same chemical structure, but the mass tags differ in molecular weight due to the presence of isotopes. In such embodiments, a single enzyme, with plural intervening enzyme deactivation steps, typically is used since each mass tag has the same chemical structure. For example, a first target may be detected by a first enzymatic reaction. Residual enzyme from the first reaction then is deactivated. For example, horseradish peroxidase can be used, and after a first mass tag is deposited at a first target, residual horseradish peroxidase can be deactivated using excess hydrogen peroxide. The second target is then detected using a second mass tag deposited using a second horseradish peroxidase reaction.

Figure 12:
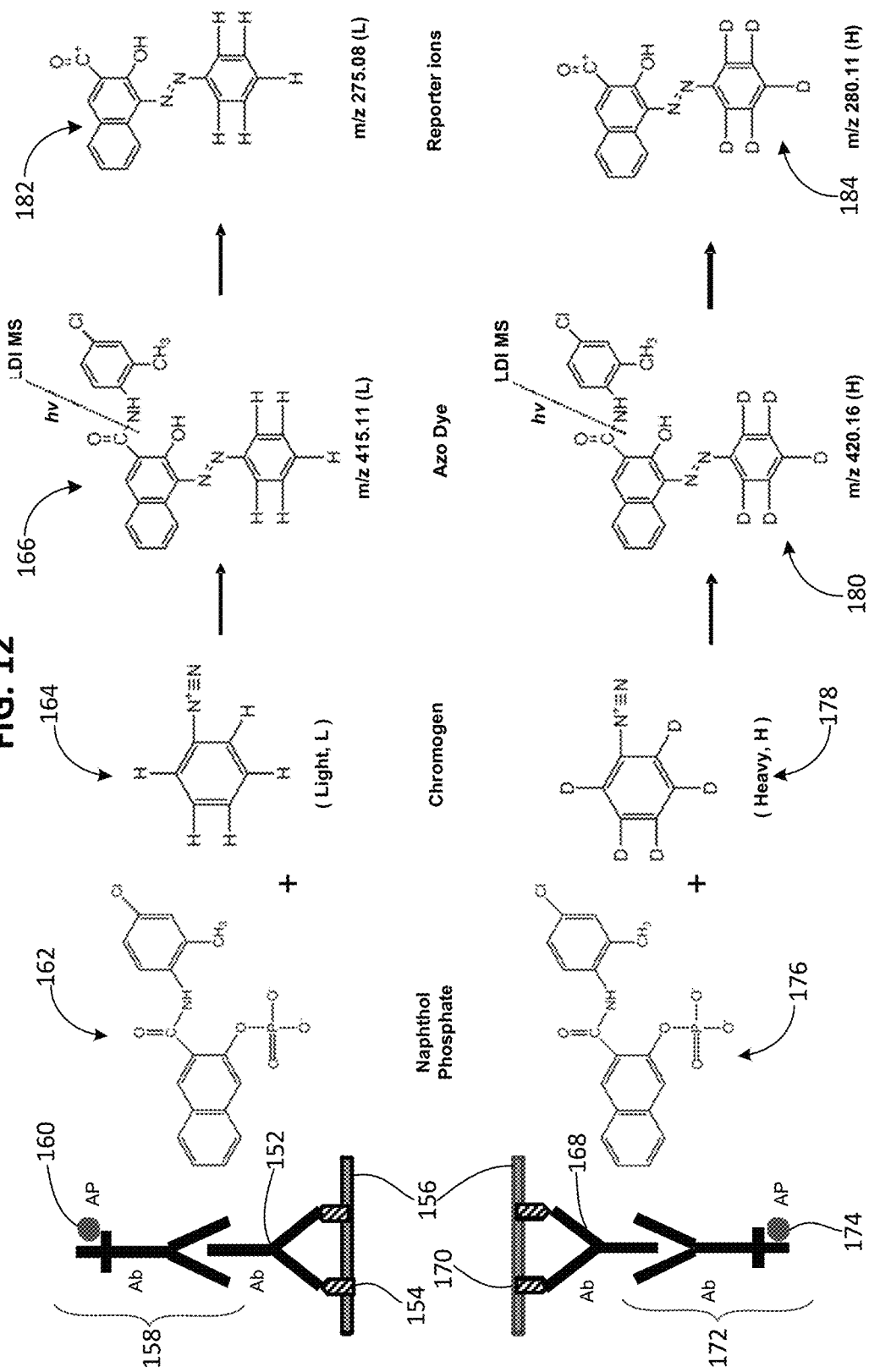
FIG. 12 is a schematic diagram illustrating one embodiment of a method for simultaneously quantifying two biomarkers on FFPE tissue.
Figure 13:
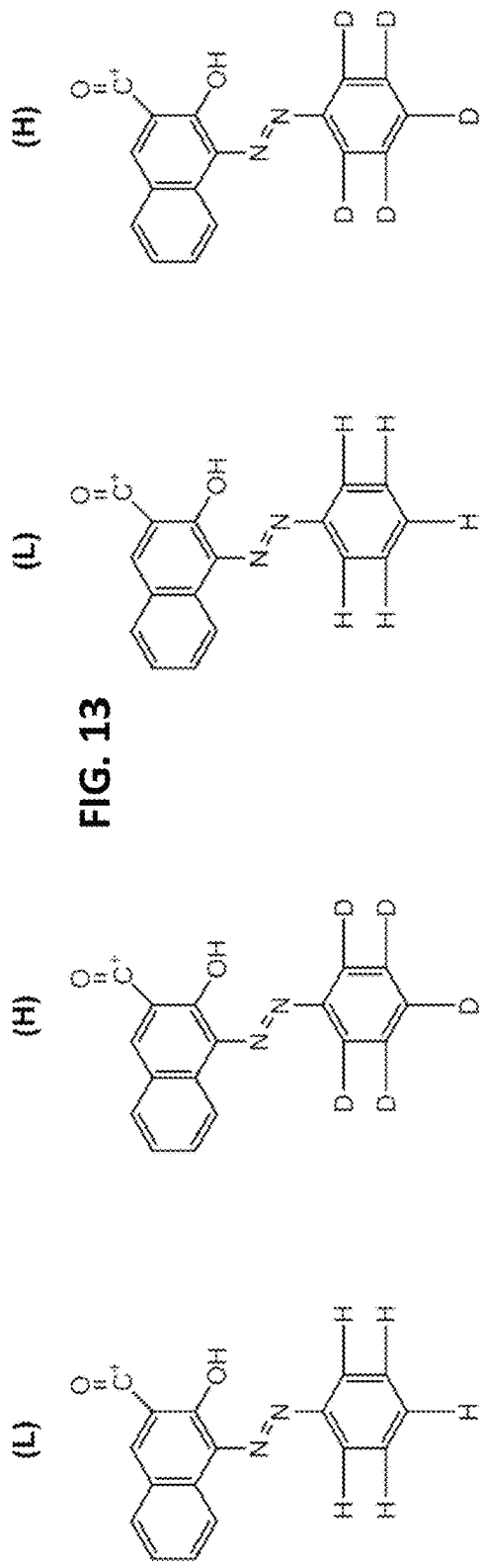
FIG. 13 illustrates the expected reporter ions and the spectra obtained when detecting two antigens with light and heavy stable-isotope-labeled mass tags.

One embodiment of a method for quantifying plural targets (e.g., cancer biomarkers) on FFPE tissue is shown in FIG. 12. A first antibody 152 capable of recognizing and binding to a first antigen 154 (e.g., a first biomarker) is applied to formalin-fixed, paraffin-embedded tissue 156 mounted on a slide. A first antibody-enzyme conjugate 158 capable of recognizing and binding to the first antibody 152 is applied. In the embodiment shown, the first antigen 154 is ER, and the antibody-enzyme conjugate 158 includes alkaline phosphatase 160. The first antigen 154 is detected by adding an enzyme substrate 162 and a first diazonium species 164. The enzyme 160 reacts with and activates the first enzyme substrate 162, which then reacts with the first diazonium 164 to deposit a first mass tag 166 in the target (i.e., antigen 154) vicinity, thereby staining first antigen 154 with a mass tag 166 (e.g., a "light" mass tag that does not include one or more heavier isotopes, such as deuterium). The first antibody-enzyme conjugate 158 is deactivated by any suitable means including chemical deactivation or physical deactivation. A second antibody 168 capable of recognizing a second antigen 170 (e.g., a second biomarker) is applied to the FFPE tissue 156. (Typically, both antigens are detected on the same tissue section on a single slide.) A second antibody-enzyme conjugate 172 capable of recognizing and binding to the second antibody 168 is applied. In the embodiment shown, the second antigen 170 is PR, and the second antibody-enzyme conjugate 172 includes alkaline phosphatase 174. The second antigen 170 is detected by adding an enzyme substrate 176 and a second diazonium salt 178. Enzyme substrates 162 and 176 have the same chemical structure. The first and second diazonium salts 164 and 178 have the same chemical structure, but differ in molecular weight. In the embodiment shown, second diazonium salt 178 has the same chemical structure as first diazonium salt 164, but the hydrogen atoms have been replaced with deuterium. A person of ordinary skill in the art will understand that the method also can be performed utilizing the heavy diazonium salt as first diazonium salt 164 and the light diazonium salt as second diazonium salt 178. The enzyme 174 reacts with and activates the second enzyme substrate 176, which then reacts with the second diazonium salt 178 to deposit a second mass tag 180 in the second antigen's vicinity, thereby staining second antigen 170 with a heavy stable-isotope-labeled mass tag 180. First and second reporter ions 182, 184 (or mass codes) are generated using laser desorption/ionization (LDI) techniques, and the first and second reporter ions 182, 184 are detected and quantified by a mass spectrometer. Because the same enzyme substrate, 162 and 176, is used with both antigens 154, 170, and the diazonium salts 164, 178 differ only in molecular weight, the azo-dye precipitates (mass tags 166, 180) also have the same chemical structure and differ only in molecular weight. Thus, in-source fragmentation of mass tags 166 and 180 upon laser irradiation will have the same efficiency with both azo dyes and will produce reporter ions 182, 184 with the same chemical structure but different molecular weights. The expected mass spectrum produced by reporter ions 182, 184 is shown in FIG. 13 (Experiment 1).

Each mass code produced is detected and the mass code's amount in the tissue sample section is quantified. The size of the tissue sample section depends, in part, on the laser beam size. For example, a laser beam with a diameter of 30 μm may ionize mass tags in a 30 μm×30 μm section of the tissue sample. The laser beam may have a diameter ranging from a just few microns to several hundred microns. In some embodiments, the laser beam has a diameter in the range of 5-200 μm, 10-100 μm, 15-75 μm or 20-50 μm. For example, the laser beam diameter may be 10 μm, 15 μm, 20 μm, 25 μm, 30 μm, 40 μm, 50 μm, 60 μm, 70 μm, 80 μm, 90 μm, or 100 μm.

In some embodiments, after mass tags have been ionized in a tissue sample section, the tissue sample and the laser are moved relative to one another. For example, the tissue sample and/or the laser is repositioned such that the laser is capable of ionizing mass tags in a subsequent section of the tissue sample. In certain embodiments, the tissue sample and/or laser is repositioned a plurality of times, and laser ionization/desorption followed by mass code detection and quantification, wherein quantification comprises determining the size of a mass peak and correlating it with the amount of a target, is performed for a plurality of tissue sample sections. In particular embodiments, rastering is performed, i.e., the tissue sample and/or laser is moved in a grid-like pattern such that mass tags in substantially each section of the tissue sample are ionized and the respective mass codes are detected and quantified. For example, if the laser beam has a diameter of 30 μm and the tissue sample size is 0.9 mm×1.2 mm, the tissue sample is "divided" into a grid of 30×40 sections and data is obtained for the resulting 1200 sections.

Thus, the mass spectrometric image data obtained correlates to regularly-spaced spatial coordinate points of the tissue sample, and each point may contain mass spectrometric information from a plurality of mass codes. The regularly spaced coordinate points taken together represent an 'image' of the sample. To visualize the mass spectra data in two dimensions correlating to the sample sections, relevant information is extracted from the mass spectra at each coordinate and converted to a single scalar value in a two-dimensional array. For example, when detecting two or more targets in a sample, data corresponding to the expected mass codes from each target is extracted from the mass spectra obtained for each tissue sample section (or coordinate) and quantitated. Analytical imaging software can be utilized to convert the data into a two-dimensional image. In a particular embodiment, an in-house program "Ventana Analytical Image" was developed and used.

For each target of interest, a two-dimensional image is created. Each image contains a two-dimensional array of quantitative (numerical) data correlating to the expected mass code produced by a mass tag deposited at a particular target. In some embodiments, the quantitative data may comprise the area, or intensity, of a mass spectrometric peak having a m/z ratio corresponding to an expected m/z ratio of the mass code. In other embodiments, a plurality of mass spectrometric peaks is measured and the measurements combined to quantify the mass code. The plurality of peaks typically includes a primary peak having a m/z ratio of x corresponding to the expected m/z ratio of the mass code and at least one secondary peak having a m/z ratio of x+1, x+2, or x+3.

To create a single image of a tissue sample, numerical data from the individual data arrays corresponding to individual targets is combined by performing mathematical operations on the numerical values to analyze the relationship(s) between values at homologous coordinates. For example, the ratio of two targets, such as ER and PR, may be of interest. In such embodiments, a numerical value corresponding to the ratio of the two targets—as determined by the relative peak sizes produced by the respective mass codes generated from mass tags deposited at each target—at each coordinate is calculated. The numerical values form a single data array representing the target ratios throughout the tissue sample. In theory, the ratio can range from zero to infinity if the mass code corresponding to either target does not produce a measurable peak, such as when there is no mass tag deposited at the target at that particular coordinate. In some embodiments, the ratios range from greater than zero to 100, such as from 0.01 to 100, 0.02 to 50, 0.04 to 25, or 0.1 to 10.

In some embodiments, a visual image representing the numerical data may be desirable. For example, a person reviewing the data may prefer to evaluate the ratios of two targets (e.g., ER and PR) by viewing a color image representing the ratios found in each tissue sample section rather than a numerical grid. In some embodiments, a color or other symbol may be assigned to a range of numerical values, thereby producing a color or symbol map with discrete colors or symbols in a grid-like pattern (see, e.g., FIGS. 14-15). For example, when the ratio is less than 0.7, the color might be green; when the ratio is between 0.7 and 1.5, the color might be yellow; and when the ratio is more than 1.5, the color might be red. In certain embodiments, a "heat map" representation is produced in which colors are assigned across a continuum of values. For example, colors may shade from blue to red as the numerical ratios increase (see, e.g., FIGS. 16-18). For example, as the ratio increases from 0.1 to 4, the colors might vary along a color continuum from blue through yellow to red. Such heat map images provide large amounts of data in a format that is readily interpreted.

Most conventional digital image data analysis software is designed to accept positive integer values typically produced by digital cameras. The ability to handle signed decimal fractions and floating point values is typically provided by mathematical array processing tools. In order to visualize floating point values as image data, a custom software interface based on widely available software libraries for scientific data processing and visualization (Python, Numpy, SciPy, VTK, ITK, wxPython) was developed. The software is capable of reading in numerical arrays in floating point format, as text files, and creating color maps in which numerical values may be assigned to different combinations of hue, saturation, value, and alpha. By applying these types of color maps to the numerical arrays resulting from processing of the mass spectrometric data, the data can be visualized and spatial organization of the tissue sample can be correlated with relationships between analytes, in a quantitative manner. The software tool also can gather statistics about data values and render a scale to understand color as a function of the data point value. In some embodiments, the distribution of values and relationship to the color scale (i.e., a color reference guide) is also provided in the same screen alongside the image. In certain embodiments, the range of data values displayed is selected to cover a specified range of interest, e.g., ratios ranging from 0.5-1.5 or 2-4. Narrowing the range displayed may facilitate comparison of data value distribution between samples. The generated heat maps can be saved to provide a convenient record of the data obtained from the sample.

In some embodiments of the disclosed method for detecting plural targets in a tissue sample, the numerical data and/or heat map images produced facilitate diagnosis, prognosis and/or treatment of a disease state. For example, knowing the ratios of cancer biomarkers, such as breast cancer biomarkers, facilitates accurate diagnosis, staging, and/or prognosis of a patient's disease state. In certain embodiments, the numerical data and/or heat map images may be utilized to tailor a treatment plan for a patient. For instance, a patient having a breast cancer tumor with high ratios of ER/PR may benefit from a different treatment plan than a patient whose breast cancer tumor has low ratios of ER/PR.

In some embodiments, the targets may be two or more forms of a particular biomarker, e.g., an intact form and one or more truncated forms. For example, the Her2 biomarker can be found in both intact and truncated forms, e.g., p95Her2 fragments (or Her2 carboxy-terminal fragments). Her2 is a transmembrane receptor with an intracellular domain and an extracellular domain. Metalloproteinases are capable of cleaving proteins like Her2, thereby producing Her2 fragments. In some instances, truncated Her2 is formed when initiation of mRNA translation encoding Her2 begins from different AUG codons within the gene. Several truncated forms of Her2 may form. Approximately 20-40% of Her2-positive tumors express a series of p95Her2 fragments. One truncated form, 110-115 kDa p95Her2, is biologically hyperactive because it easily forms dimers with itself or with Her3, and dimerization leads to breast cancer progression. Another truncated form, 95-100 kDa p95Her2, has a biological activity equivalent to intact Her2. A third truncated form, 90-95 kDa p95Her2, is biologically inactive.

Patients with Her2 positive (as detected by IHC) breast cancer typically are treated with trastuzumab (Herceptin), a monoclonal antibody drug that binds the extracellular domain of Her2 protein. The IHC-based assay for Her2 detection uses a primary antibody (4B5, Ventana Medical Systems, Inc.) capable of recognizing an epitope in the Her2 intracellular domain. In Her2 the extracellular domain is amino acids 1-652, the transmembrane region is amino acids 653-675, and the intracellular domain is amino acids 676-1255. The 4B5 antibody specifically binds to an epitope on the intracellular domain of Her2 including amino acids 1231-1250 of SEQ ID NO: 3 (GAPPSTFKGTPTAENPEYLG).

Hence, the assay cannot distinguish between intact and truncated forms of Her2 and instead detects both forms. A significant disadvantage to this assay, and to the patient's well-being, is that trastuzumab is only effective against the intact form of Her2 since it binds to the extracellular domain. Since truncated Her2 (p95Her2) has no extracellular domain, trastuzumab is therapeutically ineffective in patients with a significant amount of truncated Her2. Another drug, lapatinib, is effective against truncated forms of Her2.

If a tumor includes a significant percentage of truncated Her2, the patient can be treated with lapatinib instead of, or concurrently with, trastuzumab. Lapatinib is a tyrosine kinase inhibitor, which interrupts the Her2 growth receptor pathway. Currently, lapatinib is used when a patient's cancer continues to progress despite treatment with trastuzumab. Lapatinib also is used when a patient's cancer is "triple positive," i.e., ER+/EGFR+/Her2+. Thus, an assay that quantifies the intact and truncated forms of Her2 and/or determines a ratio of intact:truncated Her2, can be used to determine the appropriate, targeted treatment for Her2-positive tumors.

Because truncated forms of Her2 lack the extracellular domain, an antibody that binds to the extracellular domain of Her2 will detect only intact Her2 in a tissue sample. Antibodies capable of recognizing and binding to the extracellular domain of Her2 include SP3 (Spring Bioscience) and p95 D9 (Biomatik).

A tissue sample includes primarily truncated Her2 if it is Her2 positive when the 4B5 antibody is used for IHC detection, but Her2 negative when the SP3 or p95 D9 antibody is used. A tissue sample includes primarily intact Her2 if the IHC results are similar with both the 4B5 and SP3 (or p95 D9) antibodies. A tissue sample with a mixture of both intact and truncated forms will have a positive IHC result with the SP3 (or p95 D9) antibody, but will have a more strongly positive result with the 4B5 antibody.

Thus, in some embodiments (see, e.g., FIG. 12), a first antibody 152 capable of binding to an intact biomarker 154, and incapable of binding to a truncated form of the biomarker, is applied to FFPE tissue 156. A first antibody-enzyme conjugate 158 capable of recognizing and binding to the first antibody 152 is applied, followed by an enzyme substrate 162 and a first diazonium salt 164. The enzyme 160 reacts with and activates the first enzyme substrate 162, which then reacts with the first diazonium salt 164 to deposit a first mass tag 166 in the target (i.e., intact biomarker 154) vicinity, thereby staining intact biomarker 154 with a mass tag 166 (e.g., a "light" mass tag that does not include one or more heavier isotopes, such as deuterium). The first enzyme-antibody conjugate 158 then is deactivated, and a second antibody 168 capable of recognizing and binding to a truncated form of the biomarker 170 is applied to the FFPE tissue 156. (Typically, both forms of the biomarker are detected on the same tissue section on a single slide.) A second antibody-enzyme conjugate 172 capable of recognizing and binding to the second antibody 168 is applied, followed by an enzyme substrate 176 and a second diazonium salt 178. Enzyme substrates 162 and 176 have the same chemical structure. The first and second diazonium salts 164, 178 have the same chemical structure, but differ in molecular weight. In the embodiment shown, second diazonium salt 178 has the same chemical structure as first diazonium salt 164, but the hydrogen atoms have been replaced with deuterium. (One of ordinary skill in the art will understand that the method also can be performed utilizing the heavy diazonium salt as first diazonium salt 164 and the light diazonium salt as second diazonium salt 178.) The enzyme 174 reacts with and activates the second enzyme substrate 176, which then reacts with the second diazonium salt 178 to deposit a second mass tag 180 in the truncated biomarker's vicinity, thereby staining truncated biomarker 170 with a heavy stable-isotope-labeled mass tag 184. First and second reporter ions 182, 184 (or mass codes) are generated using laser desorption/ionization (LDI) techniques, and the first and second reporter ions 182, 184 are detected and quantified by a mass spectrometer as previously described herein.

In certain embodiments, second antibody 168 is capable of recognizing and binding to truncated biomarker 170 and to intact biomarker 154. In such embodiments, second mass tag 180 will be deposited in the vicinity of both truncated biomarker 170 and intact biomarker 154, thereby staining both forms of the biomarker with mass tag 180. Intact biomarker 154 is quantified by quantifying first reporter ion 182. However, quantifying second reporter ion 184 determines the total amount of both intact biomarker 154 and truncated biomarker 170. To quantify truncated biomarker 170 by itself, the peak intensity of first reporter ion 182 is subtracted from the peak intensity of second reporter ion 184.

Figure 19:
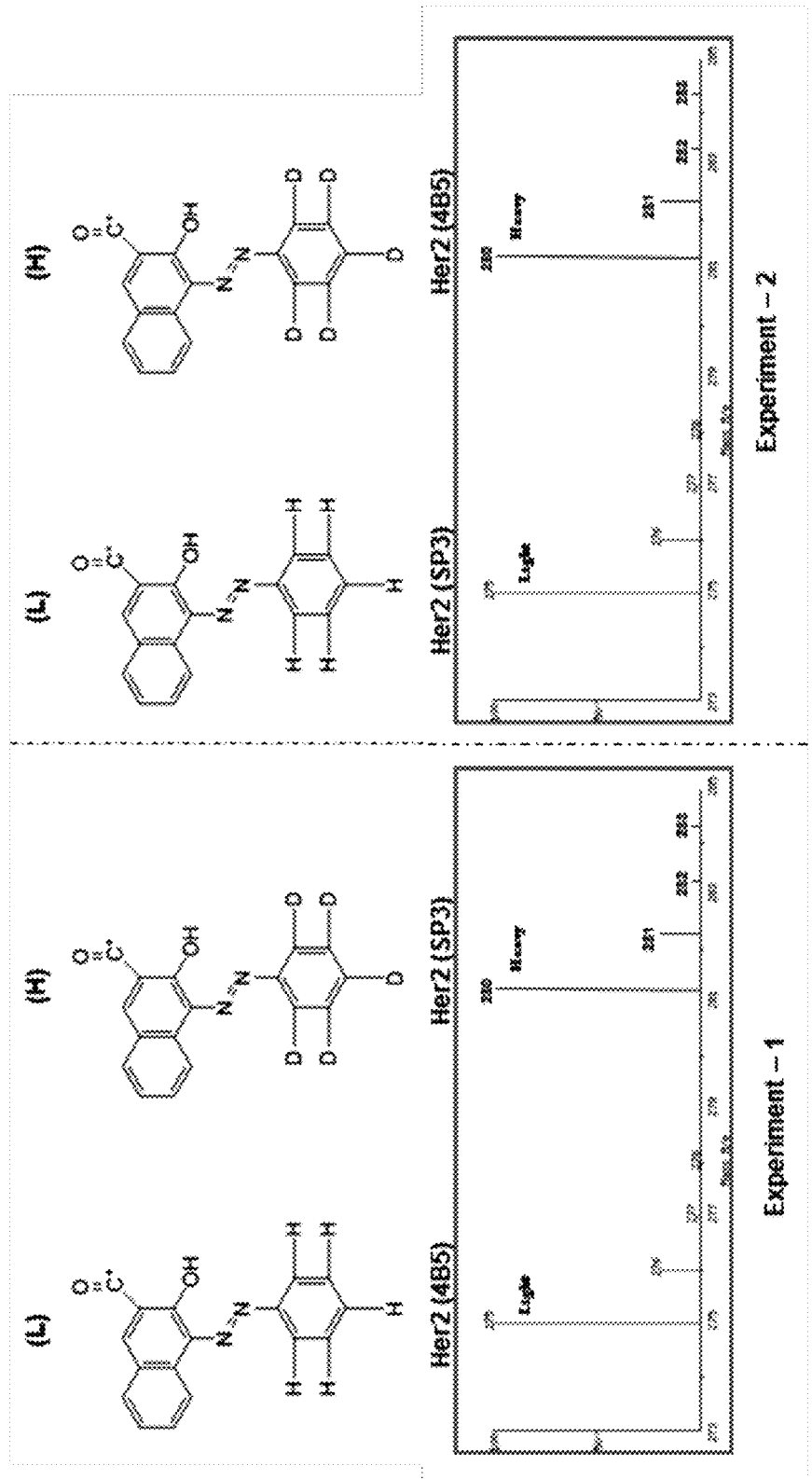
FIG. 19 illustrates the expected reporter ions (mass codes) and the spectra obtained when detecting two antigens with light and heavy stable-isotope-labeled mass tags.

In a particular embodiment, intact and truncated forms of Her2 are detected and quantified by using SP3 as first antibody 152 and 4B5 as second antibody 168. SP3 binds only to intact Her2, and 4B5 binds to both intact and truncated forms of Her2. In the embodiment shown in FIG. 12, light mass tags are deposited in the vicinity of intact Her2 and heavy mass tags are deposited in the vicinity of both intact Her2 and truncated Her2. FIG. 19 shows the expected spectra obtained when the first reporter ion (mass code) is the "light" form and the second reporter ion is the "heavy" form (e.g., labeled with deuterium) (Experiment 1), and the expected spectra obtained when the first reporter ion is the heavy form and the second reporter ion is the light form (Experiment 2). In each case, the peak corresponding to the SP3 antibody represents mass tags deposited in the vicinity of intact Her2, and the peak corresponding to the 4B5 antibody represents mass tags deposited in the vicinity of both intact and truncated Her2. By comparing the peak intensities, the ratio of intact Her2/total Her2 can be determined. With respect to Experiment 1, the amount of truncated Her2 can be determined by subtracting the peak intensity of the heavy reporter ion peak (intact Her2 only) from the peak intensity of the light reporter ion peak (intact and truncated Her2) to determine the portion of the heavy reporter ion peak due to truncated Her2. The ratio of intact Her2/truncated Her2 then can be calculated. With respect to Experiment 2, the peak intensity of the light reporter ion peak would be subtracted from the peak intensity of the heavy reporter ion peak.

In some embodiments, a visual image representing the numerical data may be desirable. For example, a person reviewing the data may prefer to evaluate the ratios of two targets (e.g., intact Her2 and truncated p95Her2) by viewing a color image representing the ratios found in each tissue sample section rather than a numerical grid. In some embodiments, a color may be assigned to a range of numerical values, thereby producing a color map with discrete colors in a grid-like pattern (similar to FIGS. 14-15). In certain embodiments, a "heat map" representation is produced in which colors are assigned across a continuum of values. For example, colors may shade from blue to red as the numerical ratios increase (similar to FIGS. 16-18).

Figure 20:
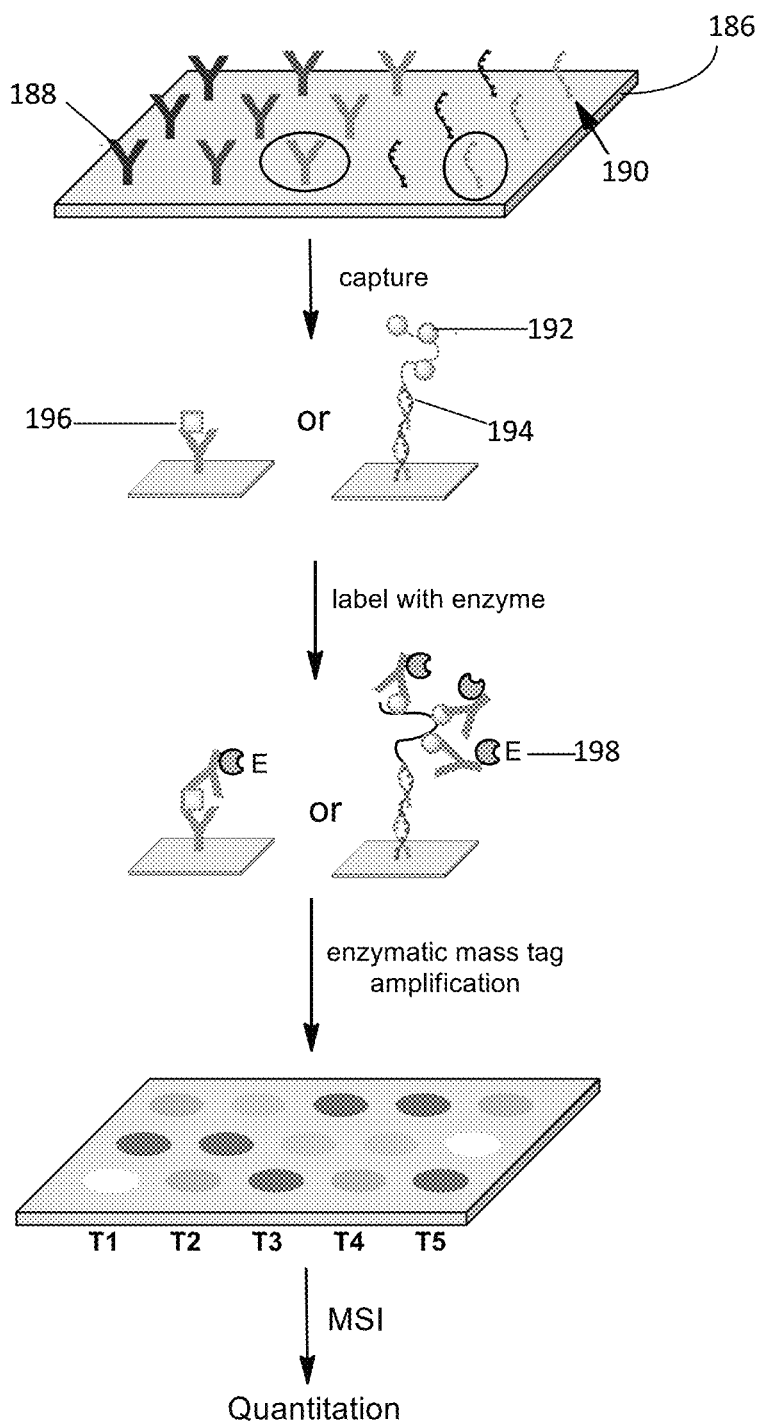
FIG. 20 is a schematic diagram illustrating using enzymatic mass tags for array-based immunoassays.

Certain embodiments also can be used for array-based immunoassays. One such array-based immunoassay is illustrated in FIG. 20. An array is produced by forming a modified surface 186 containing capture antibodies 188 and/or capture probes 190 which may or may not be further labeled, such as hapten labeled. The array is treated with a sample comprising target molecules of interest, such as proteins, nucleic acids, cells, etc. The target molecules of interest are captured by antibodies 188 and/or probes 190 to form an antibody/protein target complex 196 or a probe/nucleic acid target complexes 194. The antibody/protein target complex complexes 196 or probe/nucleic acid target complexes 194 are then labeled with the desired enzyme 198, followed by enzymatic mass tag amplification. Once the mass tag amplification has taken place, the samples can undergo laser-induced ionization to release the mass codes and provide a method for quantitation, wherein the quantity of the mass code is proportional to the signal intensity.

XIII. Kits

A kit for detecting a target in a sample by using mass spectrometry may comprise one or more mass tag precursors selected from the embodiments disclosed herein. In particular embodiments, the mass tag precursor may be conjugated with an enzyme substrate, a tyramine moiety, a tyramine derivative, an optional linker or carrier, and any combination thereof.

A kit for detecting a plurality of targets by mass spectrometry includes at least a first mass tag precursor and a second mass tag precursor. The first and second mass tag precursors have the same chemical structures, and at least one of the first mass tag precursor and the second mass tag precursor is isotopically labeled such that they differ in mass. In certain embodiments, the kit may further include one or more additional mass tag precursors having the same chemical structure as the first and second mass tag precursors. Each additional mass tag precursor is isotopically labeled such that its mass differs from the masses of the first mass tag precursor, the second mass tag precursor, and any other additional mass tag precursor.

In some embodiments, the kit further includes a specific binding moiety-enzyme conjugate, wherein the specific binding moiety is capable of recognizing and binding to a target in a tissue sample or a specific binding moiety bound to a target in a tissue sample. In certain embodiments, the kit includes a plurality of specific binding moiety-enzyme conjugates, wherein each specific binding moiety is capable of recognizing and binding to a particular target in a tissue sample or a specific binding moiety bound to a particular target in a tissue sample. In some embodiments, the specific binding moiety-enzyme conjugate is an antibody-enzyme conjugate. In particular embodiments, the enzyme in each conjugate is the same.

In some embodiments, the kit further includes an enzyme substrate, wherein the enzyme substrate is capable of reacting with an enzyme and a mass tag precursor to produce and deposit a mass tag at a target in a tissue sample. In other embodiments, each mass tag precursor is part of a mass tag precursor conjugate, wherein the enzyme substrate moiety of the mass tag precursor conjugate is capable of reacting with an enzyme to produce and deposit a mass tag at a target in a tissue sample.

In some embodiments, a kit for detecting two targets in a tissue sample includes first and second mass tag precursors, an enzyme substrate, and at least one specific binding moiety-enzyme substrate. In certain embodiments, the enzyme is a phosphatase such as alkaline phosphatase, the enzyme substrate has the chemical structure

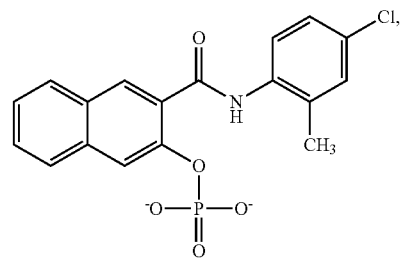

and the first and second diazonium salts have the chemical structures

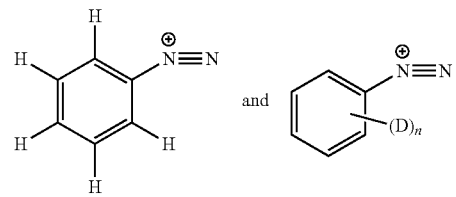

where n is 1-5. In particular embodiments, the first and second diazonium salts have the chemical structures

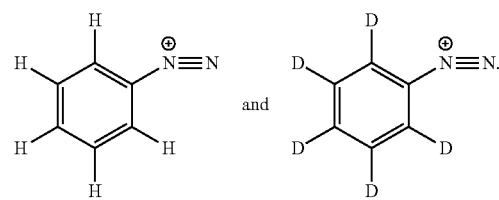 [SMILES: N#[N+]c1ccccc1 ; [2H]c1c([2H])c([2H])c([N+]#N)c([2H])c1[2H]]

In some embodiments, a kit for detecting two to four targets in a tissue sample includes a plurality of mass tag precursors, an enzyme substrate, and at least one specific binding moiety-enzyme substrate. In certain embodiments, the enzyme is a phosphatase such as alkaline phosphatase, the enzyme substrate has the chemical structure

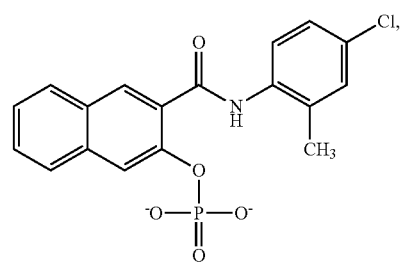

and there are two to four mass tag precursors comprising diazonium salts having chemical structures selected from

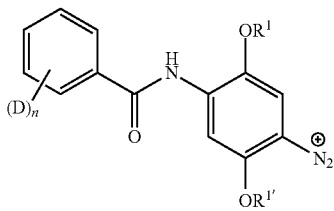

where n is 0-5, and $R^2$ and $R^{1'}$ are independently lower alkyl. $R^1$ and $R^{1'}$ independently are optionally substituted with one or more isotopes. In particular embodiments, the diazonium salts have chemical structures selected from

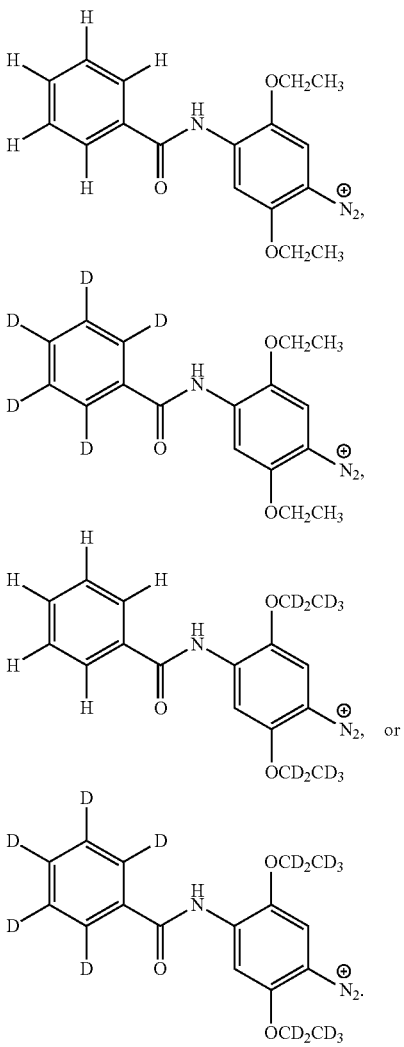

XIV. Examples

The following examples are provided to exemplify certain features of working embodiments. A person of ordinary skill in the art will appreciate that the scope of the present invention is not limited to the working features of such examples.

Certain of the following examples concern tissue staining and subsequent mass imaging. A general procedure for tissue staining and mass imaging is as follows:

A formalin fixed paraffin embedded human tissue sample was sectioned at 4 μm and tissue sections were placed on Plus or Superfrost Plus slides (VWR International) and MS tissue sections were placed on indium-tin oxide (ITO) coated glass slides (Bruker Daltonics, Bremen, Germany). Deparaffinization, cell conditioning (antigen retrieval), IHC staining, and/or mass tag application were done using a Benchmark XT or Discovery XT automated IHC instrument (Ventana Medical Systems Inc, Tucson, Arizona, US) and Ventana reagents, unless otherwise specified.

If the mass tag deposited was soluble in alcohol, the sample slides were rinsed with water following completion of the Discovery XT staining protocol, dried for 30 min. at 65° C., and rinsed with hexane before MS analysis.

If the deposited mass tags were insoluble in alcohol, the slides were dehydrated using an ethyl alcohol (80%, 80%, 90%, 90%, 100%, 100%) sequence and dried in air or under vacuum. In general, samples that were exposed under vacuum for an extended period of time provided more intense signals.

A laser desorption ionization (LDI)/time of flight (TOF) linear mass spectrometer using FlexControl acquisition software (Autoflex III, Bruker Daltonics, Bremen, Germany) was used for analysis of the mass tagged tissue sample. A suitable mass range was selected according to the mass of the tags. The mass spectra were collected at each raster point across the designated measurement region. A raster width of 25-100 μm is generally used but can be changed as desired. Unless otherwise specified, the smartbeam laser was operated at a 200 Hz frequency and accumulated 100 shots at each raster point. Laser attenuator and focus settings were chosen to generate a signal with satisfactory intensity and signal to noise ratio. Positive ion mode was used with ion source 1 at 20 kV, ion source 2 at 18.73 kV, the lens at 6 kV, and post ion extraction delay set to 0 ns.

A. In-Situ Hybridization Procedures

In-situ hybridization (ISH) of human tissues in disease states has a well-established place in cancer diagnostics, however there still remains a need for alternatives to ISH technologies that are based on fluorescent and/or chromogenic signal target detection. The embodiments disclosed herein for target detection using Mass Spectrometric Imaging (MSI) detection of genes or gene products provide such alternatives, such as MSI-based multiplexing applications. For example, probes directed to corresponding nucleic acid targets may be labeled with cognate haptens recognized by corresponding anti-hapten antibodies associated with molecular weight tags that are detectable by MSI. Further, fluorescent and chromogenic ISH technologies typically determine staining intensity with categorical values whereas MSI-based ISH allows numeric relative quantification (wherein quantification comprises determining the size of a mass peak and correlating it with the amount) and therefore offers a significant advantage over non-MSI based ISH methods.

In exemplary working embodiments performed to support embodiments of the present invention, silver was utilized as a mass tag precursor for detecting Her2 genomic DNA and human papillomavirus (HPV) genotype targets in mouse xenografts of human cancer cell lines. Exemplary working embodiments were performed utilizing alkaline phosphatase (AP) silver in situ hybridization (SISH) based detection methods as described in U.S. Pat. No. 7,632,652, which we herein incorporate by reference. After hybridizing a nucleic acid probe to the desired target mass tag precursor, deposition and detection, proceeded as previously described for IHC.

B. Indium-Tin Oxide (ITO) Slide Modification Procedures

In particular embodiments, mass tag deposition was carried out utilizing ITO-coated mass spectrometry slides that have been immersed in a gelatin. Effective slide preparation treatments concern preserving the conductive ITO layer on the mass spectrometry slides. Without being limited to a theory of operation, it is currently believed that this prevents any surface charging during the MS ionization process. Particular embodiments concern slides comprising a hydrophilic layer, which promotes mass tag deposition on VMSI's automated strainers. In particular embodiments, a suitable hydrophilic coating can be obtained by immersing the slides in 1% gelatin (from cold water fish skin, Sigma PN G7041) in 1× PBS for several hours at room temperature, rinsing with distilled water, and air drying the slide at room temperature before tissue placement. This technique was applied to particular working examples using ITO slides.

In other embodiments, the hydrophilic coating comprises a hydrophilic protein coating. Certain embodiments concern immersing the tissue-free slide in a solution of gelatin, such as gelatin from cold water fish skin, a protein, such as bovine serum albumin (BSA), a detergent, such as octylphenoxypolyethoxyethanol (IGEPAL CA-630®), and an organic compound, such as glutaraldehyde to form a cross-linked proteinaceous layer on top of the ITO coating, thus providing a hydrophilic coating to promote automated mass tag deposition without damaging the ITO coating required for mass spectrometric analysis. Particular embodiments concern using a mixture of 0.1% gelatin (Sigma G7041) and 0.1% BSA (Roche), to which was added added 10% IGEPAL CA-630 and 5% glutaraldehyde, followed by thorough mixing. ITO slides (Bruker) were used without pre-cleaning. The protein solution was added onto the non-labeled end of the slide and spread to cover the slide evenly. The solution was allowed to dry in air and placed on a hot plate at 80° C. for about 10 minutes and stored in a slide box. Additionally, applying hydrophilic coatings before tissue placement, such as poly-lysine, amino dextran, and casein, to the ITO coated MS slide can preserve the conductive ITO layer on the slide.

Other treatments for ITO slide preparation were explored; however, these treatments did not sufficiently preserve the conductive ITO layer. Examples of these treatments include cleaning procedures, wherein the slide is immersed in a sequence of different solvents, such as trichloroethylene, acetone, methanol, isopropanol, and potassium hydroxide, and is then air dried. Other cleaning procedures include submerging slides in 20% ethanolamine and sonicating at 80° C., then air drying. Additional methods include hydrophilic coating modifications, such as using Ventana reagents ChipMap Prep 1 (PN 760-4121) and ChipMap Prep 2 (PN 760-4122) during the staining procedure (i.e. after tissue placement). The main components of ChipMap Prep 1 are buffer and detergent, and the main component of ChipMap Prep 2 is casein. An additional approach involved treating the slide with a polyvinylalcohol and glutaraldehyde solution (ChipSpread™) before tissue placement. Other methods include using a combination of cleaning and coating the slides, such as first cleaning the glass slide (tissue sample not yet in place) with 6N HCl, then coating the slide with (3-aminopropyl) triethoxysilane, followed by immersion in 1,4-phenylene diisocyanate.

C. Working Embodiments

EXAMPLE 1

This example concerns using alkaline phosphatase to cleave a phosphate group from a mass tag precursor conjugate, and demonstrates the expected enzymatic reaction and subsequent detection of the mass code (Scheme 23).

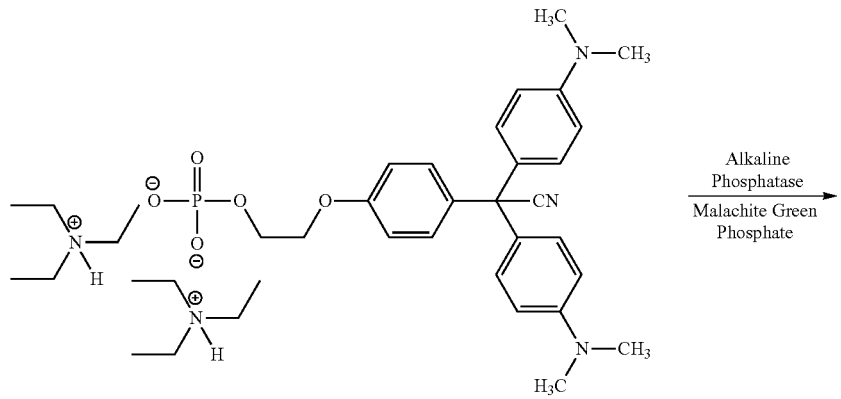

-continued

119

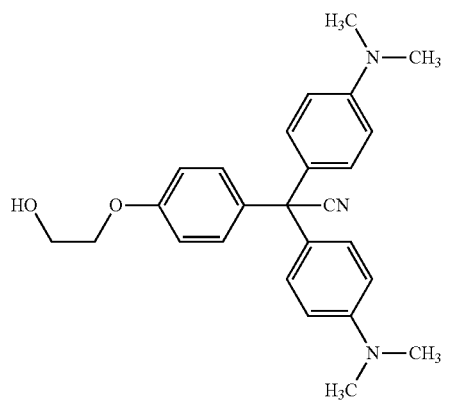

Precipitate

120

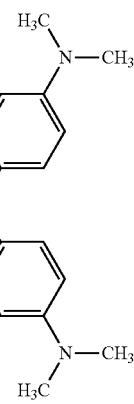

M/Z = 389.22

To test the substrate, a 1 mg/ml malachite green phosphate solution was made in water. To 200 µl of tris buffer (pH=10) was added 40 µl of the malachite green phosphate solution. The mixture was split into two tubes containing 120 µl each. 10 µl of an alkaline phosphatase (250 µl/ml) solution was added to one tube. Both tubes were then incubated at room temperature. After about 15 minutes the solution comprising alkaline phosphatase became slightly cloudy. The tube without alkaline phosphatase remained clear. Since the hydrolyzed product is not water soluble, the cloudy solution suggested that the alkaline phosphatase catalyzed hydrolysis of the substrate. After allowing the solution to stand overnight, 100 µl of acetonitrile (CH₃CN) was added to each tube to dissolve the precipitate, if any. Both sample solutions were further analyzed on MALDI (w/o matrix LDI). The mass code produced by LDI of the sample treated with alkaline phosphatase had a molecular ion peak of m/z=389.22.

EXAMPLE 2

This example demonstrates the use of styryl dyes as mass tag precursors. Styryl dyes generate comparable MS signals to that of a typical triarylmethane dye (triarylmethane dyes are proven mass tags).

LDI results of a mixture of malachite green and 4-[4-(dimethylamino)styryl] pyridine (DMA-SP; Aldrich #394211) at different concentrations produced the following mass codes: DMA-SP=224.573 and malachite green=329.266. The radical cation of DMA-SP was observed, demonstrating the use of styryl dyes as effective mass tags. Additional styryl dyes, such as (E)-4-(2-(benzo[d]thiazol-2-yl)vinyl)-N,N-dimethylaniline and (E)-2-(4-methoxystyryl)benzo[d]thiazole, demonstrated the same effect for use as mass tags.

EXAMPLE 3

This example illustrates the use of naphthol/triarylmethane diazo mass tag precursors, as described in Scheme 24.

Scheme 24

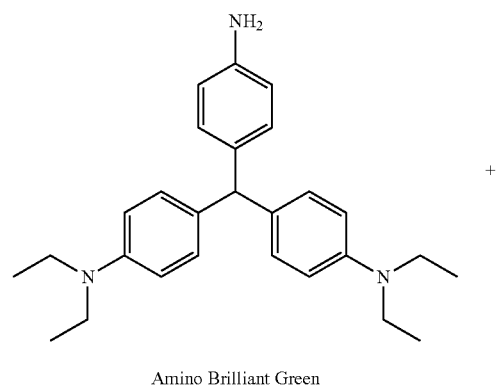

Amino Brilliant Green

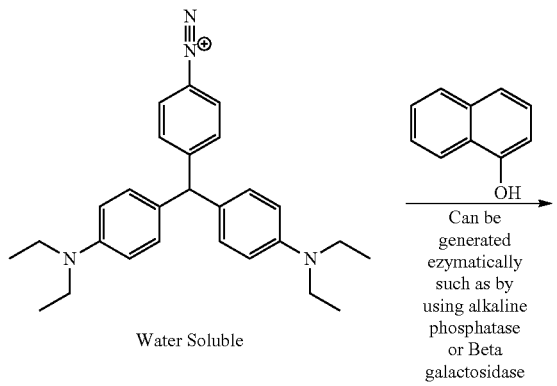

Water Soluble

Can be generated ezymatically such as by using alkaline phosphatase or Beta galactosidase -continued

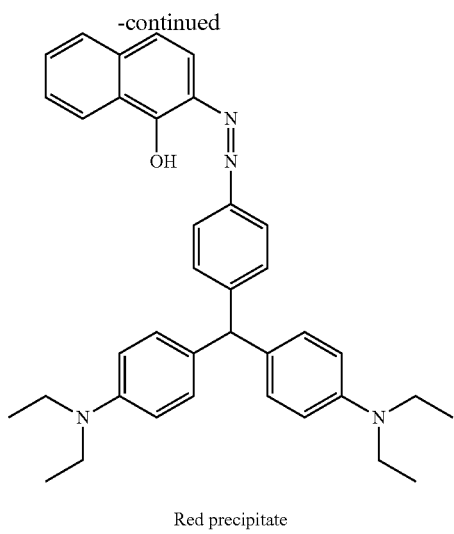

Red precipitate

Amino brilliant green (ABG) 1 mg/ml solution was made in 0.01 N hydrochloric acid (HCl) (made from 40 mg/ml ABG stock solution in DMF). $NaNO_2$ solution in water was added to the ABG solution to provide a final concentration of 0.125% sodium nitrate (NaNO2). The color of the solution changed from colorless to light yellow to green in about 0.5 hour. 1-naphthol solution (1 mg/ml) was made in tris buffer (0.1 M, pH=7.5) from a 28 mg/ml dimethylformamide (DMF) stock solution. 50 µl ABG solution was added to 100 µl of 1-naphthol solution. A red precipitate was observed in less than one minute, indicating azo dye formation. The precipitate was separated by centrifugation and the red residue was dissolved in acetonitrile ($CH_3CN$) to give a red solution. LDI of this solution resulted in a peak at m/z at 555.312, demonstrating the presence of the expected mass of the azo-triarylmethane cation.

EXAMPLE 4

Brilliant green (BG), malachite green (MG) and crystal violet (CV) were obtained from Sigma-Aldrich and used without further purification. A 0.3 mM solution of the triarylmethane mass tag precursor (BG or MG or CV) was made in deionized water and stored in a dark dispenser. Formalin fixed paraffin embedded (FFPE) human tonsil tissue was placed on MALDI compatible ITO glass slides (Bruker).

To label a specific epitope on the tissue (Ki-67 or Bcl-2, for example), the deparaffinized tissue was incubated with a primary antibody targeting the epitope (rabbit anti Ki-67 or mouse anti Bcl-2) for a period of time (e.g 16 mins). After washing, the tissue was exposed to a secondary antibody conjugated with alkaline phosphatase (AP) (e.g. ultraView AP multimer from Ventana Medical Systems, Inc.) for a period of time of about 16 to about 32 minutes. After washing, 100 □l of BCIP (Ventana Medical Systems, Inc.) and 100 ul of mass tag precursor solution (0.3 mM of triarylmethane dye) were added to the slide and allowed to incubate on the tissue for 32 minutes. For the control IHC exemplary working embodiment, 100 □l of BCIP and 100 □l of NBT solution (Ventana Medical Systems, Inc. AP Blue Kit) were used to give a dark blue signal indicating the Ki-67 epitope. After incubation, the slides were washed with reaction buffer (Ventana Medical Systems, Inc.). The above steps were all performed automatically in a Ventana Benchmark Discovery staining system.

After automated staining, the ITO slide was washed in water and finally deionized water. The slide was placed in an oven and baked for 20-30 minutes at ~65° C. to remove most of the water. The slide was rinsed with hexanes and allowed to air dry for at least 10 minutes. The tissue sample labeled with the mass tag (triarylmethane dye) was ready for MS imaging (MSI). Imagine was performed in a Bruker Autoflex III spectrometer, equipped with a linear TOF detector. No matrix material was applied. A region of interest was selected and a specific scanning step (raster) was selected (usually 30-100 micron). FIGS. 21A-21C provide an exemplary illustration of the multiple results obtained after MSI on the tonsil tissue. The results demonstrate the use of triarylmethane dyes as mass tags in identifying biomarkers in human tissue. FIG. 72A shows an ion map in one color for the BG mass code. FIG. 72B is an image of a heat map of the BG mass code, the color scale indicating intensity of the peak. FIG. 72C is an optical image of a control slide (a serial sectioned slide) stained with BCIP/NBT under identical conditions to show the specificity of mass tag staining and imaging. FIG. 72D is a mass spectrum of BG (m/z=385) as a mass code including a blown up region showing the spectrum in greater detail. FIG. 73A is an image of a heat map of the CV mass code, the color scale indicating intensity of the peak. FIG. 73B is a mass spectrum of CV.

EXAMPLE 5

Azo products formed between a naphthol and a diazonium salt can be used as mass tag precursors for tissue imaging applications. An example is the Ventana AP Red Detection Kit in which naphthol AS-TR phosphate and Fast Red KL are used to generate a red precipitate at the site of the enzyme. The product of the reaction was analyzed under LDI conditions and it was determined that the amide bond in the naphthol was susceptible to laser irradiation. The formation and detection of azo dye-based mass tags, as described in Schemes 3 and 4, is described below. 100 microliters of naphthol AS-TR phosphate was combined with 100 microliters of Fast Red and 100 microliters of alkaline phosphatase multimer as found in Ventana's AP-Red detection kit. A red precipitate formed in 5-10 minutes. The precipitate was collected by centrifugation, and washed with acetonitrile (MeCN). The washed precipitate was isolated by centrifugation, dispersed in acetonitrile (MeCN), cast on a target and analyzed by LDI. The results of this analysis indicated that the major constituent detected was a reaction product of the Fast Red and naphthol.

Figure 67:
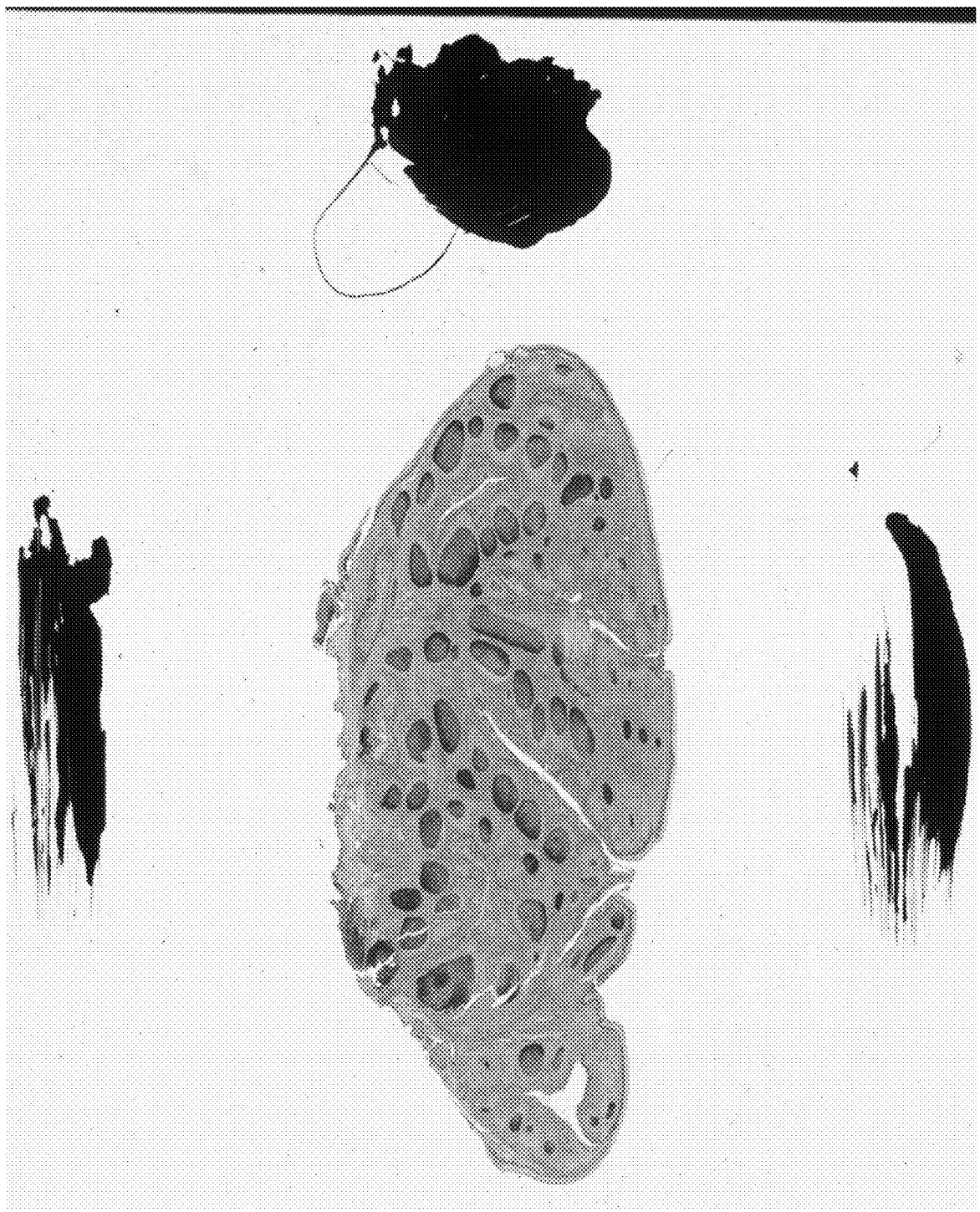
FIG. 67 is an optical image of Ki-67 staining using the Ventana AP-Red detection reagents on tonsil tissue, according to Example 5.
Figure 68:
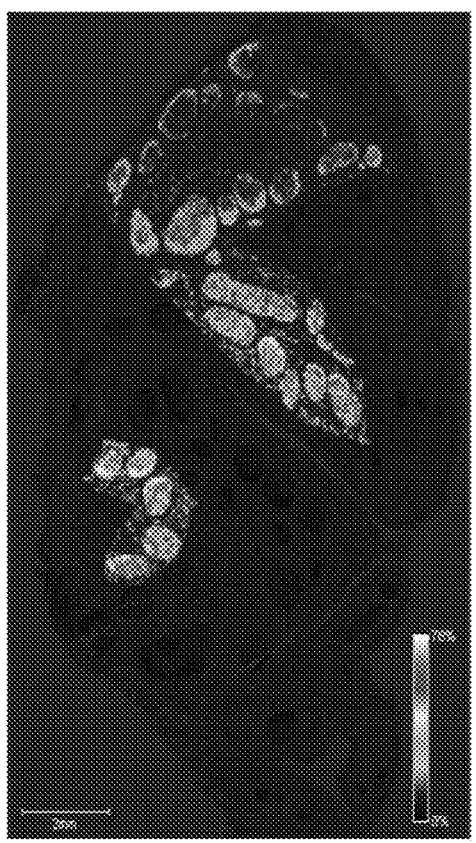
FIG. 68 is a LDI MSI of Ki-67 using the Ventana AP-Red detection reagents on tonsil tissue, according to Example 5.

To demonstrate that the mass tag precursors generated as described above could be used in human tissue, tonsil tissue was stained according to Ventana's AP Red protocol using anti-Ki67 antibody. The stained tissue was imaged under LDI conditions and the specific mass code having a m/z of 347.932 from the cleavage of the naphthol amide bond was observed. Referring now to FIG. 67, shown is an optical image of Ki-67 staining using the Ventana AP-Red detection reagents on tonsil tissue. FIG. 68 is a LDI MSI of Ki-67 using the Ventana AP-Red detection reagents on tonsil tissue. It was observed that there was strong correlation between the optical image and the heat map.

EXAMPLE 6

Figure 22:
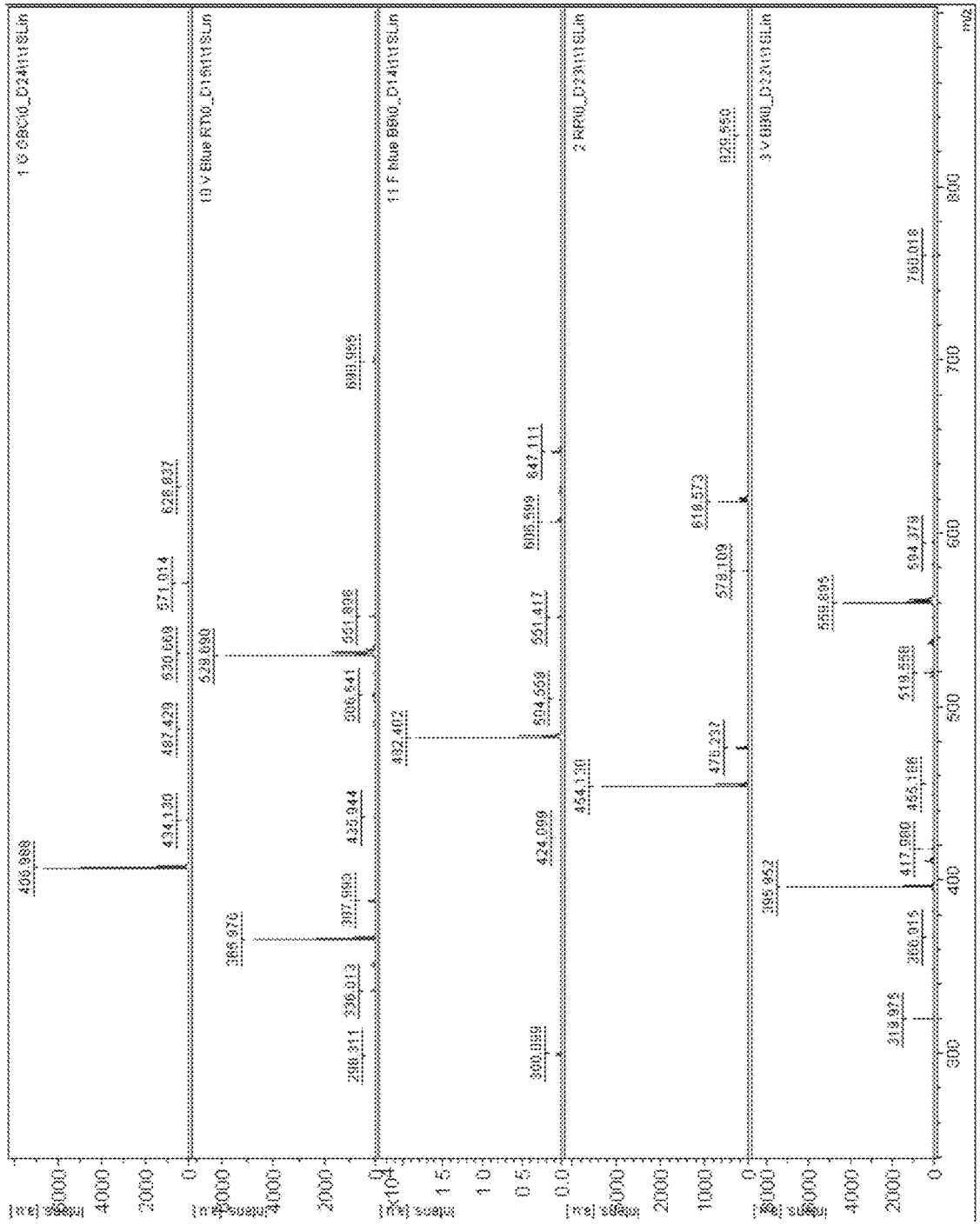
FIG. 22 is an image of the representative mass spectra for the compounds used in Example 6.
Figure 23:
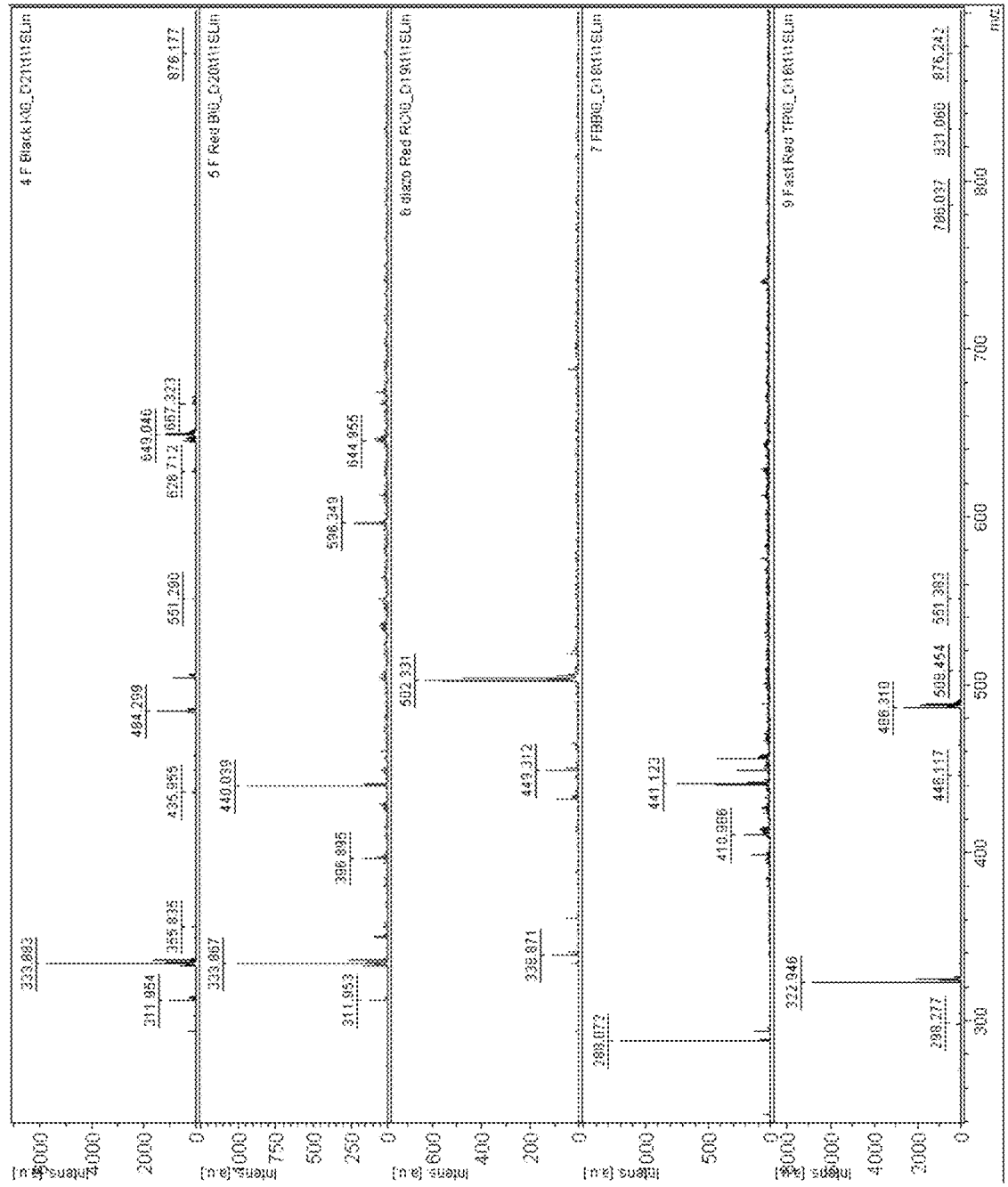
FIG. 23 is an image of the representative mass spectra for the compounds used in Example 6.

According to the method of Example 5, ten additional diazonium salts were tested. See FIGS. 22 and 23 for the mass spectra for each sample. For each reaction, 20 μL of 1 mM diazonium salt solution, as indicated in Table 1 below, was added to 20 μL of 1 mM naphthol AS-TR phosphate and mixed well. Alkaline phosphatase (10 μL of 25 μg/ml) was added and mixed well. After overnight incubation, the product (suspension of precipitation) was analyzed under LDI conditions. Without being limited to a single theory of operation, it is currently believed that the formation of the cation likely is facilitated by the electron donating groups of the diazonium salt, and is inhibited by the presence of electron withdrawing groups. Examination of the diazonium salts demonstrated a trend that the substituent groups on the diazonium salts play a role in the formation of the photo-cleavable product. In general, if electron donating groups (e.g., methoxyl, ethoxyl, etc.) are present in the diazonium salt, the azo product is readily cleaved by the laser. However, if electron withdrawing groups (e.g., $NO_2$, etc.) are present little or no photo-cleavage was observed.

TABLE 1

| R Group | Name | Mass of [cation structure] | Mass of [amide structure] | Observed Mass of Major Peak(s) |
|---|---|---|---|---|
| [O=C-NH2, methoxy benzamide] | Fast Red KL | 348.10 | 488.13 | 347.9 |
| [methoxy-chloro phenyl] | Diazo Red RC | 339.05 | 479.08, 502.1 (+Na⁺) | 338.9 502.3 |
| [methoxy-nitro phenyl] | Fast Red B | 350.08 | 490.11 | 333.9 440.0 |
| [diphenylamine] | Var Blue RT | 366.12 | 506.15 529.2 (+Na⁺) | 366.0 559.9 |
| [methoxy diphenylamine] | Var Blue B | 396.13 | 536.16 559.2 (+Na⁺) | 396 559.9 |
| [Fast Black K structure] | Fast Black K | 484.13 | 624.16 | 333.9 484.3 |

TABLE 1-continued

| R Group | Name | Mass of [naphthol-CHO azo compound] | Mass of [naphthol-amide-Cl azo compound] | Observed Mass of Major Peak(s) |
|---|---|---|---|---|
| (2-methylphenyl-azo-3-methylphenyl) | Fast Garnet GBC | 407.15 | 547.18 | 407.0 |
| (benzamido-dimethoxyphenyl) | Fast Blue RR | 454.14 | 594.17 | 454.1 |
| (4-chloro-2-methylphenyl... 3-methyl) | Fast Red TR | 323.06 | 463.09 | 322.9<br>486.3 |
| (benzamido-diethoxyphenyl) | Fast Blue BB | 482.17 | 622.20 | 482.4 |
| (dimethoxy-biphenyl-diazonium) | Fast Blue B | 438.13 | 578.16 | 288.1<br>411.0<br>441.1 |

EXAMPLE 7

This example concerns using heteroaryl compounds for forming oligomers detectable by MS under LDI conditions. Initial trials with DAB stained tissue showed detectable signal (DAB dimer) but the background was quite high. Additional compounds were tested by mixing them with HRP and $H_2O_2$ and subsequently examining the precipitates on LDI MS. For example, 1,8-DAN gave a peak at m/z=297 and 8-AQ gave peaks at m/z=426 and m/z=567.

Tissue samples were stained with 1,8-DAN and 8-AQ. The initial results indicated 8-AQ gave similar staining as DAB (Ki-67 on tonsil). A tissue sample stained by 8-AQ demonstrated that the oligomers (mostly trimers and tetramers) of 8-AQ can be readily detected on tissue samples without using a matrix (FIGS. 24A-24C).

EXAMPLE 8

A frequently used immunohistochemistry (IHC) assay employs alkaline phosphatase conjugated to a secondary antibody which binds a primary antibody to the antigen of interest. The alkaline phosphatase substrate 5-bromo-4-chloro-3-indolyl phosphate (BCIP), which tightly binds to the alkaline phosphatase active site, is then oxidized by nitro blue tetrazolium (NBT) to produce a blue precipitate. This assay is modified in a mass tag protocol to use brilliant green (BG) as presumably an oxidizing agent and a detected mass code.

An anti-phospho-4EBP1 (Thr70) rabbit polyclonal primary antibody binds phospho-4EBP1 in formalin-fixed and paraffin-embedded (FFPE) human prostate tissue. A goat-anti-rabbit secondary antibody conjugated to alkaline phosphatase binds the phospho-4EBP1 primary antibody. Following alkaline phosphatase cleavage of the BCIP phosphate group, BCIP is presumably oxidized by BG to generate a blue BCIP dimer precipitate and colorless BG precipitate. The colorless BG precipitate is then ionized by the mass spectrometer laser and detected as a mass code for phospho-4EBP1.

FFPE human prostate tissue was sectioned at 3 μm for IHC and 5 μm for mass spectrometry (MS) analysis. IHC tissue sections were placed on Superfrost Plus slides (VWR International) and MS tissue sections were placed on indium-tin oxide (ITO) coated glass slides (Bruker Daltonics, Bremen, Germany). Deparaffinization, antigen retrieval, IHC staining, and mass tag application were done using a Discovery XT automated IHC instrument (Ventana Medical Systems, Tucson, Arizona, US) and Ventana reagents, unless otherwise specified.

Control and mass tag slides were stained with p4EBP1 (Thr70) primary antibody (Cell Signaling Technology, Beverly, MA, US), which was diluted 1:5 and incubated on the tissue for 60 min. at 37° C. One IHC control slide was stained with DABMAP (Ventana Medical Systems), a detection kit using a horse-radish peroxidase conjugated secondary antibody, 3,3'-Diaminobenzidine (DAB) substrate and hydrogen peroxide oxidant. A second IHC control slide was stained with an alkaline phosphatase conjugated secondary antibody and detected with BCIP substrate and NBT oxidant. Control slides were counterstained with hematoxylin. The mass tag slide was stained with an alkaline phosphatase conjugated secondary antibody, using BCIP as a substrate and BG (Sigma-Aldrich, St. Louis, MO, US) as the oxidant and mass tag. Secondary antibodies were incubated 32 minutes at 37° C. before addition of substrates.

Mass tag sample slides were rinsed with water following completion of the Discovery XT staining protocol, dried for 30 min. at 65° C., and rinsed with hexane before MS analysis. No matrix was used.

A laser desorption ionization (LDI)/time of flight (TOF) linear mass spectrometer using FlexControl acquisition software (Autoflex III, Bruker Daltonics, Bremen, Germany) was used for analysis of the mass tagged tissue sample. Mass spectra covering the mass range of 240 Da-1,000 Da were collected at each raster point across the designated measurement region, using a 100 μm raster width. The smartbeam laser was operated at a 100 Hz frequency and accumulated 100 shots at each raster point. Laser attenuator and focus settings were chosen to produce an expected laser diameter of approximately 50 μm. Positive ion mode was used with ion source 1 at 20 kV, ion source 2 at 18.73 kV, the lens at 6 kV, and post ion extraction delay set to 0 ns. Two different cases of human prostate tissue were analyzed for p4EBP1 (Thr70) with brilliant green mass tag. Similar staining results were achieved in the HRP/DAB/H$_2$O$_2$ and AP/BCIP/NBT IHC control slides for both tissue cases. Mass tag results in FIGS. 25A-25E show similar localization for p4EBP1 in both IHC control slides and the corresponding mass tag slide. Notably, the major signal detected in the mass spectrum is that of BG at 385 Da (FIG. 25E).

The resonance stabilized BG carbocation mass code yields an intense signal with LDI mass spectrometry. Low laser powers allow detection of the BG carbocation mass code while minimizing ionization of additional analytes from the tissue, yielding high signal to noise ratios for the desired mass tag. The ability to obtain intense signals without the use of matrix eliminates numerous drawbacks associated with matrix-assisted LDI (MALDI).

MALDI direct imaging analyses were conducted on serial sections of the human prostate cases used for mass tag analysis, using sinapinic acid as matrix. While protein-rich spectra were obtained (data not shown), no signals were detected at the expected m/z ratios for either 4EBP1 or any of its phosphorylated forms. Detection of p4EBP1 using MS analysis has only been possible using the targeted mass tag approach described here. Mass tag distribution is well correlated with p4EBP1 staining as demonstrated in the IHC control slides.

Figure 69:
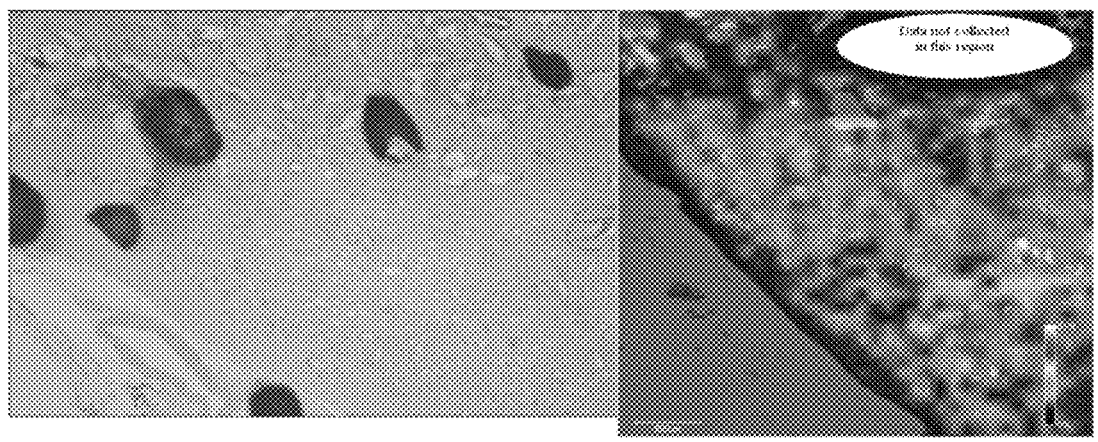
FIG. 69 is a combined image illustrating a zoomed view of a DAB control slide (red dots on DAB control slide encircle the cancer region) and an enlarged image of a BG mass code slide, according to Example 8.
Figure 70:
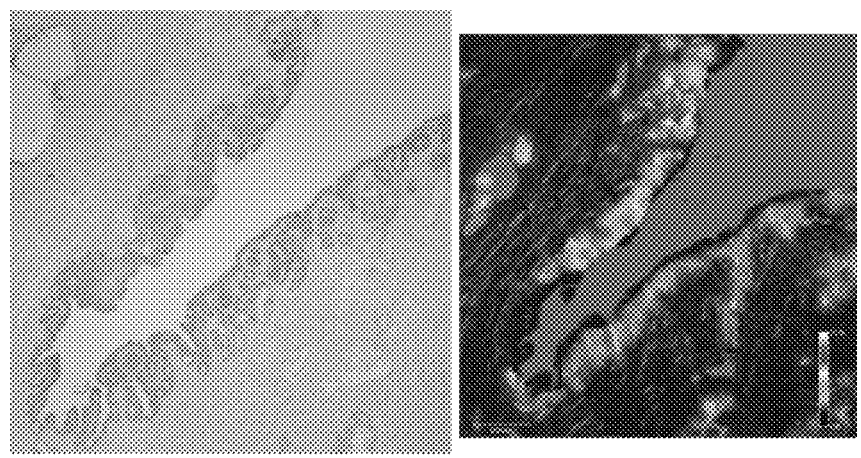
FIG. 70 is a combined image illustrating a enlarged view of a DAB control slide and an image of a BG mass code slide, showing the urethra region, according to Example 8.
Figure 71:
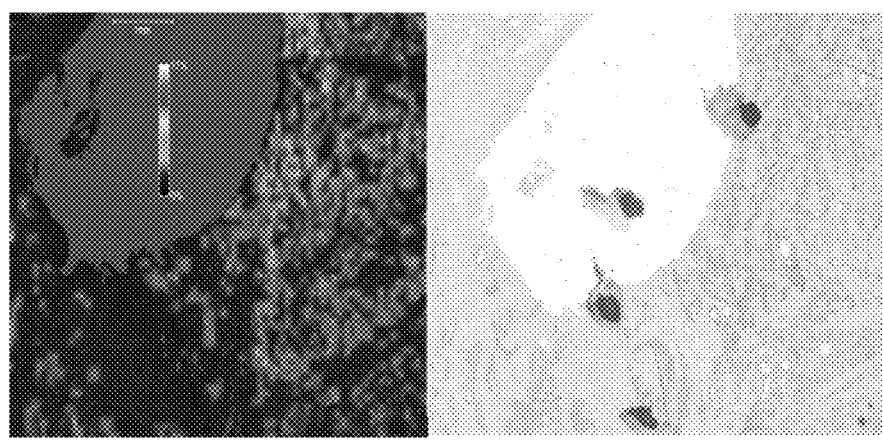
FIG. 71 is a combined image illustrating an image of a V175-H7 DAB control slide, where the area to the right of the red dots on DAB control slide is cancerous region, and an image of a BG mass code slide of the same region, according to Example 8.

Referring now to FIG. 69, shown is a combined image illustrating a zoomed view of a DAB control slide (red dots on DAB control slide encircle the cancer region) and an enlarged image of a BG mass code slide. FIG. 70 is a combined image illustrating an enlarged view of a DAB control slide and an image of a BG mass code slide, showing the urethra region. FIG. 71 is a combined image illustrating an image of a V175-H7 DAB control slide, where the area to the right of the red dots on DAB control slide is cancerous region, and an image of a BG mass code slide of the same region.

EXAMPLE 9

Figure 28A:
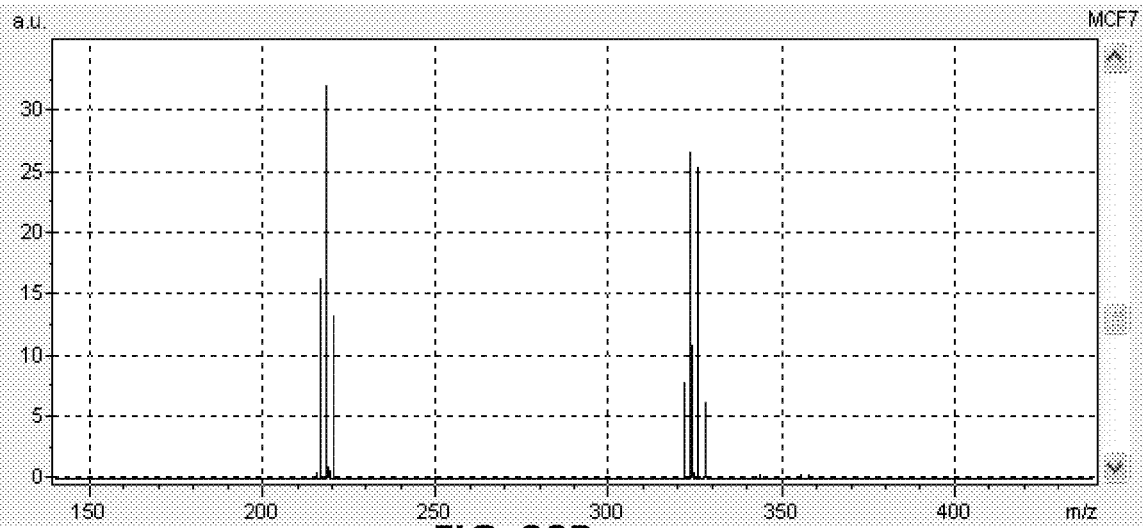
FIGS. 28A-28C are images illustrating the overall average spectra for all measured spectra in MCF-7 xenografts (FIG. 28A), ZR-751 xenografts (FIG. 28B), and Calu-3 xenografts (FIG. 28C), showing $Ag_2^+$ and $Ag_3^+$ ions detected for Her2 gene.
Figure 28B:
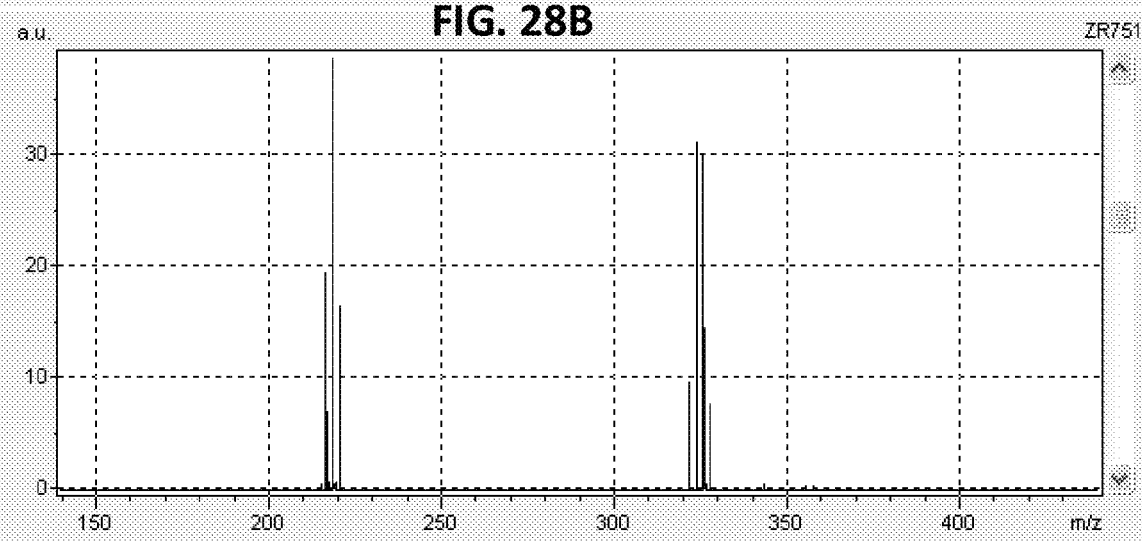
Figure 28C:
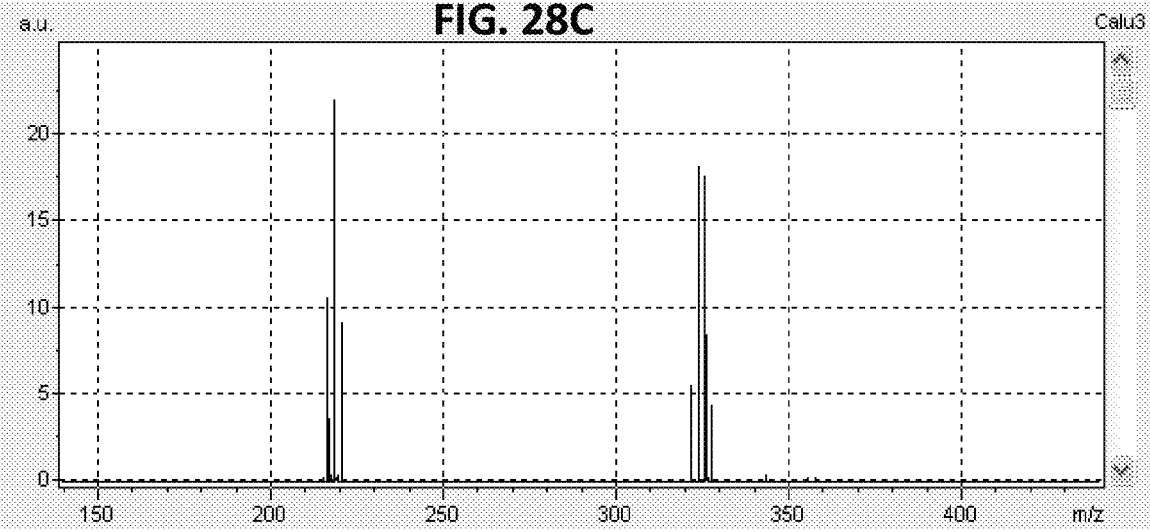

This example concerns the detection of Her2 and HPV DNA in tissue using mass tags. A FFPE multi-block of mouse xenograft tissues containing human breast cancer cell lines of differential Her 2 gene copy number MCF-7 (ATCC HTB-22™; contains 1-2 Her2 gene copies), ZR-751 (ATCC CRL-1500™; contains 2-4 Her2 gene copies), and Calu-3 (ATCC HTB-55™; contains >6 Her2 gene copies) was cut to 4 μm thickness and placed onto an ITO glass slide (Bruker). FIGS. 26A-26C, FIGS. 27A-27C, FIGS. 28A-28C, FIGS. 29A-29C, FIGS. 30A-30C, and FIGS. 31A-31C show MS results for Her2 xenografts. FIGS. 26A-26C illustrate optical images of Her2 xenografts obtained from MCF-7, ZR-751, Calu-3, respectively. FIGS. 27A-27C shows heat maps of Ag$_2$$^+$ ions observed from the exemplary working embodiments with MCF-7, ZR-751, Calu-3, respectively. The relative intensity scale for these heat maps is included in FIG. 27C. The overall average mass spectra for all measured spectra of MCF-7, ZR-751, Calu-3 in Her2 xenografts, showing the Ag$_2$$^+$ and Ag$_3$$^+$ ions are illustrated in FIGS. 29A-28C.

Figure 31A:
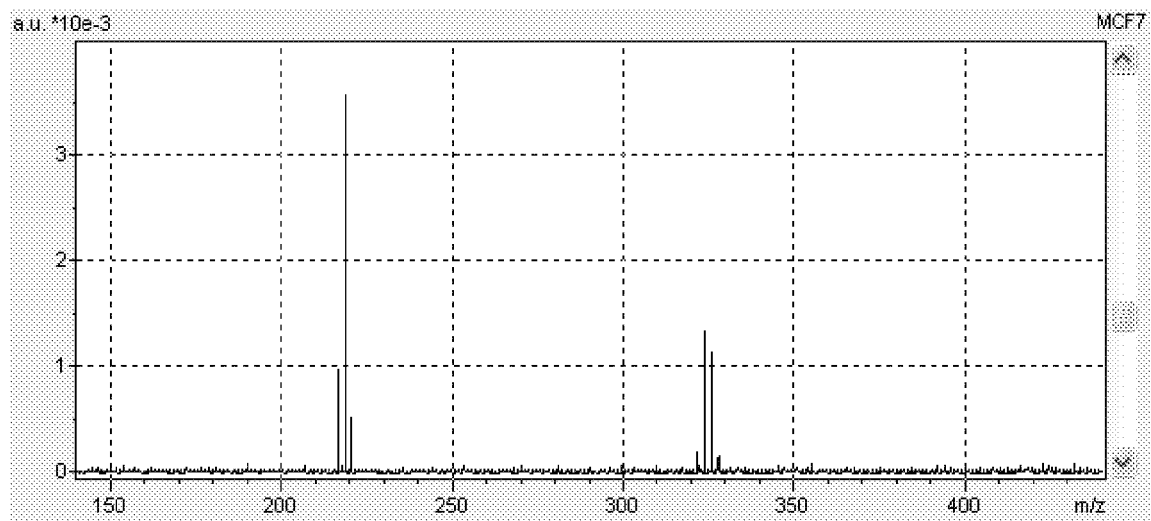
FIGS. 31A-31C are images illustrating the overall average spectra for negative control slide (no Her2 gene probe), showing $Ag_2^+$ and $Ag_3^+$ ions detected in background staining for MCF-7 (FIG. 31A), ZR-751 (FIG. 31B), and Calu-3 (FIG. 31C).
Figure 31B:
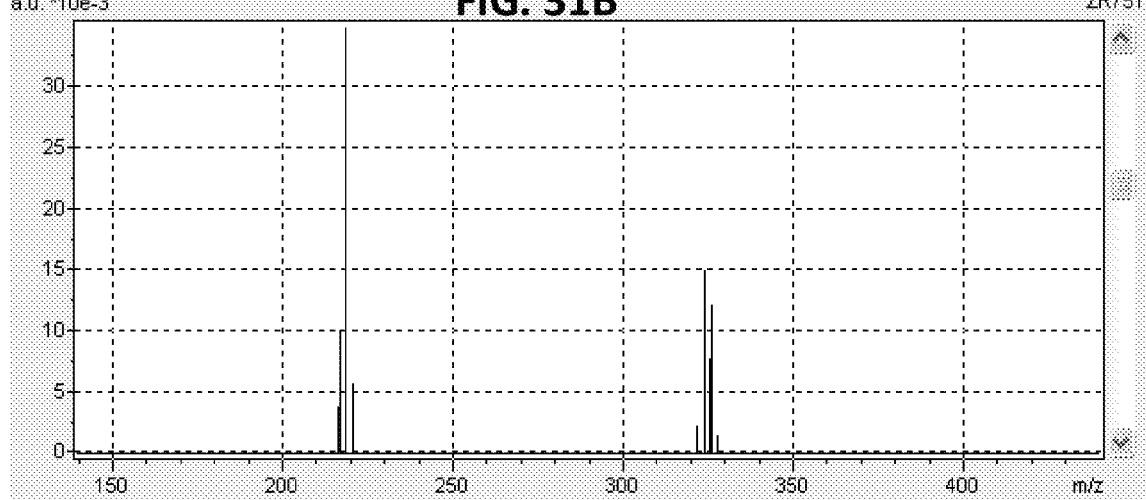
Figure 31C:
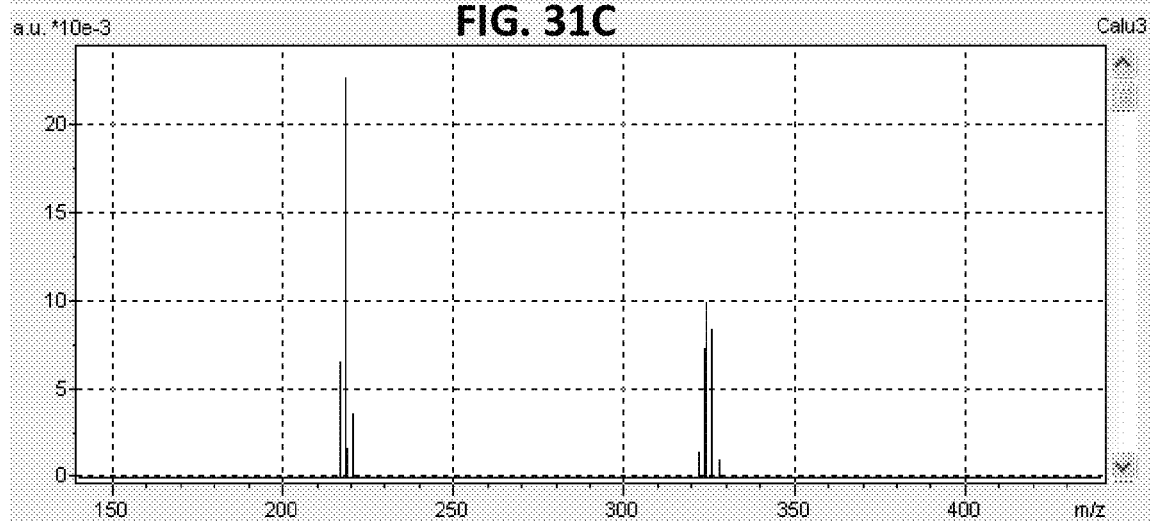

FIGS. 29A-29C illustrate optical images of Her2 xenografts negative control samples, wherein no Her2 gene probe is present, for MCF-7, ZR-751, Calu-3, respectively. FIGS. 30A-30C shows the heat maps of Ag$_2$$^+$ ions observed from the exemplary working embodiments with MCF-7, ZR-751, Calu-3, respectively, using a negative control slide (no Her2 gene probe is present). The relative intensity scale for these heat maps is included in FIG. 30C. Absolute intensity is significantly less than the sample slides with the Her2 gene probe. FIGS. 31A-31C illustrate the overall average spectra for Her2 negative control slide (no Her2 gene probe), showing Ag$_2$$^+$ and Ag$_3$$^+$ ions detected in background staining are shown for MCF-7, ZR-751, Calu-3, respectively. The overall average spectra include all spectra, with no minimum intensity requirement. Null spectra for negative cells will therefore lower the overall average spectra unless a minimum intensity threshold is defined. To accomplish this, spectra for each raster point were exported to Excel and an average intensity for all spectra with S/N ratio 10 was calculated.

The microscope images of AP SISH stained Her2 xenografts, MCF-7, ZR-751, Calu-3, respectively are illustrated in FIG. 32A-32C. The microscope images of AP SISH stained Her2 xenografts negative control samples (no Her2 gene probe) for MCF-7, ZR-751, Calu-3, are also illustrated in FIGS. 32D-32F. These samples, which were imaged in the MS, show the expected increase in silver staining with increasing Her2 gene copy number. Table 2, below, indicates the average intensity for Ag$_2$$^+$ in Her2 xenografts. The expected increase in silver staining is not captured in the mass spectral data, which may be related to small differences in Her2 gene copy number for each xenograft which the MS is unable to distinguish, or possibly due to background staining which differs with each xenograft.

TABLE 2

| | Average intensity (AU) | | |
|---|---|---|---|
| | MCF7 | ZR751 | Calu3 |
| Sample | 1686 | 1701 | 1669 |
| Neg Control | 4.4 | 5.7 | 7.4 |

A Her2 DNA probe was nick-labeled with the hapten 2,4-dinitrophenol (DNP) and incubated on the related tissues for 2 hr at 52° C. to target Her2 related genomic DNA (Ventana Medical Systems, 760-4332; 200 ul). A rabbit anti-DNP primary antibody (Ventana Medical Systems, 780-4335, 100 ul) was incubated on tissues for 20 min. at 37° C. to detect the Her2 DNA probe.

Figure 33:
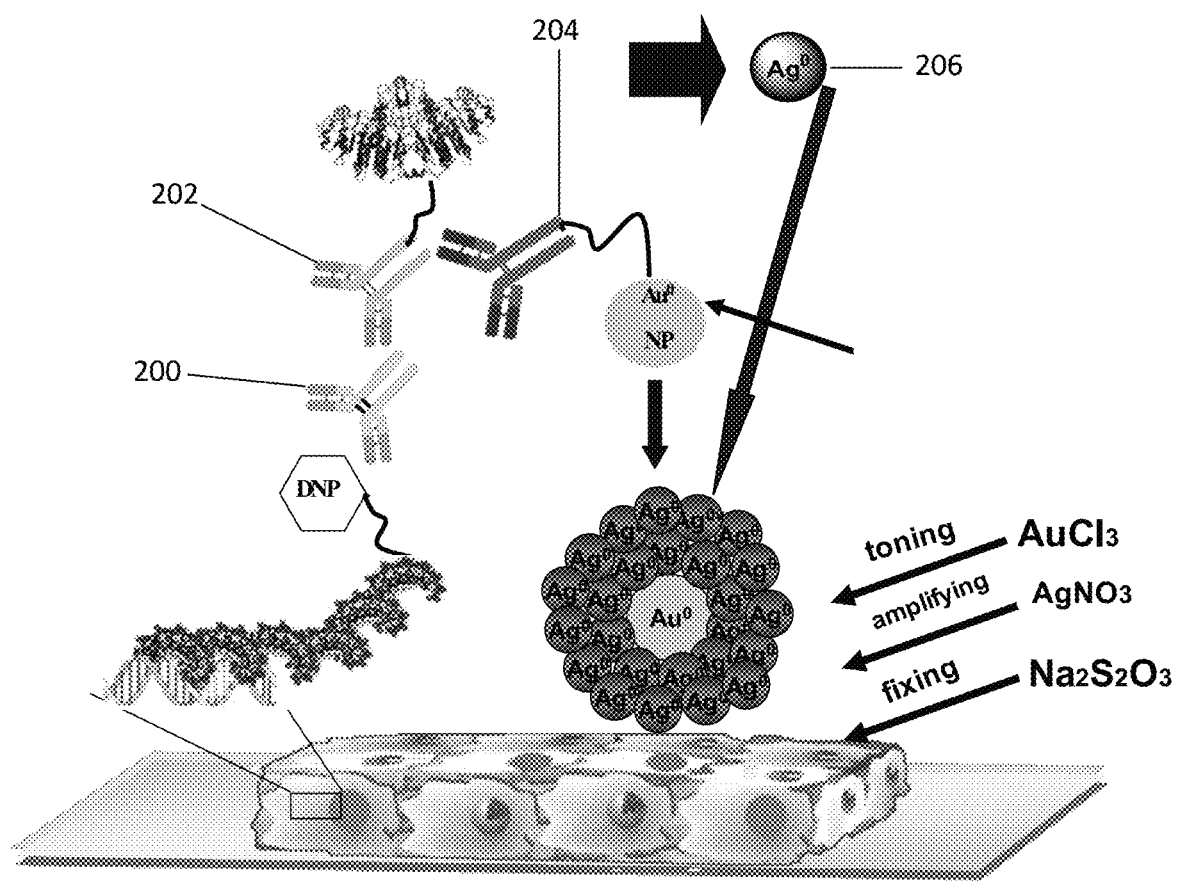
FIG. 33 is a schematic diagram illustrating an alkaline phosphatase (AP) silver in situ hybridization (SISH) based detection method.
Figure 36A:
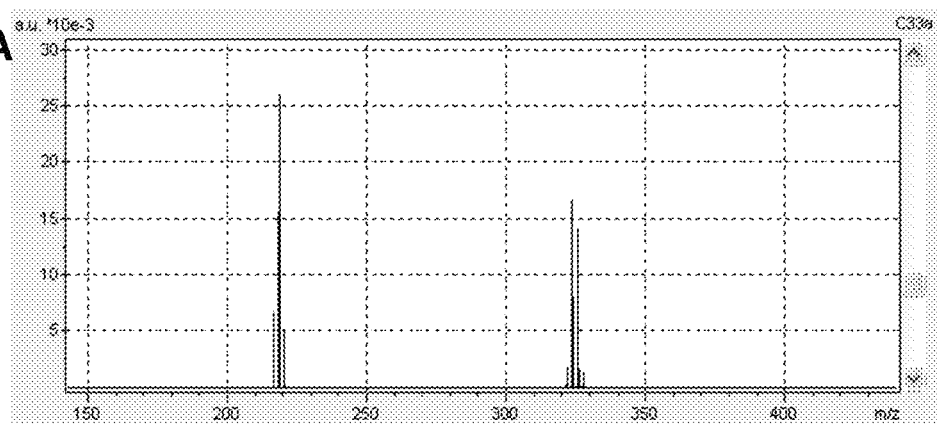
FIGS. 36A-36D are images of the overall average spectra for C-33A xenografts (FIG. 36A), SiHa xenografts (FIG. 36B), HeLa xenografts (FIG. 36C), and CaSki xenografts (FIG. 36D), showing $Ag_2^+$ and $Ag_3^+$ ions detected for HPV gene.
Figure 36B:
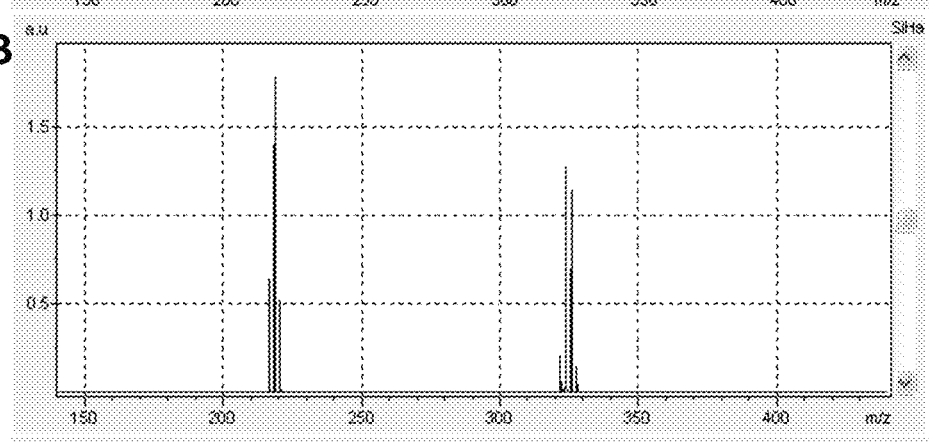
Figure 36C:
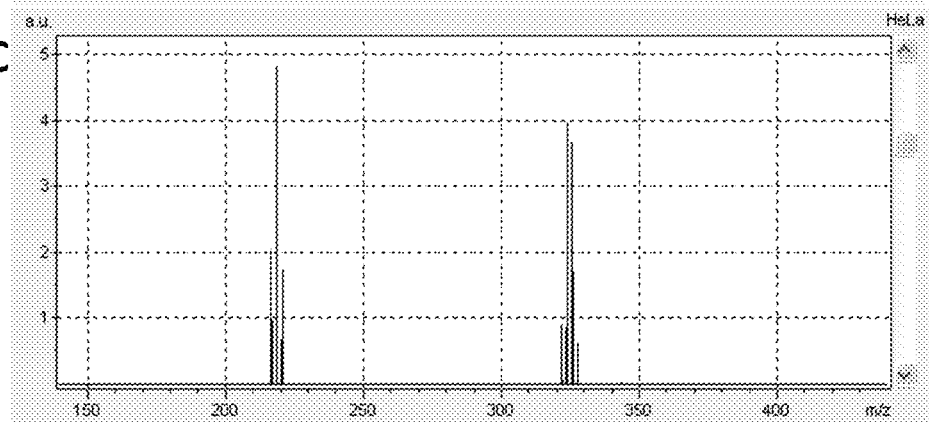
Figure 36D:
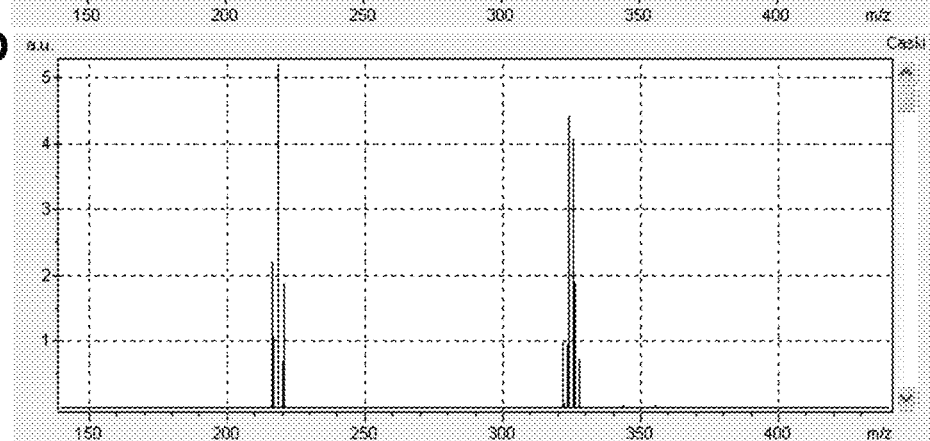
Figure 39A:
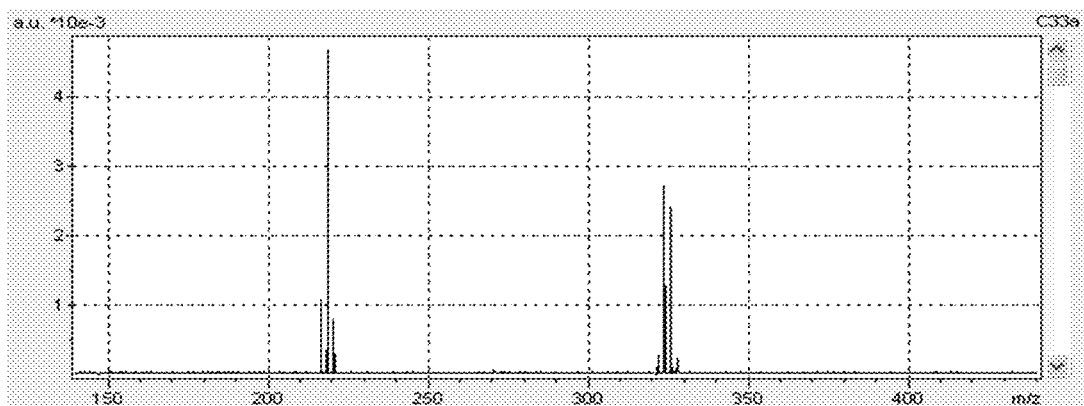
FIGS. 39A-39D are images of the overall average spectra for C-33A (FIG. 39A), SiHa (FIG. 39B), HeLa (FIG. 39C), and CaSki (FIG. 39D) negative control slides (no HPV gene probe), showing $Ag_2^+$ and $Ag_3^+$ ions detected in background staining for HPV gene.
Figure 39B:
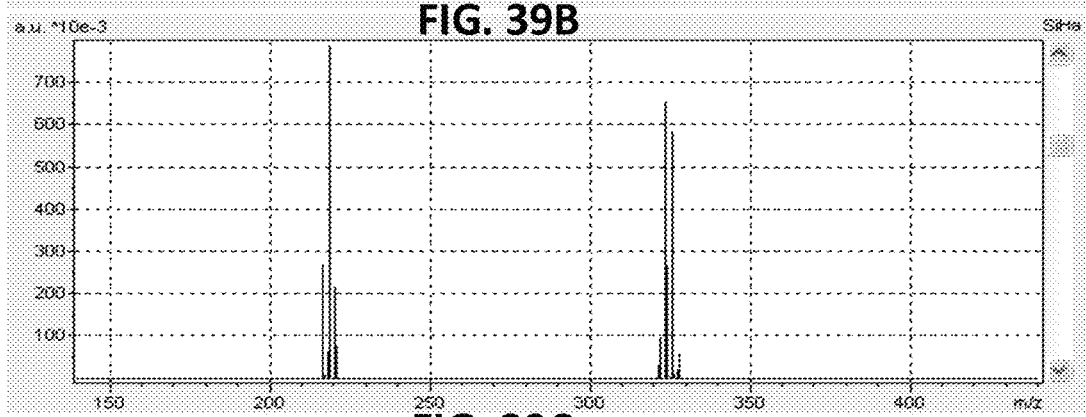
Figure 39C:
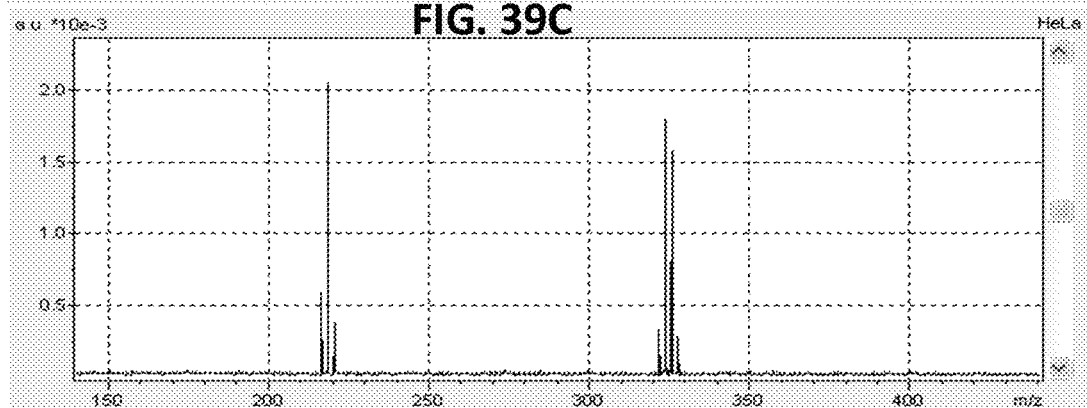
Figure 39D:
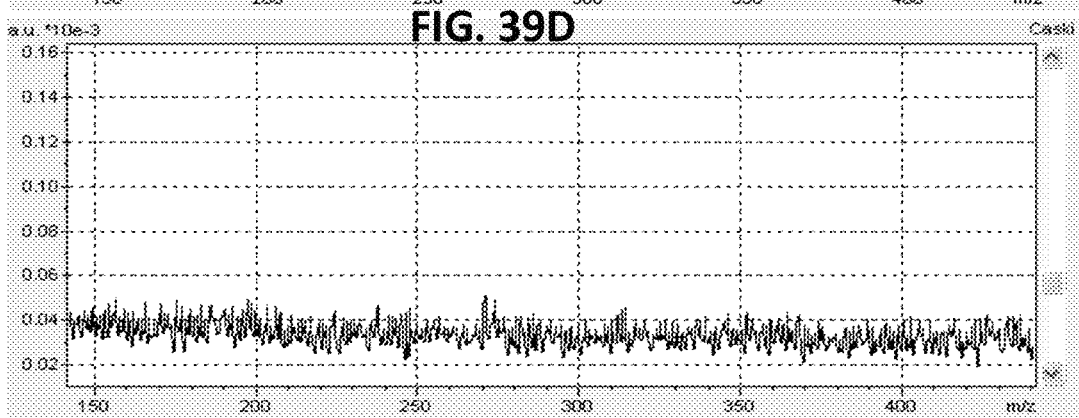

A general schematic diagram for this procedure is illustrated in FIG. 33. Following addition of the rabbit anti-hapten antibodies 200, goat anti-rabbit AP conjugated secondary antibody 202, for recognition of the rabbit primary antibody 200, are added to the slides. Rabbit anti-goat gold nanoparticle conjugated antibodies 204 are bound to the secondary antibodies, thereby functioning as a seeding site for subsequent silver deposition. Upon addition of $AgNO_3$ and BCIP to the slides, silver ions are reduced to silver atoms 206 by the alkaline phosphatase resulting in their deposition at the site of the gold nanoparticles. Toning is completed by the addition of $AuCl_3$, the signal is amplified with additional $AgNO_3$ and fixed with $Na_2S_2O_3$. $Ag_2^+$ and $Ag_3^+$ ions can be then be detected by mass spectrometry.

EXAMPLE 10

An FFPE multi-block of mouse xenograft tissues containing human cervical cancer cell lines of differential HPV genotype copy number C-33 A (ATCC HTB-31™; contains 0 HPV genes), SiHa (ATCC HTB-35™; contains 1-2 HPV genes), HeLa (ATCC CCL-2™; contains 10-50 HPV genes), and CaSki (ATCC CRL-1550™; contains 400-600 HPV genes) was cut to 4 μm thickness and placed onto an ITO glass slide (Bruker). FIGS. 34A-34D, FIGS. 35A-35D, FIGS. 36A-36D, FIGS. 37A-37D, FIGS. 38A-38D, and FIGS. 39A-39D show MS results for HPV xenografts. As with the Her2 xenograft data, the overall average spectra shown in FIGS. 52 and 55 include all spectra, with no minimum intensity requirement. Null spectra for negative cells will therefore lower the overall average spectra unless a minimum intensity threshold is defined. To accomplish this, spectra for each raster point were exported to Excel and an average intensity for all spectra with S/N ratio 10 was calculated. Overall average intensities calculated in this way for each xenograft are shown in FIGS. 39A-39D.

FIGS. 34A-34D illustrate optical images of HPV xenografts obtained from C-33 A, SiHa, HeLa, and CaSki respectively. FIGS. 35A-35D show the heat maps of $Ag_2^+$ ions observed from the exemplary working embodiments with C-33 A, SiHa, HeLa, and CaSki respectively. The relative intensity scale for these heat maps is included in FIG. 35D. The overall average mass spectra for all measured spectra of C-33 A, SiHa, HeLa, and CaSki, respectively, in HPV xenografts, showing the $Ag_2^+$ and $Ag_3^+$ ions are illustrated in FIGS. 36A-36D, respectively.

FIGS. 37A-37D illustrate optical images of HPV xenografts negative control samples, wherein no HPV gene probe is present, for C-33 A, SiHa, HeLa, and CaSki, respectively.

FIGS. 38A-38D shows the heat maps of $Ag_2^+$ ions observed from the exemplary working embodiments with C-33 A, SiHa, HeLa, and CaSki, respectively, using a negative control slide (no HPV gene probe is present). The relative intensity scale for these heat maps is included in FIG. 38D. Absolute intensity is significantly less than the sample slides with the HPV gene probe. FIGS. 39A-39D illustrate the overall average spectra for HPV negative control slide (no HPV gene probe), showing $Ag_2^+$ and $Ag_3^+$ ions detected in background staining are shown for C-33 A, SiHa, HeLa, and CaSki, respectively.

The microscope images of AP SISH stained HPV xenografts, C-33 A, SiHa, HeLa, and CaSki, respectively, are illustrated in FIGS. 40A-40D. The microscope images of AP SISH stained HPV xenografts negative control samples (no HPV gene probe) for C-33 A, SiHa, HeLa, and CaSki, respectively, are illustrated in FIGS. 40E-40H. Table 3, below, indicates the average intensity for $Ag_2^+$ in HPV xenografts.

TABLE 3

| | Average Intensity (AU) | | | |
|---|---|---|---|---|
| | C33a | SiHa | HeLa | Caski |
| Sample | 4.0 | 407 | 481 | 837 |
| Neg Control | 12 | 116 | 23 | 0 |

An HPV DNA probe, nick-labeled with the hapten digoxigenin (DIG) (Ventana Medical Systems, 200 ul of 8 ug/ml), was incubated on the related tissues for 6 hrs at 42° C. to target HPV DNA. while a rabbit anti-DIG primary antibody (Sigma-Alrich PN 07782, diluted 1:2,000, 100 ul) was incubated on tissues for 12 min. at 37° C. to detect the HPV DNA probe.

EXAMPLE 11

At this point, the protocol for both Her2 and HPV target detection are the same. As such, regardless of target, following addition of the rabbit anti-hapten antibodies, goat anti-rabbit AP conjugated secondary antibody for recognition of the rabbit primary antibody was added to the slides (100 ul of 20 ug/ml for 32 min. at 37° C.). Rabbit anti-goat gold nanoparticle conjugated antibodies were added (100 ul of 100 nM for 32 min. at 37° C.) and bound to the secondary antibodies, thereby functioning as a seeding site for subsequent silver deposition. Upon addition of AgNO3 (100 ul of 50 nM for 20 min. at 37° C.) and BCIP (Ventana Medical Systems, 95405, 100 ul for 20 min. at 37° C.) to the slides, silver ions were reduced to silver atoms by the alkaline phosphatase resulting in their deposition at the site of the gold nanoparticles. Toning was completed by the addition of $AuCl_3$ (100 ul of 0.20% solution for 4 min. at 37° C.), the signal was amplified with additional $AgNO_3$ (100 ul for 4 min. at 37° C.) and fixed with $Na_2S_2O_3$ (100 ul for 4 min. at 37° C.). $Ag_2^+$ and $Ag_3^+$ ions were detected in the MS using conditions described previously.

The above two ISH examples clearly demonstrate the capability of detecting generic materials on FFPE tissue samples using enzymatic amplified mass tag approach, which is not possible using direct or un-amplified MSI method. More importantly, in a suitable dynamic range, the enzymatic mass tag approach could also be established as a relative quantitation method for tissue diagnostics. The microscope images of AP SISH stained HPV xenografts (FIGS. 40A-40D) which were imaged in the MS show the expected increase in silver staining with increasing HPV gene copy number. However, gene copy numbers in chromogenic detection are generally not countable with more than four gene copies present, because above this level the chromogenic staining appears as an aggregate, rather than discrete countable signals. As indicated in Table 3, a trend between gene copies and MS signal intensity is captured in the MS data. Relative quantitation achieved through MSI detection of mass tags for genes or gene products of interest may therefore achieve a significant advantage over chromogenic detection.

Mutiplexing detection of three breast cancer relevant proteins (Her2, ER, PR) has been demonstrated with LDI mass tag detection in FFPE xenografts and human tissue. Mouse xenografts of the following cell lines were used for assay evaluation and development: MCF-7 (breast ductal carcinoma), ZR-75-1 (breast ductal carcinoma), and Calu-3 (non-small cell lung cancer adenocarcinoma). The assay was also demonstrated in human breast tissue samples.

The MCF-7, ZR-75-1, and Calu-3 xenografts were embedded in one paraffin block, so that all three xenografts were placed on one slide. Xenograft and breast tissue blocks were cut at 4 µm and allowed to air-dry onto SuperFrost+ or ITO coated slides. ITO slides were treated with 1% gelatin before tissue placement to facilitate successful mass tag deposition on BenchMark XT.

Figure 41:
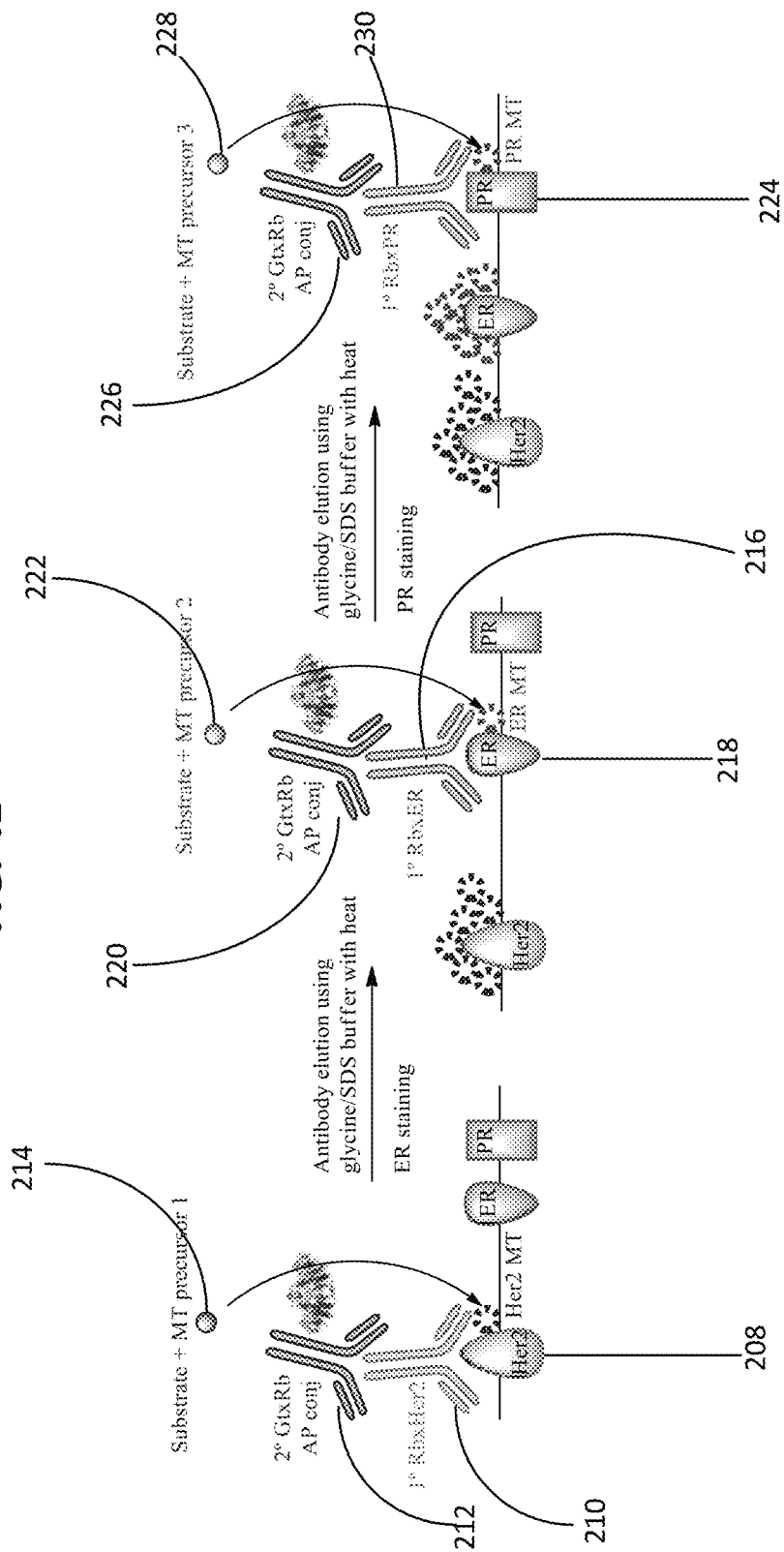
FIG. 41 is a schematic diagram for staining/mass tag deposition concerning triplexing.
Figure 42A:
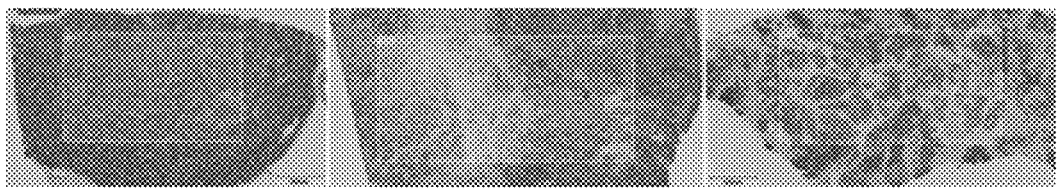
FIGS. 42A-42E are images illustrating mass spectrum heat map results for a MCF7 xenograft sample, a ZR751 xenograft sample, and a Calu3 xenograft sample wherein the measured region for the xenograft is enclosed with the white box.
Figure 42B:
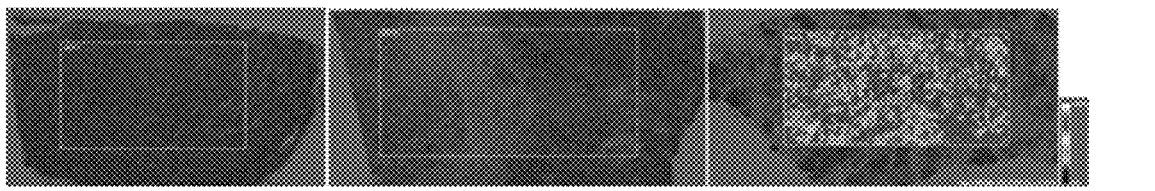
Figure 42C:
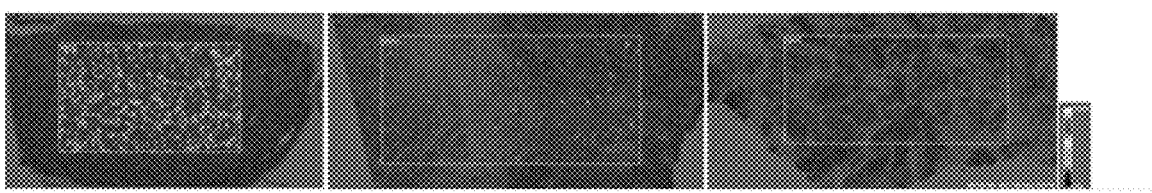
Figure 42D:
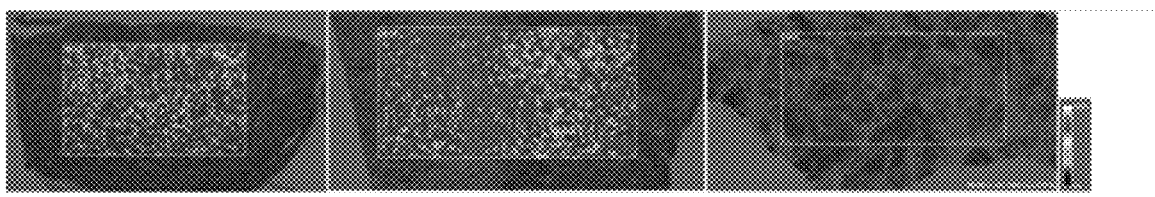
Figure 42E:
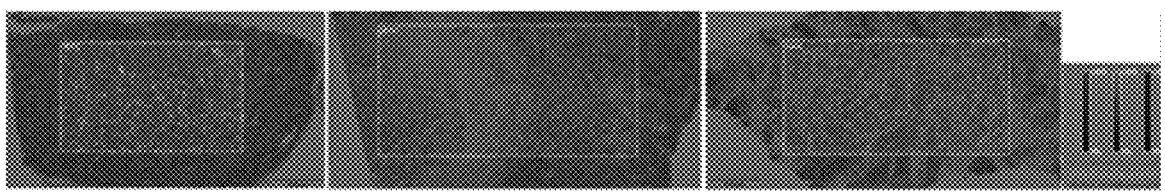

Staining/mass tag deposition was done on a BenchMark XT using an automated protocol. The general staining scheme used is shown in FIG. 41. According to FIG. 41, a primary antibody 210 recognizing a first target 208 is recognized by a secondary antibody-enzyme conjugate 212. A mass tag precursor conjugate 214 is added to the sample and deposited after reaction with the enzyme. After the primary antibody 210 and the antibody-enzyme conjugate 212 are removed via elution (i.e. the deactivation process), a second primary 216 recognizing a second target 218 is recognized by a secondary antibody-enzyme conjugate 220. A second mass tag precursor conjugate 222 is added to the sample and deposited after reaction with the enzyme. The deactivation process is repeated, and a third primary antibody 230 recognizing a third target 224 is recognized by a third antibody-enzyme conjugate 226. A third mass tag precursor conjugate 228 is added to the sample and deposited after reaction with the enzyme. All reagents used were from Ventana Medical Systems, Inc. unless otherwise noted. After antigen retrieval, an anti-Her2 primary rabbit monoclonal antibody (PN 790-2991) binds Her2 protein. A goat anti-rabbit alkaline phosphatase (AP) conjugated secondary antibody (PN 760-4314) binds the anti-Her2 antibody.

AP catalyzes the dephosphorylation of naphthol AS TR phosphate (PN 760-4308); the dephosphorylated product then undergoes an azo coupling with a diazonium salt, producing an insoluble precipitate at the antigen site. The chemistry of the AP catalyzed mass tag deposition is shown below in Scheme 25 (FIG. 76). The diazonimum salts used were fast blue BB (FB BB, Sigma-Aldrich PN F3378), fast blue RR (FB RR, Sigma-Aldrich PN F0500), and fast violet B (FV B, Sigma-Aldrich PN 201596) for Her2, ER, and PR respectively. Each diazonium salt was prepared at approximately 4 mM in buffer (10 mM $NaCH_3COOH$ pH 3.95, 250 mM $MgCl_2$, 0.37% Brij-35) and stored in a light-impenetrable dispenser.

After deposition of the Her2 mass tag, the primary and secondary antibodies are eluted from the tissue section using 1% SDS (Sigma-Aldrich PN L3771-500) 25 mM Glycine (Bio-Rad PN 161-0718) pH 2 buffer (Pirici, D., Mogoanta, L., et al. (2009) "Antibody Elution Method for Multiple Immunohistochemistry on Primary Antibodies Raised in the Same Species and of the Same Subtype."*Journal of Histochemistry and Cytochemistry* 57(6): 567-575.

ER and PR are then sequentially stained in a similar manner on the same tissue sample. The primary and secondary antibody complex used for PR mass tag deposition is not eluted from the tissue using the glycine/SDS buffer.

Upon completion of the BenchMark XT staining/mass tag deposition, the slides are washed with dilute detergent to remove hydrophobic reagents used on the automated stainer, rinsed with tap water, then dried overnight under high vacuum (~$10^{-4}$ torr) before LDI-MS analysis of the intact tissue sample with Bruker Daltonic's Autoflex III mass spectrometer.

Mass spec imaging was done using a laser diameter of approximately 20 µm. Imaging data used a raster width of 30 µm. The mass spec was operated in the positive ion mode with no post-ion extraction delay. Voltages used were: ion source 1 20 kV, ion source 2 18.85 kV, lens 6 kV, and linear detector 1.545 kV. Laser frequency was 200 Hz, and up to 100 shots were summed per raster point. Data was collected in the mass range of 400-500 Da.

Figures 44A, 44B, 44C:
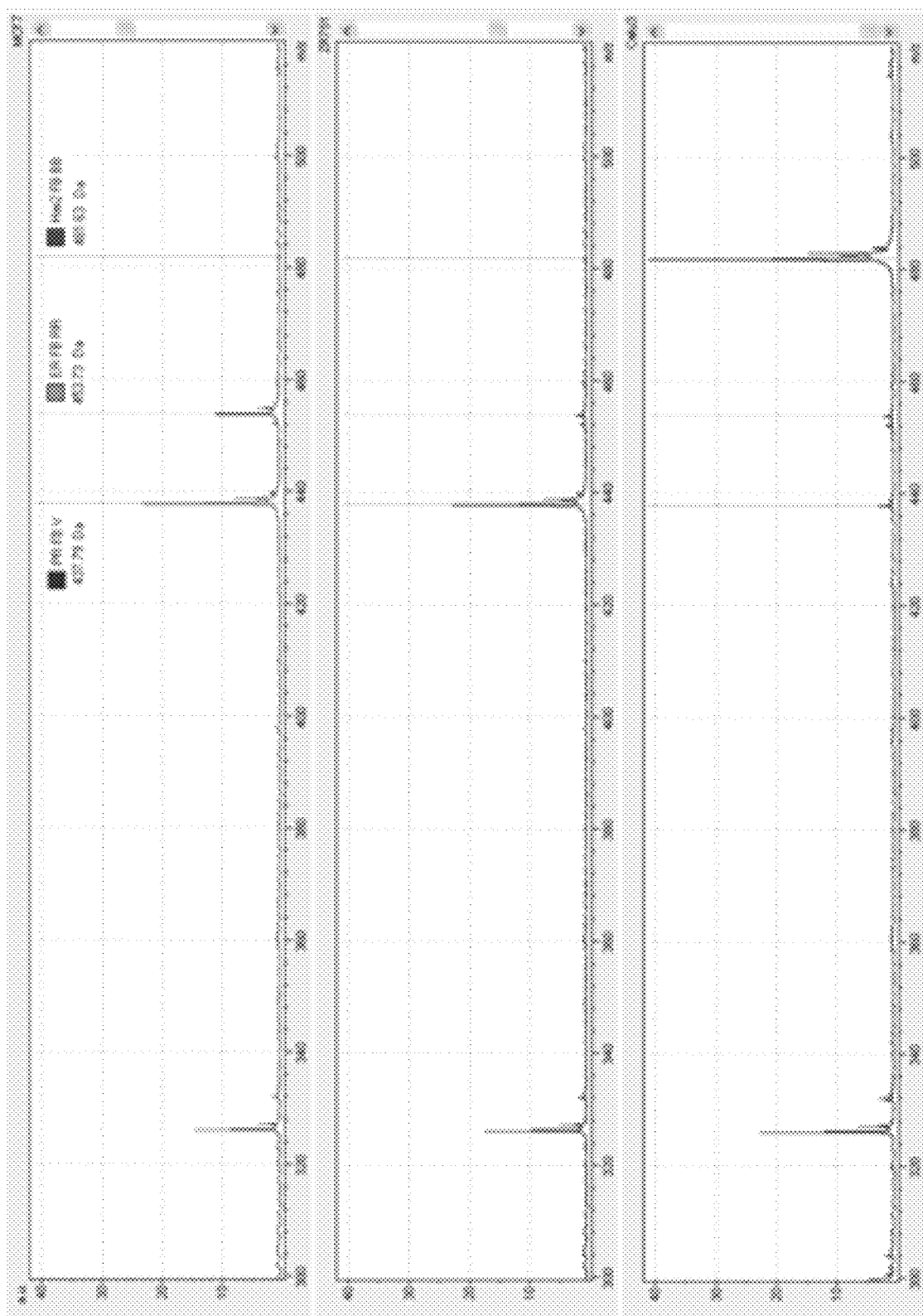

Typical data obtained for xenograft samples is shown in FIGS. 42A-42E. The mass spectra in FIGS. 44A-44C are consistent with optical staining results. Optical staining using routine immunohistochemistry (IHC) techniques show approximately equal staining for ER and PR in the MCF7 xenograft, mostly PR with little ER staining in the ZR751 xenograft, and only Her2 staining in the Calu3 xenograft.

Three different control samples were run for evaluating the xenograft model system: (1) no primary antibody for Her2, ER, or PR; (2) no secondary antibody-alkaline phosphatase conjugate; and (3) no elution of antibodies with glycine/SDS buffer before staining ER and PR. The first two types of control samples showed colorless tissue with no mass tags detected in the mass spectrometer using laser powers equal to that used on samples.

EXAMPLE 12

The exemplary disclosed embodiment described in Example 11 has been expanded to quadruplexed detection of Her2, ER, PR and Ki67 using substantially similar methods to those methods described in Example 11. Quadruplexed detection was demonstrated in a FFPE multiblock containing MCF-7, ZR-75-1, and Calu-3 xenografts. Because Her2 expression in these xenografts is substantially higher than ER, PR or Ki67, a mass tag with considerably lower ionization by LDI-MS was chosen for Her2. This allows mass tag detection for all four antigens using one laser power to sample the MCF-7, ZR-75-1 and Calu-3 xenografts contained on one slide.

In this non-limiting example, the following diazonium salts were used to generate mass tags for each antigen: fast red violet LB (FR V LB, Sigma-Aldrich PN F3381) for Her2; FB BB for ER; FB RR for PR; and FV B for Ki67 (listed in the order of sequential staining). The structure of FR V LB and the detected mass tag are illustrated below. LDI-MS results are shown in FIGS. 45A-45C. The FR V LB mass tag precursor has substantially less intense ionization by laser desorption than the three other mass tag precursors used, resulting in a small detected signal for Her2 even though the Her2 antigen concentration is high relative to the three other antigens detected.

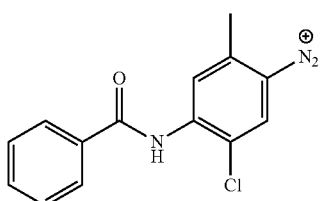

Fast Red Violet LB

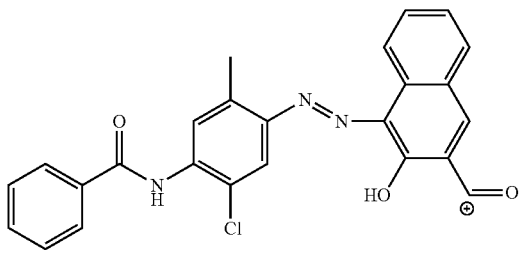

HER2 mass code
Chemical Formula: $C_{25}H_{17}ClN_3O_3^+$
Exact Mass: 442.10

Figure 46A:
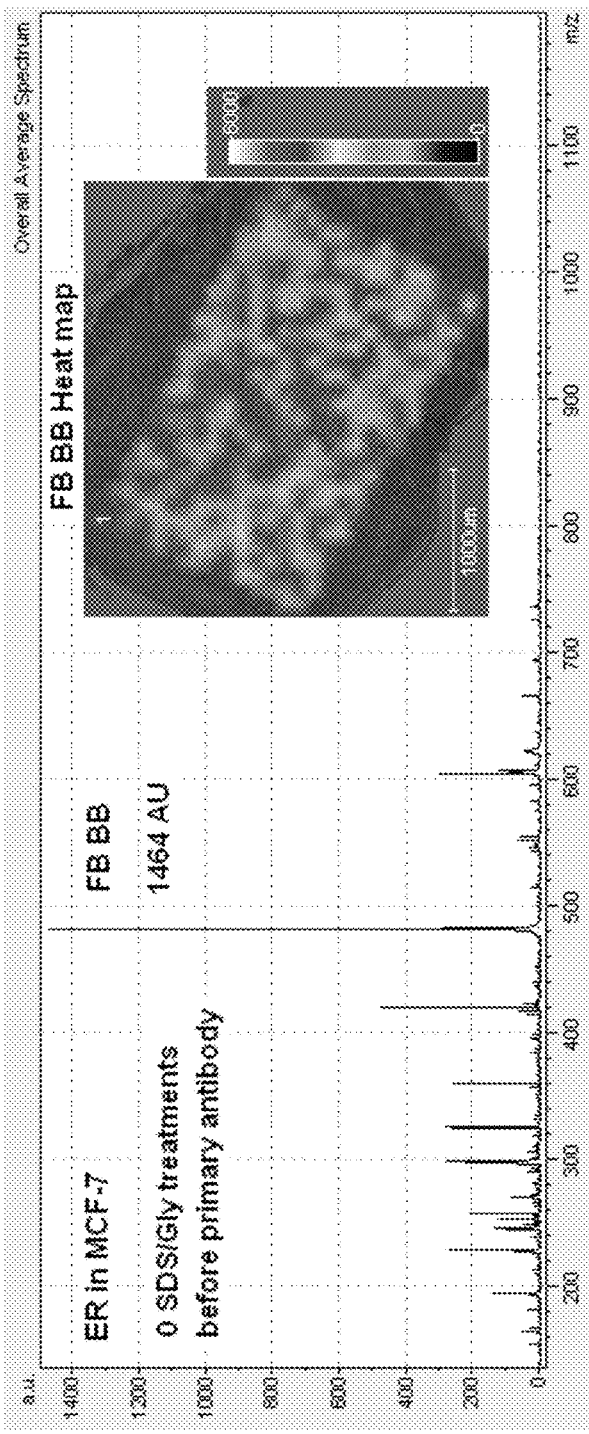
FIGS. 46A and 46B are images illustrating the results in an exemplary working embodiment wherein the effect of SDS/glycine buffer treatments on the sample were determined using a control (no SDS/glycine treatment) (FIG. 46A) and an sample washed twice with SDS/glycine treatment (FIG. 46B).
Figure 46B:
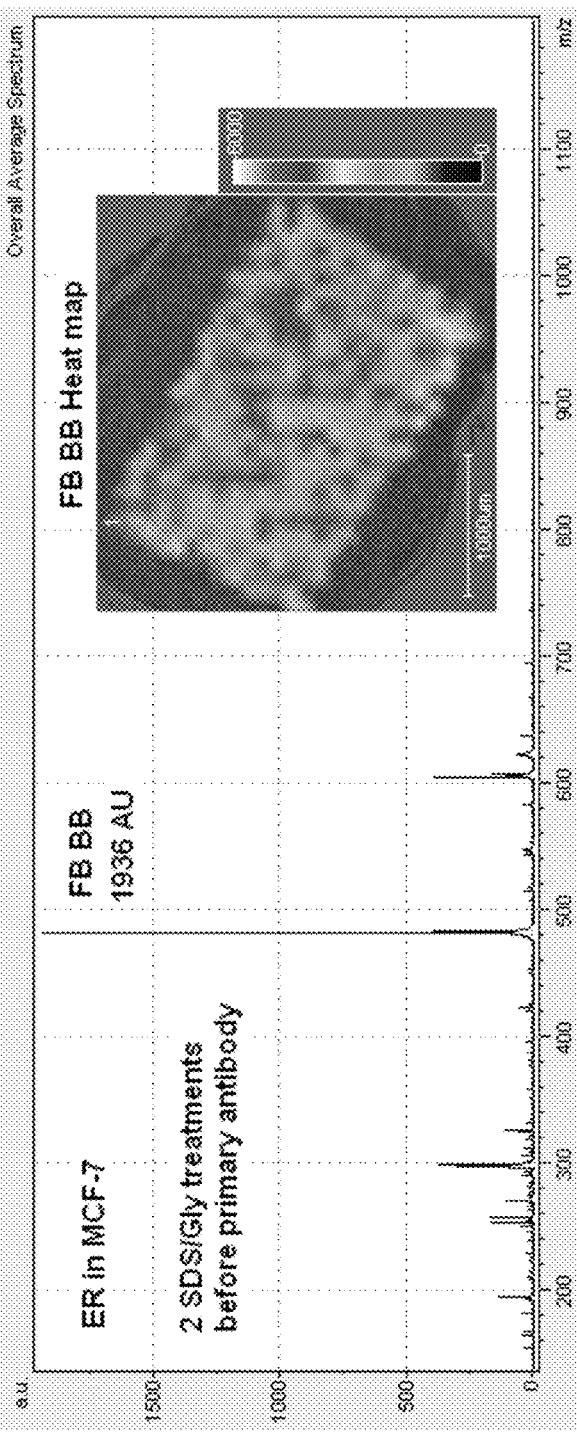
Figure 47A:
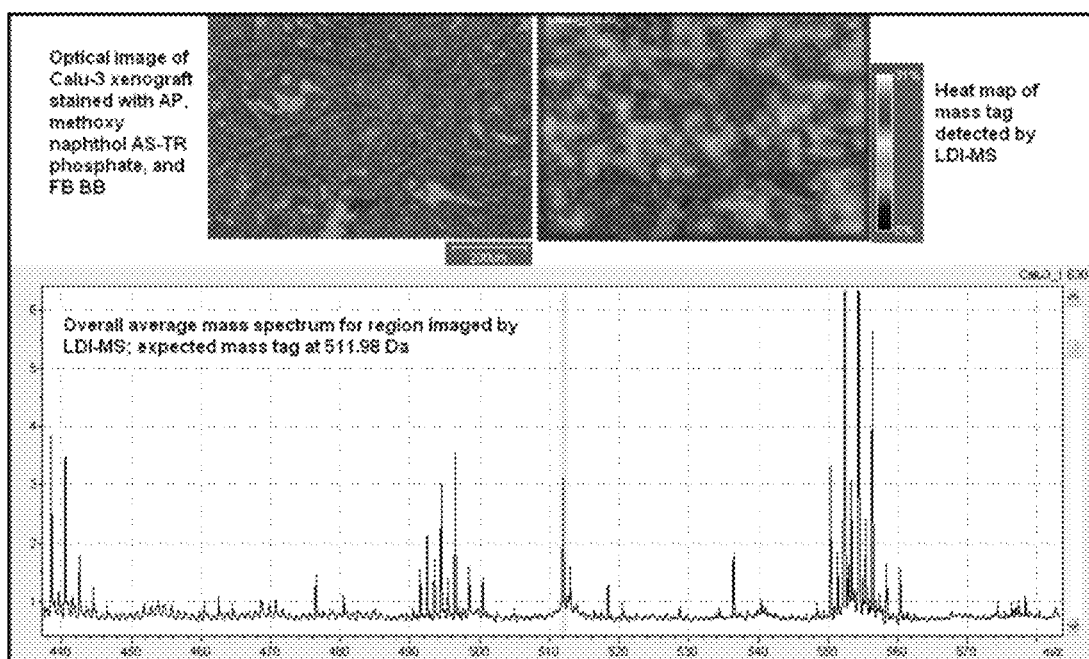
FIGS. 47A and 47B are images illustrating the exemplary results obtained by comparing different exemplary mass tag precursors.
Figure 47B:
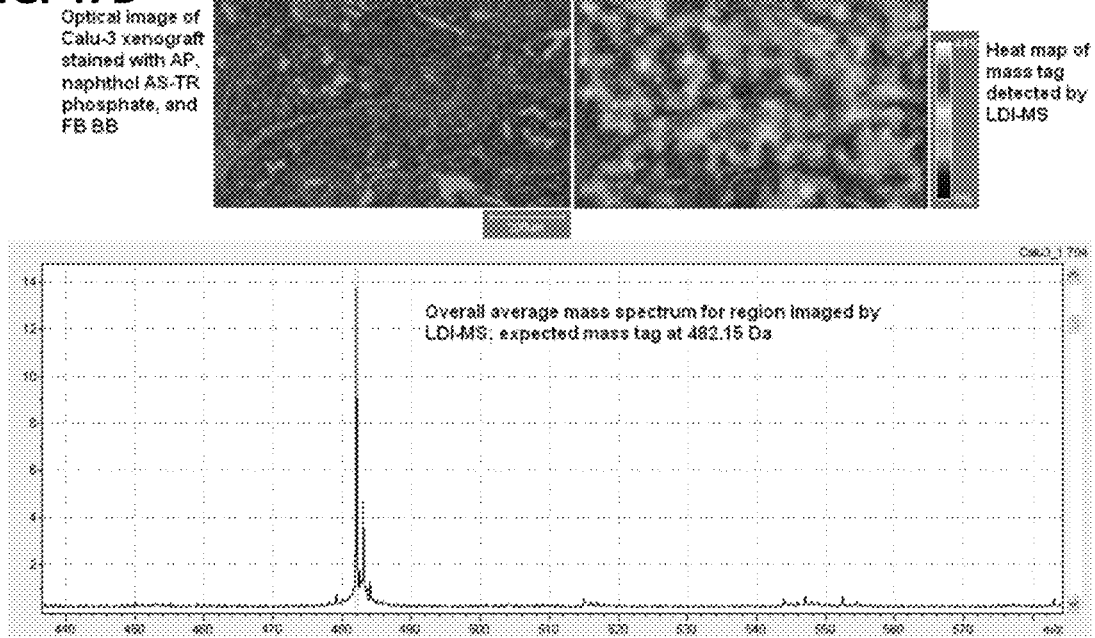

Possible antigen damage caused by the 1% SDS 25 mM glycine pH 2 antibody elution treatment was evaluated for ER, PR, Ki67, and Her2, with the evaluation for each antigen done on separate tissue sections. Xenografts were cut at 4 µm and placed on ITO coated glass slides treated with 1% gelatin. Following antigen retrieval, xenografts were subjected to zero or two cycles of 1% SDS 25 mM glycine pH 2 washing at 50° C. Detection was then completed with the addition of the following: an appropriate primary antibody; AP conjugated secondary antibody; naphthol AS TR phosphate; and FB BB. The FB BB mass tag was detected using LDI-MS. Results for ER are shown in FIGS. 46A and 46B. A summary of results for all antigens is shown in Table 4. The SDS glycine treatment did not decrease detection of the FB BB mass tag for ER and had no significant impact on the FB BB mass tag detection for Her2.

TABLE 4

Effects of SDS/Gly treatment, before primary antibody addition, on LDI-MS detection of FB BB mass tag.

| | | FB BB intensity (AU) in overall average spectrum | |
|---|---|---|---|
| Xenograft | Antigen | 0 SDS/Gly treatments | 2 SDS/Gly treatments |
| Calu-3 | Her2 | 1854 | 1950 |
| MCF-7 | Ki67 | 2280 | 2329 |
| MCF-7 | PR | 696 | 1748 |
| MCF-7 | ER | 1464 | 1936 |

Possible removal of precipitated diazonium coupling reaction products by the 1% SDS 25 mM glycine pH 2 antibody elution treatment was evaluated. Single antigen detection for ER or Her2 was done on xenograft sections. After all mass tag deposition steps were completed and the mass tag precursor was deposited at the antigen site, slides were treated with zero, one, two, or three rounds of the 1% SDS 25 mM glycine pH 2 antibody elution treatment at 50° C. The intensities of the mass tag obtained from the overall average mass spectrum for the region imaged by LDI-MS are summarized in Table 5. LDI-MS parameters were held constant for the four slides examined for one antigen and one particular mass tag, but were not necessarily held constant for analysis of another mass tag/antigen combination. The SDS glycine buffer treatment did not reduce the intensity of detected mass tags.

TABLE 5

Mass tag intensities (in arbitrary units AU) in overall average mass spectrum, following treatment with SDS/Glycine buffer after mass tag deposited. One antigen detected with one mass tag per slide.

| | | #SDS/Gly | Mass tag intensity (AU) | | | |
|---|---|---|---|---|---|---|
| Xenograft | Antigen | treatments | FB BB | FB RR | FV B | FR V LB |
| MCF-7 | ER | 0 | 41.1 | 14.8 | 45.4 | NT |
| MCF-7 | ER | 1 | 64.7 | 28.8 | 36.2 | NT |
| MCF-7 | ER | 2 | 53.6 | 37.2 | 51.1 | NT |
| MCF-7 | ER | 3 | 74.3 | 38.3 | 39.3 | NT |
| Calu-3 | Her2 | 0 | 39.8 | 25.6 | NT | 14.2 |
| Calu-3 | Her2 | 1 | 40.4 | 24.2 | NT | 21.9 |
| Calu-3 | Her2 | 2 | 53.6 | 17.4 | NT | 29.5 |
| Calu-3 | Her2 | 3 | 52.7 | 28.6 | NT | 28.8 |

NT = not tested

Quadruplexed mass tag intensities relative to single antigen mass tag intensities were examined. Quadruplexed detection for Her2, ER, PR and Ki-67 was completed on one slide containing MCF-7, ZR-75-1, and Calu-3 xenografts. Four separate serial section slides were stained individually for each separate antigen, using the same mass tag for each antigen as in the quadruplex slide. Mass tag intensities from the overall average spectrum for the region measured by LDI-MS are summarized in Table 6. The lower intensities observed in the quadruplexed slide relative to the single antigen slides is possibly due to ion suppression, a documented phenomenon in LDI-MS. Without being limited to a particular theory of operation, it is currently believed that the presence of multiple mass tags at the antigen site may lower the intensity of each detected mass tag.

TABLE 6

Mass tag intensities from overall average spectrum for quadruplex verses single antigen detection.

| Mass | | MCF-7 | | ZR-75-1 | | Calu-3 | |
|---|---|---|---|---|---|---|---|
| Tag | Antigen | Quad | Single | Quad | Single | Quad | Single |
| FV B | Ki-67 | 29.8 | 84.2 | 32.7 | 87.4 | 18.0 | 37.7 |
| FB RR | PR | 17.0 | 39.1 | 35.8 | 76.5 | 4.8 | 2.0 |
| FB BB | ER | 12.4 | 53.6 | 6.2 | 17.9 | 2.5 | ND |
| FR V LB | Her2 | ND | ND | ND | ND | 5.3 | 19.2 |

ND = not detected

EXAMPLE 13

This exemplary embodiment concerns using a small laser diameter for analysis. Laser diameter was estimated to be approximately 50 µm for data shown in Examples 9 and 10. Background silver staining varies heterogeneously across tissue sections, variably affecting the overall intensity measured when ionizing silver atoms via LDI. With a smaller laser diameter, cells showing positive silver staining can be sampled with less overlapping of the laser into negative cells having only background staining, theoretically giving a more accurate measurement of silver intensity in positive cells. Results are shown in FIGS. 67 and 68.

Figure 48:
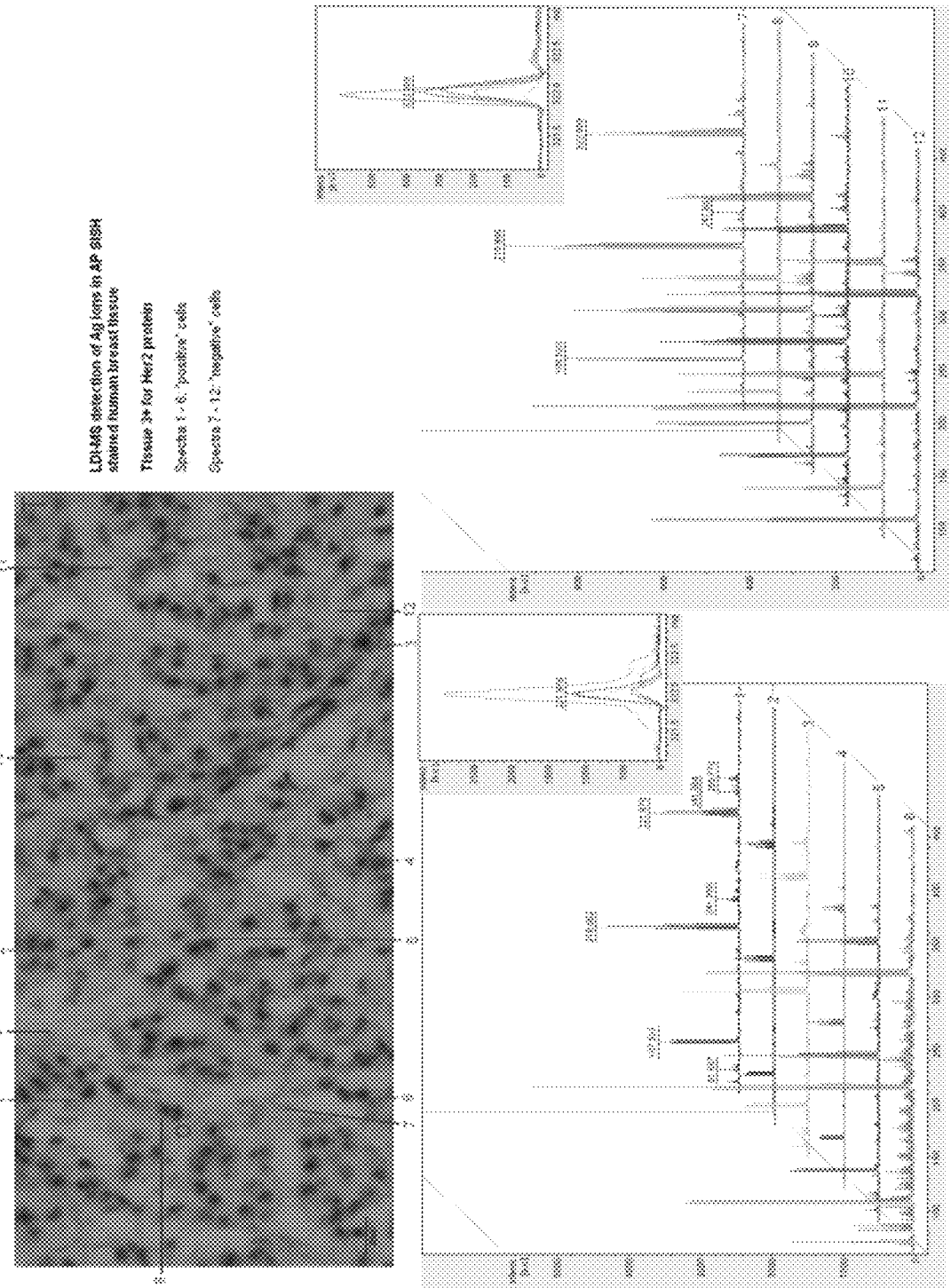
FIG. 48 is a combined image illustrating an optical image of an exemplary xenograft comprising positive cells and negative cells, a combined mass spectrum of the silver ion mass codes detected in the positive cells, and a combined mass spectrum of the silver ion mass codes detected in the negative cells.
Figure 49:
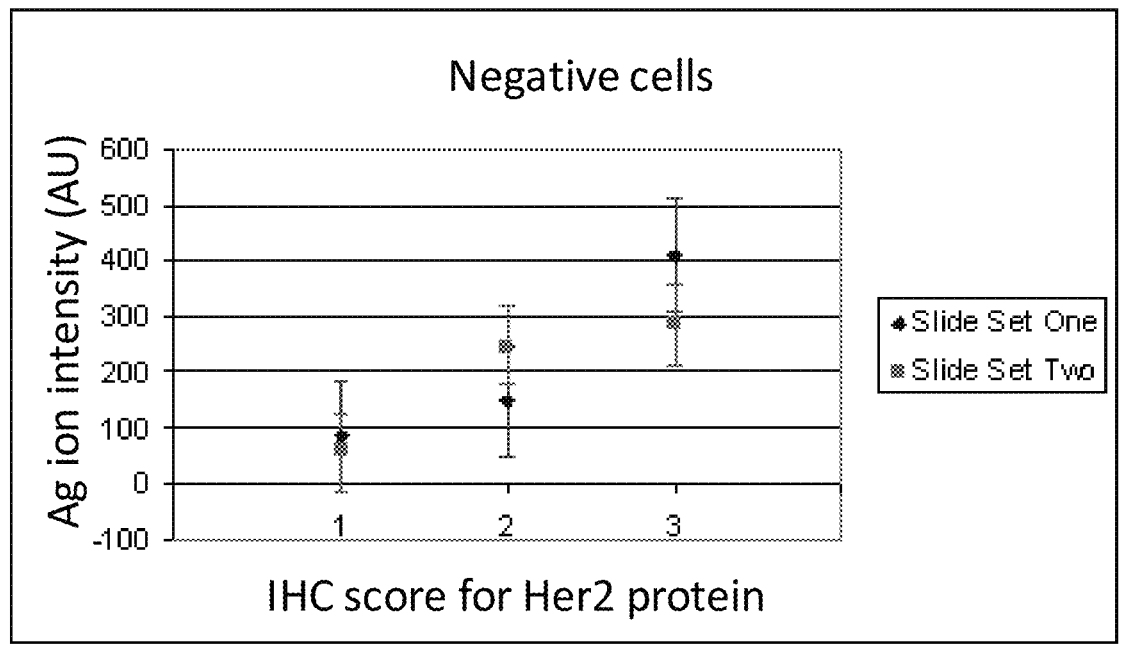
FIG. 49 is a graph of silver ion intensity (au) versus the IHC score for Her2, which summarizes the silver ion mass code intensity results obtained for the negative cells of Example 13.
Figure 50:
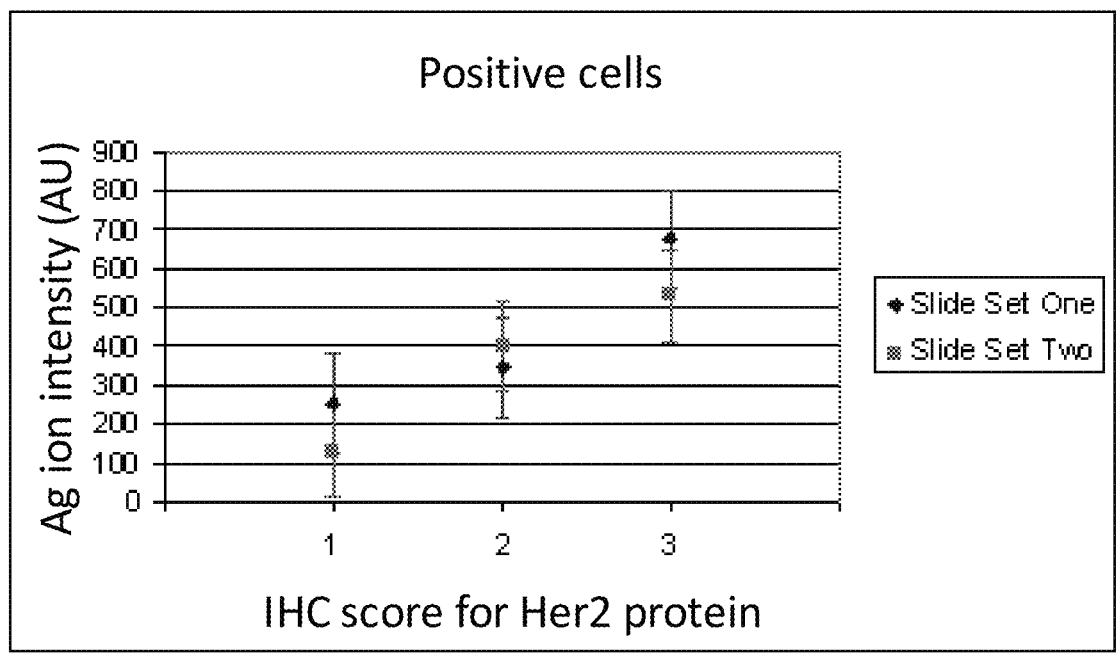
FIG. 50 is a graph of silver ion intensity (au) versus the IHC score for Her2, which summarizes the silver ion mass code intensity results obtained for the positive cells of Example 13.
Figure 51A:
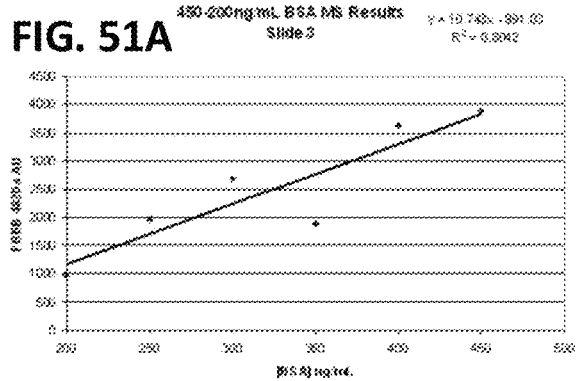
FIGS. 51A-51F are images of graphs (mass code intensity [au] versus protein concentration [ng/mL]) illustrating the mass spectral (FIG. 51A-51C) and ImageJ (FIG. 51D-51F) results for a protein covalently bound to an ITO slide.
Figure 51B:
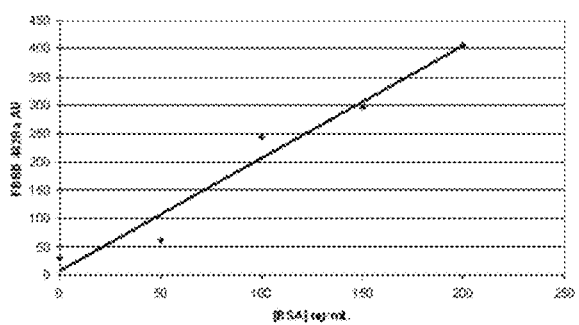
Figure 51C:
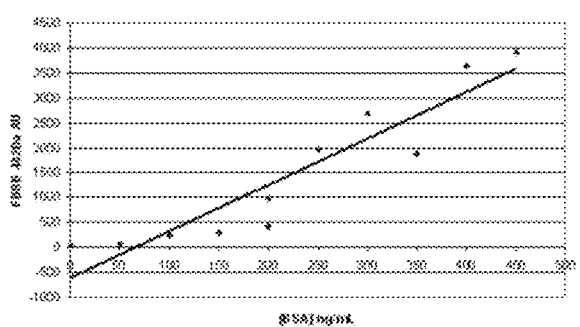
Figure 51D:
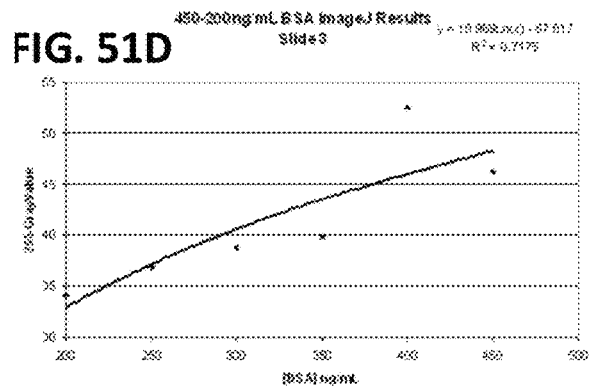
Figure 51E:
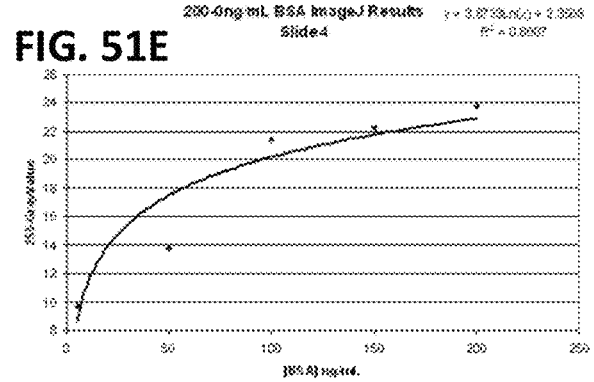
Figure 51F:
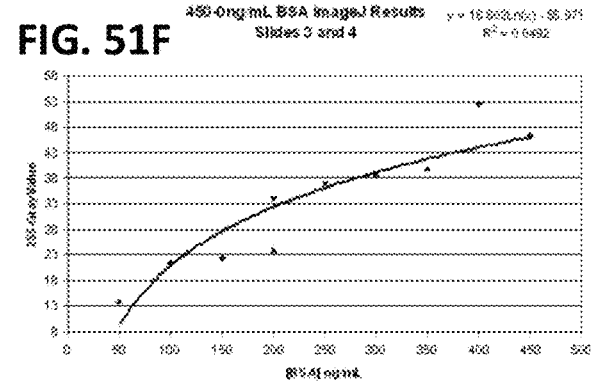

Human breast tissue 4 µm sections were placed on ITO coated glass slides treated with 1% gelatin and stained for Her2 DNA using the AP silver in-situ hybridization procedure described in Example 9. Silver ions were detected with LDI-MS in profiling mode by collecting single spectra at individual raster points. For each raster point sampled, shots were accumulated and summed until silver signal was depleted at one set laser power. The laser power and focus settings produced a diameter of approximately 15-25 μm. Exemplary results are shown in FIG. 48. A numerical summary of data is shown in Table 7, and a graphical summary in FIG. 49 and FIG. 50. Tissues were stained with traditional IHC methods for Her2 protein, with the Her2 protein status rated as 0, +1, +2, or +3 by a pathologist. These Her2 protein scores are included with the data shown in FIG. 48, FIG. 49, and FIG. 50, and Table 7. While there is substantial variability in the data, (which, without being limited to a particular theory of operation, could be a reflection of heterogeneity of cancer cells) the intensity of silver ion detected as Her2 gene mass tag does correlate with known Her2 protein expression levels.

TABLE 7

Intensities (in AU) of silver ions detected as mass tags for Her2 gene in human breast tissue. Intensities are for profiling spectra. Bkgrd = background/negative cell response.

|  | m/z = 322 (pos cell) | | m/z = 322 (Bkgrd) | |
| --- | --- | --- | --- | --- |
| IHC 1+ | Slide A | Slide B | Slide A | Slide B |
|  | 538 | 92 | ND | ND |
|  | 48 | 134 | 120 | 60 |
|  | 100 | 66 | 78 | 54 |
|  | 153 | 178 | 71 | ND |
|  | 326 | 88 | 62 | ND |
|  | 360 | 221 | ND | ND |
| Avg | 254 | 130 | 83 | 57 |
| Std Dev | 186 | 60 | 26 | 4 |
| % RSD | 73 | 46 | 31 | 7 |
| IHC 2+ | Slide C | Slide D | Slide C | Slide D |
|  | 96 | 305 | 245 | 315 |
|  | 128 | 507 | 177 | 335 |
|  | 327 | 427 | 174 | 296 |
|  | 798 | 243 | 74 | 181 |
|  | 331 | 661 | 70 | 141 |
|  | 404 | 261 | 146 | 212 |
| Avg | 347 | 401 | 148 | 247 |
| Std Dev | 252 | 163 | 67 | 79 |
| % RSD | 73 | 41 | 45 | 32 |
| IHC 3+ | Slide E | Slide F | Slide E | Slide F |
|  | 687 | 1073 | 383 | 300 |
|  | 283 | 318 | 429 | 149 |
|  | 1251 | 423 | 617 | 287 |
|  | 343 | 445 | 333 | 387 |
|  | 1188 | 309 | 389 | 293 |
|  | 299 | 594 | 308 | 298 |
| Avg | 675 | 527 | 410 | 286 |
| Std Dev | 447 | 287 | 110 | 77 |
| % RSD | 66 | 54 | 27 | 27 |

EXAMPLE 14

Particular disclosed embodiments concern quantifying enzymatically deposited mass tags. To evaluate the feasibility of quantification (wherein quantification comprises determining the size of a mass peak and correlating it with the amount of a particular target) using LDI-MS detection of enzymatically deposited mass tags, tissue-free exemplary working embodiments were performed in order to eliminate sample variation inherent in tissue samples. ITO coated glass slides were chemically modified to covalently bind protein to the slide without disturbing the ITO coating. Bovine serum albumin (BSA) was spotted on the slide in known concentrations. Staining/mass tag deposition was then completed on the Benchmark XT as described under Example 11, using a mouse anti-BSA primary antibody, and FB BB. The SDS/glycine buffer treatment was not needed in these single antigen exemplary working embodiments; however, a person of ordinary skill in the art would recognize that such a buffer treatment may be used. The FB BB mass tag was detected using LDI-MS.

To allow comparison of LDI-MS results with some orthogonal technique, ImageJ software was used to determine a gray value for each spot before slides were imaged in the MS. Because gray values vary logarithmically with antigen concentration, ImageJ data were fit with a logarithmic trendline. A correlation was observed for spotted BSA concentrations ranging from 0 to 450 ng/mL, which demonstrates the feasibility of quantification (wherein quantification comprises determining the size of a mass peak and correlating it with the amount of a particular target) of LDI-MS detection of enzymatically deposited mass tags. LDI-MS detection of FB BB and ImageJ gray value results are shown in FIGS. 51A-51F.

EXAMPLE 15

This particular exemplary embodiment concerns using heteroaryl compounds in conjunction with transition metal ions for enhanced detection by MS under LDI conditions. A particular disclosed embodiment concerns using DAB combined with nickel chloride ($NiCl_2$) for HRP catalyzed staining and subsequent MSI. For this exemplary embodiment, the following general staining procedure was used. Except for the $NiCl_2$ solution, all the other reagents (DAB inhibitor, HRP multimer, DAB chromogen, and DAB $H_2O_2$) were obtained from the Ventana ultraView™ Universal DAB detection kit (catalog number: 760-500). After applying the HRP multimer, one drop of DAB chromogen and one drop of $NiCl_2$ (16 mM in water) were applied on the tissue section and incubated for a certain period (e.g. 4-32 minutes). Alternatively, a pre-mixture of DAB chromogen and $NiCl_2$ solution was made separate from the slide and incubated prior to adding onto the tissue. Approximately one drop of DAB $H_2O_2$ was then dispensed on the slide and incubated for 8 minutes. After staining, the slides were treated as with standard DAB stain and were further dried under high vacuum. The dried slides were examined in Autoflex III under LDI conditions (e.g. no matrix material used). A representative image is shown in FIGS. 52A and 52B.

EXAMPLE 16

The staining procedure of this example was based on HRP catalyzed silver ($Ag^+$) reduction in the presence of $H_2O_2$ and hydroquinone. General staining methods, as disclosed herein, were used for the disclosed embodiments. For detection, approximately one drop of Silver A reagent was applied and incubated for 4 minutes followed by applying approximately one drop of Silver B and approximately one drop of Silver C and incubation for 8 minutes. After staining, the slides were washed and dehydrated and further dried under high vacuum. The dried slides were examined in Autoflex III under LDI conditions (e.g. no matrix material used).

EXAMPLE 17

Figure 53B:
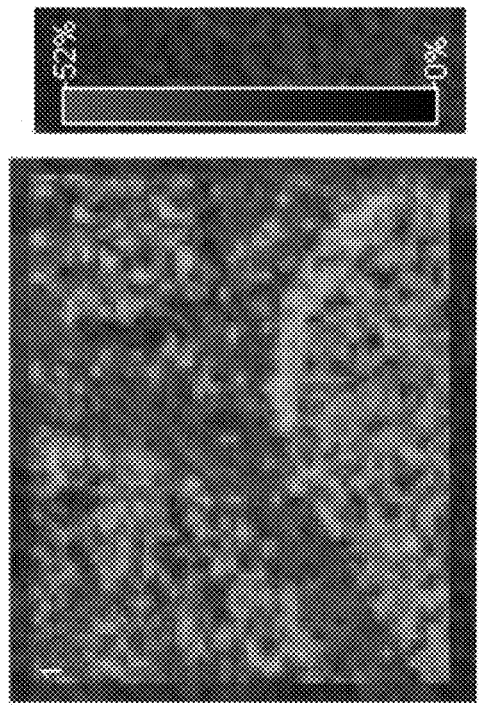
FIGS. 53A and 53B are mass spectral images of tonsil Ki-67 stained with AEC illustrating dimer molecule ions and monomer molecule ions.
Figure 53A:
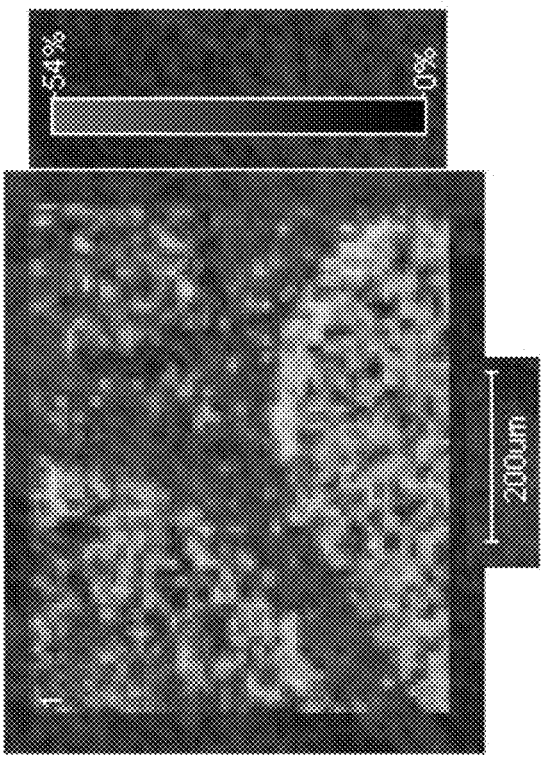

This particular disclosed embodiment concerns using 3-Amino-9-ethylcarbazole (AEC) as an additional example of using heteroaryl compounds as HRP substrate for MSI. General staining methods, as disclosed herein, were used for the disclosed embodiments. AEC chromogen and AEC $H_2O_2$ from a Ventana AEC detection kit (Catalog number: 760-020) were applied and incubated for a period of time (e.g. 8-32 minutes) on tissue. After staining, the slide was washed with soapy water and pure water before dried on vacuum. No alcohol dehydration treatment was applied since the precipitation is soluble in alcohol. The dried slide was imaged using Autoflex III under LDI. For the embodiment shown in FIGS. 53A and 53B, Ki-67 protein in tonsil tissue was stained and imaged. These particular embodiments demonstrate good signal correlation between IHC and MSI.

EXAMPLE 18

Figure 54:
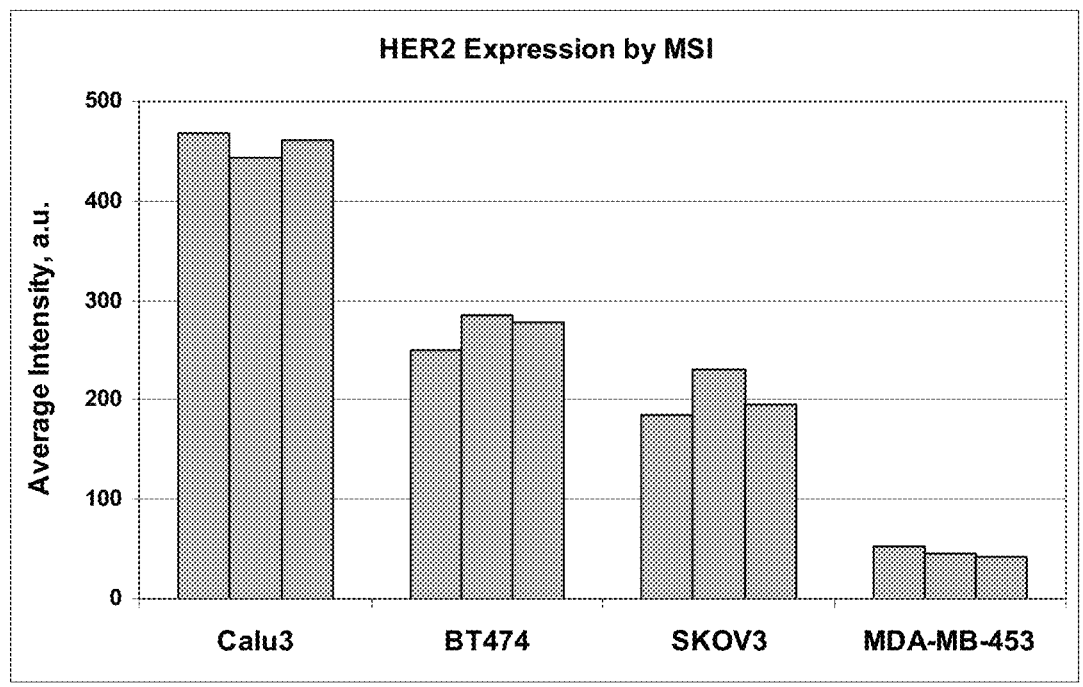
FIG. 54 is a bar graph illustrating the average intensity (au) of multiple regions imaged using mass spectrometry imaging. Four different Her2 expressing cell lines were analyzed on the same slide and each bar shown for each cell line in the graph illustrates a different region of the cell line imaged under identical conditions.

A 4-in-1 FFPE multi-cell block of Calu 3, BT-474, SKOV3, and MDA-MB-453 was used to examine whether MSI intensity can be correlated to known protein expression level. The disclosed cell lines have been reported to express different level of Her2 protein, with Calu 3 expressing a higher level of Her2 protein than BT-474, which expresses a level of Her2 protein substantially similar to that of SKOV3, both of which express a higher level of Her2 protein than MDA-MB-453 (e.g. Calu 3>BT-474~SKOV3>MDA-MB-453). The staining for this particular disclosed embodiment was based on the AP catalyzed naphthol-diazonium reaction. Fast Blue BB (Sigma F3378) was used as the diazonium component, while ultraview Red Naphthol (from Ventana ultraView™ Universal Alkaline Phosphatase Red Detection Kit) was used as the naphthol precursor. Multiple slides were stained using an identical protocol but were imaged at a different point in time in order to examine reproducibility of the intensity data. For each disclosed cell line, multiple regions within a specific cell line section were imaged and FIG. 54 shows a representative plot of the overall average intensity of the regions. A person of ordinary skill in the art will recognize that the intra-slide variation of the intensity was general very small. In addition, the trend of the intensity levels correlates with the Her2 expression level among the disclosed cell lines.

Figure 55:
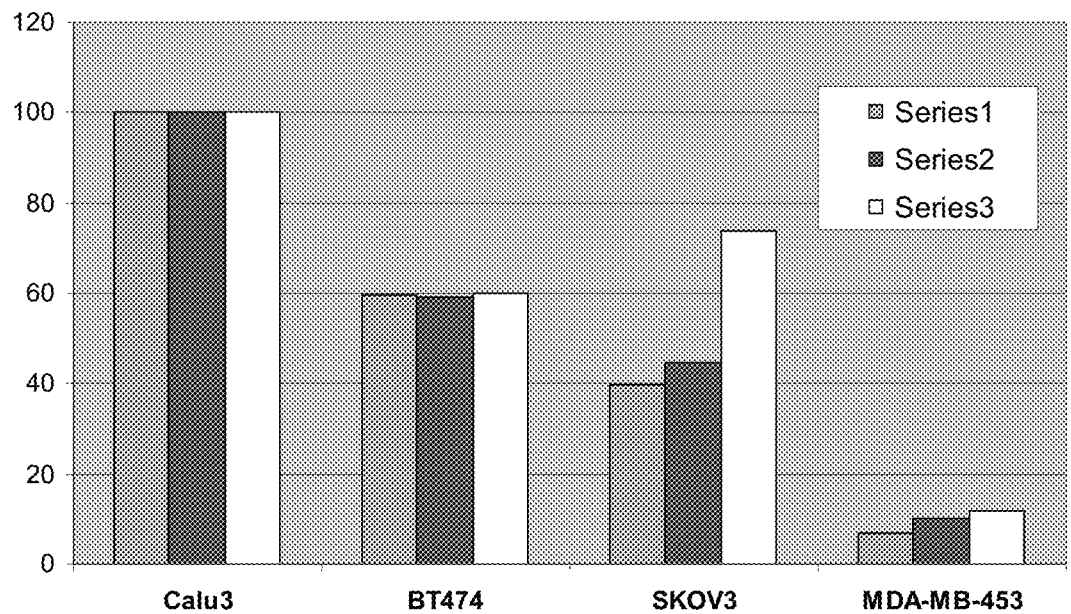
FIG. 55 is a bar graph illustrating normalized intensity of Her2 expessing cell lines (Her2 in Calu 3 =100). Each series (Series 1, 2, and 3) represents a different slide imaged at different times.

To examine inter-slide variation and reproducibility, the identically stained slides were imaged at different points in time. The average intensity values of the same cell line from different imaging exemplary working embodiments were found to be different. Without being limited to a particular theory of operation, it is currently believed that the difference in average intensity values is likely due to the different instrumental conditions and slightly different imaging set up parameter. However, in particular embodiments, the absolute intensities were normalized against one of the cell line (e.g. Her2 in Calu 3 cell line as 100 AU), with which reproducible relative intensity levels were obtained that correlated with the reported Her2 expression levels (FIG. 55). These results illustrate semi-quantification (wherein quantification comprises determining the size of a mass peak and correlating it with the amount of a particular target) information obtained from MSI using particular embodiments of the disclosed method. Also, in particular embodiments both inter- and intra-slide comparisons may be established.

EXAMPLES 19-21

An FFPE tissue block from MCF-7 nude-mouse xenograft breast cancer (block number: 20718, Ventana Medical System Inc., AZ, USA) was used as the sample for IHC staining and SILMSI analysis. The FFPE tissue block was cut in a microtome to the desired thickness (5 μm) and affixed onto the pretreated indium tin oxide (ITO) coated slide (part number: CG-811N-S115, Delta Technologies Inc, MN, USA). The ITO slide was pretreated with gelatin by immersing the ITO slide in gelatin solution 1% w/v gelatin (part number: G7041, Sigma-Aldrich, MO, USA) in 1× PBS (part number: 14190, Invitrogen, NY, USA) for 5 hours at room temperature. Then, the ITO slide was rinsed with $dH_2O$ and allowed to air dry before use.

All immunohistochemistry was performed on Ventana Benchmark XT® automated staining platforms. The tissue samples and primary antibodies were pre-qualified (i.e., assayed for suitability and performance) using ultraView Universal Alkaline Phosphatase Red Detection Kit (part number:760-501, Ventana Medical System Inc., AZ, USA). In all cases one drop of reagent is equal to 100 □L.

FFPE MCF-7 nude-mouse xenograft breast cancer tissue mounted on Superfrost Plus Micro Slide (part number: 48311, VWR, IL, USA) was stained by ultraView Universal Alkaline Phosphatase Red Detection Kit (part number:760-501, Ventana Medical System Inc., AZ, USA) for ER detection in one slide and PR detection in another slide. The same tissue section from the same tissue block was used for the IHC staining. Optical images of the IHC stained slides were taken with light microscopy (Axio Imager A2, Carl Zeiss MicroImaging Inc., Gottingen, Germany).

FFPE MCF-7 nude-mouse xenograft breast cancer tissue mounted on a gelatin-pretreated ITO slide was stained by multiplex staining protocol using in-house synthesized stable-isotope-labeled chromogens. The same slide was sequentially stained for ER detection and PR detection. There were two independent IHC staining exemplary working embodiments for LDI MS imaging analysis. In one IHC staining exemplary working embodiment (Experiment-1), IHC staining was performed using light form of chromogen for ER detection and heavy form of stable-isotope-labeled chromogen for PR detection in the one ITO slide. In another IHC staining exemplary working embodiment (Experiment-2), IHC staining was performed using light form of chromogen for PR detection and heavy form of stable-isotope-labeled chromogen for ER detection in the another ITO slide. The two IHC stained ITO slides were analyzed by LDI MS imaging analysis, separately.

EXAMPLE 19

Referring now to Scheme 16, the following was synthesized.

Stable-Isotope-Labeled (SIL) Mass Tag Synthesis and Formulation

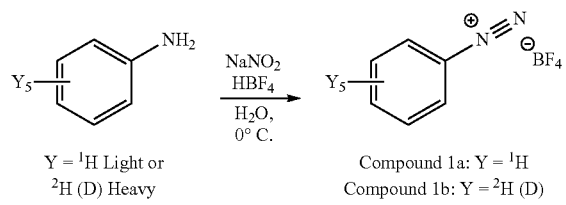

Scheme 26

Y = ¹H Light or
²H (D) Heavy

Compound 1a: Y = ¹H
Compound 1b: Y = ²H (D)

Compound (1a)—Light benzene diazonium salt: According to Scheme 26, aniline 0.3 mL (3.3 mmol, 1 equivalent, Sigma 10400) was dissolved in 1.3 ml of d.i. H$_2$O. Tetrafluoroboric acid 1.02 mL (5.6 mmol, 1.7 equivalents, Sigma 207934) was added dropwise and the mixture subsequently chilled to 0° C. Sodium nitrite 228 mg (3.3 mmol, 1 equivalent, Fluka 71759) was dissolved in 0.9 mL of d.i. H$_2$O and added dropwise to the reaction. The reaction was stirred for 30 minutes. The precipitate was filtered, washed with d.i. H$_2$O. The residue was dissolved in a minimum volume of acetone and precipitated with cold diethyl ether. The precipitate was filtered, washed with cold diethyl ether and dried under vacuum. An off-white powder was isolated in 60% yield. $^1$H NMR (400 MHz, CDCl$_3$) δ (CDCl$_3$) 8.00 (2.0H, dd, J=7.92, 8.56 Hz), 8.30 (1.0H, t, J=7.72 Hz), 8.64 (1.9H, d, J=7.84 Hz). $^{13}$C NMR (101 MHz, CD$_3$OD) δ 141.2, 132.3, 131.3. IR (cm$^{-1}$) 3105 (C—H), 2292 (N≡T), 1565, 1458, 1307, 1283, 1026, 751, 662.

Compound (1b)—Heavy benzene diazonium salt: According to Scheme 26, d$_5$-Aniline 0.3 mL (3.1 mmol, 1 equivalent, Sigma 175692) was dissolved in 1.3 ml of d.i. H$_2$O. Tetrafluoroboric acid 1.02 mL (5.6 mmol, 1.7 equivalents, Sigma 207934) was added dropwise and the mixture subsequently chilled to 0° C. Sodium nitrite 215 mg (3.1 mmol, 1 equivalent, Fluka 71759) was dissolved in 0.9 mL of d.i. H$_2$O and added dropwise to the reaction. The reaction was stirred for 30 minutes. The precipitate was filtered, washed with d.i. H$_2$O. The residue was dissolved in a minimum volume of acetone and precipitated with cold diethyl ether. The precipitate was filtered, washed with cold diethyl ether and dried under vacuum. An off-white powder was isolated in 51% yield. IR (cm$^{-1}$) 3342 (C—D), 2361, 2292 (N≡T), 1524, 1303, 1017.

Compounds 1a and 1b were each formulated in 10 mM acetate buffer to a final concentration of 5 mM.

EXAMPLE 20

Multiplex Staining Protocol—ER Light/PR Heavy (Experiment 1)

FIG. 12 is a schematic diagram of a multiplexed assay for detection of ER and PR with light and heavy mass tags. Formalin-fixed, paraffin-embedded (FFPE) MCF-7 xenograft tissue mounted on gelatin pretreated ITO slides was deparaffinized (EZ Prep, Ventana #950-100) and antigen retrieved (CC1 standard, Ventana #950-124). After retrieval, one drop of anti-ER (SP1) antibody (Ventana #790-4324) was added and incubated at 37° C. for 16 minutes. After washing, one drop of UltraMap anti-rabbit-alkaline phosphatase conjugate (Ventana #760-4314) was added and incubated for 16 minutes. Detection was achieved by adding one drop of naphthol phosphate (Ventana #253-4328) and one drop of a solution of compound 1a and incubating for 12 minutes (Light SIL). Antibody elution was achieved by adding three drops of a elution buffer (25 mM glycine, 0.1% SDS, pH 2.0)[4], heating the slide to 50° C., and incubating for 28 minutes. After washing, one drop of anti-PR (1E2) antibody (VMSI #790-4296) was added and incubated at 37° C. for 16 minutes. Then one drop of anti-rabbit-alkaline phosphatase conjugate was added and incubated for 16 minutes. Detection was achieved by adding one drop of naphthol phosphate and one drop of a solution of compound 1b and incubating for 12 minutes (Heavy SIL). The slides were rinsed with water and air dried. The expected reporter ions and spectra are illustrated in FIG. 13.

Multiplex Staining Protocol—PR Light/ER Heavy (Experiment 2)

The experiment above was repeated with PR being stained with compound 1a and ER being stained with compound 1b to determine whether there was a quantifiable difference when labeling a given antigen with a light or heavy mass tags. The expected reporter ions and spectra are illustrated in FIG. 13.

LDI MS Imaging Analysis

Figure 56:
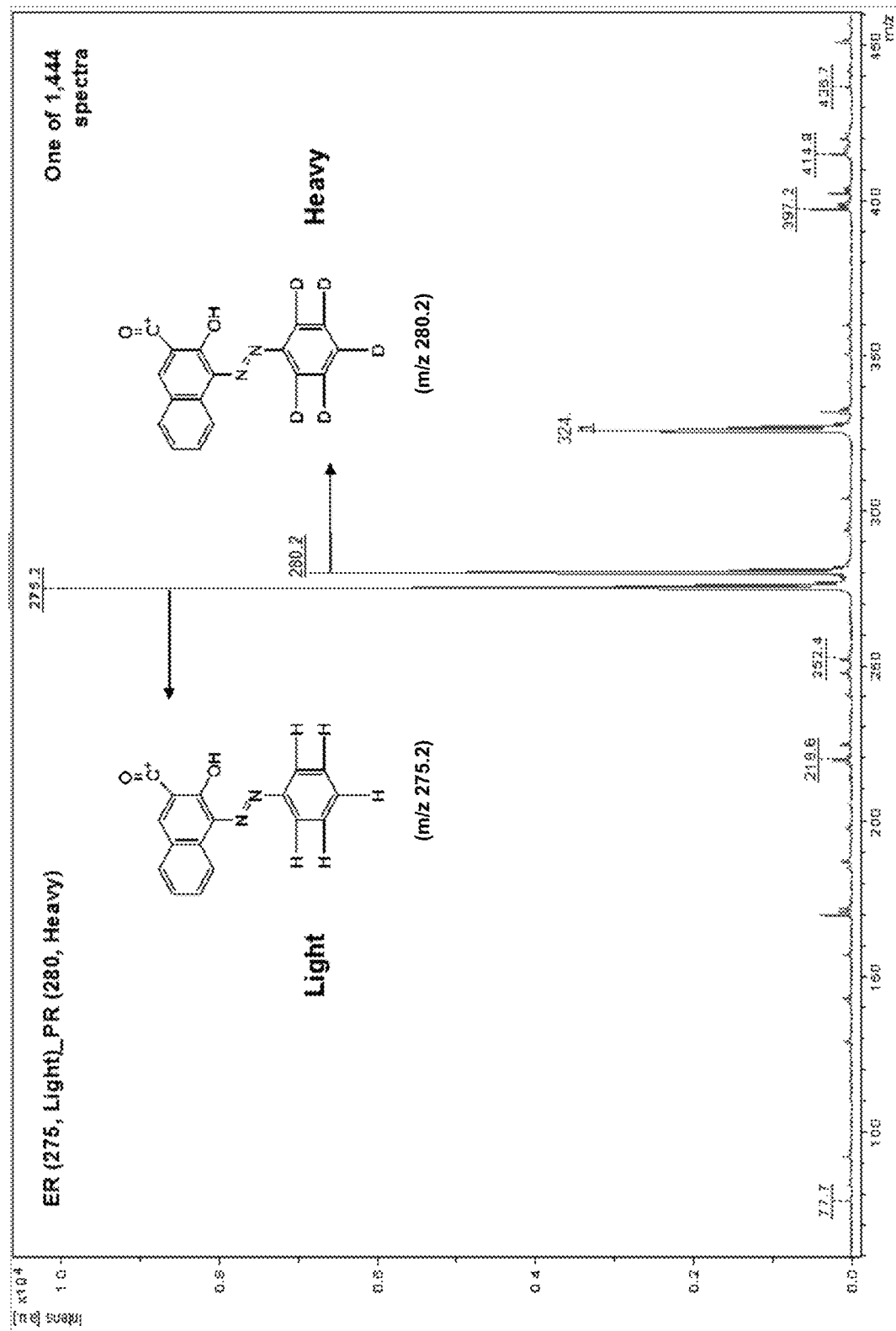
FIG. 56 is a mass spectrum obtained from a multiplexed assay using stable-isotope-labeled mass tags to detect and quantify two antigens in FFPE tissue.

LDI-TOF MS measurements were done on an autoflex III™ MALDI-TOF mass spectrometer equipped with a Smartbeam Laser™ (Bruker Daltonics Inc, Bremen, Germany). The sample was measured with the LDI-TOF MS (linear mode) controlled with flexControl software (version 3.3) and flexImaging software (version 2.1). The laser diameter was set to "small" with a 30 μm of laser-diameter and 30 μm of imaging resolution. Laser frequency was 200 Hz with 100-shot per data acquisition. The laser power was set to 40%, and the mass range of data acquisition was 60-600 Da. The other instrument parameters were set as followings: Ion Source 1 (20 kV), Ion Source 2 (18.85 kV), Lens (6 kV), Detector Electronic Gain (Enhanced), Detector Gain Voltage Offset (linear, 1,300 V). Moving the laser in increments of 30 μm across the tissue sample, 1,444 spectra were obtained from Experiment 1 and 1,177 spectra were obtained from Experiment 2. FIG. 56 shows one mass spectrum obtained from Experiment 1 (ER light/PR heavy).

The chromogens used in the IHC staining, i.e., the light form of chromogen (compound 1a) and the heavy stable-isotope-labeled chromogen (compound 1b), have the exact chemical structure and composition. The only difference is the replacement of hydrogen in light form of chromogen with deuterium in heavy stable-isotope-labeled chromogen. Thus, the efficiency of IHC chemical reaction should be exactly the same in the two independent experiments (see FIG. 12). This provides one pre-requisite to ensure accurate quantitative detection by LDI-TOF MS.

Moreover, the IHC chemical reaction generated azo-dye precipitates (FIG. 12) also have exact same chemical structure and composition except for the replacement of hydrogen in the light form of azo dye with deuterium in the heavy form of stable-isotope-labeled azo dye; therefore, in-source fragmentation of both forms of azo dye upon the laser irradiation will have exact same efficiency. This, in turn, provides another pre-requisite to ensure accurate quantitative detection by LDI-TOF MS. In the MS spectrum, the peak intensity of reporter ions generated by the in-source fragmentation of azo dye will be solely correlated with the detected antigen (ER or PR) concentration in FFPE tissue, thereby enabling accurate quantification (wherein quantification comprises determining the size of a mass peak and correlating it with the amount of the two antigens in the tissue sample).

Acquired LDI MS imaging measurements were exported from flexImaging to Excel (Microsoft Office 2003, SP3, Microsoft Corporation, WA, USA) for quantitative analysis. Data from each measurement is composed of the peak intensity and its corresponding coordinates for ER and PR, separately. The relative quantization (i.e., the ratio of ER/PR) was calculated by the comparison of the peak intensity of ER versus PR in two independent experiments. The quantitative results were saved as a .txt file and exported to in-house developed software for imaging analysis (Ventana Analytical Image, Ventana Medical System Inc., AZ, USA).

Figure 57B:
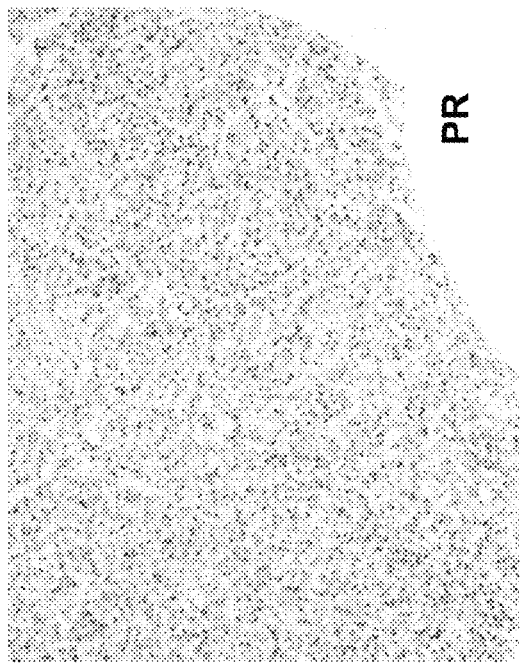
FIGS. 57A-57C are optical images of ER and PR antigens on FFPE MCF-7 nude-mouse xenograft breast cancer tissue.
Figure 57A:
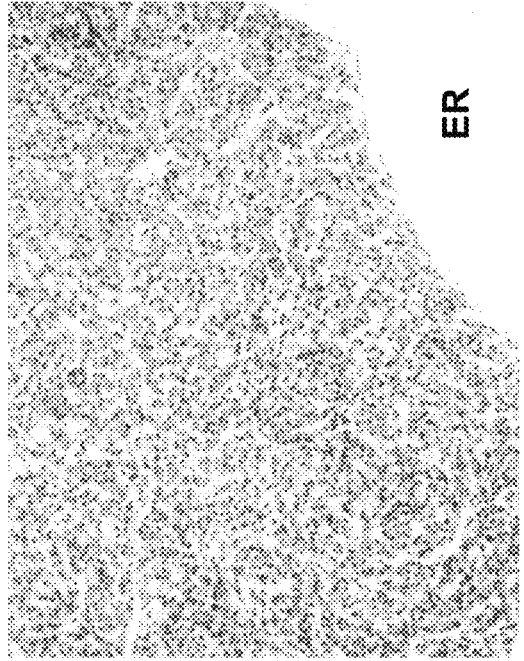
Figure 57C:
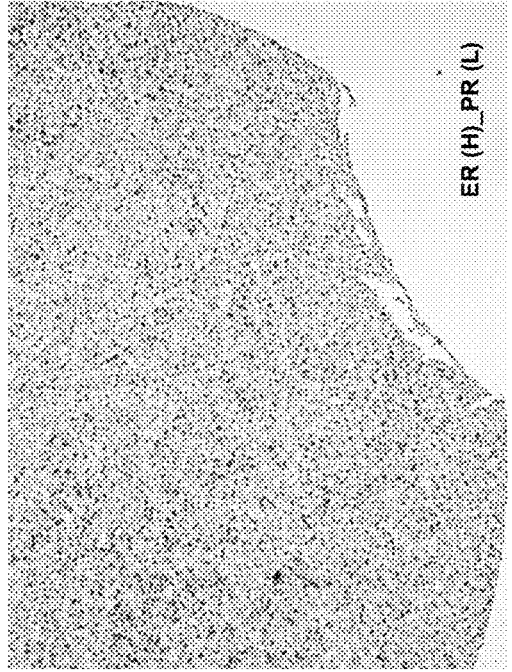

FFPE MCF-7 nude-mouse xenograft breast cancer tissue mounted on Superfrost Plus micro slide was stained by ultraView Universal Alkaline Phosphatase Red Detection Kit for ER detection in one slide and PR detection in another slide. The optical images of the IHC stained slides were taken with light microscopy. As shown in FIGS. 57A-57B, with optical staining, the tissue appears to have more ER antigen than PR antigen. FIG. 57C is an optical image of FFPE MCF-7 nude-mouse xenograft breast cancer tissue mounted on a gelatin-pretreated ITO slide after multiplex IHC staining as described above in Experiment 2 where ER was stained with the heavy mass tag and PR was stained with the light form. Since both forms of the mass tag/chromogen have the same chemical structure and composition, the only difference is the replacement of hydrogen in light form with deuterium in heavy form. Thus, the azo dye color for both ER and PR detection is the same.

Quantitative results of the ER/PR analysis by the SILMSI technique from Experiments 1 and 2 were processed by comparing the peak intensity of the reporter-ion for ER and the reporter-ion for PR. Ten representative data points from Experiment 1 are shown in Table 8.

TABLE 8

Experiment 1

| #spot-location | Peak intensity ER_275 (Light) | Peak intensity PR_280 (Heavy) | Ratio ER/PR |
|---|---|---|---|
| 0_R00X215Y073 | 6.50 | 2.50 | 2.60 |
| 0_R00X216Y073 | 7.97 | 6.10 | 1.31 |
| 0_R00X217Y073 | 5.71 | 3.33 | 1.72 |
| 0_R00X218Y073 | 4.90 | 6.80 | 0.72 |
| 0_R00X219Y073 | 7.16 | 6.32 | 1.13 |
| 0_R00X220Y073 | 53.65 | 35.34 | 1.52 |
| 0_R00X221Y073 | 3286.10 | 2058.26 | 1.60 |
| 0_R00X222Y073 | 6.50 | 4.29 | 1.52 |
| 0_R00X223Y073 | 6.06 | 3.86 | 1.57 |
| 0_R00X224Y073 | 143.57 | 96.59 | 1.49 |

Table 9 summarizes the results and compares the two experiments using four categories of ER/PR ratio, i.e., ER/PR≤0.67, ER/PR∈(0.67, 1.50), ER/PR∈(1.50, 4.0), and ER/PR≥4.00. Each "MS event" is one MS spectrum obtained as the laser was rastered across the tissue sample in 30 μm increments.

TABLE 9

Summary of SILMSI results (MCF-7 nude-mouse xenograft breast cancer)

|  | ER/PR | ≤0.67 | ∈ (0.67, 1.50) | ∈ (1.50, 4.00) | ≥4.00 |
|---|---|---|---|---|---|
| No. of MS events | Experiment-1 | 61 | 739 | 636 | 8 |
|  | Experiment-2 | 32 | 603 | 540 | 2 |
| % of MS events | Experiment-1 | 4.22 | 51.18 | 44.17 | 0.55 |
|  | Experiment-2 | 2.72 | 51.23 | 45.88 | 0.17 |
| Mean | Experiment-1 | 0.55 | 1.14 | 1.97 | 6.53 |
|  | Experiment-2 | 0.54 | 1.17 | 2.04 | 4.72 |
| Standard Deviation | Experiment-1 | 0.10 | 0.22 | 0.40 | 3.50 |
|  | Experiment-2 | 0.11 | 0.21 | 0.46 | 0.74 |
| Standard Error of Mean | Experiment-1 | 0.01 | 0.01 | 0.02 | 1.24 |
|  | Experiment-2 | 0.02 | 0.01 | 0.02 | 0.52 |

Figure 58A:
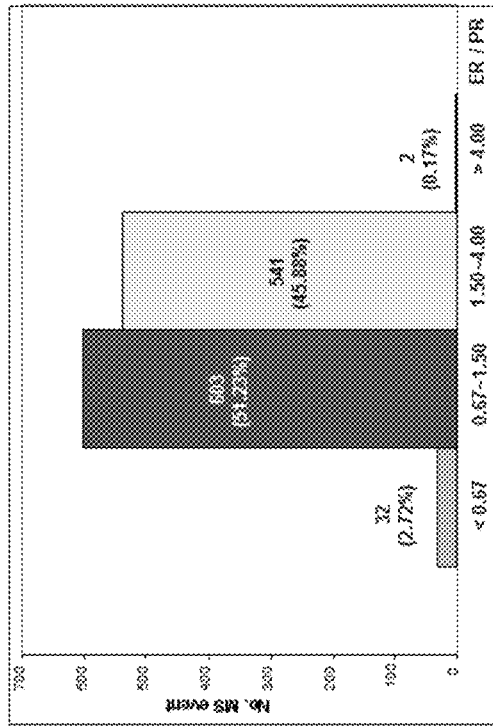
FIGS. 58A-58B are bar graphs illustrating the number of mass spectrometric events versus ER/PR ratio for two exemplary working embodiments in which ER and PR antigens were stained according to one embodiment of the disclosed method for multiplex staining with stable-isotope-labeled mass tags.
Figure 58B:
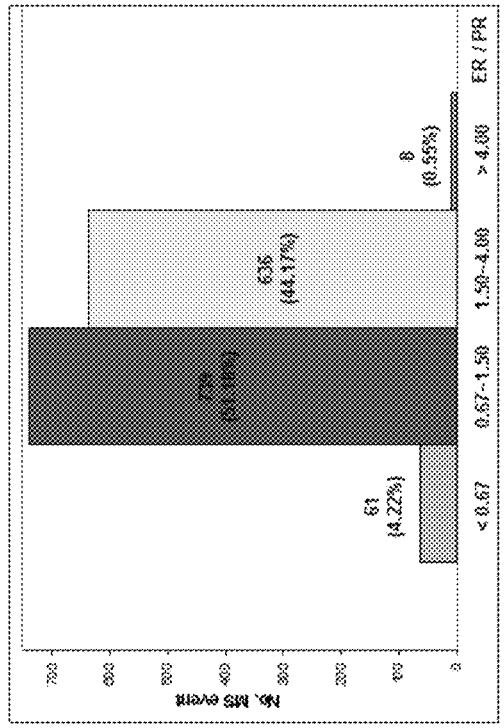

By analyzing the quantitative results from the two independent experiments, it is clear that the ER expression level is higher than that of PR in MCF-7 nude-mouse xenograft breast cancer tissue. In the category of ER/PR E (1.50, 4.00), there are 44.17% of measurements in Experiment-1 and 45.88% of measurement in Experiment-2. Interestingly, in the category of ER/PR E (0.67, 1.50), there are 51.18% of measurements in Experiment-1 and 51.23% of measurement in Experiment-2. These results indicate that about 45% of measurements show up-regulated ER compared to PR expression in the MCF-7 nude-mouse xenograft breast cancer tissue, and about 50% of measurements show that ER and PR have similar expression levels. Only 4.22% of measurements from Experiment-1 show ER/PR≤0.67, and 2.72% of measurements from Experiment-2 show ER/PR≤0.67. FIGS. 58A-58B are bar graphs summarizing the results of Experiments 1 and 2, respectively. Although the overall expression level of ER is seen to be higher than that of PR by visualizing optical images from the IHC staining using ultraView Universal Alkaline Phosphatase Red Detection Kit, the accurate ratio of ER/PR cannot be determined across the conventionally IHC-stained tissue section. However, by applying an embodiment of the disclosed SILMSI technique, the ER/PR ratios can be quantitatively determined across the stained tissue section. This, in turn, will provide valuable information in cancer histological evaluation.

Figure 59:
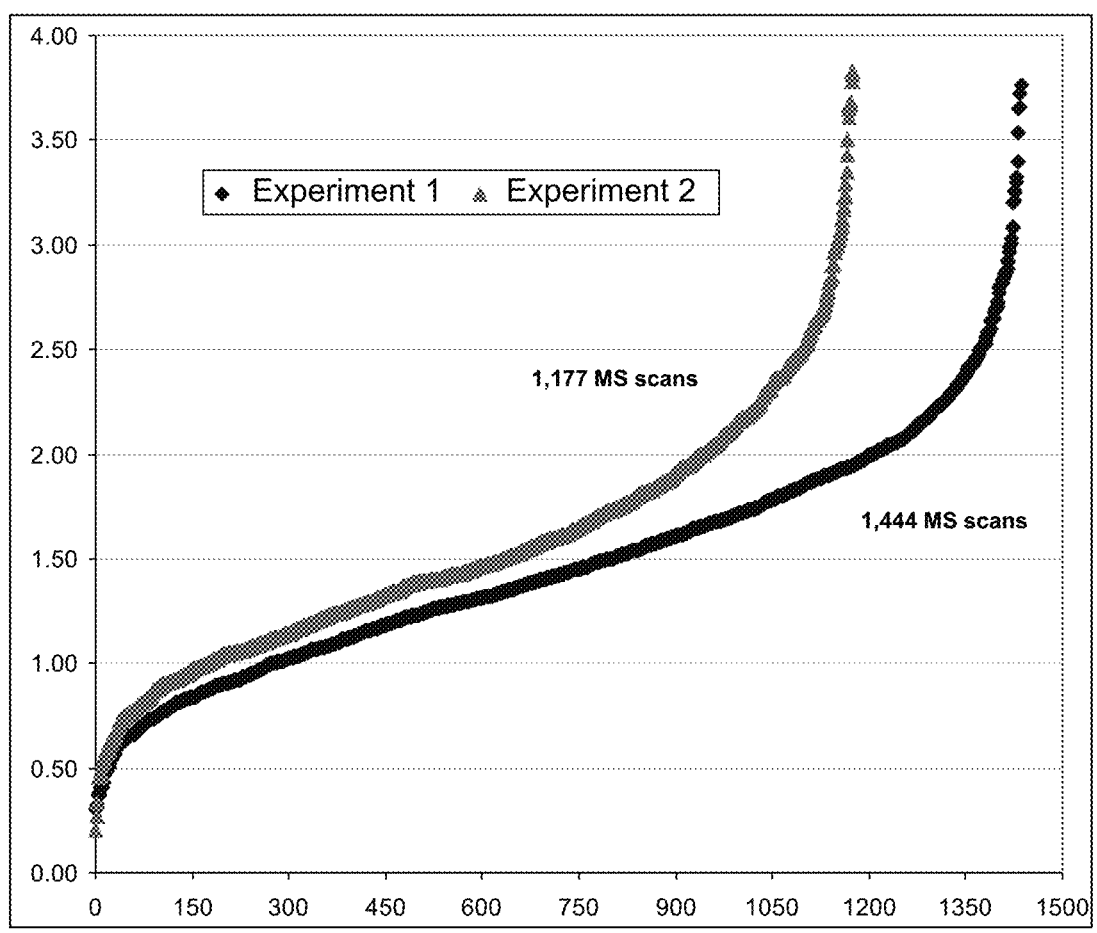
FIG. 59 is a graph of ER/PR mass peak ratio versus the spectrum number determined by sorting the ER/PR ratios from low to high for two exemplary working embodiments in which ER and PR antigens were stained according to one embodiment of the disclosed method for multiplex staining with stable-isotope-labeled mass tags.

To investigate the influence of stable-isotope-label order (direction) on the quantitative analysis of ER/PR by SILMSI, two independent experiments were performed as described above to demonstrate that the results were not affected based on which antigen was labeled with the light mass tag and which antigen was labeled with the heavy mass tag. FIG. 59 shows the similar trend/relation profile of the ratios of ER/PR across the measurements (or MS events) from the two independent experiments with reversed direction of stable-isotope-label. For each experiment, the ER/PR ratios calculated from the spectra obtained were sorted from low to high and plotted. The graph demonstrates that there is no significant influence of the stable-isotope-label direction on the quantitative results. In other words, substantially similar results were obtained whether ER was labeled with the light mass tag and PR was labeled with the heavy mass tag, or vice versa.

Figure 60:
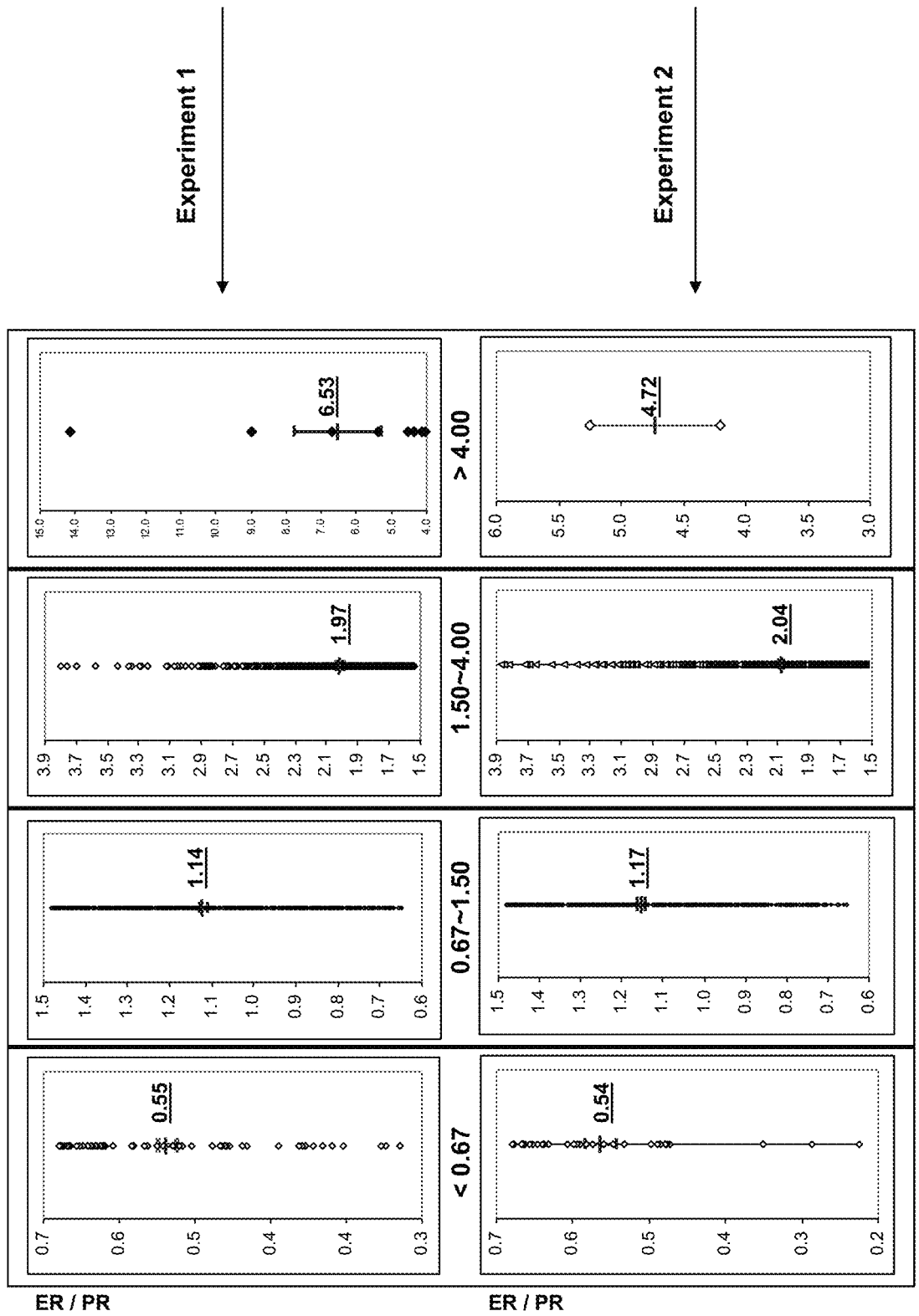
FIG. 60 is a series of graphs showing the mean values of the ER/PR ratio and the error bars for two exemplary working embodiments in which ER and PR antigens were stained according to one embodiment of the disclosed method for multiplex staining with stable-isotope-labeled mass tags. The ER/PR ratios were sorted into four groups, i.e., $\leq 0.67$, $\in(0.67, 1.50)$, $\in(1.50, 4.00)$, and $\geq 4.00$.

To investigate the reliability, or reproducibility, of the SILMSI technique, the results from Experiments 1 and 2 were statistically analyzed (FIG. 60). A side-by-side comparison of the ratio of ER/PR between the two experiments shows that the mean value was 0.55 with a 0.01 error-bar in Experiment-1, and the mean value was 0.54 with a 0.02 error-bar in Experiment-2 for the bin of ER/PR≤0.67. The mean value was 1.14 with a 0.01 error-bar in Experiment-1, and the mean value was 1.17 with a 0.01 error-bar in Experiment-2 for the bin of ER/PR∈(0.67, 1.50). The mean value was 1.97 with a 0.02 error-bar in Experiment-1, and the mean value was 2.04 with a 0.02 error-bar in Experiment-2 for the bin of ER/PR∈(1.50, 4.00). Thus, both the mean values and error-bars of the quantitative analysis of ER/PR in the three different bins were very close and there is no significant difference found between the two experiments in the same bin. Although the mean value was 6.53 with a 1.24 error-bar in Experiment-1, and the mean value was 4.72 with a 0.52 error-bar in Experiment-2 for the bin of ER/PR≥4.00, there were only 8 measurements (0.55% of total measurements) in Experiment-1 and 2 measurements (0.17% of total measurements) Experiment-2 for the bin of ER/PR≥4.00. The results from this bin were considered to be outliers. Thus, the SILMSI technique provides an accurate and reliable quantitative analysis for multiple biomarkers (ER and PR) on FFPE tissue.

Figure 61:
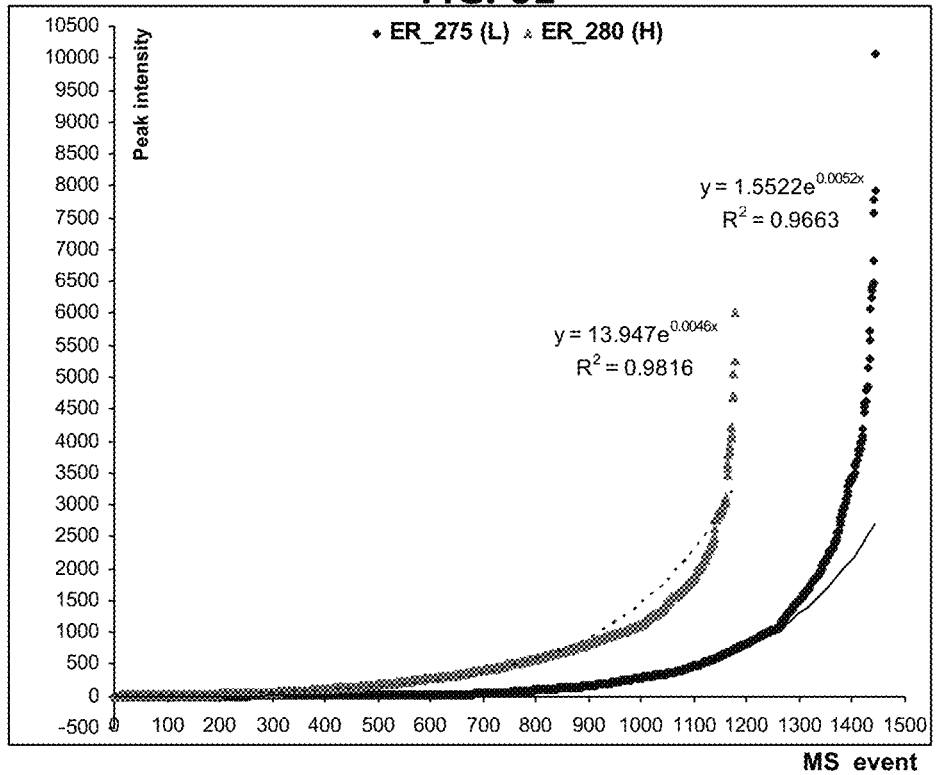
FIG. 61 is a graph of ER peak intensity versus MS event for two exemplary working embodiments in which ER and PR antigens were stained according to one embodiment of the disclosed method for multiplex staining with stable-isotope-labeled mass tags.
Figure 62:
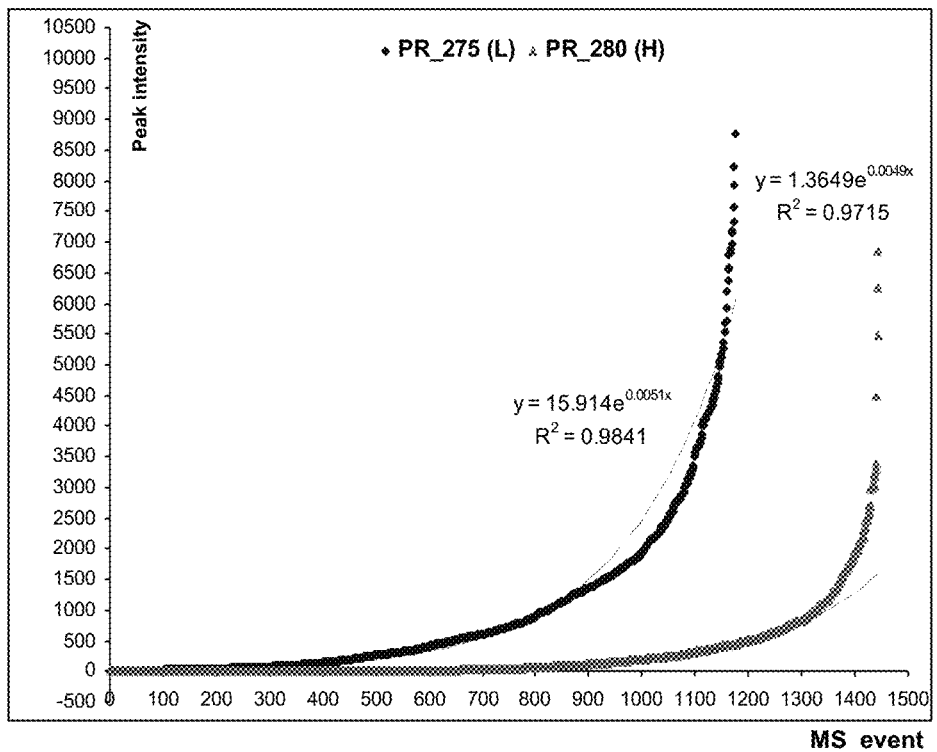
FIG. 62 is a graph of PR peak intensity versus MS event for two exemplary working embodiments in which ER and PR antigens were stained according to one embodiment of the disclosed method for multiplex staining with stable-isotope-labeled mass tags.
Figure 63:
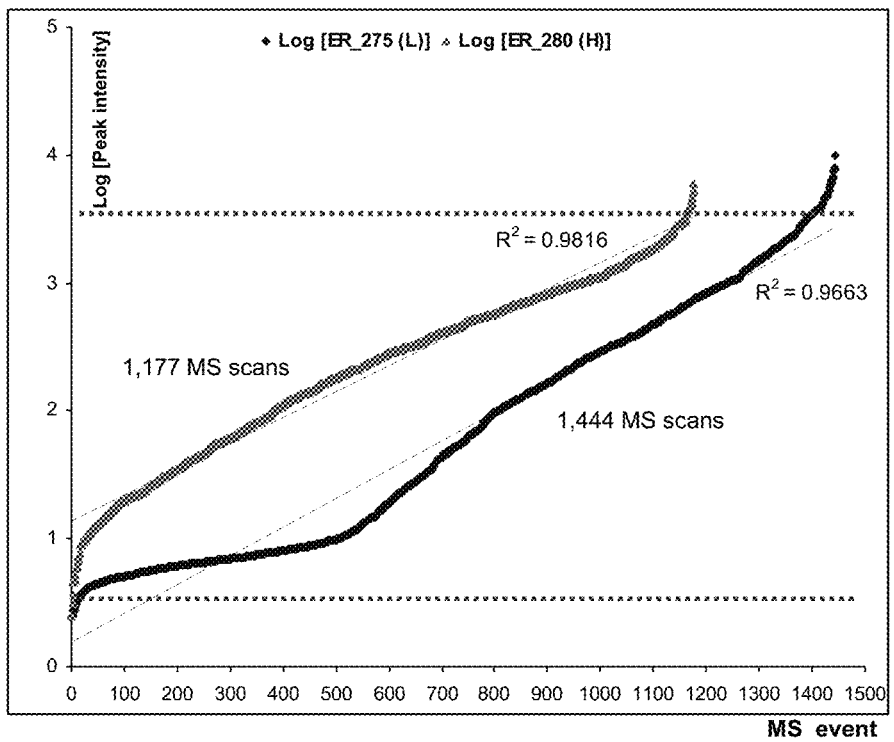
FIG. 63 is a graph of log ER peak intensity versus MS event for two exemplary working embodiments in which ER and PR antigens were stained according to one embodiment of the disclosed method for multiplex staining with stable-isotope-labeled mass tags.
Figure 64:
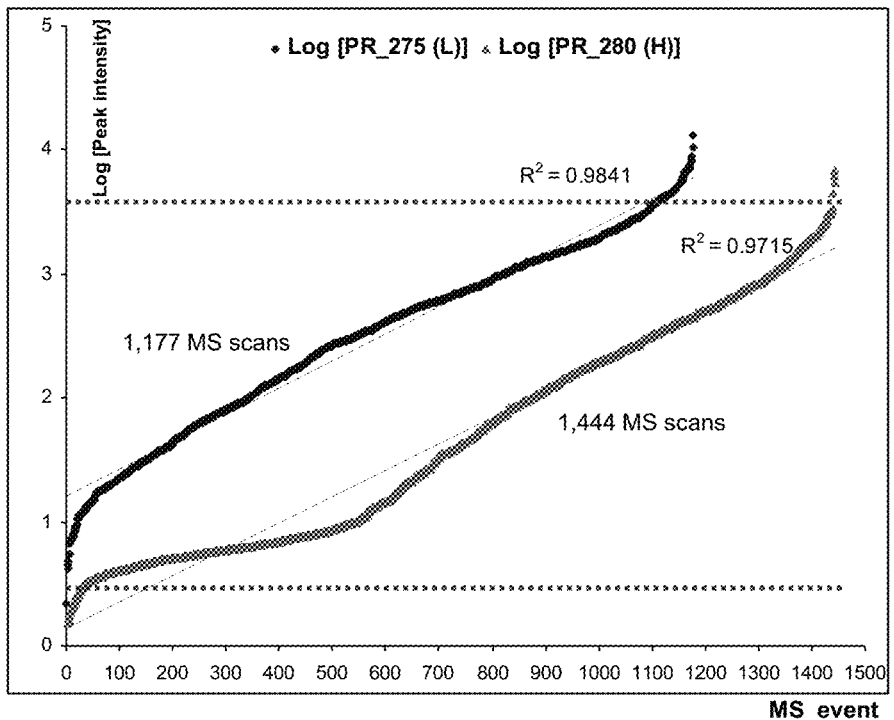
FIG. 64 is a graph of log PR peak intensity versus MS event for two exemplary working embodiments in which ER and PR antigens were stained according to one embodiment of the disclosed method for multiplex staining with stable-isotope-labeled mass tags.

To investigate the dynamic range and linearity of the SILMSI technique, the peak intensities for ER (FIG. 61) and PR (FIG. 62) were sorted from low to high and plotted against the measurements (MS events) for Experiment 1 (ER labeled with light mass tag) and Experiment 2 (ER labeled with heavy mass tag). As shown in FIGS. 81 and 82, IHC staining produces an observable relationship between the peak intensity of reporter ion and ER or PR concentration on the FFPE tissue. FIGS. 83 and 84 illustrate the log of ER and PR peak intensity with the measurement. This result is indicative of the dynamic range. The peak intensity measurement was observed over the range of about 5-3500.

Figure 14:
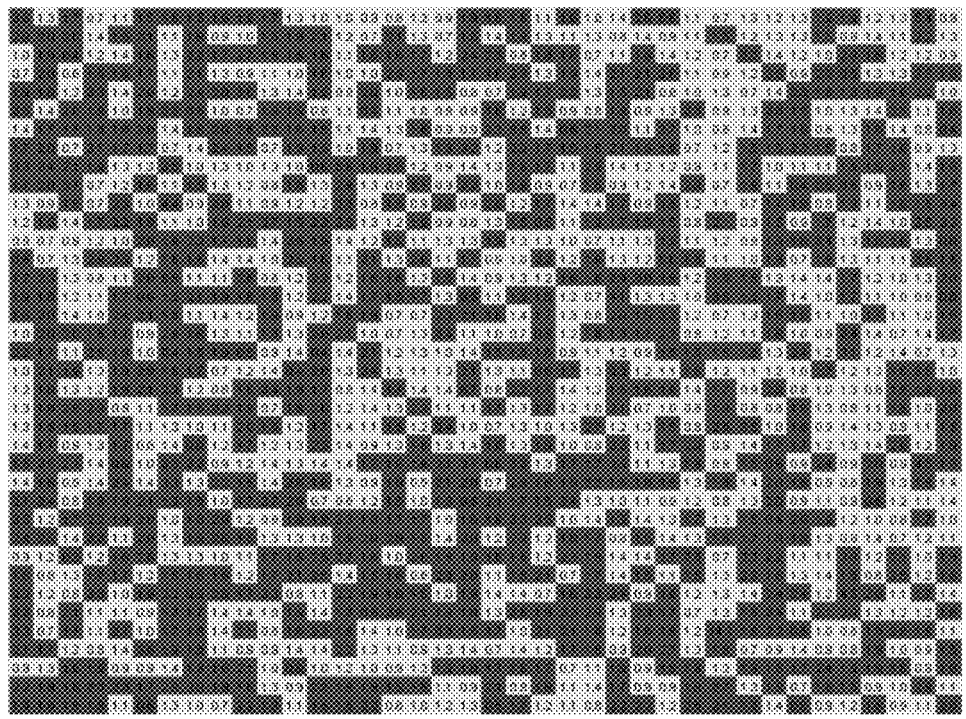
FIGS. 14 and 15 are color-coded and numerical representations of the ER/PR ratios found in tissue sample sections for two working embodiments in which ER and PR antigens were stained according to one embodiment of the disclosed method for multiplex staining with stable-isotope-labeled mass tags.
Figure 15:
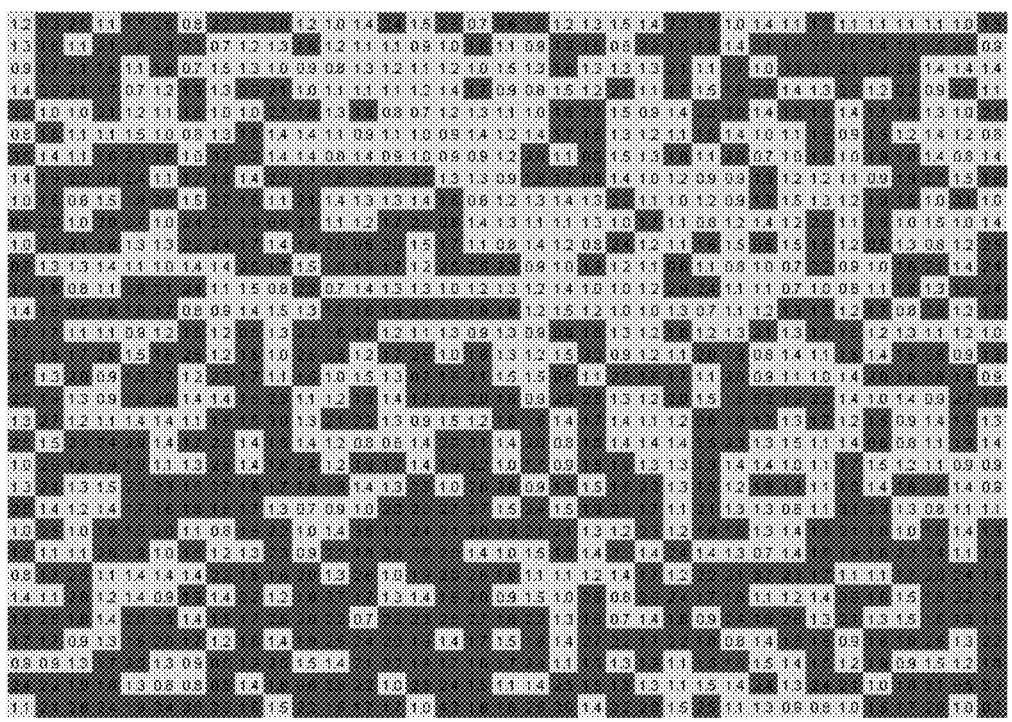

The ER/PR ratio of each 30×30 μm section of the tissue samples from Experiments 1 and 2 was processed in Microsoft $^{Excel}$®, and "heat-maps" were generated using three different cutoffs of ER/PR. When ER/PR≤0.67, the corresponding section on the heat map was colored green. When ER/PR≥1.50, the corresponding section was colored red. When ER/PR∈(0.67, 1.50), the corresponding section was colored yellow. The number in each box is the numerical ratio of ER/PR determined from the actual measurement on the tissue section. The tissue sample from experiment 1 measured 1.14 mm×1.14 mm, and the tissue sample from Experiment 2 measured 1.05 mm×0.96 mm. FIG. 14 is the heat map from Experiment-1, and FIG. 15 is the heat map from Experiment-2.

Figure 16:
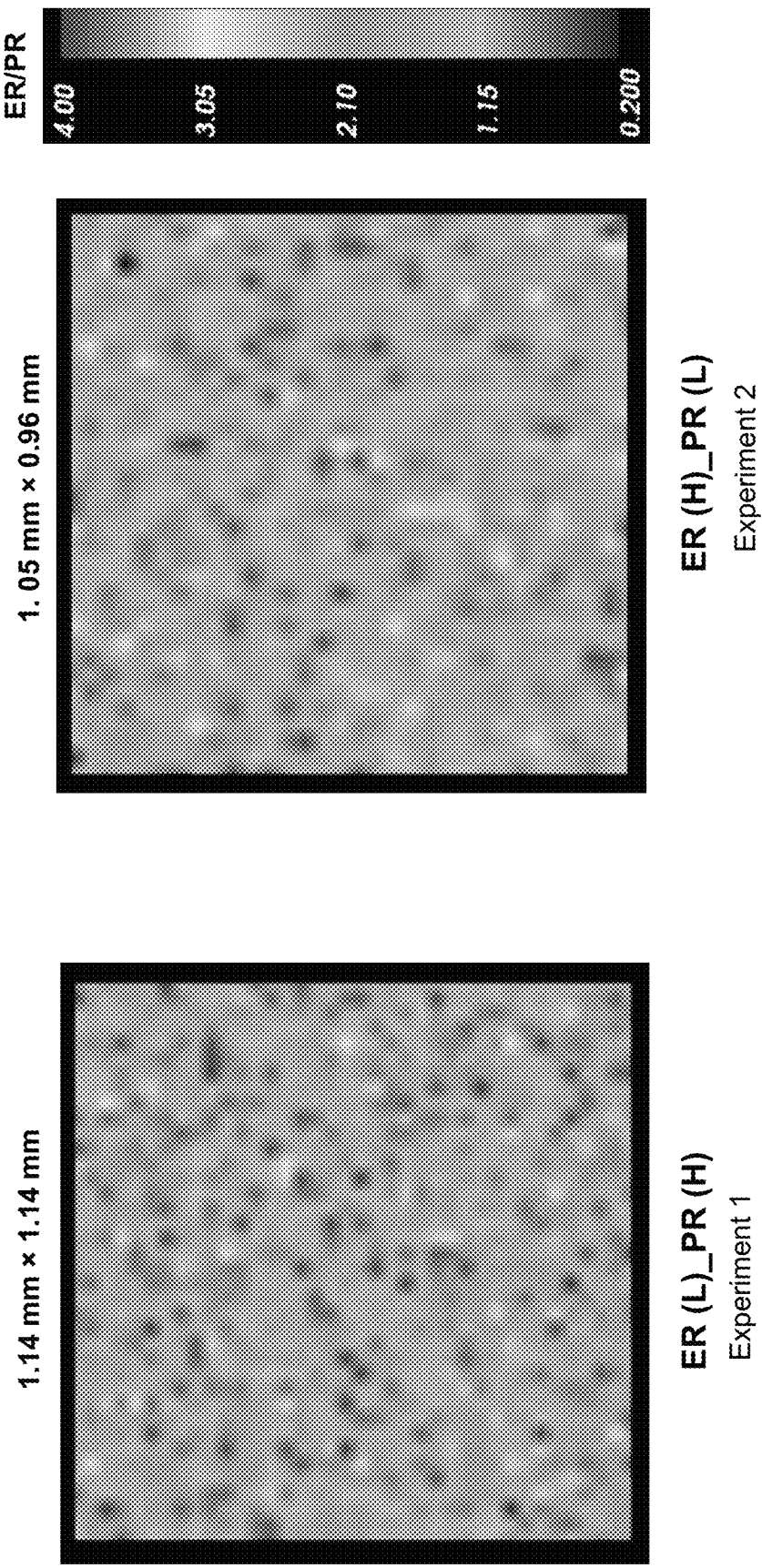
FIGS. 16-18 are color-coded, "heat map" representations of the ER/PR ratios found in in tissue sample sections for two exemplary working embodiments in which ER and PR antigens were stained according to one embodiment of the disclosed method for multiplex staining with stable-isotope-labeled mass tags.
Figure 17:
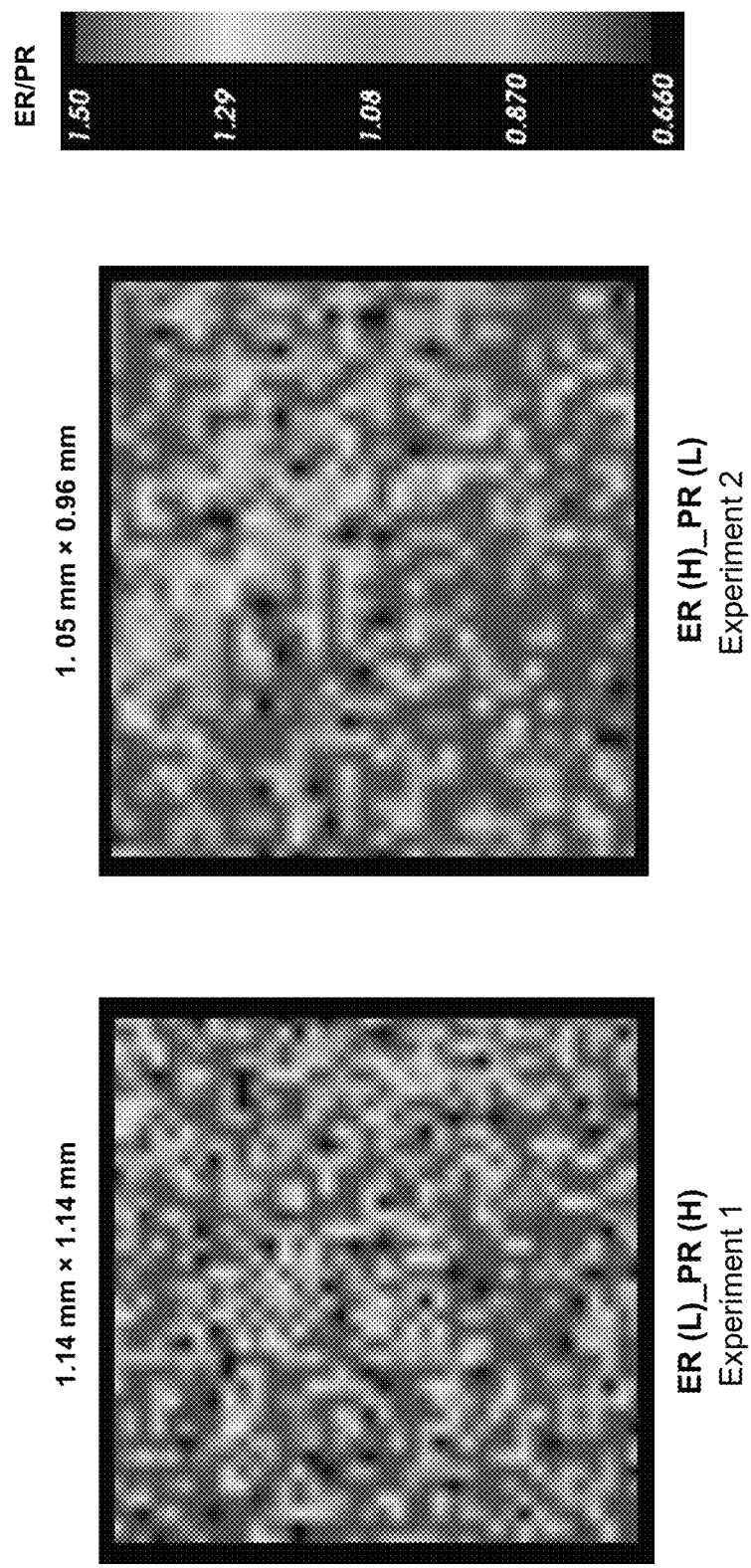
Figure 18:
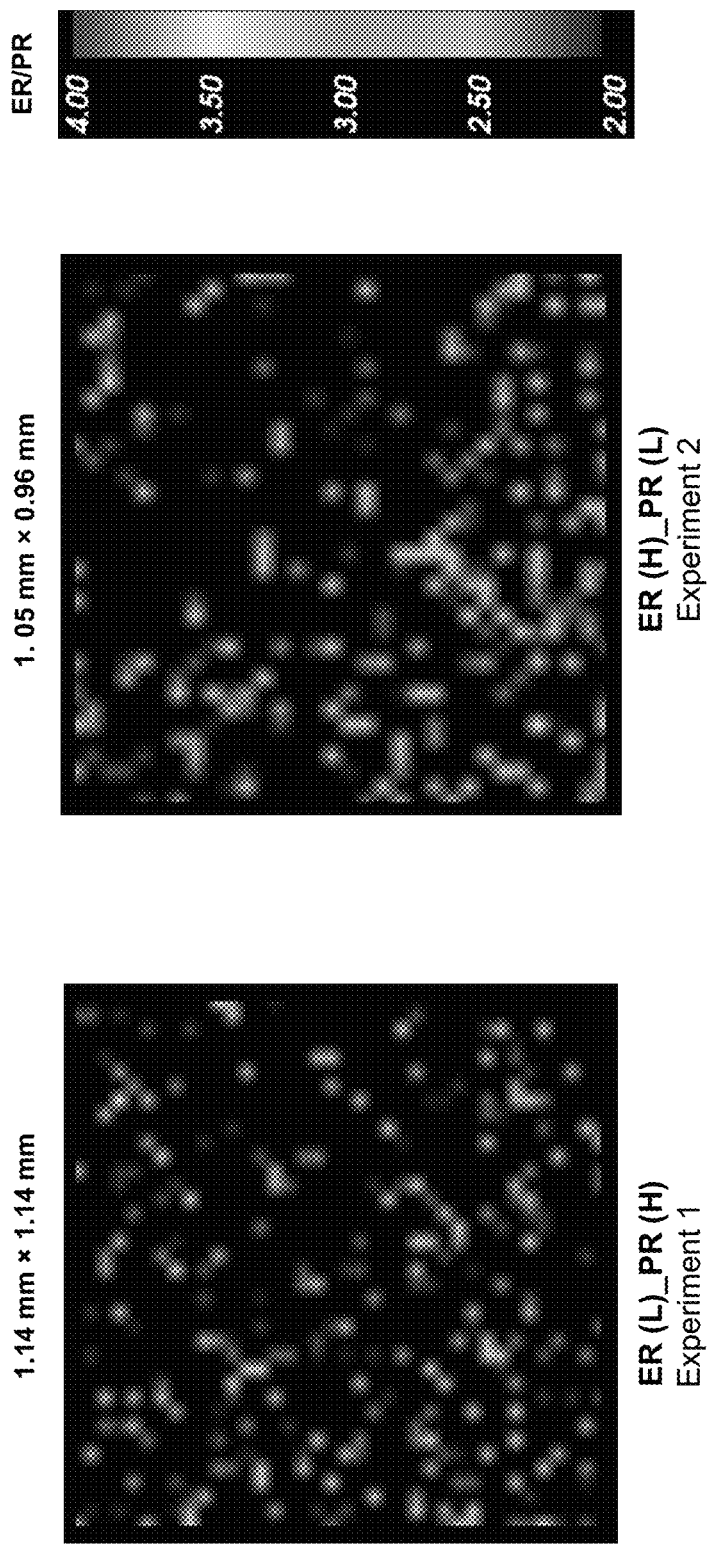

FIGS. 16-18 are other "heat map" representations of the ER/PR data shown in FIGS. 24-27. The data processed in Microsoft Excel® was exported to an in-house software program, Ventana Analytical Image (described herein), and converted to an image with colors shading from blue to red as the ER/PR ratio increased. The image resolution for FIGS. 16-18 is 30 μm. FIG. 16 depicts ER/PR ratios ranging from 0.2 to 4.0 for Experiments 1 and 2. FIG. 17 depicts a subset of the ER/PR ratios ranging from 0.66 to 1.5 for Experiments 1 and 2. FIG. 18 depicts a subset of the ER/PR ratios ranging from 2.0 to 4.0 for Experiments 1 and 2.

EXAMPLE 21

Multiplexed Detection of Intact and Truncated Her2

FIG. 12 is a schematic diagram of a multiplexed assay for detection of intact and truncated Her2 with light and heavy mass tags. Formalin-fixed, paraffin-embedded (FFPE) tissue mounted on gelatin-pretreated ITO slides is deparaffinized and antigen retrieved. After retrieval, SP3 antibody is added and incubated. SP3 antibody will bind to intact Her2. After washing, an anti-SP3 antibody/alkaline phosphatase conjugate is added and incubated. Detection is achieved by adding naphthol phosphate and compound 1a and incubating. Antibody elution is achieved by adding elution buffer and incubating. After washing, 4B5 antibody is added and incubated. 4B5 antibody will bind to truncated and intact Her2. After washing, an anti-4B5 antibody-alkaline phosphatase conjugate is added and incubated. Detection is achieved by adding naphthol phosphate and compound 1b and incubating. The slide is rinsed with water and air dried.

LDI-TOF MS measurements are performed. Multiple spectra are obtained by moving the laser in increments across the tissue sample. Imaging measurements are exported for quantitative analysis. Data for each measurement is composed of the peak intensity and its corresponding coordinates for the light mass code (intact Her2 only) and heavy mass code (truncated and intact Her2). For each measurement, the relative quantization (i.e., the ratio of intact Her2/total Her2) is calculated by comparison of the peak intensity of the light mass code versus the heavy mass code. The ratio of intact Her2/truncated Her2 is calculated by comparing the peak intensity of the light mass code to the difference between the peak intensities of the heavy and light mass codes (i.e., heavy mass code peak intensity—light mass code peak intensity).

General Procedures for Tissue Staining and Mass Imaging using Exemplary Embodiments of the Disclosed Mass Tag Precursor Conjugate: A formalin fixed paraffin embedded (FFPE) tissue sample can be stained on a Ventana Benchmark XT instrument with standard reagents. After deparaffinization and suitable cell conditioning (antigen retrieval), the specific target of interest in the tissue sample is labeled with an antibody-HRP conjugate to localize peroxidase on the target. The tissue is exposed to a mixture of 100 μL of $H_2O_2$ from a Ventana UltraView™ Detection Kit and 100 μL of tyramine or tyramine derivative substrate solution at a suitable concentration, usually in the range of 1 to 200 μM. The reaction is allowed to proceed at 37° C. for a certain period of time (e.g., 4-60 minutes). After the reaction, the slide is washed thoroughly with buffers and water. The slide can be dried under vacuum or in an oven to remove water. Matrix material such as CHCA, SA or DHB is applied on the tissue using a Bruker Imageprep sprayer. The matrix-coated sample is imaged using an AutoFlex III MALDI spectrometer (Bruker). Reference is made to FIGS. 4 and 5 for the examplary staining procedure. Tonsil Ki-67 was targeted with Rb-anti-Ki-67 to produce a labeled target. The target was further labeled with an enzyme-specific binding moiety conjugate, comprising goat-anti-rabbit antibody and horseradish peroxidase (HRP). A mass tag precursor conjugate [e.g. Dabsyl-PEG8-PL-tyramine (68 μM)] was used as the substrate. The sample was then ionized and the mass codes were detected. Peaks at m/z=about 728 and 750 correspond to the mass code and its sodium adduct. α-Cyano-4-hydroxycinnamic acid was used as the matrix.

EXAMPLE 22

With reference to Scheme 18, a nitrophenyl photo-cleavable linker 166 (Advanced ChemTech, RT1095) was first loaded onto a trityl chloride resin 164. The Fmoc protective group of protected amine 168 was removed in 2% 1,8-diazabicyclo[5.4.0]undec-7-ene/dimethylformamide (DBU/DMF) for 10 minutes to provide amine 170. An Fmoc-protected amino acid was activated using standard peptide coupling reagents diisopropylcarbodiimide (DIC)/hydroxybenzotriazole (HOBt) and conjugated to the amino group of the nitrophenyl linker on resin 172. After the coupling reaction, the Fmoc group was subsequently removed in 2% DBU/DMF. The final conjugate 174 was cleaved from the resin in a suitable trifluoroacetic acid (TFA) cocktail to afford a nitrophenyl conjugate 176 with a free carboxylic acid group for further conjugation with tyramine.

EXAMPLE 23

With reference to Scheme 19, tyramine was conjugated to the nitrophenyl photo-cleavable linker carboxylic acid 176 through a standard carbodiimide-mediated coupling reaction. To one equivalent of 1 in DMF was added 1.5 eq of DCC and NHS to afford the active ester 178. The NHS ester 178 was used without separation in the next reaction by adding 2 to 5 eq of tyramine. After stirring at room temperature for at least 4 hours, the insoluble material was removed by filtration and the solution was concentrated. The tyramide conjugate 180 was further purified by HPLC. This method is used to produce a variety of detectable mass codes, having, for example the following m/z ratios.

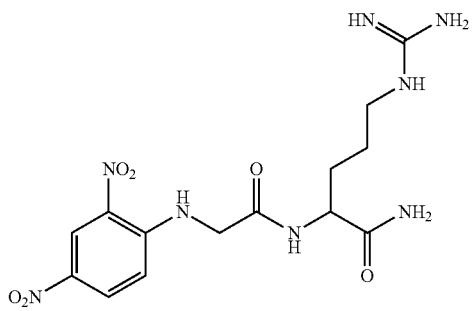
Chemical Formula: C₁₄H₂₀N₈O₆
Exact Mass: 396.151
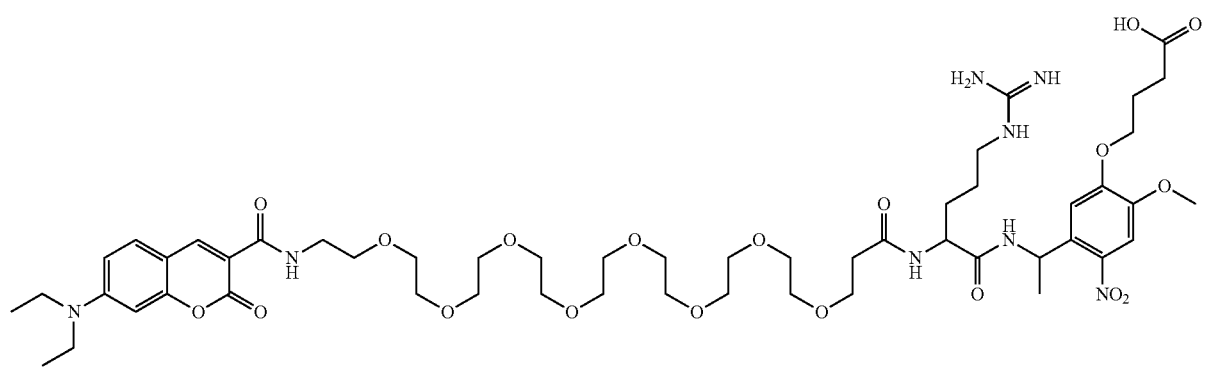
Chemical Formula: C₅₂H₈₀N₈O₁₉
Exact Mass: 1120.554
Molecular Weight: 1121.234
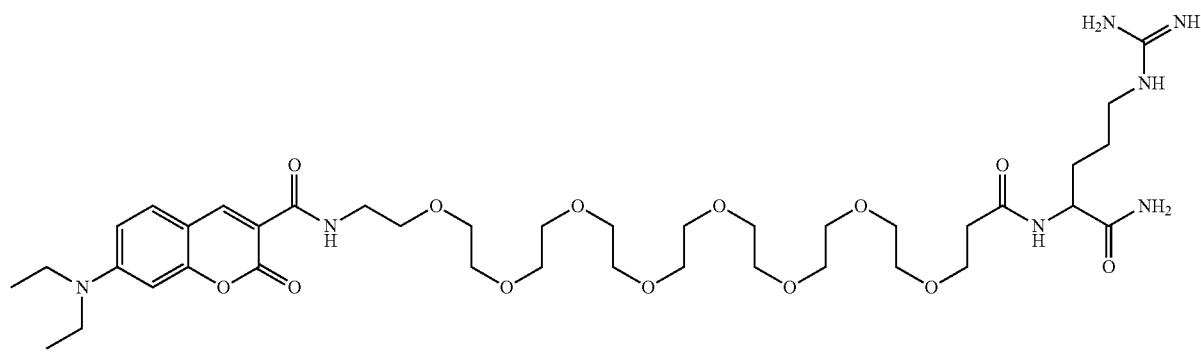
Chemical Formula: C₃₉H₆₅N₇O₁₃
Exact Mass: 839.464
Molecular Weight: 839.973

EXAMPLE 24

A tyramide conjugate, CDO-PEG8-Arg-PL-Tyr (illustrated below) was synthesized according to the general methods described in Example 1 and 2. The molecule was cleaved under MALDI conditions to give a detectable ion at m/z=840.

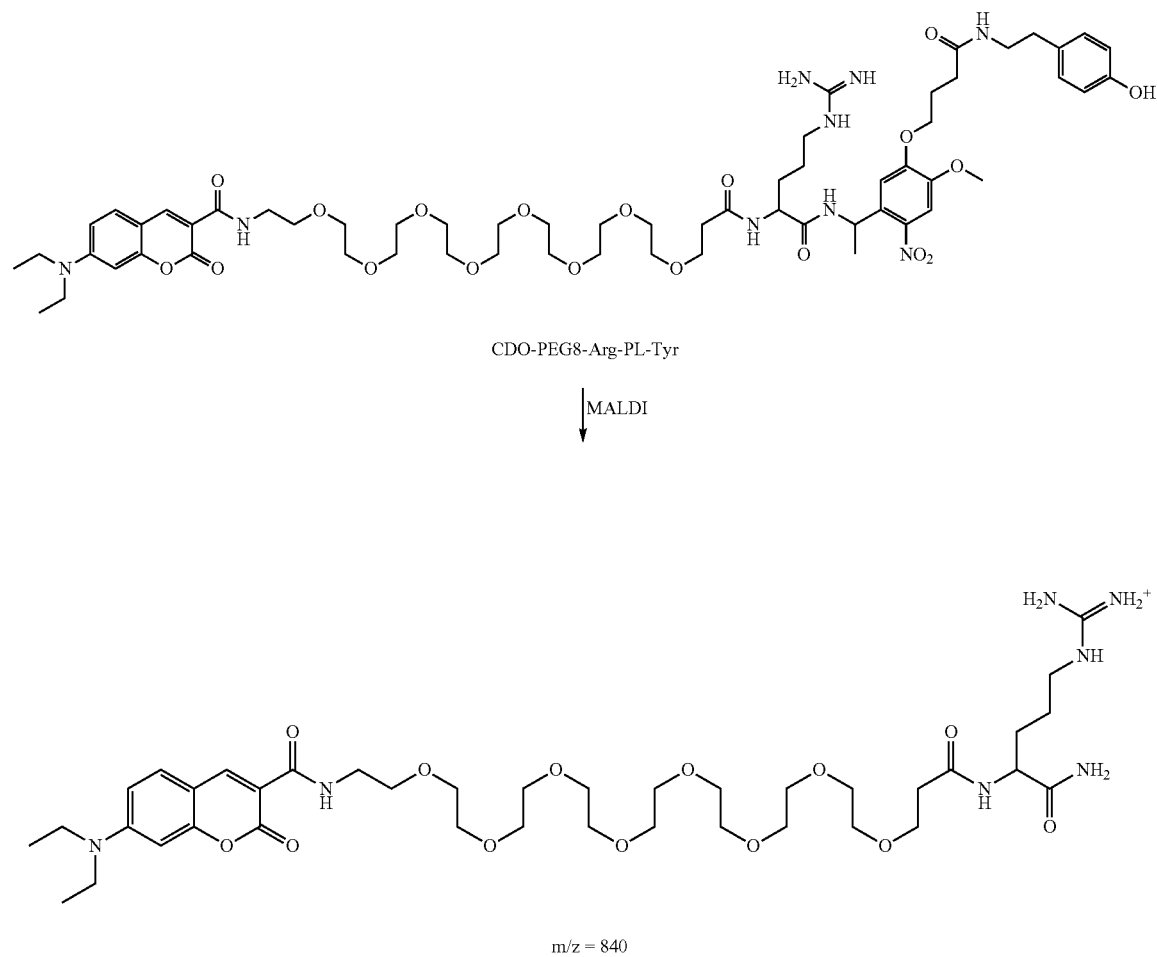

CDO-PEG8-Arg-PL-Tyr

↓ MALDI m/z = 840

The tyramide tag was deposited at tissue target (Ki-67 on tonsil tissue) through HRP mediated oxidative addition reaction using the general tissue staining procedure and scheme in FIG. 85. A control slide (AP instead of HRP added) was also run in parallel with the sample of interest, with the same post-staining treatment being used. After matrix (CHCA) application, the slides were imaged using Bruker Autoflex III. The results are shown in FIGS. 65A-65C. The expected mass tag ion of m/z=840 was observed in the sample with HRP, while this particular mass tag ion was absent from the control slide (no HRP).

EXAMPLE 25

Another exemplary working embodiment was performed on a Her2 3-in-1 xenograft slide with anti-Her2 (Ventana 4B5) as the primary antibody. A substantially similar procedure to that of Example 3 was followed. FIGS. 66A-66C show the heat map of m/z=840 obtained from the MSI exemplary working embodiment. As expected, a strong signal was observed for the Calu 3 xenograft while little signal was recorded from the other two xenografts (ZR-75-1 and MCF7).

The following U.S. Patent, patent publications, and applications are assigned to Ventana Medical Systems, Inc., the assignee of the present application, and each is incorporated herein by reference: U.S. Pat. No. 7,695,929; U.S. Patent Publication No. 2007/0117153; U.S. Patent Publication No. 2006/0246524; U.S. Patent Publication No. 2006/0246423; U.S. patent application Ser. No. 12/154,472; U.S. Provisional Application No. 61/328,494; U.S. Provisional Application No. 61/398,946; and U.S. Provisional Application No. 61/464,216.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A conjugate comprising having a formula:

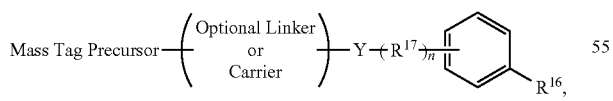

wherein the 'Mass Tag Precursor' is a nitrophenyl moiety or a heteroaryl moiety;

$R^{16}$ is selected from ether, hydroxyl, —N(H)($R^{11}$) or —NH$_2$;

$R^{11}$ is selected from an aliphatic group having between 1 and 10 carbon atoms, a heteroaliphatic group having between 1 and 10 carbon atoms, an aryl group, a heteroaryl group;

$R^{17}$ is selected from an aliphatic group having between 1 and 10 carbon atoms, a heteroaliphatic group having between 1 and 10 carbon atoms, an aryl group having 5 or 6 carbon atoms, or a heteroaryl group having 4 or 5 carbon atoms;

n is an integer ranging from 1 to 20;

Y is selected from oxygen, sulfur, or —N($R^{11}$)—, or —NH—;

the optional linker is selected from an aliphatic group, a heteroaliphatic group, or heterobifunctional linkers; and the optional carrier is selected from a polymer, a biomolecule, a liposome, a micelle, or a nanoparticle;

wherein the nitrophenyl moiety has the formula:

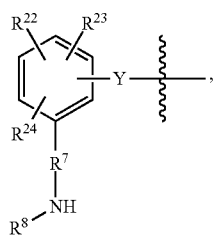

where $R^{22}$, $R^{23}$, and $R^{24}$ are independently selected from an aliphatic group, a heteroaliphatic group, an aryl group, a heteroaryl group, a carbonyl group, a halogen, a hydrogen, a hydroxyl group, an isothiocyanate group, an isocyanate group, a nitrile group, a nitro group, a thiol, or any combination thereof, at least one of $R^{22}$, $R^{23}$, and $R^{24}$ is nitro;

Y is selected from oxygen, sulfur, or -(nitrogen —$R^{11}$)—;

$R^7$ is selected from aliphatic or heteroaliphatic;

$R^8$ is selected from an aliphatic group, a heteroaliphatic group, a heterobifunctional linker, a charged moiety, a chromophore, or any combination thereof; and $R^{11}$ is an aliphatic group, a heteroaliphatic group, an aryl group, or a heteroaryl group; and wherein the heteroaryl moiety has a formula:

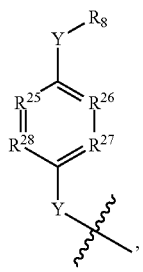

where $R^{25}$, $R^{26}$, and $R^{28}$ are independently selected from carbon or nitrogen, where at least one of $R^{25}$, $R^{26}$, $R^{27}$, and $R^{28}$ is nitrogen;

each Y is independently selected from oxygen, sulfur, or -(nitrogen —$R^{11}$)—;

$R^8$ comprises an aliphatic group, a heteroaliphatic group, a heterobifunctional linker, a charged moiety, a chromophore, or any combination thereof; and $R^{11}$ is an aliphatic group, a heteroaliphatic group, an aryl group, or a heteroaryl group.

2. The conjugate of claim 1, wherein the linker has the following general formula

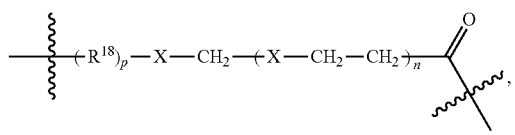

where each X is independently selected from $CH_2$, oxygen, sulfur, or -(nitrogen —$R^{11}$)—;

$R^{18}$ is carbonyl or sulfoxyl; n is an integer ranging from 1 to 20; and p is 0 or 1.

3. The conjugate of claim 1, wherein the nitrophenyl moiety has any of the formulas:

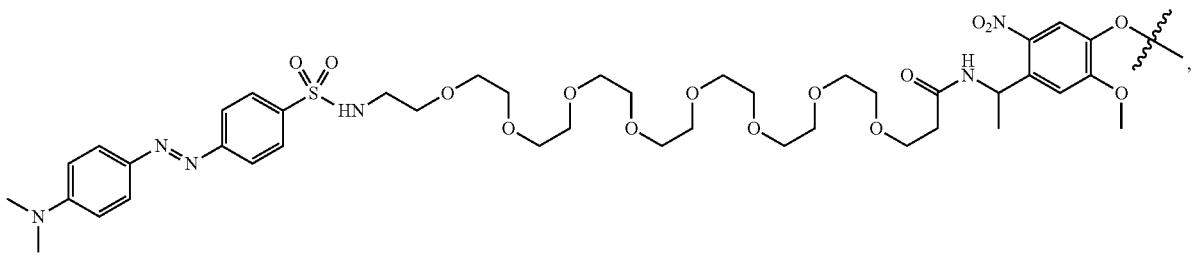

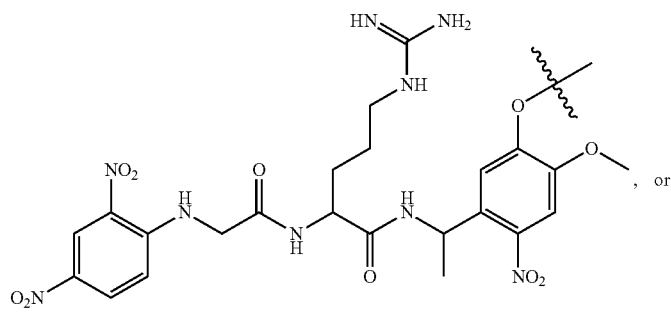, or

-continued

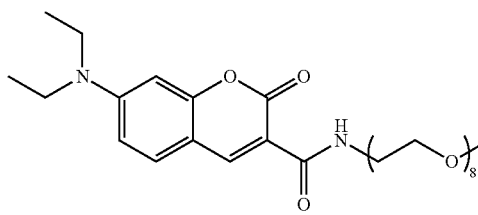
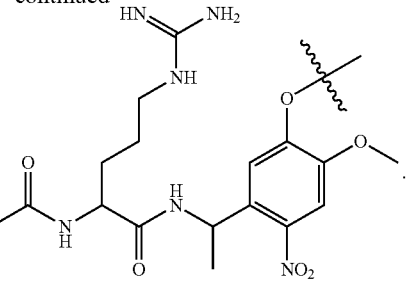

4. The conjugate of claim 1, wherein the linker has the following general formula

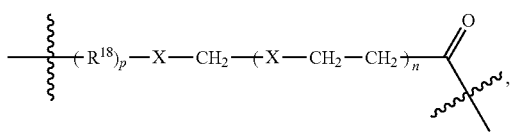

where each X is independently selected from CH$_2$, oxygen, sulfur, or -(nitrogen —R$^{11}$)—; R$^{18}$ is carbonyl or sulfoxyl; n is an integer ranging from 1 to 20; and p is 0 or 1.

5. The conjugate of claim 1, wherein the heteroaryl moiety has a formula:

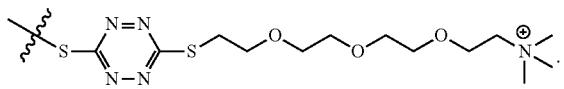 [SMILES: *Sc1nnc(SCCOCCOCCOCC[N+](C)(C)C)nn1]

6. The conjugate of claim 1, wherein

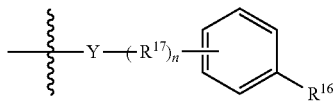

is tyramide or a tyramide derivative.

7. The conjugate of claim 1, wherein the 'Mass Tag Precursor' includes a nitrophenyl moiety and wherein the charged moiety is a charged amino acid moiety or a tetraalkyl ammonium species.

8. The conjugate of claim 7, wherein the charged amino acid moiety is one of arginine, lysine, or histidine.

9. The conjugate of claim 1, wherein the 'Mass Tag Precursor' includes a nitrophenyl moiety and wherein R$^{23}$ is nitro.

10. The conjugate of claim 9, wherein R$^{23}$ is located ortho to the group R$^7$.

11. The conjugate of claim 1, wherein the 'Mass Tag Precursor' includes a nitrophenyl moiety and wherein R$^7$ is —[CH(Me)]—.

12. The conjugate of claim 1, wherein the 'Mass Tag Precursor' includes a nitrophenyl moiety and wherein R$^8$ is substituent having a m/z value ranging from about 100 to about 5000.

13. The conjugate of claim 12, wherein the m/z value ranges from about 500 to about 2000.

14. The conjugate of claim 1, the 'Mass Tag Precursor' includes a heteroaryl moiety and wherein Y is sulfur.

15. The conjugate of claim 1, the 'Mass Tag Precursor' includes a heteroaryl moiety and wherein each of R$^{25}$, R$^{26}$, R$^{27}$, and R$^{28}$ are nitrogen.

16. The conjugate of claim 1, the 'Mass Tag Precursor' includes a heteroaryl moiety.

17. The conjugate of claim 1, wherein the 'Mass Tag Precursor' includes a nitrophenyl moiety.

18. A conjugate comprising having a formula:

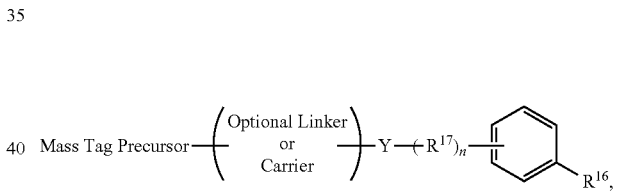

wherein the 'Mass Tag Precursor' is a nitrophenyl moiety or a heteroaryl moiety;

R$^{16}$ is hydroxyl;

R$^{11}$ is selected from an aliphatic group, a heteroaliphatic group, an aryl group, a heteroaryl group;

R$^{17}$ is selected from an aliphatic group, a heteroaliphatic group; n is an integer ranging from 1 to 20;

Y is selected from oxygen, sulfur, or —N(R$^{11}$)—, or —NH—;

the optional linker is selected from an aliphatic group, a heteroaliphatic group, or heterobifunctional linkers; and the optional carrier is selected from a polymer, a biomolecule, a liposome, a micelle, or a nanoparticle;

213 wherein the nitrophenyl moiety has the formula:

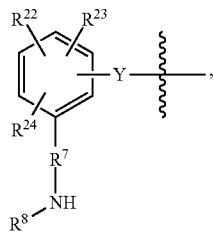

where $R^{22}$, $R^{23}$, and $R^{24}$ are independently selected from an aliphatic group, a heteroaliphatic group, an aryl group, a heteroaryl group, a carbonyl group, a halogen, a hydrogen, a hydroxyl group, an isothiocyanate group, an isocyanate group, a nitrile group, a nitro group, a thiol, or any combination thereof, at least one of $R^{22}$, $R^{23}$, and $R^{24}$ is nitro;

Y is selected from oxygen, sulfur, or -(nitrogen —$R^{11}$)—;

$R^7$ is selected from aliphatic or heteroaliphatic;

$R^8$ is selected from an aliphatic group, a heteroaliphatic group, a heterobifunctional linker, a charged moiety, a chromophore, or any combination thereof; and $R^{11}$ is an aliphatic group, a heteroaliphatic group, an aryl group, or a heteroaryl group; and

214 wherein the heteroaryl moiety has a formula:

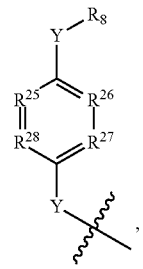

where $R^{25}$, $R^{26}$, $R^{27}$, and $R^{28}$ are independently selected from carbon or nitrogen, where at least one of $R^{25}$, $R^{26}$, $R^{27}$, and $R^{28}$ is nitrogen;

each Y is independently selected from oxygen, sulfur, or -(nitrogen —$R^{11}$)—;

$R^8$ comprises an aliphatic group, a heteroaliphatic group, a heterobifunctional linker, a charged moiety, a chromophore, or any combination thereof; and $R^{11}$ is an aliphatic group, a heteroaliphatic group, an aryl group, or a heteroaryl group.

* * * * *